US012760303B2

(12) United States Patent
Ostertag et al.

(10) Patent No.: US 12,760,303 B2
(45) **Date of Patent: *Oct. 13, 2026**

(54) COMPOSITIONS AND METHODS FOR DIRECTING PROTEINS TO SPECIFIC LOCI IN THE GENOME

(71) Applicant: Poseida Therapeutics, Inc., San Diego, CA (US)

(72) Inventors: Eric M. Ostertag, San Diego, CA (US); Tseten Yeshi, San Diego, CA (US); Xianghong Li, San Diego, CA (US)

(73) Assignee: Poseida Therapeutics, Inc., San Diego, CA (US)

( * ) Notice: Subject to any disclaimer, the term of this patent is extended or adjusted under 35 U.S.C. 154(b) by 936 days.

This patent is subject to a terminal disclaimer.

(21) Appl. No.: 17/822,240

(22) Filed: Aug. 25, 2022

(65) Prior Publication Data

US 2023/0257737 A1 Aug. 17, 2023

Related U.S. Application Data

(63) Continuation of application No. 15/580,675, filed as application No. PCT/US2016/037922 on Jun. 16, 2016, now Pat. No. 11,473,082.

(60) Provisional application No. 62/181,162, filed on Jun. 17, 2015.

(51) Int. Cl.

| | |
|---|---|
| ***C12N 15/11*** | (2006.01) |
| ***A61K 48/00*** | (2006.01) |
| ***C12N 9/16*** | (2006.01) |
| ***C12N 9/22*** | (2006.01) |

(52) U.S. Cl.

CPC .............. *C12N 15/11* (2013.01); *A61K 48/00* (2013.01); *C12N 9/16* (2013.01); *C12N 9/22* (2013.01); *C12N 9/222* (2025.05); *C07K 2319/00* (2013.01); *C12N 2310/20* (2017.05)

(58) Field of Classification Search

CPC . C12N 15/11; C12N 9/16; C12N 9/22; C12N 9/222; C12N 2310/20; A61K 48/00; C07K 2319/00

USPC ......................... 435/196, 440; 514/44 R, 1.1

See application file for complete search history.

(56) References Cited

U.S. PATENT DOCUMENTS

| | | | |
|---|---|---|---|
| 4,554,101 | A | 11/1985 | Hopp |
| 4,873,192 | A | 10/1989 | Kunkel |
| 5,240,846 | A | 8/1993 | Collins et al. |
| 5,380,831 | A | 1/1995 | Adang et al. |
| 5,399,346 | A | 3/1995 | Anderson et al. |
| 5,436,146 | A | 7/1995 | Shenk et al. |
| 5,436,391 | A | 7/1995 | Fujimoto et al. |
| 5,529,774 | A | 6/1996 | Barba et al. |
| 5,547,932 | A | 8/1996 | Curiel et al. |
| 5,639,642 | A | 6/1997 | Kjeldsen et al. |
| 5,645,829 | A | 7/1997 | Shockley et al. |
| 5,656,465 | A | 8/1997 | Panicali et al. |
| 5,670,488 | A | 9/1997 | Gregory et al. |
| 5,672,344 | A | 9/1997 | Kelley et al. |
| 5,741,486 | A | 4/1998 | Pathak et al. |
| 5,817,492 | A | 10/1998 | Saito et al. |
| 5,830,880 | A | 11/1998 | Sedlacek et al. |
| 5,854,019 | A | 12/1998 | Sedlacek et al. |
| 5,869,040 | A | 2/1999 | Oin |
| 5,910,488 | A | 6/1999 | Nabel et al. |
| 5,911,983 | A | 6/1999 | Barranger et al. |
| 5,928,214 | A | 7/1999 | Rubinstein et al. |
| 5,928,914 | A | 7/1999 | Leboulch et al. |
| 6,596,509 | B1 | 7/2003 | Bauer et al. |
| 6,824,978 | B1 | 11/2004 | Cox, III et al. |
| 6,933,113 | B2 | 8/2005 | Case et al. |
| 6,979,539 | B2 | 12/2005 | Cox, III et al. |
| 7,001,768 | B2 | 2/2006 | Wolffe |
| 7,013,219 | B2 | 3/2006 | Case et al. |
| 7,070,934 | B2 | 7/2006 | Cox, III et al. |
| 7,163,824 | B2 | 1/2007 | Cox, III et al. |
| 7,220,719 | B2 | 5/2007 | Case et al. |
| 7,262,054 | B2 | 8/2007 | Jamieson et al. |
| 7,273,923 | B2 | 9/2007 | Jamieson et al. |
| 7,285,416 | B2 | 10/2007 | Choo et al. |
| 7,361,635 | B2 | 4/2008 | Miller et al. |

(Continued)

FOREIGN PATENT DOCUMENTS

| | | | |
|---|---|---|---|
| CA | 2246005 | A1 | 4/2000 |
| CN | 104450785 | A | 3/2015 |

(Continued)

OTHER PUBLICATIONS

Guilinger et al. (2014) Nat. Biotech., vol. 32(6), 577-583, published online Apr. 25, 2014.*
Merriam-Webster Online Dictionary definition of "separate", merriam-webster.com/dictionary/separate, accessed 2025.*
Abe, R. et al. (Apr. 11, 2014) "Ultra Q-bodies: quench-based antibody probes that utilize dye-dye interactions with enhanced antigen-dependent fluorescence" Scientific Reports, 4:4640; DOI: 10.1038/srep04640, 9 pages.

(Continued)

*Primary Examiner* — Anne Marie S Wehbe
(74) *Attorney, Agent, or Firm* — Leason Ellis LLP; Brian M. Gummow; Maha M. Saber

(57) ABSTRACT

Disclosed are compositions and methods for directing proteins to specific loci in the genome and uses thereof. In one aspect, the disclosed methods allow for directing proteins to specific loci in the genome of an organism, including the steps of providing a fusion protein comprising a DNA localization component and an effector molecule. Preferred embodiments of the disclosure include, but are not limited to, the following fusion proteins: dSaCas9-Clo051, dCas9-Clo051, *Xanthomonas*-TALE-Clo051, and *Ralstonia*-TALE-Clo051.

13 Claims, 12 Drawing Sheets

Specification includes a Sequence Listing.

(56) References Cited

U.S. PATENT DOCUMENTS

| | | | | |
|---|---|---|---|---|
| 7,521,241 | B2 | 4/2009 | Choo et al. | |
| 7,790,379 | B2 | 9/2010 | Laemmli et al. | |
| 8,586,526 | B2 | 11/2013 | Gregory et al. | |
| 9,410,134 | B2 * | 8/2016 | Kühn | C12N 15/8509 |
| 9,499,592 | B2 | 11/2016 | Zhang et al. | |
| 10,415,024 | B2 | 9/2019 | Ostertag et al. | |
| 10,844,361 | B2 | 11/2020 | Ostertag et al. | |
| 11,473,082 | B2 | 10/2022 | Ostertag et al. | |
| 2003/0138850 | A1 | 7/2003 | Mossner et al. | |
| 2005/0272107 | A1 | 12/2005 | Rabbitts et al. | |
| 2006/0099654 | A1 | 5/2006 | Huster | |
| 2006/0252140 | A1 | 11/2006 | Yant et al. | |
| 2009/0305402 | A1 | 12/2009 | Liljedahl et al. | |
| 2010/0261177 | A1 | 10/2010 | Weiner et al. | |
| 2011/0059502 | A1 | 3/2011 | Chalasani | |
| 2011/0117625 | A1 | 5/2011 | Lippow et al. | |
| 2012/0270273 | A1 | 10/2012 | Zhang et al. | |
| 2013/0117869 | A1 | 5/2013 | Duchateau et al. | |
| 2014/0068797 | A1 * | 3/2014 | Doudna | C12N 15/907 435/375 |
| 2014/0087426 | A1 | 3/2014 | Liu et al. | |
| 2014/0186958 | A1 | 7/2014 | Zhang et al. | |
| 2014/0298505 | A1 | 10/2014 | Kuhn | |
| 2014/0304847 | A1 | 10/2014 | Kuhn et al. | |
| 2015/0044772 | A1 | 2/2015 | Zhao | |
| 2016/0060610 | A1 | 3/2016 | Ostertag et al. | |
| 2017/0107541 | A1 | 4/2017 | Ostertag et al. | |
| 2017/0114149 | A1 | 4/2017 | Ostertag et al. | |
| 2018/0187185 | A1 | 7/2018 | Ostertag et al. | |
| 2020/0199553 | A1 | 6/2020 | Ostertag et al. | |
| 2021/0062170 | A1 | 3/2021 | Ostertag et al. | |

FOREIGN PATENT DOCUMENTS

| | | | |
|---|---|---|---|
| EP | 2522726 | A1 | 11/2012 |
| JP | 2003500051 | A | 1/2003 |
| JP | 2006518188 | A | 8/2006 |
| JP | 2007159512 | A | 6/2007 |
| JP | 2010209068 | A | 9/2010 |
| JP | 2012518398 | A | 8/2012 |
| JP | 2014506131 | A | 3/2014 |
| JP | 2014511698 | A | 5/2014 |
| JP | 2017518082 | A | 7/2017 |
| JP | 6206893 | B2 | 10/2017 |
| WO | WO-0071702 | A1 | 11/2000 |
| WO | WO-02099104 | A1 | 12/2002 |
| WO | WO-2004046185 | A2 | 6/2004 |
| WO | WO-2007060495 | A1 | 5/2007 |
| WO | WO-2007122511 | A2 | 11/2007 |
| WO | WO-2009095793 | A1 | 8/2009 |
| WO | WO-2010097385 | A1 | 9/2010 |
| WO | WO-2011146121 | A1 | 11/2011 |
| WO | WO-2012092970 | A1 | 7/2012 |
| WO | WO-2012093833 | A2 | 7/2012 |
| WO | WO-2012138927 | A2 | 10/2012 |
| WO | WO-2012158986 | A2 | 11/2012 |
| WO | WO-2012168304 | A1 | 12/2012 |
| WO | WO-2013088446 | A1 | 6/2013 |
| WO | WO-2013152220 | A2 | 10/2013 |
| WO | WO-2013177231 | A1 | 11/2013 |
| WO | WO-2014064277 | A1 | 5/2014 |
| WO | WO-2014089290 | A1 | 6/2014 |
| WO | WO-2015195798 | A1 | 12/2015 |
| WO | WO-2015195803 | A1 | 12/2015 |
| WO | WO-2016205554 | A1 | 12/2016 |

OTHER PUBLICATIONS

Addgene, "Talen Expression Vectors for REAL, REAL-Fast and FLASH" [online]. Retrieved from the Internet: www.addgene.org/talengineering/expressionvectors/. Retrieved on Aug. 22, 2018; 1 page.

Allison, R. (Oct. 15, 1986) "The nucleotide sequence of the coding region of tobacco etch virus genomic RNA: evidence for the synthesis of a single polyprotein" Virology, 154:9-20.

An, G. et al. (1986) "Transformation of Tobacco, Tomato, Potato, and *Arabidopsis thaliana* Using a Binary Ti Vector System", Plant Physiol., 81:301-305.

Arora, N. & Leppla, S.H. (1993) "Residues 1-254 of Anthrax Toxin Lethal Factor Are Sufficient to Cause Cellular Uptake of Fused Polypeptides" J Biol Chem, 268(5):3334-3341.

Asano, et al. (1994) "Transgenic plants of Agrostis alba obtained by electroporation-mediated direct gene transfer into protoplasts", Plant Cell Reports 13:243-246.

Auf Der Maur, A. et al. (2002) "Direct in vivo screening of intrabody libraries constructed on a highly stable single-chain framework", Journal of Biological Chemistry, vol. 277, No. 47, pp. 45075-45085.

Ayres, N.M. and Park, W.D. (1994) "Genetic Transformation of Rice", Critical Reviews in Plant Sciences, 13:219-239.

Baim et al. (Jun. 1991) "A chimeric mammalian transactivator based on the lac repressor that is regulated by temperature and isopropyl-D-thiogalactopyranoside", Proc. Natl. Acad. Sci. USA, 88:5072-5076.

Ballas, N. et al. (1989) "Efficient functioning of plant promoters and poly(A) sites in Xenopus oocytes" Nucleic Acids Res, 17(19):7891-7903.

Banta, S. et al. (2013) "Replacing Antibodies: Engineering New Binding Proteins" Annual Reviews Biomedical Engineering, 15:93-113.

Barcelo, P. et al. (1994) "Transgenic cereal (tritordeum) plants obtained at high efficiency by microprojectile bombardment of inflorescence tissue", Plant Journal, 5:583-592.

Barkley, M.D. et al. (1980) "Repressor Recognition of Operator and Effectors", The Operon, p. 177-220.

Barlos, K. et. al. (1989) "Darstellung geschtzter peptid-fragmente unter einsatz substituierter triphenylmethyl-harze" Tetrahedron Lett, 30(30):3943-3946. German with English Summary on p. 3943.

Becker, D. et al. (1994) "Fertile transgenic wheat from microprojectile bombardment of scutellar tissue", Plant. Journal, 5:299-307.

Bibikova, M. et al. (May 2, 2003) "Enhancing Gene Targeting with Designed Zinc Finger Nucleases", Science, 300:764.

Biocca, S. (2011) "Intrabody Expression in Mammalian Cells" in Antibody Expression and Production. Cell Engineering, vol. 7. Mohamed Al-Rubeai (Ed.) New York: Springer Science+Business Media; pp. 179-195.

Bochtler, M. (Oct. 2012) "Structural basis of the TAL effector-DNA interaction" Biol. Chem, 393(10):1055-1066.

Bolte, S. et al. (2004) "The N-myristoylated Rab-GTPase m-Rabmc is involved in post-Golgi trafficking events to the lytic vacuole in plant cells", Journal of Cell Science, 117:943-954.

Borkowska, M. et al. (1994) "Transformation of diploid potato with an Agrobacterium tumefaciens binary vector system: I. Methodological approach" Acta. Physiol Plant. 16(3):225-230.

Brooks, A.I. et al. "Reproducible and efficient murine CNS gene delivery using a microprocessor-controlled injector", Journal of Neuroscience Methods, 1998, vol. 80, p. 137-147.

Brown, M. et al. (Jun. 5, 1987) "lac Repressor Can Regulate Expression from a Hybrid SV40 Early Promoter Containing a lac Operator in Animal Cells" Cell, 49:603-612.

Campbell, W.H. and G. Gowri (1990) "Codon Usage in Higher Plants, Green Algae, and Cyanobacteria" Plant Physiol, 92:1-11.

Carbonetti, N. et al. (1995) "Use of Perussis toxin Vaccine Molecule PT9K/129G to Deliver Peptide Epitopes for Stimulation of a Cytotoxic T Lymphocyte Response" Abstr. Annu. Meet. Am Soc. Microbiol., 95:295, Abstract E-86.

Casas, A.M. et al. (Dec. 1993) "Transgenic sorghum plants via microprojectile bombardment" Proc. Nat. Acad Sci. USA, 90:11212-11216.

Chee, P.P. and J.L. Slightom (1992) "Transformation of cucumber tissues by microprojectile bombardment: identification of plants containing functional and non-functional transferred genes" (1992) Gene, 118:255-260.

Chevalier, B.S. et al. "Design, activity, and structure of a highly specific artificial endonuclease." Mol Cell. Oct. 2002;10(4):895-905. doi: 10.1016/s1097-2765(02)00690-1.

(56) References Cited

OTHER PUBLICATIONS

Choulika et al., "Induction of homologous recombination in mammalian chromosomes by using the I-Seel system of *Saccharomyces cerevisiae*," Mol. Cell. Biol., 15(4):1968-73, Apr. 1995.
Christian et al., "Targeting DNA Double-Strand Breaks with TAL Effector Nucleases," Genetics. Oct. 2010;186(2):757-61.
Christopherson, K.S. et al. (Jul. 1992) "Ecdysteroid-dependent regulation of genes in mammalian cells by a *Drosophila* ecdysone receptor and chimeric transactivators" Proc. Natl. Acad. Sci. USA, 89:6314-6318.
Christou, P. (Jul. 1993) "Philosophy and practive of variety-independent gene transfer into recalcitrant crops" In Vitro Cell. Dev. Biol., 29p. 119-124.
Christou, P. (Mar./Apr. 1994) "Genetic engeenering of crop legumes and cereals: current status and recent advances" Agro. Food. Ind. Hi Tech., 5:17-27.
Christou, P. et al. (1992) "The development of a variety-independent gene-transfer method for rice" Tibtech, 10:239-246.
Cong et al., "Multiplex Genome Engineering Using CRISPR/Cas Systems," Science 2013, 339:819-823.
Cousins, Y.L. et al. (1991) "Transformation of an Australian Cotton Cultivar: Prospects for Cotton Improvement through Genetic Engineering", Aust. J. Plant Physiol., 18:481-494.
Davies, D.R. et al. (1993) "Transformation of peas" Plant Cell Rep, 12:180-183.
De Block, M. (1988) "Genotype-independent leaf disc transformation of potato (*Solanum tuberosum*) using Agrobacterium tumefaciens", Theor. Appl Genet. 76:767-774.
De Lange, O. et al. (May 2013) "Breaking the DNA-binding code of Ralstonia solanacearum TAL effectors provides new possibilities to generate plant resistance genes against bacterial wilt disease" New Phytologist, 199(3):773-786 (with Supplementary Information, 47 pages).
Degenkolb, J. et al. (Aug. 1991) "Structural Requirements of Tetracycline-Tet Repressor Interaction: Determination of Equilibrium Binding Constants for Tetracycline Analogs with the Tet Repressor" Antimicrob. Agents Chemother., 35:1591-1595.
Della-Cioppa, G. et al. (1987) "Protein trafficking in plant cells" Plant Physiol, 84(4):965-968.
Derossi et al. "The third helix of Antennapedia homeodomain translocates through biological membranes", J Biol. Chem. (1994), 269(14, Issue 8):10444-10450.
Deuschle, U. et al. (Jul. 1989) "Regulated expression of foreign genes in mammalian cells under the control of coliphage T3 RNA polymerase and lac repressor" Proc. Natl. Acad. Aci. USA, 86:5400-5404.
Deuschle, U. et al. (1990) "RNA Polymerase II Transcription Blocked by *Escherichia coli* Lac Repressor" Science, 248:480-483.
D'Halluin, K. et al. (Mar. 1992) "Transformation of Sugarbeet (*Beta vulgaris* I.) and evaluation of herbicide resistance in transgenic plants" Bio/Technol, 10:309-314.
Dhir, S.K. et al. (1992) "Regeneration of Transgenic Soybean (*Glycine max*) Plants from Electroporated Protoplasts" Plant Physiol, 99:81-88. Includes "Notice of Retraction", May 10, 1993, 102:331.
Dong, J-Z. and Mchughen, A. (1993) "Transgenic flax plants from Agrobacterium mediated transformation: incidence of chimeric regenerants and inheritance of transgenic plants" Plant Sci., 91:139-148.
Donnelly, J.J. et al. (Apr. 1993) "Targeted delivery of peptide epitopes to class I major histocompatibility molecules by a modified Pseudomonas exotoxin" Proc Natl Acad Sci, 90(8):3530-3534.
Eapen, S. and L. George (1994) "Agrobacterium tumefaciens mediated gene transfer in peanut (*Arachis hypogaea* L.)" Plant Cell Rep., 13:582-586.
Elliott, G. & O'Hare, P. (1997) "Intercellular Trafficking and Protein Delivery by a Herpesvirus Structural Protein" Cell, 88(2):223-233.
Elroy-Stein, O. et al. (Aug. 1989) "Cap-independent translation of mRNA conferred by encephalomyocarditis virus 5' sequence improves the performance of the vaccinia virus/bacteriophage T7 hybrid expression system" Proc Natl Acad Sci USA, 86(16):6126-6130.
Fajardo-Sanchez, E. et al. (2008) "Computer design of obligate heterodimer meganucleases allows efficient cutting of custom DNA sequences" Nucl Acids Res, 36(7):2163-2173.
Fetter et al. (Jan. 2004) "Interactions between Plasma Membrane Aquaporins Modulate Their Water Channel Activity", Plant Cell, 16:215-228.
Fhraeus, R. et al. (1996) "Inhibition of pRb phosphorylation and cell-cycle progression by a 20-residue peptide derived from p16CDKN2/INK4A" Curr Biol, 6(1):84-91.
Fields, S. and O-k Song (Jul. 1989) "A Novel Genetic System to Detect Protein-Protein Interactions" Nature, vol. 340, No. 6230, pp. 245-246.
Figge, J. et al. (Mar. 11, 1988) "Stringent Regulation of Stably Integrated Chloramphenicol Acetyl Transferase Genes by *E. coli* lac Repressor in Monkey Cells", Cell, 52:713-722.
Franklin, C. I. and T.N. Trieu (May 1993) "Transformation of the forage grass caucasian bluestem via biolistic bombardment-mediated DNA transfer" Plant. Physiol. Suppl., 102(1):167, Abstract 958.
Fry, J. et al. (1987) "Transformation of *Brassica napus* with Agrobacterium tumefaciens based vectors", Plant Cell Rep, 6:321-325.
Fuerst, T.R. et al. (Apr. 1989) "Transfer of the inducible lac repressor/operator system from *Escherichia coli* to a vaccinia virus expression vector", Proc. Natl. Acad. Sci. USA, 86:2549-2553.
Gallie, D.R. et al. (1989) "Eukaryotic viral 5'-leader sequences act as translational enhancers in eukaryotes and prokaryotes" in Molecular Biology of RNA. Thomas R. Cech (Ed.), New York: Alan R. Liss, Inc.; pp. 237-256.
Gallie, D.R. et al. (1995) "The tobacco etch viral 5' leader and poly(A) tail are functionally synergistic regulators of translation" Gene, 165(2):233-238.
Galn, J.E. and A. Collmer (May 21, 1999) "Type III Secretion Machines: Bacterial Devices for Protein Delivery into Host Cells" Science, 284:1322-1328.
GenBank Accession No. AAA25728 (Jul. 26, 1993) "avirulence protein [Pseudomonas syringae]" National Center For Biotechnology Information (NCBI).gov [online]. Retrieved from: http://www.ncbi.nlm.nih.gov/protein/AAA25728; retrieved on Feb. 15, 2019; 1 page.
GenBank Accession No. AAA26525 (Apr. 26, 1993) "IpaA protein, partial [Shigella flexneri]" National Center For Biotechnology Information (NCBI).gov [online]. Retrieved from: http://www.ncbi.nlm.nih.gov/protein/AAA26525; retrieved on Feb. 15, 2019; 1 page.
GenBank Accession No. AAC02071 (Oct. 4, 1999) "SopE [*Salmonella enterica* subsp. enterica serovar Typhimurium str. SL1344]" National Center For Biotechnology Information (NCBI).gov [online]. Retrieved from: http://www.ncbi.nlm.nih.gov/protein/AAC02071; retrieved on Feb. 15, 2019; 1 page.
GenBank Accession No. AAC44349 (Sep. 4, 1996) "protein tyrosine phosphatase SptP [*Salmonella enterica* subsp. enterica serovar Typhimurium str. SL1344]" National Center For Biotechnology Information (NCBI).gov [online]. Retrieved from: http://www.ncbi.nlm.nih.gov/protein/AAC44349; retrieved on Feb. 15, 2019; 2 pages.
GenBank Accession No. AAC69765 (Jul. 26, 2016) "secreted protein kinase (plasmid) [Yersinia pestis]" National Center For Biotechnology Information (NCBI).gov [online]. Retrieved from: http://www.ncbi.nlm.nih.gov/protein/AAC69765; retrieved on Feb. 15, 2019; 2 pages.
GenBank Accession No. AAC69766 (Jul. 26, 2016) "targeted effector protein (plasmid) [Yersinia pestis]" National Center For Biotechnology Information (NCBI).gov [online]. Retrieved from: http://www.ncbi.nlm.nih.gov/protein/AAC69766; retrieved on Feb. 15, 2019; 1 page.
GenBank Accession No. AAC69768 (Jul. 26, 2016) "targeted effector protein (plasmid) [Yersinia pestis]" National Center For Biotechnology Information (NCBI).gov [online]. Retrieved from: http://www.ncbi.nlm.nih.gov/protein/AAC69768; retrieved on Feb. 15, 2019; 2 pages.
GenBank Accession No. AAD11434 (Feb. 1, 1999) "avirulence protein AvrBs2 [Xanthomonas euvesicatoria]" National Center For

(56) References Cited

OTHER PUBLICATIONS

Biotechnology Information (NCBI).gov [online]. Retrieved from: http://www.ncbi.nlm.nih.gov/protein/AAD11434; retrieved on Feb. 21, 2019; 2 pages.
GenBank Accession No. AAF21057 (Dec. 29, 1999) "invasion protein D, partial [*Salmonella typhimurium*]" National Center For Biotechnology Information (NCBI).gov [online]. Retrieved from: http://www.ncbi.nlm.nih.gov/protein/AAF21057.1; retrieved on Feb. 21, 2019; 1 page.
GenBank Accession No. AAF71481.1 (May 23, 2000) "type III effector protein [Pseudomonas syringae pv. syringae]" National Center For Biotechnology Information (NCBI).gov [online]. Retrieved from: http://www.ncbi.nlm.nih.gov/protein/AAF71481.1; retrieved on Feb. 21, 2019; 1 page.
GenBank Accession No. AAG03434 (Jan. 31, 2014) "exoenzyme T [Pseudomonas aeruginosa PAO1]" National Center For Biotechnology Information (NCBI).gov [online]. Retrieved from: http://www.ncbi.nlm.nih.gov/protein/AAG03434; retrieved on Feb. 15, 2019; 2 pages.
GenBank Accession No. AAG05579 (Jan. 31, 2014) "adenylate cyclase ExoY [Pseudomonas aeruginosa PAO1]" National Center For Biotechnology Information (NCBI).gov [online]. Retrieved from: http://www.ncbi.nlm.nih.gov/protein/AAG05579; retrieved on Feb. 15, 2019; 2 pages.
GenBank Accession No. AAG07228 (Jan. 31, 2014) "exoenzyme S [Pseudomonas aeruginosa PAO1]" National Center For Biotechnology Information (NCBI).gov [online]. Retrieved from: http://www.ncbi.nlm.nih.gov/protein/AAG07228; retrieved on Feb. 15, 2019; 2 pages.
GenBank Accession No. AF232006 (May 23, 2000) "Pseudomonas syringae pv. tomato strain DC3000 AvrE (avrE), HrpW (hrpW), and GstA (gstA) genes, complete cds; and unknown genes" National Center For Biotechnology Information (NCBI).gov [online]. Retrieved from: http://www.ncbi.nlm.nih.gov/protein/AF232006.1; retrieved on Feb. 21, 2019; 8 pages.
GenBank Accession No. BAA96815 (Jun. 22, 2000) "Tir [*Escherichia coli*]" National Center For Biotechnology Information (NCBI).gov [online]. Retrieved from: http://www.ncbi.nlm.nih.gov/protein/BAA96815; retrieved on Feb. 15, 2019; 2 pages.
GenBank Accession No. CAA34257 (Jul. 26, 2016) "avirulence protein avrBs3 (plasmid) [Xanthomonas vesicatoria]" National Center For Biotechnology Information (NCBI).gov [online]. Retrieved from: http://www.ncbi.nlm.nih.gov/protein/CAA34257; retrieved on Feb. 15, 2019; 2 pages.
GenBank Accession No. CAA63302 (Jul. 23, 2016) "sipA, partial [*Salmonella enterica* subsp. enterica serovar Typhi str. Ty2]" National Center For Biotechnology Information (NCBI).gov [online]. Retrieved from: http://www.ncbi.nlm.nih.gov/protein/CAA63302; retrieved on Feb. 15, 2019; 1 page.
GenBank Accession No. EFW82095 (Jan. 28, 2011) "chemotaxis-specific methylesterase [Pseudomonas savastanoi pv. glycinea str. B076]" National Center For Biotechnology Information (NCBI).gov [online]. Retrieved from: http://www.ncbi.nlm.nih.gov/protein/EFW82095; retrieved on Feb. 15, 2019; 2 pages.
GenBank Accession No. EFW86187 (Jan. 28, 2011) "chemotaxis-specific methylesterase [Pseudomonas savastanoi pv. glycinea str. race 4]" National Center For Biotechnology Information (NCBI).gov [online]. Retrieved from: http://www.ncbi.nlm.nih.gov/protein/EFW86187; retrieved on Feb. 15, 2019; 2 pages.
GenBank Accession No. EGH06695 (May 22, 2012) "chemotaxis-specific methylesterase [Pseudomonas amygdali pv. morsprunorum str. M302280]" National Center For Biotechnology Information (NCBI).gov [online]. Retrieved from: http://www.ncbi.nlm.nih.gov/protein/EGH06695; retrieved on Feb. 15, 2019; 2 pages.
GenBank Accession No. EGH23390 (Apr. 28, 2011) "chemotaxis-specific methylesterase [Pseudomonas amygdali pv. mori str. 301020]" National Center For Biotechnology Information (NCBI).gov [online]. Retrieved from: http://www.ncbi.nlm.nih.gov/protein/EGH23390; retrieved on Feb. 15, 2019; 2 pages.
GenBank Accession No. EGH31878 (May 22, 2012) "chemotaxis-specific methylesterase, partial [Pseudomonas syringae pv. japonica str. M301072]" National Center For Biotechnology Information (NCBI).gov [online]. Retrieved from: http://www.ncbi.nlm.nih.gov/protein/EGH31878; retrieved on Feb. 15, 2019; 2 pages.
GenBank Accession No. EGH48032 (Apr. 28, 2011) "chemotaxis-specific methylesterase, partial [Pseudomonas syringae pv. pisi str. 1704B]" National Center For Biotechnology Information (NCBI).gov [online]. Retrieved from: http://www.ncbi.nlm.nih.gov/protein/EGH48032; retrieved on Feb. 15, 2019; 2 pages.
GenBank Accession No. EGH54563 (Apr. 28, 2011) "chemotaxis-specific methylesterase [Pseudomonas syringae Cit 7]" National Center For Biotechnology Information (NCBI).gov [online]. Retrieved from: http://www.ncbi.nlm.nih.gov/protein/EGH54563; retrieved on Feb. 15, 2019; 2 pages.
GenBank Accession No. EGH56182 (Apr. 28, 2011) "amino acid adenylation, partial [Pseudomonas syringae Cit 7]" National Center For Biotechnology Information (NCBI).gov [online]. Retrieved from: http://www.ncbi.nlm.nih.gov/protein/EGH51682; retrieved on Feb. 15, 2019; 1 page.
GenBank Accession No. EGH61007 (Apr. 28, 2011) "chemotaxis-specific methylesterase [Pseudomonas syringae pv. maculicola str. ES4326]" National Center For Biotechnology Information (NCBI).gov [online]. Retrieved from: http://www.ncbi.nlm.nih.gov/protein/EGH61007; retrieved on Feb. 15, 2019; 2 pages.
GenBank Accession No. EGH66597 (Apr. 28, 2011) "chemotaxis-specific methylesterase [Pseudomonas syringae pv. actinidiae str. M302091]" National Center For Biotechnology Information (NCBI).gov [online]. Retrieved from: http://www.ncbi.nlm.nih.gov/protein/EGH66597; retrieved on Feb. 15, 2019; 2 pages.
GenBank Accession No. EGH71924 (May 22, 2012) "chemotaxis-specific methylesterase, partial [Pseudomonas syringae pv. aceris str. M302273]" National Center For Biotechnology Information (NCBI).gov [online]. Retrieved from: http://www.ncbi.nlm.nih.gov/protein/EGH71924; retrieved on Feb. 15, 2019; 2 pages.
GenBank Accession No. EGH77388 (Apr. 28, 2011) "chemotaxis-specific methylesterase [Pseudomonas syringae pv. aptata str. DSM 50252]" National Center For Biotechnology Information (NCBI).gov [online]. Retrieved from: http://www.ncbi.nlm.nih.gov/protein/EGH77388; retrieved on Feb. 15, 2019; 2 pages.
GenBank Accession No. EJ092907 (Aug. 13, 2012) "response regulator receiver modulated CheB methylesterase [Pseudomonas mendocinaDLHK]" National Center For Biotechnology Information (NCBI).gov [online]. Retrieved from: http://www.ncbi.nlm.nih.gov/protein/EJ092907; retrieved on Feb. 15, 2019; 2 pages.
GenBank Accession No. EKE17764 (Sep. 26, 2012) "hypothetical protein ACD_10C00285G0003 [uncultured bacterium]" National Center For Biotechnology Information (NCBI).gov [online]. Retrieved from: http://www.ncbi.nlm.nih.gov/protein/EKE17764; retrieved on Feb. 15, 2019; 1 page.
GenBank Accession No. J04623 (Apr. 26, 1993) "F.okeanokoites methylase (MFokl) and endonuclease (RFokl) genes, complete cds" National Center For Biotechnology Information (NCBI).gov [online]. Retrieved from: https://www.ncbi.nlm.nih.gov/nuccore/J04623.1; retrieved on Feb. 21, 2019, 2 pages.
GenBank Accession No. M28828 (Apr. 26, 1993) "F.okeanokoites fokIR and fokIM genes encoding endonuclease and methyltransferase, complete cds" National Center For Biotechnology Information (NCBI).gov [online]. Retrieved from: https://www.ncbi.nlm.nih.gov/nuccore/M28828.1/; retrieved on Feb. 21, 2019, 3 pages.
GenPept Accession No. A34965 (Jul. 16, 1999) "62K membrane antigen ipaB—Shigella flexneri plasmid" National Center For Biotechnology Information (NCBI).gov [online]. Retrieved from: http://www.ncbi.nlm.nih.gov/protein/96918?report=genpept; retrieved on Feb. 21, 2019; 2 pages.
GenPept Accession No. NP_790747 (Aug. 6, 2012) "protein-glutamate methylesterase CheB [Pseudomonas syringae pv. tomato str. DC3000]" National Center For Biotechnology Information (NCBI).gov [online]. Retrieved from: http://www.ncbi.nlm.nih.gov/protein/NP_790747; retrieved on Feb. 20, 2019, 2 pages.
GenPept Accession No. S14242 (Oct. 8, 1999) "yopE protein—Yersinia enterocolitica virulence plasmid pYVe439-80" National Center For Biotechnology Information (NCBI).gov [online]. Retrieved

(56) References Cited

OTHER PUBLICATIONS from: https://www.ncbi.nlm.nih.gov/protein/96986?report=genpept; retrieved on Feb. 21, 2019, 2 pages.

GenPept Accession No. S15579 (Aug. 26, 1999) "ipaD protein—Shigella dysenteriae" National Center For Biotechnology Information (NCBI).gov [online]. Retrieved from: https://www.ncbi.nlm.nih.gov/protein/96907?report=genpept; retrieved on Feb. 21, 2019, 1 page.

GenPept Accession No. YP_001187060 (Sep. 27, 2012) "response regulator receiver modulated CheB methylesterase [Pseudomonas mendocina ymp]" National Center For Biotechnology Information (NCBI).gov [online]. Retrieved from: http://www.ncbi.nlm.nih.gov/protein/YP_001187060; retrieved on Feb. 20, 2019; 2 pages.

GenPept Accession No. YP_001792820 (Jan. 25, 2012) "chemotaxis-specific methylesterase [Leptothrix cholodnii SP-6]" National Center For Biotechnology Information (NCBI).gov [online]. Retrieved from: http://www.ncbi.nlm.nih.gov/protein/YP_001792820; retrieved on Feb. 20, 2019; 2 pages.

GenPept Accession No. YP_003847734 (Jan. 25, 2012) "response regulator receiver modulated CheB methylesterase [Gallionella capsiferriformansES-2]" National Center For Biotechnology Information (NCBI).gov [online]. Retrieved from: http://www.ncbi.nlm.nih.gov/protein/YP_003847734; retrieved on Feb. 20, 2019; 2 pages.

GenPept Accession No. YP_003907367 (Jun. 18, 2012) "response regulator receiver modulated CheB methylesterase [*Burkholderia* sp. CCGE1003]" National Center For Biotechnology Information (NCBI).gov [online]. Retrieved from: http://www.ncbi.nlm.nih.gov/protein/YP_003907367; retrieved on Feb. 20, 2019; 2 pages.

GenPept Accession No. YP_004030667 (Apr. 25, 2011) "hypothetical protein RBRH_01777 (plasmid) [Burkholderia rhizoxinica HKI 454]" National Center For Biotechnology Information (NCBI).gov [online]. Retrieved from: http://www.ncbi.nlm.nih.gov/protein/YP_004030667; retrieved on Feb. 20, 2019; 1 page.

GenPept Accession No. YP_004846745 (Sep. 28, 2012) "response regulator receiver modulated CheB methylesterase [*Pseudogulbenkiania* sp.NH8B]" National Center For Biotechnology Information (NCBI).gov [online]. Retrieved from: http://www.ncbi.nlm.nih.gov/protein/YP_004846745; retrieved on Feb. 20, 2019; 2 pages.

GenPept Accession No. YP_005027668 (Jun. 25, 2012) "chemotaxis response regulator containing a CheY-like receiver domain and a methylesterasedomain [Dechlorosoma suillum PS]" National Center For Biotechnology Information (NCBI).gov [online]. Retrieved from: http://www.ncbi.nlm.nih.gov/protein/YP_005027668; retrieved on Feb. 20, 2019; 2 pages.

GenPept Accession No. YP_233877 (Sep. 27, 2012) "chemotaxis-specific methylesterase [Pseudomonas syringae pv. syringae B728a]" National Center For Biotechnology Information (NCBI).gov [online]. Retrieved from: http://www.ncbi.nlm.nih.gov/protein/YP_233877; retrieved on Feb. 20, 2019; 2 pages.

GenPept Accession No. YP_273082 (Sep. 27, 2012) "chemotaxis-specific methylesterase [Pseudomonas syringae pv. phaseolicola 1448A]" National Center For Biotechnology Information (NCBI).gov [online]. Retrieved from: http://www.ncbi.nlm.nih.gov/protein/YP_273082; retrieved on Feb. 20, 2019; 2 pages.

GenPept Accession No. ZP_03698248 (Nov. 9, 2010) "response regulator receiver modulated CheB methylesterase [Pseudogulbenkiania ferrooxidans 2002]" National Center For Biotechnology Information (NCBI).gov [online]. Retrieved from: http://www.ncbi.nlm.nih.gov/protein/ZP_03698248; retrieved on Feb. 20, 2019; 2 pages.

GenPept Accession No. ZP_04590480 (Nov. 14, 2012) "chemotaxis-specific methylesterase [Pseudomonas syringae pv. oryzae str. 1_6]" National Center For Biotechnology Information (NCBI).gov [online]. Retrieved from: http://www.ncbi.nlm.nih.gov/protein/ZP_04590480; retrieved on Feb. 20, 2019; 1 page.

GenPept Accession No. ZP_05638023 (Nov. 14, 2012) "chemotaxis-specific methylesterase [Pseudomonas syringae pv. tabaci str. ATCC 11528]" National Center For Biotechnology Information (NCBI).gov [online]. Retrieved from: http://www.ncbi.nlm.nih.gov/protein/ZP_05638023; retrieved on Feb. 20, 2019; 1 page.

GenPept Accession No. ZP_06457223 (Nov. 14, 2012) "chemotaxis-specific methylesterase [Pseudomonas syringae pv. aesculi str. NCPPB 3681]" National Center For Biotechnology Information (NCBI).gov [online]. Retrieved from: http://www.ncbi.nlm.nih.gov/protein/ZP_06457223; retrieved on Feb. 20, 2019; 1 page.

GenPept Accession No. ZP_06495900 (Nov. 14, 2012) "chemotaxis-specific methylesterase, partial [Pseudomonas syringae pv. syringae FF5]" National Center For Biotechnology Information (NCBI).gov [online]. Retrieved from: http://www.ncbi.nlm.nih.gov/protein/ZP_06495900; retrieved on Feb. 20, 2019; 1 page.

GenPept Accession No. ZP_07003572 (Jun. 22, 2010) "Chemotaxis response regulator protein-glutamate methylesterase CheB [Pseudomonas savastanoi pv. savastanoi NCPPB 3335]" National Center For Biotechnology Information (NCBI).gov [online]. Retrieved from: http://www.ncbi.nlm.nih.gov/protein/ZP_07003572; retrieved on Feb. 20, 2019; 1 page.

GenPept Accession No. ZP_07251539 (Dec. 10, 2010) "chemotaxis-specific methylesterase [Pseudomonas syringae pv. tomato K40]" National Center For Biotechnology Information (NCBI).gov [online]. Retrieved from: http://www.ncbi.nlm.nih.gov/protein/ZP_07251539; retrieved on Feb. 20, 2019; 2 pages.

GenPept Accession No. ZP_07265841 (Dec. 10, 2010) "chemotaxis-specific methylesterase [Pseudomonas syringae pv. syringae 642]" National Center For Biotechnology Information (NCBI).gov [online]. Retrieved from: http://www.ncbi.nlm.nih.gov/protein/ZP_07265841; retrieved on Feb. 20, 2019; 2 pages.

GenPept Accession No. ZP_08780698 (Nov. 15, 2011) "response regulator receiver modulated CheB methylesterase [Methylobacter tundripaludum SV96]" National Center For Biotechnology Information (NCBI).gov [online]. Retrieved from: http://www.ncbi.nlm.nih.gov/protein/ZP_08780698; retrieved on Feb. 20, 2019; 2 pages.

GenPept Accession No. ZP_10381001 (Jul. 11, 2012) "chemotaxis-specific methylesterase [Sulfuricella denitrificans skB26]" National Center For Biotechnology Information (NCBI).gov [online]. Retrieved from: http://www.ncbi.nlm.nih.gov/protein/ZP_10381001; retrieved on Feb. 20, 2019; 1 page.

GenPept Accession No. ZP_10442431 (Jul. 18, 2012) "response regulator receiver modulated cheb methylesterase [Janthinobacterium lividumPAMC 25724]" National Center For Biotechnology Information (NCBI).gov [online]. Retrieved from: http://www.ncbi.nlm.nih.gov/protein/ZP_10442431; retrieved on Feb. 20, 2019; 2 pages.

GenPept Accession No. ZP_10991552 (Nov. 14, 2012) "chemotaxis-specific protein-glutamate methyltransferase [Pseudomonas fuscovaginae UPB0736]" National Center For Biotechnology Information (NCBI).gov [online]. Retrieved from: http://www.ncbi.nlm.nih.gov/protein/ZP_10991552; retrieved on Feb. 20, 2019; 2 pages.

GenPept Accession No. ZP_10995147 (Sep. 13, 2012) "response regulator receiver modulated CheB methylesterase [Pseudomonas fuscovaginae UPB0736]" National Center For Biotechnology Information (NCBI).gov [online]. Retrieved from: http://www.ncbi.nlm.nih.gov/protein/ZP_10995147; retrieved on Feb. 20, 2019; 2 pages.

Gilbert, L. et al. (Jul. 18, 2013) "CRISPR-Mediated Modular RNA-Guided Regulation of Transcription in Eukaryotes" Cell, 154(2):442-451, including "Supplemental Information. Extended Experimental Procedures", pp. S1-S5.

Gill, G. and M. Ptashne (1988) "Negative effect of the transcriptional activator GAL4" Nature, 334:721-724.

Golovkin, M. et al. (1993) "Production of transgenic maize plants by direct DNA uptake into embryogenic protoplasts" Plant Science, 90:41-52.

Gossen, M. and Bujard, H., "Tight control of gene expression in mammalian cells by tetracycline-responsive promoters," PNAS, vol. 89, pp. 5547-5551 (Jun. 1992).

Guerineau, F. et al. (1991) "Effect of deletions in the cauliflower mosaic virus polyadenylation sequence on the choice of the polyadenylation sites in tobacco protoplasts" Mol. Gen. Genet., 262:141-144.

Guglielmi, L. et al. (2011) "Selection for intrabody solubility in mammalian cells using GFP fusions" Protein Engineering, Design & Selection, 24(12):873-881.

Guilinger, J.P. et al. (Jun. 2014) "Fusion of catalytically inactive Cas9 to FokI nuclease improves the specificity of genome modification" Nature Biotechnology, vol. 32, No. 6, pp. 577-582.

(56) References Cited

OTHER PUBLICATIONS

Guo et al. (Dec. 1993) "Transgenic Plants Obtained From Wheat Protoplasts Transformed by PEGmediated Direct Gene Transfer", Chinese Science Bulletin, 38(24):2072-2078.
Hartman, C.L. et al. (Sep. 1994) "Herbicide resistant turfgrass (*Agrostis palustris* Huds.) by biolistic transformation", Bio-Technology, 12:919-923.
Hassanzadeh-Ghassabeh, G. et al. (2013) "Nanobodies and their potential applications" Nanomedicine, 8(6):1013-1026.
Herbers et. al., "Race-specificity of plant resistance to bacterial spot disease determined by repetitive motifs in a bacterial avirulence protein" Nature, vol. 356, pp. 172-174 (1992).
Hillen, W. and Wissmann, A. (1989) "Tet repressor-tet operator interaction", In: Saenger W., Heinemann U. (eds) Protein-Nucleic Acid Interaction. Series: Topics in Molecular and Structural Biology, 10:143-162.
Hinchee, M.A.W. et al. (1990) "Transformation and regeneration of non-solanaceous crop plants", in Gene Manipulation in Plant Improvement II. J.P. Gustafson (Ed.), New York: Plenum Press; p. 203-212.
Holliger P., et al., "Engineered Antibody Fragments and the Rise of Single Domains," Nature Biotechnology, Sep. 2005, vol. 23, No. 9, pp. 1126-1136, XP008076746.
Hu, M.C.-T. and N. Davidson (Feb. 27, 1987) "The Inducible lac Operator-Repressor System Is Functional in Mammalian Cells", Cell, 48:555-566.
Jobling, S.A. et al. "Enhanced translation of chimaeric messenger RNAs containing a plant viral untranslated leader sequence", (1987) Nature 325:622-625.
Joshi, C.P. (1987) "Putative polyadenylation signals in nuclear genes of higher plants: a compilation and analysis" Nucleic Acids Res, 15(23):9627-9640.
Kato, N. et al. (Jul. 2002) "Spectral Profiling for the Simultaneous Observation of Four Distinct Fluorescent Proteins and Detection of Protein-Protein Interaction via Fluorescence Resonance Energy Transfer in Tobacco Leaf Nuclei", Plant Physiology, 129:931-942.
Kay et. al., "A bacterial effector acts as a plant transcription factor and induces a cell size regulator" Science. Oct. 26, 2007; 318 (5850): 648-651.
Kim, Y-G. et al. (1996) "Hybird restriction enzymes: Zinc finger fusions to Fok I cleavage domain" Proc Natl Acad Sci, 93(3):1156-1160.
Kleinschmidt, C. et al. (1988) "Dynamics of Repressor-Operator Recognition: The Tn10-Encoded Tetracycline Resistance Control", Biochemistry, 27:1094-1104.
Klimpel, K.R. et al. (Nov. 1992) "Anthrax toxin protective antigen is activated by a cell surface protease with the sequence specificity and catalytic properties of furin" Proc Natl Acad Sci USA, 89(21):10277-10281.
Kulinski, J. et al. "CEL I Enzymatic Mutation Detection Assay", BioTechniques (2000), 29(1):44-48.
Kunkel T.A., et al., "Rapid and Efficient Site-Specific Mutagenesis Without Phenotypic Selection," Methods in Enzymology, 1987, vol. 154 pp. 367-382.
Kunkel T.A., "Rapid And Efficient Site-specific Mutagenesis Without Phenotypic Selection," Proceedings of the National Academy of Sciences USA, Jan. 1985, vol. 82(2), pp. 488-492.
Kyte, J. and R.F. Doolittle (May 5, 1982) "A simple method for displaying the hydropathic character of a protein" J Mol Biol, 157(1):105-132.
Labow, M.A. et al. (Jul. 1990) "Conversion of the lac Repressor into an Allosterically Regulated Transcriptional Activator for Mammalian Cells", Molecular and Cellular Biology, 10(7):3343-3356.
Lehninger, A.L., Biochemistry. The Molecular Basis of Cell Structure and Function. Second Edition. New York, NY: Worth Publishers, Inc., 1975; pp. 71-77.
Li, L. et al. (May 1992) "Functional domains in Fok I restriction endonuclease" Proc Natl Acad Sci USA, 89(10):4275-4279.
Li, L. et al. (Jul. 2013) "Characterization and DNA-Binding Specificities of Ralstonia TAL-Like Effectors" Mol Plant, 6(4):1318-1330.
Li, Y. et al. (Aug. 2011) "Molecular recognition code between pathogenic bacterial TAL-effectors and host target genes: a review" Chinese Journal of Biotechnology, 27(8):1132-1141 (English Abstract and Figure Legends included).
Li, Y. et al. (Nov. 28, 2012) "Transcription activator-like effector hybrids for conditional control and rewiring of chromosomal transgene expression", Scientific Reports, vol. 2, No. 897, DOI: 10.1038/srep00897; 7 pages.
Lippow, S.M. et al. (2009) "Creation of a type IIS restriction endonuclease with a long recognition sequence" Nucleic Acids Research, 37(9):3061-3073.
Lommel, S.A. et al. (1991) "Identification of the Maize Chlorotic Mottle Virus Capsid Protein Cistron and Characterization of its Subgenomic Messenger RNA", Virology, 181:382-385.
Luo, Y. et al. (1997) "Mammalian Two-Hybrid System: A Complementary Approach to the Yeast Two-Hybrid System" Biotechniques, vol. 22, No. 2, pp. 350-352.
Macejak, D.G. and P. Sarnow (Sep. 5, 1991) "Internal initiation of translation mediated by the 5' leader of a cellular mRNA", Nature, 353:90-94.
Mali., et al., "RNA-Guided Human Genome Engineering via Cas9," Science, Feb. 15, 2013, vol. 339(6121), pp. 823-826 (8 total pages).
Mali, P. et al. (Sep. 2013) "CAS9 transcriptional activators for target specificity screening and paired nickases for cooperative genome engineering", Nature Biotechnology, vol. 31, No. 9, p. 833-840.
Maynard, J. and G. Georgiou et al. (2000) "Antibody Engineering" Annual Reviews Biomedical Engineering, 2(1):339-376.
Miller, J.C. et al. (Feb. 2011) "A TALE nuclease architecture for efficient genome editing" Nat Biotechnol, 29(2):143-148 (with Supplementary Information, 2 pages).
Mino, T. et al. (2009) "Efficient double-stranded DNA cleavage by artificial zinc-finger nucleases composed of one zinc-finger protein and a single-chain Fokl dimer" J. Biotechnol., 140:156-161.
Mogen, B.D. et al. (Dec. 1990) "Upstream sequences other than AAUAAA are required for efficient messenger RNA 3'-end formation in plants" Plant Cell, 2(12):1261-1272.
Mssner, E. et al. (2001) "Fast selection of antibodies without antigen purification: adaptation of the protein fragment complementation assay to select antigen-antibody pairs" Journal of Molecular Biology, vol. 308, No. 2, pp. 115-122.
Munroe, D. and A. Jacobson (1990) "Tales of poly(A): a review", Gene, 91:151-158.
Muramatsu, T. et al. (Jan. 1998) "In vivo electroporation: a powerful and convenient means of nonviral gene transfer to tissues of living animals (Review)" Int. J. Mol. Med., 1:55-62.
Murray, Elizabeth E., et al., "Codon usage in plant genes", Nucleic Acids Research (Jan. 25, 1989); 17(2): 477-498.
Novak, J.M. et al. (Aug. 25, 1992) "Functional Characterization of Protease-treated Bacillus anthracis Protective Antigen" J Biol Chem, 267(24):17186-17193.
Oliva, B. et al. (May 1992) "Evidence that Tetracycline Analogs Whose Primary Target Is Not the Bacterial Ribosome Cause Lysis of *Escherichia coli*", Antimicrobial Agents and Chemotherapy, 36:913-919.
Perelle, S. et al. (1993) "Characterization of Clostridium perfringens Iota-Toxin Genes and Expression in *Escherichia coli*" Infect Immun, 61(12):5147-5156.
Phelan, A. et al. (May 1998) "Intercellular Delivery of Functional p53 by the Herpesvirus Protein VP22" Nat. Biotechnol., 16:440-443.
Proudfoot, N. (Feb. 22, 1991) "Poly(A) Signals", Cell, 64:671-674.
Puchta, H. et al. (1993) "Homologous recombination in plant cells is enhanced by in vivo induction of double strand breaks into DNA by a site-specific endonuclease" Nucleic Acids Res, 21(22):5034-5040.
Reines, D. and J. Mote, Jr. (Mar. 1993) "Elongation factor SII-dependent transcription by RNA polymerase II through a sequence-specific DNA-binding protein", Proc. Natl. Acad. Sci. USA, 90:1917-1921.
Remenant, B. et al. (2012) "Sequencing of K60, Type Strain of the Major Plant Pathogen Ralstonia solanacearum" J Bacteriol, 194(10):2742-2743.

(56) References Cited

OTHER PUBLICATIONS

Remenent, B. et al. (2010) "Genomes of three tomato pathogens within the Ralstonia solanacearum species complex reveal significant evolutionary divergence" BMC Genomics, 11:379, 16 pages.
Reyon, D et al. (May 2012) "FLASH assembly of TALENs for high-throughput genome editing" Nat Biotechnol, 30(5):460-465, including Online Methods, 2 pages.
Reznikoff, W.S. (1992) "The lactose operon-controlling elements: a complex paradigm", Molecular Microbiology, 6(17):2419-2422.
Ritala, A. et al. (1994) "Fertile transgenic barley by particle bombardment of immature embryos", Plant. Mol. Biol., 24:317-325.
Salanoubat, M. et al. (Jan. 2002) "Genome sequence of the plant pathogen Ralstonia solanacearum" Nature, 415:497-502.
Sanfaon, et al. (1991) "A dissection of the cauliflower mosaic virus polyadenylaion signal" Genes Dev, 5(1):141-149.
Schandry, N. et al. (Aug. 17, 2016) "TALE-Like Effectors Are an Ancestral Feature of the Ralstonia solanacearum Species Complex and Converge in DNA Targeting Specificity" Frontiers in Plant Science, 7:Article 1225, doi:10.3389/fpls.2016.01225, 16 pages.
Schwarze, S.R. et al. (Jul. 2000) "Protein Transduction: Unrestricted Delivery Into All Cells?" Trends Cell Biol, 10:290-295.
Sebo, P. et al. (Oct. 1995) "Cell-invasive activity of epitope-tagged adenylate cyclase of Bordetella pertussis allows in vitro presentation of a foreign epitope to CD8+ cytotoxic T cells" Infect Immun, 63(10):3851-3857.
Secco, P. et al. (2009) "Antibody library selection by the-lactamase protein fragment complementation assay", Protein Engineering, Design and Selection, vol. 22, No. 3, pp. 149-158.
Segal, D.J. and D. Carroll (Jan. 1995) "Endonuclease-induced, targeted homologous extrachromosomal recombination in Xenopus oocytes" Proc Natl Acad Sci USA, 92(3):806-810.
Shulka, V.K. et al. (2009) "Precise genome modification in the crop species *Zea mays* using zinc-finger nucleases" Nature, 459:437-441, including "Methods", 2 pages.
Smolarek, D. et al. (2010) "A recombinant dromedary antibody fragment (VHH or nanobody) directed against human Duffy antigen receptor for chemokines" Cell Mol Life Sci, 67(19):3371-3387. Author Manuscript, HAL Archives Ouvertes—France [online]. Retrieved from: https://www.ncbi.nlm.nih.gov/pmc/articles/PMC2966875/?report=printable; retreived on Jun. 18, 2018, 30 pages.
Stenmark, H. et al., "Peptides fused to the amino-terminal end of diphtheria toxin are translocated to the cytosol," The Journal of Cell Biology, vol. 113, No. 5, Jun. 1991, pp. 1025-1032.
Su, W.W. et al. (2004) "High-Level Secretion of Functional Green Fluorescent Protein From Transgenic Tobacco Cell Cultures: Characterization and Sensing", Biotechnol Bioeng, 85:610-619.
Tanenbaum, M. et al. (Oct. 2014) "A Protein-Tagging System for Signal Amplification in Gene Expression and Fluorescence Imaging" Cell, vol. 159, No. 3, pp. 635-646.
Tatusova et al., "Blast 2 Sequences—a new tool for comparing protein and nucleotide sequences." FEMS Microbiol Lett. 174:247-250 (1999).
Thierry, A. et al. (1991) "Cleavage of yeast and bacteriophage T7 genomes at a single site using the rare cutter endonuclease I-Sce I" Nucleic Acids Res, 9(1):189-190.
Townsend, J.A. et al. (May 21, 2009) "High-frequency modification of plant genes using engineered zinc-finger nucleases" Nature, 459:442-445, including "Methods", 1 page.
Tsai, S. et al. (Jun. 2014) "Dimeric CRISPR RNA-guided Fokl nucleases for highly specific genome editing", Nature Biotechnology, vol. 32, No. 6, p. 569-576, including "Methods", 1 page.
UniProtKB Sequence Accession No. D8N2L9 (Jun. 7, 2017) "Type III effector AvrBs3 family" [online]. Retrieved from: www.uniprot.org/uniprot/D8N2L9.txt?version=27, on Apr. 9, 2019, 1 page.
Urnov, F.D. et al. "Highly efficient endogenous human gene correction using designed zinc-finger nucleases." Nature. Jun. 2, 2005;435(7042):646-51. doi: 10.1038/nature03556.
Vannocci, T. et al. (2014) "Nuclease-stimulated homologous recombination at the human beta-globin gene", The Journal of Gene Medicine, vol. 16, No. 1-2, p. 1-10.
Vielemeyer, O. et al. (2010) "Characterization of single chain antibody targets through yeast two hybrid" BMC Biotechnology, 10:59, 13 pages.
Visintin, M. et al. (Oct. 1999) "Selection of antibodies for intracellular function using a two-hybrid in vivo system", Proceedings of the National Academy of Sciences, USA, vol. 96, No. 21, pp. 11723-11728.
Wan, Y. C. and P.G. Lemaux (1994) "Generation of Large Numbers of Independently Transformed Fertile Barley Plants" Plant Physiol., 104:37-48.
Wright, D.A. et al. (2005) "High-frequency homologous recombination in plants mediated by zinc-finger nucleases" The Plant Journal, 44:693-705.
Wyborski, D.L. and J.M. Short (1991) "Analysis of inducers of the *E.coli* lac repressor system in mammalian cells and whole animals", Nucleic Acids Res, 19:4647-4653.
Yao, T-P. et al. (Oct. 2, 1992) "*Drosophila* ultraspiracle modulates ecdysone receptor function via heterodimer formation" Cell, 71:63-72.
Yarranton, G.T. (1992) "Inducible vectors for expression in mammalian cells" Curr. Opin. Biotech., 3:506-511.
Zambretti, G.P. et al. (May 1992) "A mutant p53 protein is required for maintenance of the transformed phenotype in cells transformed with p53 plus ras cDNAs" Proc. Natl Acad. Sci. USA, 89:3952-3956.

* cited by examiner

Lane1: Xanthomonas TALEN transfected sample
Lane2: Ralstonia TALEN transfected sample
Lane3: WT sample
Lane4: DNA Ladder Dual Reporter plasmid: validating efficiency of targeted nucleases 1. Constitutive RFP for transfection efficiency.
2. GFP induced by targeted double stranded break and subsequent NHEJ.

Endonuclease cutting of AAVS1 Indicator Vector 22hrs post Transfection.
Transfection was done 11:00am, 3/29/15.
24 Well Plate. 250ng of DNA per TALEN half-site. 250 ng of InVec/well.

Cel1 Assay with TALE-Clo51

1. pCagsClo51C4RGN
+ non-specific gRNA
+ indicator
(negative control)

2. pCagsClo51C4RGN
+ NG-AAVS1-gRNA
+ indicator 3. pCagsC4RGN
+ NG-AAVS1-gRNA
+ indicator
(positive control)

Test of TAL-BfiI and TAL-BmrI in HEK293 cells

AAVS1 XTN F/R + indicator: pictures 3 days post transfection

SEQUENCE LISTING

```
Sequence total quantity: 301
SEQ ID NO: 1            moltype = AA  length = 35
FEATURE                 Location/Qualifiers
VARIANT                 12..13
source                  1..35
                        mol_type = protein
                        organism = synthetic construct
SEQUENCE: 1
LSTEQVVAIA SXXGGKQALE AVKAQLLVLR AAPYE                             35

SEQ ID NO: 2            moltype = AA  length = 35
FEATURE                 Location/Qualifiers
source                  1..35
                        mol_type = protein
                        organism = synthetic construct
SEQUENCE: 2
LSTEQVVAIA SSIGGKQALE AVKAQLLVLR AAPYE                             35

SEQ ID NO: 3            moltype = AA  length = 35
FEATURE                 Location/Qualifiers
source                  1..35
                        mol_type = protein
                        organism = synthetic construct
SEQUENCE: 3
LSTEQVVAIA SSNGGKQALE AVKAQLLVLR AAPYE                             35

SEQ ID NO: 4            moltype = AA  length = 35
FEATURE                 Location/Qualifiers
source                  1..35
                        mol_type = protein
                        organism = synthetic construct
SEQUENCE: 4
LSTEQVVAIA SSHGGKQALE AVKAQLLVLR AAPYE                             35

SEQ ID NO: 5            moltype = AA  length = 35
FEATURE                 Location/Qualifiers
```

```
source                  1..35
                        mol_type = protein
                        organism = synthetic construct
SEQUENCE: 5
LSTEQVVAIA SNPGGKQALE AVKAQLLVLR AAPYE                        35

SEQ ID NO: 6            moltype = AA  length = 35
FEATURE                 Location/Qualifiers
source                  1..35
                        mol_type = protein
                        organism = synthetic construct
SEQUENCE: 6
LSTEQVVAIA SNHGGKQALE AVKAQLLVLR AAPYE                        35

SEQ ID NO: 7            moltype = AA  length = 35
FEATURE                 Location/Qualifiers
source                  1..35
                        mol_type = protein
                        organism = synthetic construct
SEQUENCE: 7
LSTEQVVAIA SNTGGKQALE AVKAQLLVLR AAPYE                        35

SEQ ID NO: 8            moltype = AA  length = 35
FEATURE                 Location/Qualifiers
source                  1..35
                        mol_type = protein
                        organism = synthetic construct
SEQUENCE: 8
LSTEQVVAIA SNKGGKQALE AVKAQLLVLR AAPYE                        35

SEQ ID NO: 9            moltype = AA  length = 35
FEATURE                 Location/Qualifiers
source                  1..35
                        mol_type = protein
                        organism = synthetic construct
SEQUENCE: 9
LSTEQVVAIA SNPGGKQALE AVKAQLLVLR AAPYE                        35

SEQ ID NO: 10           moltype = AA  length = 35
FEATURE                 Location/Qualifiers
source                  1..35
                        mol_type = protein
                        organism = synthetic construct
SEQUENCE: 10
LSTEQVVAIA SNNGGKQALE AVKAQLLVLR AAPYE                        35

SEQ ID NO: 11           moltype = AA  length = 35
FEATURE                 Location/Qualifiers
source                  1..35
                        mol_type = protein
                        organism = synthetic construct
SEQUENCE: 11
LSTEQVVAIA SNDGGKQALE AVKAQLLVLR AAPYE                        35

SEQ ID NO: 12           moltype = AA  length = 35
FEATURE                 Location/Qualifiers
source                  1..35
                        mol_type = protein
                        organism = synthetic construct
SEQUENCE: 12
LSTEQVVAIA SNGGGKQALE AVKAQLLVLR AAPYE                        35

SEQ ID NO: 13           moltype = AA  length = 35
FEATURE                 Location/Qualifiers
source                  1..35
                        mol_type = protein
                        organism = synthetic construct
SEQUENCE: 13
LSTEQVVAIA SHNGGKQALE AVKAQLLVLR AAPYE                        35

SEQ ID NO: 14           moltype = AA  length = 35
FEATURE                 Location/Qualifiers
source                  1..35
                        mol_type = protein
                        organism = synthetic construct
SEQUENCE: 14
LSTEQVVAIA SHYGGKQALE AVKAQLLVLR AAPYE                        35

SEQ ID NO: 15           moltype = AA  length = 35
```

```
FEATURE                Location/Qualifiers
source                 1..35
                       mol_type = protein
                       organism = synthetic construct
SEQUENCE: 15
LSTEQVVAIA SHDGGKQALE AVKAQLLVLR AAPYE                          35

SEQ ID NO: 16          moltype = AA  length = 35
FEATURE                Location/Qualifiers
source                 1..35
                       mol_type = protein
                       organism = synthetic construct
SEQUENCE: 16
LSTEQVVAIA SHHGGKQALE AVKAQLLVLR AAPYE                          35

SEQ ID NO: 17          moltype = AA  length = 35
FEATURE                Location/Qualifiers
source                 1..35
                       mol_type = protein
                       organism = synthetic construct
SEQUENCE: 17
LSTEQVVAIA SRNGGKQALE AVKAQLLVLR AAPYE                          35

SEQ ID NO: 18          moltype = AA  length = 35
FEATURE                Location/Qualifiers
source                 1..35
                       mol_type = protein
                       organism = synthetic construct
SEQUENCE: 18
LSTEQVVAIA SRSGGKQALE AVKAQLLVLR AAPYE                          35

SEQ ID NO: 19          moltype = AA  length = 35
FEATURE                Location/Qualifiers
source                 1..35
                       mol_type = protein
                       organism = synthetic construct
SEQUENCE: 19
LSTEQVVAIA SGSGGKQALE AVKAQLLVLR AAPYE                          35

SEQ ID NO: 20          moltype = AA  length = 1053
FEATURE                Location/Qualifiers
source                 1..1053
                       mol_type = protein
                       organism = Staphylococcus aureus
SEQUENCE: 20
MKRNYILGLD IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                            1053

SEQ ID NO: 21          moltype = AA  length = 1368
FEATURE                Location/Qualifiers
source                 1..1368
                       mol_type = protein
                       organism = synthetic construct
SEQUENCE: 21
MDKKYSIGLD IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG  120
NIVDEVAYHE KYPTIYHLRK KLVDSTDKAD LRLIYLALAH MIKFRGHFLI EGDLNPDNSD  180
VDKLFIQLVQ TYNQLFEENP INASGVDAKA ILSARLSKSR RLENLIAQLP GEKKNGLFGN  240
LIALSLGLTP NFKSNFDLAE DAKLQLSKDT YDDDLDNLLA QIGDQYADLF LAAKNLSDAI  300
LLSDILRVNT EITKAPLSAS MIKRYDEHHQ DLTLLKALVR QQLPEKYKEI FFDQSKNGYA  360
GYIDGGASQE EFYKFIKPIL EKMDGTEELL VKLNREDLLR KQRTFDNGSI PHQIHLGELH  420
AILRRQEDFY PFLKDNREKI EKILTFRIPY YVGPLARGNS RFAWMTRKSE ETITPWNFEE  480
VVDKGASAQS FIERMTNFDK NLPNEKVLPK HSLLYEYFTV YNELTKVKYV TEGMRKPAFL  540
```

```
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD            1368

SEQ ID NO: 22          moltype = AA  length = 1053
FEATURE                Location/Qualifiers
source                 1..1053
                       mol_type = protein
                       organism = Staphylococcus aureus
SEQUENCE: 22
MKRNYILGLD IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEN SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                              1053

SEQ ID NO: 23          moltype = AA  length = 1053
FEATURE                Location/Qualifiers
source                 1..1053
                       mol_type = protein
                       organism = Staphylococcus aureus
SEQUENCE: 23
MKRNYILGLA IGITSVGYGI IDYETRDVID AGVRLFKEAN VENNEGRRSK RGARRLKRRR  60
RHRIQRVKKL LFDYNLLTDH SELSGINPYE ARVKGLSQKL SEEEFSAALL HLAKRRGVHN  120
VNEVEEDTGN ELSTKEQISR NSKALEEKYV AELQLERLKK DGEVRGSINR FKTSDYVKEA  180
KQLLKVQKAY HQLDQSFIDT YIDLLETRRT YYEGPGEGSP FGWKDIKEWY EMLMGHCTYF  240
PEELRSVKYA YNADLYNALN DLNNLVITRD ENEKLEYYEK FQIIENVFKQ KKKPTLKQIA  300
KEILVNEEDI KGYRVTSTGK PEFTNLKVYH DIKDITARKE IIENAELLDQ IAKILTIYQS  360
SEDIQEELTN LNSELTQEEI EQISNLKGYT GTHNLSLKAI NLILDELWHT NDNQIAIFNR  420
LKLVPKKVDL SQQKEIPTTL VDDFILSPVV KRSFIQSIKV INAIIKKYGL PNDIIIELAR  480
EKNSKDAQKM INEMQKRNRQ TNERIEEIIR TTGKENAKYL IEKIKLHDMQ EGKCLYSLEA  540
IPLEDLLNNP FNYEVDHIIP RSVSFDNSFN NKVLVKQEEA SKKGNRTPFQ YLSSSDSKIS  600
YETFKKHILN LAKGKGRISK TKKEYLLEER DINRFSVQKD FINRNLVDTR YATRGLMNLL  660
RSYFRVNNLD VKVKSINGGF TSFLRRKWKF KKERNKGYKH HAEDALIIAN ADFIFKEWKK  720
LDKAKKVMEN QMFEEKQAES MPEIETEQEY KEIFITPHQI KHIKDFKDYK YSHRVDKKPN  780
RELINDTLYS TRKDDKGNTL IVNNLNGLYD KDNDKLKKLI NKSPEKLLMY HHDPQTYQKL  840
KLIMEQYGDE KNPLYKYYEE TGNYLTKYSK KDNGPVIKKI KYYGNKLNAH LDITDDYPNS  900
RNKVVKLSLK PYRFDVYLDN GVYKFVTVKN LDVIKKENYY EVNSKCYEEA KKLKKISNQA  960
EFIASFYNND LIKINGELYR VIGVNNDLLN RIEVNMIDIT YREYLENMND KRPPRIIKTI  1020
ASKTQSIKKY STDILGNLYE VKSKKHPQII KKG                              1053

SEQ ID NO: 24          moltype = AA  length = 1787
FEATURE                Location/Qualifiers
source                 1..1787
                       mol_type = protein
                       organism = Staphylococcus aureus
SEQUENCE: 24
MGDHYLDIRL RPDPEFPPAQ LMSVLFGKLH QALVAQGGDR IGVSFPDLDE SRSRLGERLR  60
IHASADDLRA LLARPWLEGL RDHLQFGEPA VVPHPTPYRQ VSRVQAKSNP ERLRRRLMRR  120
HDLSEEEARK RIPDTVARAL DLPFVTLRSQ STGQHFRLFI RHGPLQVTAE EGGFTCYGLS  180
KGGFVPWFGT EGRGSLLTCG DVEENPGPMP KKKRKVEGIK SNISLLKDEL RGQISHISHE  240
YLSLIDLAFD SKQNRLFEMK VLELLVNEYG FKGRHLGGSR KPDGIVYSTT LEDNFGIIVD  300
TKAYSEGYSL PISQADEMER YVRENSNRDE EVNPNKWWEN FSEEVKKYYF VFISGSFKGK  360
FEEQLRRLSM TTGVNGSAVN VVNLLLGAEK IRSGEMTIEE LERAMFNNSE FILKYGGGGS  420
DKKYSIGLAI GTNSVGWAVI TDEYKVPSKK FKVLGNTDRH SIKKNLIGAL LFDSGETAEA  480
```

```
TRLKRTARRR YTRRKNRICY LQEIFSNEMA KVDDSFFHRL EESFLVEEDK KHERHPIFGN  540
IVDEVAYHEK YPTIYHLRKK LVDSTDKADL RLIYLALAHM IKFRGHFLIE GDLNPDNSDV  600
DKLFIQLVQT YNQLFEENPI NASGVDAKAI LSARLSKSRR LENLIAQLPG EKKNGLFGNL  660
IALSLGLTPN FKSNFDLAED AKLQLSKDTY DDDLDNLLAQ IGDQYADLFL AAKNLSDAIL  720
LSDILRVNTE ITKAPLSASM IKRYDEHHQD LTLLKALVRQ QLPEKYKEIF FDQSKNGYAG  780
YIDGGASQEE FYKFIKPILE KMDGTEELLV KLNREDLLRK QRTFDNGSIP HQIHLGELHA  840
ILRRQEDFYP FLKDNREKIE KILTFRIPYY VGPLARGNSR FAWMTRKSEE TITPWNFEEV  900
VDKGASAQSF IERMTNFDKN LPNEKVLPKH SLLYEYFTVY NELTKVKYVT EGMRKPAFLS  960
GEQKKAIVDL LFKTNRKVTV KQLKEDYFKK IECFDSVEIS GVEDRFNASL GTYHDLLKII  1020
KDKDFLDNEE NEDILEDIVL TLTLFEDREM IEERLKTYAH LFDDKVMKQL KRRRYTGWGR  1080
LSRKLINGIR DKQSGKTILD FLKSDGFANR NFMQLIHDDS LTFKEDIQKA QVSGQGDSLH  1140
EHIANLAGSP AIKKGILQTV KVVDELVKVM GRHKPENIVI EMARENQTTQ KGQKNSRERM  1200
KRIEEGIKEL GSQILKEHPV ENTQLQNEKL YLYYLQNGRD MYVDQELDIN RLSDYDVDAI  1260
VPQSFLKDDS IDNKVLTRSD KNRGKSDNVP SEEVVKKMKN YWRQLLNAKL ITQRKFDNLT  1320
KAERGGLSEL DKAGFIKRQL VETRQITKHV AQILDSRMNT KYDENDKLIR EVKVITLKSK  1380
LVSDFRKDFQ FYKVREINNY HHAHDAYLNA VVGTALIKKY PKLESEFVYG DYKVYDVRKM  1440
IAKSEQEIGK ATAKYFFYSN IMNFFKTEIT LANGEIRKRP LIETNGETGE IVWDKGRDFA  1500
TVRKVLSMPQ VNIVKKTEVQ TGGFSKESIL PKRNSDKLIA RKKDWDPKKY GGFDSPTVAY  1560
SVLVVAKVEK GKSKKLKSVK ELLGITIMER SSFEKNPIDF LEAKGYKEVK KDLIIKLPKY  1620
SLFELENGRK RMLASAGELQ KGNELALPSK YVNFLYLASH YEKLKGSPED NEQKQLFVEQ  1680
HKHYLDEIIE QISEFSKRVI LADANLDKVL SAYNKHRDKP IREQAENIIH LFTLTNLGAP  1740
AAFKYFDTTI DRKRYTSTKE VLDATLIHQS ITGLYETRID LSQLGGD                1787

SEQ ID NO: 25          moltype = AA  length = 199
FEATURE                Location/Qualifiers
source                 1..199
                       mol_type = protein
                       organism = Staphylococcus aureus
SEQUENCE: 25
EGIKSNISLL KDELRGQISH ISHEYLSLID LAFDSKQNRL FEMKVLELLV NEYGFKGRHL  60
GGSRKPDGIV YSTTLEDNFG IIVDTKAYSE GYSLPISQAD EMERYVRENS NRDEEVNPNK  120
WWENFSEEVK KYYFVFISGS FKGKFEEQLR RLSMTTGVNG SAVNVVNLLL GAEKIRSGEM  180
TIEELERAMF NNSEFILKY                                              199

SEQ ID NO: 26          moltype = AA  length = 193
FEATURE                Location/Qualifiers
source                 1..193
                       mol_type = protein
                       organism = Staphylococcus aureus
SEQUENCE: 26
MNFFSLHPNV YATGRPKGLI GMLENVWVSN HTPGEGTLYL ISGFSNYNGG VRFYETFTEH  60
INQGGRVIAI LGGSTSQRLS SRQVVEELLN RGVEVHIINR KRILHAKLYG TSNNLGESLV  120
VSSGNFTGPG MSQNIEASLL LDNNTTQSMG FSWNDMISEM LNQNWHIHNM TNATDASPGW  180
NLLYDERTTN LTL                                                    193

SEQ ID NO: 27          moltype = AA  length = 193
FEATURE                Location/Qualifiers
source                 1..193
                       mol_type = protein
                       organism = Staphylococcus aureus
SEQUENCE: 27
MNYFSLHPNV YATGRPKGLI NMLESVWISN QKPGDGTMYL ISGFANYNGG IRFYETFTEH  60
INHGGKVIAI LGGSTSQRLS SKQVVAELVS RGVDVYIINR KRLLHAKLYG SSSNSGESLV  120
VSSGNFTGPG MSQNVEASLL LDNNTTSSMG FSWNGMVNSM LDQKWQIHNL SNSNPTSPSW  180
NLLYDERTTN LTL                                                    193

SEQ ID NO: 28          moltype = AA  length = 176
FEATURE                Location/Qualifiers
source                 1..176
                       mol_type = protein
                       organism = synthetic construct
SEQUENCE: 28
MDYKDHDGDY KDHDIDYKDD DDKMAPKKKR KVGIHRGVPM VDLRTLGYSQ QQQEKIKPKV  60
RSTVAQHHEA LVGHGFTHAH IVALSQHPAA LGTVAVKYQD MIAALPEATH EAIVGVGKQW  120
SGARALEALL TVAGELRGPP LQLDTGQLLK IAKRGGVTAV EAVHAWRNAL TGAPLN      176

SEQ ID NO: 29          moltype = AA  length = 23
FEATURE                Location/Qualifiers
source                 1..23
                       mol_type = protein
                       organism = synthetic construct
SEQUENCE: 29
MDYKDHDGDY KDHDIDYKDD DDK                                         23

SEQ ID NO: 30          moltype = AA  length = 153
FEATURE                Location/Qualifiers
source                 1..153
                       mol_type = protein
                       organism = synthetic construct
```

```
SEQUENCE: 30
MAPKKKRKVG IHRGVPMVDL RTLGYSQQQQ EKIKPKVRST VAQHHEALVG HGFTHAHIVA  60
LSQHPAALGT VAVKYQDMIA ALPEATHEAI VGVGKQWSGA RALEALLTVA GELRGPPLQL  120
DTGQLLKIAK RGGVTAVEAV HAWRNALTGA PLN                              153

SEQ ID NO: 31          moltype = AA  length = 85
FEATURE                Location/Qualifiers
source                 1..85
                       mol_type = protein
                       organism = synthetic construct
VARIANT                11..13
SEQUENCE: 31
LTPEQVVAIA XXXGGRPALE SIVAQLSRPD PALAALTNDH LVALACLGGR PALDAVKKGL  60
PHAPALIKRT NRRIPERTSH RVAGS                                       85

SEQ ID NO: 32          moltype = AA  length = 85
FEATURE                Location/Qualifiers
source                 1..85
                       mol_type = protein
                       organism = synthetic construct
SEQUENCE: 32
LTPEQVVAIA NNNGGRPALE SIVAQLSRPD PALAALTNDH LVALACLGGR PALDAVKKGL  60
PHAPALIKRT NRRIPERTSH RVAGS                                       85

SEQ ID NO: 33          moltype = AA  length = 85
FEATURE                Location/Qualifiers
source                 1..85
                       mol_type = protein
                       organism = synthetic construct
SEQUENCE: 33
LTPEQVVAIA SNGGGRPALE SIVAQLSRPD PALAALTNDH LVALACLGGR PALDAVKKGL  60
PHAPALIKRT NRRIPERTSH RVAGS                                       85

SEQ ID NO: 34          moltype = AA  length = 85
FEATURE                Location/Qualifiers
source                 1..85
                       mol_type = protein
                       organism = synthetic construct
SEQUENCE: 34
LTPEQVVAIA SHDGGRPALE SIVAQLSRPD PALAALTNDH LVALACLGGR PALDAVKKGL  60
PHAPALIKRT NRRIPERTSH RVAGS                                       85

SEQ ID NO: 35          moltype = AA  length = 85
FEATURE                Location/Qualifiers
source                 1..85
                       mol_type = protein
                       organism = synthetic construct
SEQUENCE: 35
LTPEQVVAIA SNIGGRPALE SIVAQLSRPD PALAALTNDH LVALACLGGR PALDAVKKGL  60
PHAPALIKRT NRRIPERTSH RVAGS                                       85

SEQ ID NO: 36          moltype = AA  length = 199
FEATURE                Location/Qualifiers
source                 1..199
                       mol_type = protein
                       organism = synthetic construct
SEQUENCE: 36
EGIKSNISLL KDELRGQISH ISHEYLSLID LAFDSKQNRL FEMKVLELLV NEYGFKGRHL  60
GGSRKPDGIV YSTTLEDNFG IIVDTKAYSE GYSLPISQAD EMERYVRENS NRDEEVNPNK  120
WWENFSEEVK KYYFVFISGS FKGKFEEQLR RLSMTTGVNG SAVNVVNLLL GAEKIRSGEM  180
TIEELERAMF NNSEFILKY                                              199

SEQ ID NO: 37          moltype = AA  length = 193
FEATURE                Location/Qualifiers
source                 1..193
                       mol_type = protein
                       organism = synthetic construct
SEQUENCE: 37
MNFFSLHPNV YATGRPKGLI GMLENVWVSN HTPGEGTLYL ISGFSNYNGG VRFYETFTEH  60
INQGGRVIAI LGGSTSQRLS SRQVVEELLN RGVEVHIINR KRILHAKLYG TSNNLGESLV  120
VSSGNFTGPG MSQNIEASLL LDNNTTQSMG FSWNDMISEM LNQNWHIHNM TNATDASPGW  180
NLLYDERTTN LTL                                                    193

SEQ ID NO: 38          moltype = AA  length = 193
FEATURE                Location/Qualifiers
source                 1..193
                       mol_type = protein
                       organism = synthetic construct
SEQUENCE: 38
```

```
MNYFSLHPNV YATGRPKGLI NMLESVWISN QKPGDGTMYL ISGFANYNGG IRFYETFTEH  60
INHGGKVIAI LGGSTSQRLS SKQVVAELVS RGVDVYIINR KRLLHAKLYG SSSNSGESLV  120
VSSGNFTGPG MSQNVEASLL LDNNTTSSMG FSWNGMVNSM LDQKWQIHNL SNSNPTSPSW  180
NLLYDERTTN LTL                                                    193

SEQ ID NO: 39          moltype = AA  length = 35
FEATURE                Location/Qualifiers
source                 1..35
                       mol_type = protein
                       organism = synthetic construct
SEQUENCE: 39
LSTEQVVAIA SNKGGKQALE AVKAHLLDLL GAPYV                            35

SEQ ID NO: 40          moltype = AA  length = 35
FEATURE                Location/Qualifiers
source                 1..35
                       mol_type = protein
                       organism = synthetic construct
SEQUENCE: 40
LSTEQVVAIA SNNGGKQALE AVKAQLLELR AAPYE                            35

SEQ ID NO: 41          moltype = AA  length = 35
FEATURE                Location/Qualifiers
source                 1..35
                       mol_type = protein
                       organism = synthetic construct
SEQUENCE: 41
LSTAQVVAIA SNGGGKQALE GIGEQLLKLR TAPYG                            35

SEQ ID NO: 42          moltype = AA  length = 35
FEATURE                Location/Qualifiers
source                 1..35
                       mol_type = protein
                       organism = synthetic construct
SEQUENCE: 42
LSTAQVVAIA SHDGGKPALE AVWAKLPVLR GVPYA                            35

SEQ ID NO: 43          moltype = AA  length = 35
FEATURE                Location/Qualifiers
source                 1..35
                       mol_type = protein
                       organism = synthetic construct
SEQUENCE: 43
LSTEQVVTIA SSIGGKQALE AVKVQLPVLR AAPYE                            35

SEQ ID NO: 44          moltype = DNA  length = 24
FEATURE                Location/Qualifiers
source                 1..24
                       mol_type = other DNA
                       organism = synthetic construct
SEQUENCE: 44
tctagagaag acaagaacct gacc                                        24

SEQ ID NO: 45          moltype = DNA  length = 24
FEATURE                Location/Qualifiers
source                 1..24
                       mol_type = other DNA
                       organism = synthetic construct
SEQUENCE: 45
ggatccggtc tcttaaggcc gtgg                                        24

SEQ ID NO: 46          moltype = DNA  length = 28
FEATURE                Location/Qualifiers
source                 1..28
                       mol_type = other DNA
                       organism = synthetic construct
SEQUENCE: 46
gacggtggct gtcaaatacc aagatatg                                    28

SEQ ID NO: 47          moltype = DNA  length = 30
FEATURE                Location/Qualifiers
source                 1..30
                       mol_type = other DNA
                       organism = synthetic construct
SEQUENCE: 47
tctcctccag ttcacttttg actagttggg                                  30

SEQ ID NO: 48          moltype = DNA  length = 20
FEATURE                Location/Qualifiers
```

```
source                  1..20
                        mol_type = other DNA
                        organism = synthetic construct
SEQUENCE: 48
agtaacagcg gtagaggcag                                          20

SEQ ID NO: 49           moltype = DNA  length = 20
FEATURE                 Location/Qualifiers
source                  1..20
                        mol_type = other DNA
                        organism = synthetic construct
SEQUENCE: 49
attgggctac gatggactcc                                          20

SEQ ID NO: 50           moltype = DNA  length = 25
FEATURE                 Location/Qualifiers
source                  1..25
                        mol_type = other DNA
                        organism = synthetic construct
SEQUENCE: 50
ttaattcaat atattcatga ggcac                                    25

SEQ ID NO: 51           moltype = DNA  length = 146
FEATURE                 Location/Qualifiers
source                  1..146
                        mol_type = other DNA
                        organism = synthetic construct
SEQUENCE: 51
atgcatctag agaagacaac tgagcaccga gcaggtggtg gccatcgcca gcaacaaggg  60
cggcaagcag gccctggagg ccgtgaaggc ccacctgctg gacctgctgg gcgcccccta  120
cgagctgaag agaccggatc ccgggc                                       146

SEQ ID NO: 52           moltype = DNA  length = 146
FEATURE                 Location/Qualifiers
source                  1..146
                        mol_type = other DNA
                        organism = synthetic construct
SEQUENCE: 52
atgcatctag agaagacaac tgagcaccga gcaggtggtg gccatcgcca gcaacaacgg  60
cggcaagcag gccctggagg ccgtgaaggc ccagctgctg gagctgaggg ccgcccccta  120
cgagctgaag agaccggatc ccgggc                                       146

SEQ ID NO: 53           moltype = DNA  length = 146
FEATURE                 Location/Qualifiers
source                  1..146
                        mol_type = other DNA
                        organism = synthetic construct
SEQUENCE: 53
atgcatctag agaagacaac tgagcaccga gcaggtggtg gccatcgcca gcaacggcgg  60
cggcaagcag gccctggagg gcatcggcga gcagctgctg aagctgagga ccgcccccta  120
cgagctgaag agaccggatc ccgggc                                       146

SEQ ID NO: 54           moltype = DNA  length = 146
FEATURE                 Location/Qualifiers
source                  1..146
                        mol_type = other DNA
                        organism = synthetic construct
SEQUENCE: 54
atgcatctag agaagacaac tgagcaccga gcaggtggtg gccatcgcca gccacgacgg  60
cggcaagccc gccctggagg ccgtgtgggc caagctgccc gtgctgaggg gcgtgcccta  120
cgagctgaag agaccggatc ccgggc                                       146

SEQ ID NO: 55           moltype = DNA  length = 146
FEATURE                 Location/Qualifiers
source                  1..146
                        mol_type = other DNA
                        organism = synthetic construct
SEQUENCE: 55
atgcatctag agaagacaac tgagcaccga gcaggtggtg accatcgcca gcagcatcgg  60
cggcaagcag gccctggagg ccgtgaaggt gcagctgccc gtgctgaggg ccgcccccta  120
cgagctgaag agaccggatc ccgggc                                       146

SEQ ID NO: 56           moltype = AA  length = 34
FEATURE                 Location/Qualifiers
source                  1..34
                        mol_type = protein
                        organism = synthetic construct
SEQUENCE: 56
LTPDQVVAIA SNGGGKQALE TVQRLLPVLC QDHG                          34
```

```
SEQ ID NO: 57          moltype = AA  length = 34
FEATURE                Location/Qualifiers
source                 1..34
                       mol_type = protein
                       organism = synthetic construct
SEQUENCE: 57
LTPEQVVAIA NNNGGKQALE TVQRLLPVLC QAHG                              34

SEQ ID NO: 58          moltype = AA  length = 34
FEATURE                Location/Qualifiers
source                 1..34
                       mol_type = protein
                       organism = synthetic construct
SEQUENCE: 58
LTPDQVVAIA SHDGGKQALE TVQRLLPVLC QAHG                              34

SEQ ID NO: 59          moltype = AA  length = 34
FEATURE                Location/Qualifiers
source                 1..34
                       mol_type = protein
                       organism = synthetic construct
SEQUENCE: 59
LTPAQVVAIA SNIGGKQALE TVQRLLPVLC QDHG                              34

SEQ ID NO: 60          moltype = AA  length = 29
FEATURE                Location/Qualifiers
source                 1..29
                       mol_type = protein
                       organism = synthetic construct
SEQUENCE: 60
TTDRVVALGT STGGTQALEV VLRQLPVDC                                    29

SEQ ID NO: 61          moltype = AA  length = 29
FEATURE                Location/Qualifiers
source                 1..29
                       mol_type = protein
                       organism = synthetic construct
SEQUENCE: 61
TTDRVVALGT STGGTQALEV VLRQLPVDC                                    29

SEQ ID NO: 62          moltype = AA  length = 30
FEATURE                Location/Qualifiers
source                 1..30
                       mol_type = protein
                       organism = synthetic construct
SEQUENCE: 62
MTSEQIVAIG TSTGGTQALE AVLTALPRVC                                   30

SEQ ID NO: 63          moltype = AA  length = 29
FEATURE                Location/Qualifiers
source                 1..29
                       mol_type = protein
                       organism = synthetic construct
SEQUENCE: 63
TTDRVVAIGT STGGTQALEV VLTALPRVC                                    29

SEQ ID NO: 64          moltype = AA  length = 29
FEATURE                Location/Qualifiers
source                 1..29
                       mol_type = protein
                       organism = synthetic construct
SEQUENCE: 64
TTERIVAIGT STGGTQALET VLHRLPATC                                    29

SEQ ID NO: 65          moltype = AA  length = 29
FEATURE                Location/Qualifiers
source                 1..29
                       mol_type = protein
                       organism = synthetic construct
SEQUENCE: 65
TTDKIIAIGT STGGTQALEA VLTKLPAVC                                    29

SEQ ID NO: 66          moltype = AA  length = 29
FEATURE                Location/Qualifiers
source                 1..29
                       mol_type = protein
                       organism = synthetic construct
SEQUENCE: 66
```

```
TTERIVAIGT STGGTQALET VLTALPRVC                                    29

SEQ ID NO: 67          moltype = AA  length = 29
FEATURE                Location/Qualifiers
source                 1..29
                       mol_type = protein
                       organism = synthetic construct
SEQUENCE: 67
TTERVVALGT STGGTQALEV VLRTLPRVC                                    29

SEQ ID NO: 68          moltype = AA  length = 29
FEATURE                Location/Qualifiers
source                 1..29
                       mol_type = protein
                       organism = synthetic construct
SEQUENCE: 68
TTDQLIAIGT STGGTQALEA ILTKLPATC                                    29

SEQ ID NO: 69          moltype = AA  length = 29
FEATURE                Location/Qualifiers
source                 1..29
                       mol_type = protein
                       organism = synthetic construct
SEQUENCE: 69
TTERIVAIGT STGGTQALET VLPRLPATC                                    29

SEQ ID NO: 70          moltype = AA  length = 29
FEATURE                Location/Qualifiers
source                 1..29
                       mol_type = protein
                       organism = synthetic construct
SEQUENCE: 70
TTERIVAIGT STGGTQALEA VLTALPRVC                                    29

SEQ ID NO: 71          moltype = AA  length = 29
FEATURE                Location/Qualifiers
source                 1..29
                       mol_type = protein
                       organism = synthetic construct
SEQUENCE: 71
TTERIVAIGT STGGTQALEA VLTALPRVC                                    29

SEQ ID NO: 72          moltype = AA  length = 29
FEATURE                Location/Qualifiers
source                 1..29
                       mol_type = protein
                       organism = synthetic construct
SEQUENCE: 72
TTERIVAIGT STGGTQALEA VLTALPRVC                                    29

SEQ ID NO: 73          moltype = AA  length = 29
FEATURE                Location/Qualifiers
source                 1..29
                       mol_type = protein
                       organism = synthetic construct
SEQUENCE: 73
TSDKVVAIGA STGGTQALEL LLTGLPAVC                                    29

SEQ ID NO: 74          moltype = AA  length = 29
FEATURE                Location/Qualifiers
source                 1..29
                       mol_type = protein
                       organism = synthetic construct
SEQUENCE: 74
TTERIVAIGT STGGTQALET VLTALPRVC                                    29

SEQ ID NO: 75          moltype = AA  length = 29
FEATURE                Location/Qualifiers
source                 1..29
                       mol_type = protein
                       organism = synthetic construct
SEQUENCE: 75
TTERIVAIGT STGGTQALEA VLTALPRVC                                    29

SEQ ID NO: 76          moltype = AA  length = 29
FEATURE                Location/Qualifiers
source                 1..29
                       mol_type = protein
                       organism = synthetic construct
```

```
SEQUENCE: 76
TTERIVAIGT STGGTQALEA VLTALPRVC                                     29

SEQ ID NO: 77          moltype = AA  length = 29
FEATURE                Location/Qualifiers
source                 1..29
                       mol_type = protein
                       organism = synthetic construct
SEQUENCE: 77
TTERIVAIGT STGGTQALEA VLTALPRVC                                     29

SEQ ID NO: 78          moltype = AA  length = 29
FEATURE                Location/Qualifiers
source                 1..29
                       mol_type = protein
                       organism = synthetic construct
SEQUENCE: 78
TTERIVAIGT STGGTQALEA VLTALPRVC                                     29

SEQ ID NO: 79          moltype = AA  length = 29
FEATURE                Location/Qualifiers
source                 1..29
                       mol_type = protein
                       organism = synthetic construct
SEQUENCE: 79
TTERIVAIGT STGGTQALEA VLTALPRVC                                     29

SEQ ID NO: 80          moltype = AA  length = 29
FEATURE                Location/Qualifiers
source                 1..29
                       mol_type = protein
                       organism = synthetic construct
SEQUENCE: 80
TTERIVAIGT STGGTQALEA VLTALPRVC                                     29

SEQ ID NO: 81          moltype = AA  length = 29
FEATURE                Location/Qualifiers
source                 1..29
                       mol_type = protein
                       organism = synthetic construct
SEQUENCE: 81
TTERIVAIGT STGGTQALEA VLTALPRVC                                     29

SEQ ID NO: 82          moltype = AA  length = 29
FEATURE                Location/Qualifiers
source                 1..29
                       mol_type = protein
                       organism = synthetic construct
SEQUENCE: 82
TTERIVAIGT STGGTQALEA VLTALPRVC                                     29

SEQ ID NO: 83          moltype = AA  length = 29
FEATURE                Location/Qualifiers
source                 1..29
                       mol_type = protein
                       organism = synthetic construct
SEQUENCE: 83
TTERIVAIGT STGGTQALEA VLTALPRVC                                     29

SEQ ID NO: 84          moltype = AA  length = 29
FEATURE                Location/Qualifiers
source                 1..29
                       mol_type = protein
                       organism = synthetic construct
SEQUENCE: 84
TTERIVAIGT STGGTQALEA VLTALPRVC                                     29

SEQ ID NO: 85          moltype = AA  length = 29
FEATURE                Location/Qualifiers
source                 1..29
                       mol_type = protein
                       organism = synthetic construct
SEQUENCE: 85
TTERIVAIGT STGGTQALEA VLTALPRVC                                     29

SEQ ID NO: 86          moltype = AA  length = 29
FEATURE                Location/Qualifiers
source                 1..29
                       mol_type = protein
```

```
                        organism = synthetic construct
SEQUENCE: 86
TTERIVAIGT STGGTQALEA VLTALPRVC                                      29

SEQ ID NO: 87           moltype = AA  length = 29
FEATURE                 Location/Qualifiers
source                  1..29
                        mol_type = protein
                        organism = synthetic construct
SEQUENCE: 87
TTERIVAIGT STGGTQALEA VLTALPRVC                                      29

SEQ ID NO: 88           moltype = AA  length = 29
FEATURE                 Location/Qualifiers
source                  1..29
                        mol_type = protein
                        organism = synthetic construct
SEQUENCE: 88
TTERIVAIGT STGGTQALEA VLTALPRVC                                      29

SEQ ID NO: 89           moltype = AA  length = 29
FEATURE                 Location/Qualifiers
source                  1..29
                        mol_type = protein
                        organism = synthetic construct
SEQUENCE: 89
TTERIVAIGT STGGTQALEA VLTALPRVC                                      29

SEQ ID NO: 90           moltype = AA  length = 29
FEATURE                 Location/Qualifiers
source                  1..29
                        mol_type = protein
                        organism = synthetic construct
SEQUENCE: 90
TTERIVAIGT STGGTQALEA VLTALPRVC                                      29

SEQ ID NO: 91           moltype = AA  length = 29
FEATURE                 Location/Qualifiers
source                  1..29
                        mol_type = protein
                        organism = synthetic construct
SEQUENCE: 91
TTERIVAIGT STGGTQALEA VLTALPRVC                                      29

SEQ ID NO: 92           moltype = AA  length = 29
FEATURE                 Location/Qualifiers
source                  1..29
                        mol_type = protein
                        organism = synthetic construct
SEQUENCE: 92
TTERIVAIGT STGGTQALEA VLTALPRVC                                      29

SEQ ID NO: 93           moltype = AA  length = 29
FEATURE                 Location/Qualifiers
source                  1..29
                        mol_type = protein
                        organism = synthetic construct
SEQUENCE: 93
TTERIVAIGT STGGTQALEA VLTALPRVC                                      29

SEQ ID NO: 94           moltype = AA  length = 29
FEATURE                 Location/Qualifiers
source                  1..29
                        mol_type = protein
                        organism = synthetic construct
SEQUENCE: 94
TTERIVAIGT STGGTQALEA VLTALPRVC                                      29

SEQ ID NO: 95           moltype = AA  length = 29
FEATURE                 Location/Qualifiers
source                  1..29
                        mol_type = protein
                        organism = synthetic construct
SEQUENCE: 95
TTERIVAIGT STGGTQALEA VLTALPRVC                                      29

SEQ ID NO: 96           moltype = AA  length = 29
FEATURE                 Location/Qualifiers
source                  1..29
```

```
                        mol_type = protein
                        organism = synthetic construct
SEQUENCE: 96
FSQADIVRIA DNIGGAQALK AVLEHGPTL                                     29

SEQ ID NO: 97           moltype = AA  length = 28
FEATURE                 Location/Qualifiers
source                  1..28
                        mol_type = protein
                        organism = synthetic construct
SEQUENCE: 97
ADIVKIASNG GGAQALEAVA MHGSTLCE                                      28

SEQ ID NO: 98           moltype = AA  length = 28
FEATURE                 Location/Qualifiers
source                  1..28
                        mol_type = protein
                        organism = synthetic construct
SEQUENCE: 98
ADIVKIAGNG GGARALKAVV MHGPTLCE                                      28

SEQ ID NO: 99           moltype = AA  length = 29
FEATURE                 Location/Qualifiers
source                  1..29
                        mol_type = protein
                        organism = synthetic construct
SEQUENCE: 99
TTDRVVALGC STGGTQALEF ILRQLPRDC                                     29

SEQ ID NO: 100          moltype = AA  length = 24
FEATURE                 Location/Qualifiers
source                  1..24
                        mol_type = protein
                        organism = synthetic construct
SEQUENCE: 100
ALAAAVGGKG ALEVPANLIP ANCE                                          24

SEQ ID NO: 101          moltype = AA  length = 23
FEATURE                 Location/Qualifiers
source                  1..23
                        mol_type = protein
                        organism = synthetic construct
SEQUENCE: 101
RIVAIGTSTG GTQALEVVLT ALP                                           23

SEQ ID NO: 102          moltype = AA  length = 34
FEATURE                 Location/Qualifiers
source                  1..34
                        mol_type = protein
                        organism = synthetic construct
SEQUENCE: 102
LTPDQVVAIA SNGGGKQALE TVQRLLPVLC QDHG                               34

SEQ ID NO: 103          moltype = AA  length = 34
FEATURE                 Location/Qualifiers
source                  1..34
                        mol_type = protein
                        organism = synthetic construct
SEQUENCE: 103
LTPAQVVAIA SNIGGKQALE TVQRLLPVLC QDHG                               34

SEQ ID NO: 104          moltype = AA  length = 34
FEATURE                 Location/Qualifiers
source                  1..34
                        mol_type = protein
                        organism = synthetic construct
SEQUENCE: 104
LTPDQVVAIA SHDGGKQALE TVQRLLPVLC QAHG                               34

SEQ ID NO: 105          moltype = AA  length = 34
FEATURE                 Location/Qualifiers
source                  1..34
                        mol_type = protein
                        organism = synthetic construct
SEQUENCE: 105
LTPEQVVAIA NNNGGKQALE TVQRLLPVLC QAHG                               34

SEQ ID NO: 106          moltype = AA  length = 29
FEATURE                 Location/Qualifiers
```

```
source                1..29
                      mol_type = protein
                      organism = synthetic construct
SEQUENCE: 106
TTERIVAIGT STGGTQALEA VLTALPRVC                                  29

SEQ ID NO: 107        moltype = AA  length = 29
FEATURE               Location/Qualifiers
source                1..29
                      mol_type = protein
                      organism = synthetic construct
SEQUENCE: 107
TTERIVAIGT STGGTQALEA VLTALPRVC                                  29

SEQ ID NO: 108        moltype = AA  length = 29
FEATURE               Location/Qualifiers
source                1..29
                      mol_type = protein
                      organism = synthetic construct
SEQUENCE: 108
TTERIVAIGT STGGTQALEA VLTALPRVC                                  29

SEQ ID NO: 109        moltype = AA  length = 29
FEATURE               Location/Qualifiers
source                1..29
                      mol_type = protein
                      organism = synthetic construct
SEQUENCE: 109
TTERIVAIGT STGGTQALEA VLTALPRVC                                  29

SEQ ID NO: 110        moltype = AA  length = 29
FEATURE               Location/Qualifiers
source                1..29
                      mol_type = protein
                      organism = synthetic construct
SEQUENCE: 110
TTERIVAIGT STGGTQALEA VLTALPRVC                                  29

SEQ ID NO: 111        moltype = AA  length = 29
FEATURE               Location/Qualifiers
source                1..29
                      mol_type = protein
                      organism = synthetic construct
SEQUENCE: 111
TTERIVAIGT STGGTQALEA VLTALPRVC                                  29

SEQ ID NO: 112        moltype = AA  length = 29
FEATURE               Location/Qualifiers
source                1..29
                      mol_type = protein
                      organism = synthetic construct
SEQUENCE: 112
TTERIVAIGT STGGTQALEA VLTALPRVC                                  29

SEQ ID NO: 113        moltype = AA  length = 29
FEATURE               Location/Qualifiers
source                1..29
                      mol_type = protein
                      organism = synthetic construct
SEQUENCE: 113
TTERIVAIGT STGGTQALEA VLTALPRVC                                  29

SEQ ID NO: 114        moltype = AA  length = 29
FEATURE               Location/Qualifiers
source                1..29
                      mol_type = protein
                      organism = synthetic construct
SEQUENCE: 114
TTERIVAIGT STGGTQALEA VLTALPRVC                                  29

SEQ ID NO: 115        moltype = AA  length = 29
FEATURE               Location/Qualifiers
source                1..29
                      mol_type = protein
                      organism = synthetic construct
SEQUENCE: 115
TTERIVAIGT STGGTQALEA VLTALPRVC                                  29

SEQ ID NO: 116        moltype = AA  length = 29
```

```
FEATURE                 Location/Qualifiers
source                  1..29
                        mol_type = protein
                        organism = synthetic construct
SEQUENCE: 116
TTERIVAIGT STGGTQALEA VLTALPRVC                                     29

SEQ ID NO: 117          moltype = AA  length = 29
FEATURE                 Location/Qualifiers
source                  1..29
                        mol_type = protein
                        organism = synthetic construct
SEQUENCE: 117
TTERIVAIGT STGGTQALEA VLTALPRVC                                     29

SEQ ID NO: 118          moltype = AA  length = 29
FEATURE                 Location/Qualifiers
source                  1..29
                        mol_type = protein
                        organism = synthetic construct
SEQUENCE: 118
TTERIVAIGT STGGTQALEA VLTALPRVC                                     29

SEQ ID NO: 119          moltype = AA  length = 29
FEATURE                 Location/Qualifiers
source                  1..29
                        mol_type = protein
                        organism = synthetic construct
SEQUENCE: 119
TTERIVAIGT STGGTQALEA VLTALPRVC                                     29

SEQ ID NO: 120          moltype = AA  length = 29
FEATURE                 Location/Qualifiers
source                  1..29
                        mol_type = protein
                        organism = synthetic construct
SEQUENCE: 120
TTERIVAIGT STGGTQALEA VLTALPRVC                                     29

SEQ ID NO: 121          moltype = AA  length = 29
FEATURE                 Location/Qualifiers
source                  1..29
                        mol_type = protein
                        organism = synthetic construct
SEQUENCE: 121
TTERIVAIGT STGGTQALEA VLTALPRVC                                     29

SEQ ID NO: 122          moltype = AA  length = 29
FEATURE                 Location/Qualifiers
source                  1..29
                        mol_type = protein
                        organism = synthetic construct
SEQUENCE: 122
TTERIVAIGT STGGTQALEA VLTALPRVC                                     29

SEQ ID NO: 123          moltype = AA  length = 29
FEATURE                 Location/Qualifiers
source                  1..29
                        mol_type = protein
                        organism = synthetic construct
SEQUENCE: 123
TTERIVAIGT STGGTQALEA VLTALPRVC                                     29

SEQ ID NO: 124          moltype = AA  length = 29
FEATURE                 Location/Qualifiers
source                  1..29
                        mol_type = protein
                        organism = synthetic construct
SEQUENCE: 124
TTERIVAIGT STGGTQALEA VLTALPRVC                                     29

SEQ ID NO: 125          moltype = AA  length = 29
FEATURE                 Location/Qualifiers
source                  1..29
                        mol_type = protein
                        organism = synthetic construct
SEQUENCE: 125
TTERIVAIGT STGGTQALEA VLTALPRVC                                     29
```

```
SEQ ID NO: 126          moltype = AA  length = 29
FEATURE                 Location/Qualifiers
source                  1..29
                        mol_type = protein
                        organism = synthetic construct
SEQUENCE: 126
TTERIVAIGT STGGTQALEA VLTALPRVC                                    29

SEQ ID NO: 127          moltype = AA  length = 29
FEATURE                 Location/Qualifiers
source                  1..29
                        mol_type = protein
                        organism = synthetic construct
SEQUENCE: 127
TTERIVAIGT STGGTQALEA VLTALPRVC                                    29

SEQ ID NO: 128          moltype = AA  length = 29
FEATURE                 Location/Qualifiers
source                  1..29
                        mol_type = protein
                        organism = synthetic construct
SEQUENCE: 128
TTERIVAIGT STGGTQALEA VLTALPRVC                                    29

SEQ ID NO: 129          moltype = AA  length = 29
FEATURE                 Location/Qualifiers
source                  1..29
                        mol_type = protein
                        organism = synthetic construct
SEQUENCE: 129
TTERIVAIGT STGGTQALEA VLTALPRVC                                    29

SEQ ID NO: 130          moltype = AA  length = 30
FEATURE                 Location/Qualifiers
source                  1..30
                        mol_type = protein
                        organism = synthetic construct
SEQUENCE: 130
MTSEQIVAIG TSTGGTQALE AVLTALPRVC                                   30

SEQ ID NO: 131          moltype = AA  length = 29
FEATURE                 Location/Qualifiers
source                  1..29
                        mol_type = protein
                        organism = synthetic construct
SEQUENCE: 131
TTERIVAIGT STGGTQALET VLTALPRVC                                    29

SEQ ID NO: 132          moltype = AA  length = 29
FEATURE                 Location/Qualifiers
source                  1..29
                        mol_type = protein
                        organism = synthetic construct
SEQUENCE: 132
TTERIVAIGT STGGTQALET VLTALPRVC                                    29

SEQ ID NO: 133          moltype = AA  length = 23
FEATURE                 Location/Qualifiers
source                  1..23
                        mol_type = protein
                        organism = synthetic construct
SEQUENCE: 133
RIVAIGTSTG GTQALEVVLT ALP                                          23

SEQ ID NO: 134          moltype = AA  length = 29
FEATURE                 Location/Qualifiers
source                  1..29
                        mol_type = protein
                        organism = synthetic construct
SEQUENCE: 134
TTDRVVALGT STGGTQALEV VLRQLPVDC                                    29

SEQ ID NO: 135          moltype = AA  length = 29
FEATURE                 Location/Qualifiers
source                  1..29
                        mol_type = protein
                        organism = synthetic construct
SEQUENCE: 135
TTDRVVALGT STGGTQALEV VLRQLPVDC                                    29
```

```
SEQ ID NO: 136          moltype = AA  length = 29
FEATURE                 Location/Qualifiers
source                  1..29
                        mol_type = protein
                        organism = synthetic construct
SEQUENCE: 136
TTDRVVALGC STGGTQALEF ILRQLPRDC                                     29

SEQ ID NO: 137          moltype = AA  length = 29
FEATURE                 Location/Qualifiers
source                  1..29
                        mol_type = protein
                        organism = synthetic construct
SEQUENCE: 137
TTERVVALGT STGGTQALEV VLRTLPRVC                                     29

SEQ ID NO: 138          moltype = AA  length = 29
FEATURE                 Location/Qualifiers
source                  1..29
                        mol_type = protein
                        organism = synthetic construct
SEQUENCE: 138
TTDRVVAIGT STGGTQALEV VLTALPRVC                                     29

SEQ ID NO: 139          moltype = AA  length = 29
FEATURE                 Location/Qualifiers
source                  1..29
                        mol_type = protein
                        organism = synthetic construct
SEQUENCE: 139
TTERIVAIGT STGGTQALET VLHRLPATC                                     29

SEQ ID NO: 140          moltype = AA  length = 29
FEATURE                 Location/Qualifiers
source                  1..29
                        mol_type = protein
                        organism = synthetic construct
SEQUENCE: 140
TTERIVAIGT STGGTQALET VLPRLPATC                                     29

SEQ ID NO: 141          moltype = AA  length = 29
FEATURE                 Location/Qualifiers
source                  1..29
                        mol_type = protein
                        organism = synthetic construct
SEQUENCE: 141
TTDKIIAIGT STGGTQALEA VLTKLPAVC                                     29

SEQ ID NO: 142          moltype = AA  length = 29
FEATURE                 Location/Qualifiers
source                  1..29
                        mol_type = protein
                        organism = synthetic construct
SEQUENCE: 142
TTDQLIAIGT STGGTQALEA ILTKLPATC                                     29

SEQ ID NO: 143          moltype = AA  length = 29
FEATURE                 Location/Qualifiers
source                  1..29
                        mol_type = protein
                        organism = synthetic construct
SEQUENCE: 143
TSDKVVAIGA STGGTQALEL LLTGLPAVC                                     29

SEQ ID NO: 144          moltype = AA  length = 28
FEATURE                 Location/Qualifiers
source                  1..28
                        mol_type = protein
                        organism = synthetic construct
SEQUENCE: 144
ADIVKIASNG GGAQALEAVA MHGSTLCE                                      28

SEQ ID NO: 145          moltype = AA  length = 28
FEATURE                 Location/Qualifiers
source                  1..28
                        mol_type = protein
                        organism = synthetic construct
SEQUENCE: 145
```

```
ADIVKIAGNG GGARALKAVV MHGPTLCE                              28

SEQ ID NO: 146          moltype = AA  length = 29
FEATURE                 Location/Qualifiers
source                  1..29
                        mol_type = protein
                        organism = synthetic construct
SEQUENCE: 146
FSQADIVRIA DNIGGAQALK AVLEHGPTL                             29

SEQ ID NO: 147          moltype = AA  length = 24
FEATURE                 Location/Qualifiers
source                  1..24
                        mol_type = protein
                        organism = synthetic construct
SEQUENCE: 147
ALAAAVGGKG ALEVPANLIP ANCE                                  24

SEQ ID NO: 148          moltype = DNA  length = 52
FEATURE                 Location/Qualifiers
source                  1..52
                        mol_type = other DNA
                        organism = synthetic construct
SEQUENCE: 148
ttgatagtcg ccttatgttt tggatacaga atgttgacag gtaaacgaaa ta   52

SEQ ID NO: 149          moltype = DNA  length = 16
FEATURE                 Location/Qualifiers
source                  1..16
                        mol_type = other DNA
                        organism = synthetic construct
SEQUENCE: 149
tgatagtcgc cttatg                                           16

SEQ ID NO: 150          moltype = DNA  length = 16
FEATURE                 Location/Qualifiers
source                  1..16
                        mol_type = other DNA
                        organism = synthetic construct
SEQUENCE: 150
atttggttta cctgtc                                           16

SEQ ID NO: 151          moltype = AA  length = 35
FEATURE                 Location/Qualifiers
source                  1..35
                        mol_type = protein
                        organism = synthetic construct
SEQUENCE: 151
LSTAQVVAIA SNGGGKQALE GIGEQLLKLR TAPYG                      35

SEQ ID NO: 152          moltype = AA  length = 35
FEATURE                 Location/Qualifiers
source                  1..35
                        mol_type = protein
                        organism = synthetic construct
SEQUENCE: 152
LSTEQVVAIA SNKGGKQALE AVKAHLLDLL GAPYV                      35

SEQ ID NO: 153          moltype = AA  length = 35
FEATURE                 Location/Qualifiers
source                  1..35
                        mol_type = protein
                        organism = synthetic construct
SEQUENCE: 153
LSTEQVVAIA SNNGGKQALE AVKAQLLELR AAPYE                      35

SEQ ID NO: 154          moltype = AA  length = 35
FEATURE                 Location/Qualifiers
source                  1..35
                        mol_type = protein
                        organism = synthetic construct
SEQUENCE: 154
LSTAQVVAIA SNGGGKQALE GIGEQLLKLR TAPYG                      35

SEQ ID NO: 155          moltype = AA  length = 35
FEATURE                 Location/Qualifiers
source                  1..35
                        mol_type = protein
                        organism = synthetic construct
```

```
SEQUENCE: 155
LSTEQVVAIA SNNGGKQALE AVKAQLLELR AAPYE                        35

SEQ ID NO: 156          moltype = AA  length = 35
FEATURE                 Location/Qualifiers
source                  1..35
                        mol_type = protein
                        organism = synthetic construct
SEQUENCE: 156
LSTEQVVAIA SNKGGKQALE AVKAHLLDLL GAPYV                        35

SEQ ID NO: 157          moltype = AA  length = 35
FEATURE                 Location/Qualifiers
source                  1..35
                        mol_type = protein
                        organism = synthetic construct
SEQUENCE: 157
LSTAQVVAIA SNGGGKQALE GIGEQLLKLR TAPYG                        35

SEQ ID NO: 158          moltype = AA  length = 35
FEATURE                 Location/Qualifiers
source                  1..35
                        mol_type = protein
                        organism = synthetic construct
SEQUENCE: 158
LSTAQVVAIA SHDGGKPALE AVWAKLPVLR GVPYA                        35

SEQ ID NO: 159          moltype = AA  length = 35
FEATURE                 Location/Qualifiers
source                  1..35
                        mol_type = protein
                        organism = synthetic construct
SEQUENCE: 159
LSTEQVVAIA SNKGGKQALE AVKAHLLDLL GAPYV                        35

SEQ ID NO: 160          moltype = AA  length = 35
FEATURE                 Location/Qualifiers
source                  1..35
                        mol_type = protein
                        organism = synthetic construct
SEQUENCE: 160
LSTAQVVAIA SHDGGKPALE AVWAKLPVLR GVPYA                        35

SEQ ID NO: 161          moltype = AA  length = 35
FEATURE                 Location/Qualifiers
source                  1..35
                        mol_type = protein
                        organism = synthetic construct
SEQUENCE: 161
LSTAQVVAIA SHDGGKPALE AVWAKLPVLR GVPYA                        35

SEQ ID NO: 162          moltype = AA  length = 35
FEATURE                 Location/Qualifiers
source                  1..35
                        mol_type = protein
                        organism = synthetic construct
SEQUENCE: 162
LSTAQVVAIA SNGGGKQALE GIGEQLLKLR TAPYG                        35

SEQ ID NO: 163          moltype = AA  length = 35
FEATURE                 Location/Qualifiers
source                  1..35
                        mol_type = protein
                        organism = synthetic construct
SEQUENCE: 163
LSTAQVVAIA SNGGGKQALE GIGEQLLKLR TAPYG                        35

SEQ ID NO: 164          moltype = AA  length = 35
FEATURE                 Location/Qualifiers
source                  1..35
                        mol_type = protein
                        organism = synthetic construct
SEQUENCE: 164
LSTEQVVAIA SNNGGKQALE AVKAQLLELR AAPYE                        35

SEQ ID NO: 165          moltype = AA  length = 35
FEATURE                 Location/Qualifiers
source                  1..35
                        mol_type = protein
```

```
                         organism = synthetic construct
SEQUENCE: 165
LSTAQVVAIA SNGGGKQALE GIGEQLLKLR TAPYG                           35

SEQ ID NO: 166           moltype = AA  length = 35
FEATURE                  Location/Qualifiers
source                   1..35
                         mol_type = protein
                         organism = synthetic construct
SEQUENCE: 166
LSTEQVVAIA SNKGGKQALE AVKAHLLDLL GAPYV                           35

SEQ ID NO: 167           moltype = DNA  length = 8106
FEATURE                  Location/Qualifiers
source                   1..8106
                         mol_type = other DNA
                         organism = synthetic construct
SEQUENCE: 167
gacggatcgg gagatctccc gatcccctat ggtcgactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tggactttcc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
accatggact acaaagacca tgacggtgat tataaagatc atgacatcga ttacaaggat  960
gacgatgaca agatggcccc caagaagaag aggaaggtgg gcattcaccg cggggtacct  1020
atggtggact tgaggacact cggttattcg caacagcaac aggagaaaat caagcctaag  1080
gtcaggagca ccgtcgcgca acaccacgag gcgcttgtgg ggcatggctt cactcatgcg  1140
catattgtcg cgctttcaca gcaccctgcg gcgcttggga cggtggctgt caaataccaa  1200
gatatgattg cggccctgcc cgaagccacg cacgaggcaa ttgtaggggt cggtaaacag  1260
tggtcgggag cgcgagcact tgaggcgctg ctgactgtgg cgggtgagct tagggggcct  1320
ccgctccagc tcgacaccgg gcagctgctg aagatcgcga agagaggggg agtaacagcg  1380
gtagaggcag tgcacgcctg gcgcaatgcg ctcaccgggg ccccccttgaa cctgagcacc  1440
gcccaggtgg tggccatcgc cagcaacggc ggcggcaagc aggccctgga gggcatcggc  1500
gagcagctgc tgaagctgag gaccgccccc tacggcctga gcaccgagca ggtggtggcc  1560
atcgccagca acaagggcgg caagcaggcc ctggaggccg tgaaggccca cctgctggac  1620
ctgctgggcg ccccctacgt gctgagcacc gagcaggtgg tggccatcgc cagcaacaac  1680
ggcggcaagc aggccctgga ggccgtgaag gcccagctgc tggagctgag ggccgccccc  1740
tacgagctga gcaccgccca ggtggtggcc atcgccagca acggcggcgg caagcaggcc  1800
ctggagggca tcggcgagca gctgctgaag ctgaggaccg ccccctacgg cctgagcacc  1860
gagcaggtgg tggccatcgc cagcaacaac ggcggcaagc aggccctgga ggccgtgaag  1920
gcccagctgc tggagctgag ggccgccccc tacgagctga gcaccgagca ggtggtggcc  1980
atcgccagca acaagggcgg caagcaggcc ctggaggccg tgaaggccca cctgctggac  2040
ctgctgggcg ccccctacgt gctgagcacc gcccaggtgg tggccatcgc cagcaacggc  2100
ggcggcaagc aggccctgga gggcatcggc gagcagctgc tgaagctgag gaccgccccc  2160
tacggcctga gcaccgccca ggtggtggcc atcgccagcc acgacggcgg caagcccgcc  2220
ctggaggccg tgtgggccaa gctgcccgtg ctgaggggcg tgccctacgc cctgagcacc  2280
gagcaggtgg tggccatcgc cagcaacaag ggcggcaagc aggccctgga ggccgtgaag  2340
gcccacctgc tggacctgct gggcgccccc tacgtgctga gcaccgccca ggtggtggcc  2400
atcgccagcc acgacggcgg caagcccgcc ctggaggccg tgtgggccaa gctgcccgtg  2460
ctgaggggcg tgccctacgc cctgagcacc gcccaggtgg tggccatcgc cagccacgac  2520
ggcggcaagc ccgccctgga ggccgtgtgg gccaagctgc ccgtgctgag ggcgtgccc  2580
tacgccctga gcaccgccca ggtggtggcc atcgccagca acggcggcgg caagcaggcc  2640
ctggagggca tcggcgagca gctgctgaag ctgaggaccg ccccctacgg cctgagcacc  2700
gcccaggtgg tggccatcgc cagcaacggc ggcggcaagc aggccctgga gggcatcggc  2760
gagcagctgc tgaagctgag gaccgccccc tacggcctga gcaccgagca ggtggtggcc  2820
atcgccagca acaacggcgg caagcaggcc ctggaggccg tgaaggccca gctgctggag  2880
ctgagggccg cccccctacga gctgagcacc gcccaggtgg tggccatcgc cagcaacggc  2940
ggcggcaagc aggccctgga gggcatcggc gagcagctgc tgaagctgag gaccgccccc  3000
tacggcctga gcaccgagca ggtggtggcc atcgccagca acaagggcgg caagcaggcc  3060
ctggaggccg tgaaggccca cctgctggac ctgctgggcg ccccctacgt gctgagcacc  3120
gcccaggtgg tggccatcgc cagcaacggc ggaggacggc cagccttgga gtccatcgta  3180
gcccaattgt ccaggcccga tcccgcgttg gctgcgttaa cgaatgacca tctggtggcg  3240
ttggcatgtc ttggtggacg acccgcgctc gatgcagtca aaaagggtct gcctcatgct  3300
cccgcattga tcaaaagaac caaccggcgg attcccgaga gaacttccca tcgagtcgcg  3360
ggatcccaac tagtcaaaag tgaactggag gagaagaaat ctgaacttcg tcataaattg  3420
aaatatgtgc ctcatgaata tattgaatta attgaaattg ccagaaattc cactcaggat  3480
agaattcttg aaatgaaggt aatggaattt tttatgaaag tttatggata tagaggtaaa  3540
catttgggtg gatcaaggaa accggacgga gcaatttata ctgtcggatc tcctattgat  3600
tacggtgtga tcgtggatac taaagcttat agcggaggtt ataatctgcc aattggccaa  3660
```

```
gcagatgaaa tgcaacgata tgtcgaagaa aatcaaacac gaaacaaaca tatcaaccct  3720
aatgaatggt ggaaagtcta tccatcttct gtaacggaat ttaagttttt atttgtgagt  3780
ggtcacttta aaggaaacta caaagctcag cttacacgat taaatcatat cactaattgt  3840
aatggagctg ttcttagtgt agaagagctt ttaattggtg gagaaatgat taaagccggc  3900
acattaacct tagaggaagt cagacggaaa tttaataacg gcgagataaa cttttaaggg  3960
cccttcgaag gtaagcctat ccctaaccct ctcctcggtc tcgattctac gcgtaccggt  4020
catcatcacc atcaccattg agtttaaacc cgctgatcag cctcgactgt gccttctagt  4080
tgccagccat ctgttgtttg cccctccccc gtgccttcct tgaccctgga aggtgccact  4140
cccactgtcc tttcctaata aaatgaggaa attgcatcgc attgtctgag taggtgtcat  4200
tctattctgg ggggtggggt ggggcaggac agcaaggggg aggattggga agacaatagc  4260
aggcatgctg gggatgcggt gggctctatg gcttctgagg cggaaagaac cagctggggc  4320
tctagggggt atccccacgc gccctgtagc ggcgcattaa gcgcggcggg tgtggtggtt  4380
acgcgcagcg tgaccgctac acttgccagc gccctagcgc ccgctccttt cgctttcttc  4440
ccttcctttc tcgccacgtt cgccggcttt ccccgtcaag ctctaaatcg ggcatccct   4500
ttagggttcc gatttagtgc tttacggcac ctcgacccca aaaaacttga ttagggtgat  4560
ggttcacgta gtgggccatc gccctgatag acggtttttc gccctttgac gttggagtcc  4620
acgttcttta atagtggact cttgttccaa actggaacaa cactcaaccc tatctcggtc  4680
tattcttttg atttataagg gattttgggg atttcggcct attggttaaa aaatgagctg  4740
atttaacaaa aatttaacgc gaattaattc tgtggaatgt gtgtcagtta gggtgtggaa  4800
agtccccagg ctccccaggc aggcagaagt atgcaaagca tgcatctcaa ttagtcagca  4860
accaggtgtg gaaagtcccc aggctcccca gcaggcagaa gtatgcaaag catgcatctc  4920
aattagtcag caaccatagt cccgccccta actccgccca tcccgcccct aactccgccc  4980
agttccgccc attctccgcc ccatggctga ctaatttttt ttatttatgc agaggccgag  5040
gccgcctctg cctctgagct attccagaag tagtgaggag gcttttttgg aggcctaggc  5100
ttttgcaaaa agctcccggg agcttgtata tccattttcg gatctgatca gcacgtgttg  5160
acaattaatc atcggcatag tatatcggca tagtataata cgacaaggtg aggaactaaa  5220
ccatggccaa gcctttgtct caagaagaat ccaccctcat tgaaagagca acggctacaa  5280
tcaacagcat ccccatctct gaagactaca gcgtcgccag cgcagctctc tctagcgacg  5340
gccgcatctt cactggtgtc aatgtatatc attttactgg gggaccttgt gcagaactcg  5400
tggtgctggg cactgctgct gctgcggcag ctggcaacct gacttgtatc gtcgcgatcg  5460
gaaatgagaa caggggcatc ttgagcccct gcggacggtg tcgacaggtg cttctcgatc  5520
tgcatcctgg gatcaaagcg atagtgaagg acagtgatgg acagccgacg gcagttggga  5580
ttcgtgaatt gctgccctct ggttatgtgt gggagggcta agcacttcgt ggccgaggag  5640
caggactgac acgtgctacg agatttcgat tccaccgccg ccttctatga aaggttgggc  5700
ttcggaatcg ttttccggga cgccggctgg atgatcctcc agcgcgggga tctcatgctg  5760
gagttcttcg cccaccccaa cttgtttatt gcagcttata atggttacaa ataaagcaat  5820
agcatcacaa atttcacaaa taaagcattt ttttcactgc attctagttg tggtttgtcc  5880
aaactcatca atgtatctta tcatgtctgt ataccgtcga cctctagcta gagcttggcg  5940
taatcatggt catagctgtt tcctgtgtga aattgttatc cgctcacaat tccacacaac  6000
atacgagccg gaagcataaa gtgtaaagcc tggggtgcct aatgagtgag ctaactcaca  6060
ttaattgcgt tgcgctcact gcccgctttc cagtcgggaa acctgtcgtg ccagctgcat  6120
taatgaatcg gccaacgcgc ggggagaggc ggtttgcgta ttgggcgctc ttccgcttcc  6180
tcgctcactg actcgctgcg ctcggtcgtt cggctgcggc gagcggtatc agctcactca  6240
aaggcggtaa tacggttatc cacagaatca ggggataacg caggaaagaa catgtgagca  6300
aaaggccagc aaaaggccag gaaccgtaaa aaggccgcgt tgctggcgtt tttccatagg  6360
ctccgccccc ctgacgagca tcacaaaaat cgacgctcaa gtcagaggtg gcgaaacccg  6420
acaggactat aaagatacca ggcgtttccc cctggaagct ccctcgtgcg ctctcctgtt  6480
ccgaccctgc cgcttaccgg atacctgtcc gcctttctcc cttcgggaag cgtggcgctt  6540
tctcaatgct cacgctgtag gtatctcagt tcggtgtagg tcgttcgctc caagctgggc  6600
tgtgtgcacg aaccccccgt tcagcccgac cgctgcgcct tatccggtaa ctatcgtctt  6660
gagtccaacc cggtaagaca cgacttatcg ccactggcag cagccactgg taacaggatt  6720
agcagagcga ggtatgtagg cggtgctaca gagttcttga agtggtggcc taactacggc  6780
tacactagaa ggacagtatt tggtatctgc gctctgctga agccagttac cttcggaaaa  6840
agagttggta gctcttgatc cggcaaacaa accaccgctg gtagcggtgg tttttttgtt  6900
tgcaagcagc agattacgcg cagaaaaaaa ggatctcaag aagatccttt gatcttttct  6960
acggggtctg acgctcagtg gaacgaaaac tcacgttaag ggattttggt catgagatta  7020
tcaaaaagga tcttcaccta gatcctttta aattaaaaat gaagttttaa atcaatctaa  7080
agtatatatg agtaaacttg gtctgacagt taccaatgct taatcagtga ggcacctatc  7140
tcagcgatct gtctatttcg ttcatccata gttgcctgac tccccgtcgt gtagataact  7200
acgatacggg agggcttacc atctggcccc agtgctgcaa tgataccgcg agacccacgc  7260
tcaccggctc cagatttatc agcaataaac cagccagccg gaagggccga gcgcagaagt  7320
ggtcctgcaa ctttatccgc ctccatccag tctattaatt gttgccggga agctagagta  7380
agtagttcgc cagttaatag tttgcgcaac gttgttgcca ttgctacagg catcgtggtg  7440
tcacgctcgt cgtttggtat ggcttcattc agctccggtt cccaacgatc aaggcgagtt  7500
acatgatccc ccatgttgtg caaaaaagcg gttagctcct tcggtcctcc gatcgttgtc  7560
agaagtaagt tggccgcagt gttatcactc atggttatgg cagcactgca taattctctt  7620
actgtcatgc catccgtaag atgcttttct gtgactggtg agtactcaac caagtcattc  7680
tgagaatagt gtatgcggcg accgagttgc tcttgcccgg cgtcaatacg ggataatacc  7740
gcgccacata gcagaacttt aaaagtgctc atcattggaa aacgttcttc ggggcgaaaa  7800
ctctcaagga tcttaccgct gttgagatcc agttcgatgt aacccactcg tgcacccaac  7860
tgatcttcag catcttttac tttcaccagc gtttctgggt gagcaaaaac aggaaggcaa  7920
aatgccgcaa aaaagggaat aagggcgaca cggaaatgtt gaatactcat actcttcctt  7980
tttcaatatt attgaagcat ttatcagggt tattgtctca tgagcggata catatttgaa  8040
tgtatttaga aaaataaaca aataggggtt ccgcgcacat ttccccgaaa agtgccacct  8100
gacgtc                                                             8106
```

```
SEQ ID NO: 168          moltype = AA  length = 35
FEATURE                 Location/Qualifiers
source                  1..35
```

```
                        mol_type = protein
                        organism = synthetic construct
SEQUENCE: 168
LSTEQVVAIA SNNGGKQALE AVKAQLLELR AAPYE                        35

SEQ ID NO: 169          moltype = AA  length = 35
FEATURE                 Location/Qualifiers
source                  1..35
                        mol_type = protein
                        organism = synthetic construct
SEQUENCE: 169
LSTAQVVAIA SNGGGKQALE GIGEQLLKLR TAPYG                        35

SEQ ID NO: 170          moltype = AA  length = 35
FEATURE                 Location/Qualifiers
source                  1..35
                        mol_type = protein
                        organism = synthetic construct
SEQUENCE: 170
LSTAQVVAIA SNGGGKQALE GIGEQLLKLR TAPYG                        35

SEQ ID NO: 171          moltype = AA  length = 35
FEATURE                 Location/Qualifiers
source                  1..35
                        mol_type = protein
                        organism = synthetic construct
SEQUENCE: 171
LSTAQVVAIA SNGGGKQALE GIGEQLLKLR TAPYG                        35

SEQ ID NO: 172          moltype = AA  length = 35
FEATURE                 Location/Qualifiers
source                  1..35
                        mol_type = protein
                        organism = synthetic construct
SEQUENCE: 172
LSTAQVVAIA SHDGGKPALE AVWAKLPVLR GVPYA                        35

SEQ ID NO: 173          moltype = AA  length = 35
FEATURE                 Location/Qualifiers
source                  1..35
                        mol_type = protein
                        organism = synthetic construct
SEQUENCE: 173
LSTEQVVAIA SNKGGKQALE AVKAHLLDLL GAPYV                        35

SEQ ID NO: 174          moltype = AA  length = 35
FEATURE                 Location/Qualifiers
source                  1..35
                        mol_type = protein
                        organism = synthetic construct
SEQUENCE: 174
LSTAQVVAIA SNGGGKQALE GIGEQLLKLR TAPYG                        35

SEQ ID NO: 175          moltype = AA  length = 35
FEATURE                 Location/Qualifiers
source                  1..35
                        mol_type = protein
                        organism = synthetic construct
SEQUENCE: 175
LSTAQVVAIA SNGGGKQALE GIGEQLLKLR TAPYG                        35

SEQ ID NO: 176          moltype = AA  length = 35
FEATURE                 Location/Qualifiers
source                  1..35
                        mol_type = protein
                        organism = synthetic construct
SEQUENCE: 176
LSTAQVVAIA SNGGGKQALE GIGEQLLKLR TAPYG                        35

SEQ ID NO: 177          moltype = AA  length = 35
FEATURE                 Location/Qualifiers
source                  1..35
                        mol_type = protein
                        organism = synthetic construct
SEQUENCE: 177
LSTEQVVAIA SNNGGKQALE AVKAQLLELR AAPYE                        35

SEQ ID NO: 178          moltype = AA  length = 35
FEATURE                 Location/Qualifiers
```

```
source                  1..35
                        mol_type = protein
                        organism = synthetic construct
SEQUENCE: 178
LSTAQVVAIA SHDGGKPALE AVWAKLPVLR GVPYA                              35

SEQ ID NO: 179          moltype = AA  length = 35
FEATURE                 Location/Qualifiers
source                  1..35
                        mol_type = protein
                        organism = synthetic construct
SEQUENCE: 179
LSTAQVVAIA SHDGGKPALE AVWAKLPVLR GVPYA                              35

SEQ ID NO: 180          moltype = AA  length = 35
FEATURE                 Location/Qualifiers
source                  1..35
                        mol_type = protein
                        organism = synthetic construct
SEQUENCE: 180
LSTAQVVAIA SNGGGKQALE GIGEQLLKLR TAPYG                              35

SEQ ID NO: 181          moltype = AA  length = 35
FEATURE                 Location/Qualifiers
source                  1..35
                        mol_type = protein
                        organism = synthetic construct
SEQUENCE: 181
LSTEQVVAIA SNKGGKQALE AVKAHLLDLL GAPYV                              35

SEQ ID NO: 182          moltype = AA  length = 35
FEATURE                 Location/Qualifiers
source                  1..35
                        mol_type = protein
                        organism = synthetic construct
SEQUENCE: 182
LSTAQVVAIA SNGGGKQALE GIGEQLLKLR TAPYG                              35

SEQ ID NO: 183          moltype = AA  length = 35
FEATURE                 Location/Qualifiers
source                  1..35
                        mol_type = protein
                        organism = synthetic construct
SEQUENCE: 183
LSTAQVVAIA SHDGGKPALE AVWAKLPVLR GVPYA                              35

SEQ ID NO: 184          moltype = DNA  length = 8102
FEATURE                 Location/Qualifiers
source                  1..8102
                        mol_type = other DNA
                        organism = synthetic construct
SEQUENCE: 184
gacggatcgg gagatctccc gatcccctat ggtcgactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
accatggact acaaagacca tgacggtgat tataaagatc atgacatcga ttacaaggat  960
gacgatgaca agatggcccc caagaagaag aggaaggtgg gcattcaccg cggggtacct  1020
atggtggact tgaggacact cggttattcg caacagcaac aggagaaaat caagcctaag  1080
gtcaggagca ccgtcgcgca acaccacgag gcgcttgtgg ggcatggctt cactcatgcg  1140
catattgtcg cgctttcaca gcaccctgcg gcgcttggga cggtggctgt caaataccaa  1200
gatatgattg cggccctgcc cgaagccacg cacgaggcaa ttgtaggggt cggtaaacag  1260
tggtcgggag cgcgagcact tgaggcgctg ctgactgtgg cgggtgagct tagggggcct  1320
ccgctccagc tcgacaccgg gcagctgctg aagatcgcga agagaggggg agtaacagcg  1380
gtagaggcag tgcacgcctg gcgcaatgcg ctcaccgggg cccccttctg agcaccgagc  1440
aggtggtggc catcgccagc aacaacggcg gcaagcaggc cctggaggcc gtgaaggccc  1500
agctgctgga gctgagggcc gcccccctacg agctgagcac cgcccaggtg gtggccatcg  1560
ccagcaacgg cggcggcaag caggccctgg agggcatcgg cgagcagctg ctgaagctga  1620
```

```
ggaccgcccc ctacggcctg agcaccgccc aggtggtggc catcgccagc aacggcggcg  1680
gcaagcaggc cctggagggc atcggcgagc agctgctgaa gctgaggacc gccccctacg  1740
gcctgagcac cgcccaggtg gtggccatcg ccagcaacgg cggcggcaag caggccctgg  1800
agggcatcgg cgagcagctg ctgaagctga ggaccgcccc ctacggcctg agcaccgccc  1860
aggtggtggc catcgccagc cacgacggcg gcaagcccgc cctggaggcc gtgtgggcca  1920
agctgcccgt gctgaggggc gtgccctacg ccctgagcac cgagcaggtg gtggccatcg  1980
ccagcaacaa gggcggcaag caggccctgg aggccgtgaa ggcccacctg ctggacctgc  2040
tgggcgcccc ctacgtgctg agcaccgccc aggtggtggc catcgccagc aacggcggcg  2100
gcaagcaggc cctggagggc atcggcgagc agctgctgaa gctgaggacc gccccctacg  2160
gcctgagcac cgcccaggtg gtggccatcg ccagcaacgg cggcggcaag caggccctgg  2220
agggcatcgg cgagcagctg ctgaagctga ggaccgcccc ctacggcctg agcaccgccc  2280
aggtggtggc catcgccagc aacggcggcg gcaagcaggc cctggagggc atcggcgagc  2340
agctgctgaa gctgaggacc gccccctacg gcctgagcac cgagcaggtg gtggccatcg  2400
ccagcaacaa cggcggcaag caggccctgg aggccgtgaa ggcccagctg ctggagctga  2460
gggccgcccc ctacgagctg agcaccgccc aggtggtggc catcgccagc cacgacggcg  2520
gcaagcccgc cctggaggcc gtgtgggcca agctgcccgt gctgaggggc gtgccctacg  2580
ccctgagcac cgcccaggtg gtggccatcg ccagccacga cggcggcaag cccgccctgg  2640
aggccgtgtg ggccaagctg cccgtgctga ggggcgtgcc ctacgccctg agcaccgccc  2700
aggtggtggc catcgccagc aacggcggcg gcaagcaggc cctggagggc atcggcgagc  2760
agctgctgaa gctgaggacc gccccctacg gcctgagcac cgagcaggtg gtggccatcg  2820
ccagcaacaa gggcggcaag caggccctgg aggccgtgaa ggcccacctg ctggacctgc  2880
tgggcgcccc ctacgtgctg agcaccgccc aggtggtggc catcgccagc aacggcggcg  2940
gcaagcaggc cctggagggc atcggcgagc agctgctgaa gctgaggacc gccccctacg  3000
gcctgagcac cgcccaggtg gtggccatcg ccagccacga cggcggcaag cccgccctgg  3060
aggccgtgtg ggccaagctg cccgtgctga ggggcgtgcc ctacgccctg agcaccgagc  3120
aggtggtgac catcgccagc agcatcggag gacggccagc cttggagtcc atcgtagccc  3180
aattgtccag gcccgatccc gcgttggctg cgttaacgaa tgaccatctg gtggcgttgg  3240
catgtcttgg tggacgaccc gcgctcgatg cagtcaaaaa gggtctgcct catgctcccg  3300
cattgatcaa aagaaccaac cggcggattc ccgagagaac ttcccatcga gtcgcgggat  3360
cccaactagt caaaagtgaa ctggaggaga agaaatctga acttcgtcat aaattgaaat  3420
atgtgcctca tgaatatatt gaattaattg aaattgccag aaattccact caggatagaa  3480
ttcttgaaat gaaggtaatg gaatttttta tgaaagttta tggatataga ggtaaacatt  3540
tgggtggatc aaggaaaccg gacggagcaa tttatactgt cggatctcct attgattacg  3600
gtgtgatcgt ggatactaaa gcttatagcg gaggttataa tctgccaatt ggccaagcag  3660
atgaaatgca acgatatgtc gaagaaaatc aaacacgaaa caaacatatc aaccctaatg  3720
aatggtggaa agtctatcca tcttctgtaa cggaatttaa gtttttattt gtgagtggtc  3780
actttaaagg aaactacaaa gctcagctta cacgattaaa tcatatcact aattgtaatg  3840
gagctgttct tagtgtagaa gagcttttaa ttggtggaga aatgattaaa gccggcacat  3900
taaccttaga ggaagtcaga cggaaattta ataacggcga gataaacttt taagggccct  3960
tcgaaggtaa gcctatccct aaccctctcc tcggtctcga ttctacgcgt accggtcatc  4020
atcaccatca ccattgagtt taaacccgct gatcagcctc gactgtgcct tctagttgcc  4080
agccatctgt tgtttgcccc tcccccgtgc cttccttgac cctggaaggt gccactccca  4140
ctgtcctttc ctaataaaat gaggaaattg catcgcattg tctgagtagg tgtcattcta  4200
ttctgggggg tggggtgggg caggacagca agggggagga ttgggaagac aatagcaggc  4260
atgctgggga tgcggtgggc tctatggctt ctgaggcgga aagaaccagc tggggctcta  4320
gggggtatcc ccacgcgccc tgtagcggcg cattaagcgc ggcgggtgtg gtggttacgc  4380
gcagcgtgac cgctacactt gccagcgccc tagcgcccgc tcctttcgct ttcttccctt  4440
cctttctcgc cacgttcgcc ggctttcccc gtcaagctct aaatcggggg atccctttag  4500
ggttccgatt tagtgcttta cggcacctcg accccaaaaa acttgattag ggtgatggtt  4560
cacgtagtgg gccatcgccc tgatagacgg tttttcgccc tttgacgttg gagtccacgt  4620
tctttaatag tggactcttg ttccaaactg gaacaacact caaccctatc tcggtctatt  4680
cttttgattt ataagggatt ttggggattt cggcctattg gttaaaaaat gagctgattt  4740
aacaaaaatt taacgcgaat taattctgtg gaatgtgtgt cagttagggt gtggaaagtc  4800
cccaggctcc ccaggcaggc agaagtatgc aaagcatgca tctcaattag tcagcaacca  4860
ggtgtggaaa gtccccaggc tccccagcag gcagaagtat gcaaagcatg catctcaatt  4920
agtcagcaac catagtcccg cccctaactc cgcccatccc gcccctaact ccgcccagtt  4980
ccgcccattc tccgccccat ggctgactaa ttttttttat ttatgcagag gccgaggccg  5040
cctctgcctc tgagctattc cagaagtagt gaggaggctt ttttggaggc ctaggctttt  5100
gcaaaaagct cccgggagct tgtatatcca ttttcggatc tgatcagcac gtgttgacaa  5160
ttaatcatcg gcatagtata tcggcatagt ataatacgac aaggtgagga actaaaccat  5220
ggccaagcct ttgtctcaag aagaatccac cctcattgaa agagcaacgg ctacaatcaa  5280
cagcatcccc atctctgaag actacagcgt cgccagcgca gctctctcta gcgacggccg  5340
catcttcact ggtgtcaatg tatatcattt tactggggga ccttgtgcag aactcgtggt  5400
gctgggcact gctgctgctg cggcagctgg caacctgact tgtatcgtcg cgatcggaaa  5460
tgagaacagg ggcatcttga gcccctgcgg acggtgtcga caggtgcttc tcgatctgca  5520
tcctgggatc aaagcgatag tgaaggacag tgatggacag ccgacggcag ttgggattcg  5580
tgaattgctg ccctctggtt atgtgtggga gggctaagca cttcgtggcc gaggagcagg  5640
actgacacgt gctacgagat ttcgattcca ccgccgcctt ctatgaaagg ttgggcttcg  5700
gaatcgtttt ccgggacgcc ggctggatga tcctccagcg cggggatctc atgctggagt  5760
tcttcgccca ccccaacttg tttattgcag cttataatgg ttacaaataa agcaatagca  5820
tcacaaattt cacaaataaa gcattttttt cactgcattc tagttgtggt ttgtccaaac  5880
tcatcaatgt atcttatcat gtctgtatac cgtcgacctc tagctagagc ttggcgtaat  5940
catggtcata gctgtttcct gtgtgaaatt gttatccgct cacaattcca cacaacatac  6000
gagccggaag cataaagtgt aaagcctggg gtgcctaatg agtgagctaa ctcacattaa  6060
ttgcgttgcg ctcactgccc gctttccagt cgggaaacct gtcgtgccag ctgcattaat  6120
gaatcggcca acgcgcgggg agaggcggtt tgcgtattgg gcgctcttcc gcttcctcgc  6180
tcactgactc gctgcgctcg gtcgttcggc tgcggcgagc ggtatcagct cactcaaagg  6240
cggtaatacg gttatccaca gaatcagggg ataacgcagg aaagaacatg tgagcaaaag  6300
gccagcaaaa ggccaggaac cgtaaaaagg ccgcgttgct ggcgtttttc cataggctcc  6360
```

```
gccccccctga cgagcatcac aaaaatcgac gctcaagtca gaggtggcga aacccgacag  6420
gactataaag ataccaggcg tttccccctg gaagctccct cgtgcgctct cctgttccga  6480
ccctgccgct taccggatac ctgtccgcct ttctcccttc gggaagcgtg gcgctttctc  6540
aatgctcacg ctgtaggtat ctcagttcgg tgtaggtcgt tcgctccaag ctgggctgtg  6600
tgcacgaacc ccccgttcag cccgaccgct gcgccttatc cggtaactat cgtcttgagt  6660
ccaacccggt aagacacgac ttatcgccac tggcagcagc cactggtaac aggattagca  6720
gagcgaggta tgtaggcggt gctacagagt tcttgaagtg gtggcctaac tacggctaca  6780
ctagaaggac agtatttggt atctgcgctc tgctgaagcc agttaccttc ggaaaaagag  6840
ttggtagctc ttgatccggc aaacaaacca ccgctggtag cggtggtttt tttgtttgca  6900
agcagcagat tacgcgcaga aaaaaaggat ctcaagaaga tcctttgatc ttttctacgg  6960
ggtctgacgc tcagtggaac gaaaactcac gttaagggat tttggtcatg agattatcaa  7020
aaaggatctt cacctagatc cttttaaatt aaaaatgaag ttttaaatca atctaaagta  7080
tatatgagta aacttggtct gacagttacc aatgcttaat cagtgaggca cctatctcag  7140
cgatctgtct atttcgttca tccatagttg cctgactccc cgtcgtgtag ataactacga  7200
tacgggaggg cttaccatct ggccccagtg ctgcaatgat accgcgagac ccacgctcac  7260
cggctccaga tttatcagca ataaaccagc cagccggaag ggccgagcgc agaagtggtc  7320
ctgcaacttt atccgcctcc atccagtcta ttaattgttg ccgggaagct agagtaagta  7380
gttcgccagt taatagtttg cgcaacgttg ttgccattgc tacaggcatc gtggtgtcac  7440
gctcgtcgtt tggtatggct tcattcagct ccggttccca acgatcaagg cgagttacat  7500
gatcccccat gttgtgcaaa aaagcggtta gctccttcgg tcctccgatc gttgtcagaa  7560
gtaagttggc cgcagtgtta tcactcatgg ttatggcagc actgcataat tctcttactg  7620
tcatgccatc cgtaagatgc ttttctgtga ctggtgagta ctcaaccaag tcattctgag  7680
aatagtgtat gcggcgaccg agttgctctt gcccggcgtc aatacgggat aataccgcgc  7740
cacatagcag aactttaaaa gtgctcatca ttggaaaacg ttcttcgggg cgaaaactct  7800
caaggatctt accgctgttg agatccagtt cgatgtaacc cactcgtgca cccaactgat  7860
cttcagcatc ttttactttc accagcgttt ctgggtgagc aaaaacagga aggcaaaatg  7920
ccgcaaaaaa gggaataagg gcgacacgga aatgttgaat actcatactc ttcctttttc  7980
aatattattg aagcatttat cagggttatt gtctcatgag cggatacata tttgaatgta  8040
tttagaaaaa taaacaaata ggggttccgc gcacatttcc ccgaaaagtg ccacctgacg  8100
tc                                                                 8102
```

```
SEQ ID NO: 185          moltype = DNA  length = 2706
FEATURE                 Location/Qualifiers
source                  1..2706
                        mol_type = other DNA
                        organism = synthetic construct
SEQUENCE: 185
ggatcccggg cccgtcgact gcagaggcct gcatgcaagc ttggcgtaat catggtcata  60
gctgtttcct gtgtgaaatt gttatccgct cacaattcca cacaacatac gagccggaag  120
cataaagtgt aaagcctggg gtgcctaatg agtgagctaa ctcacattaa ttgcgttgcg  180
ctcactgccc gctttccagt cgggaaacct gtcgtgccag ctgcattaat gaatcggcca  240
acgcgcgggg agaggcggtt tgcgtattgg gcgctcttcc gcttcctcgc tcactgactc  300
gctgcgctcg gtcgttcggc tgcggcgagc ggtatcagct cactcaaagg cggtaatacg  360
gttatccaca gaatcagggg ataacgcagg aaagaacatg tgagcaaaag gccagcaaaa  420
ggccaggaac cgtaaaaagg ccgcgttgct ggcgtttttc cataggctcc gcccccctga  480
cgagcatcac aaaaatcgac gctcaagtca gaggtggcga aacccgacag gactataaag  540
ataccaggcg tttccccctg gaagctccct cgtgcgctct cctgttccga ccctgccgct  600
taccggatac ctgtccgcct ttctcccttc gggaagcgtg gcgctttctc atagctcacg  660
ctgtaggtat ctcagttcgg tgtaggtcgt tcgctccaag ctgggctgtg tgcacgaacc  720
ccccgttcag cccgaccgct gcgccttatc cggtaactat cgtcttgagt ccaacccggt  780
aagacacgac ttatcgccac tggcagcagc cactggtaac aggattagca gagcgaggta  840
tgtaggcggt gctacagagt tcttgaagtg gtggcctaac tacggctaca ctagaagaac  900
agtatttggt atctgcgctc tgctgaagcc agttaccttc ggaaaaagag ttggtagctc  960
ttgatccggc aaacaaacca ccgctggtag cggtggtttt tttgtttgca agcagcagat  1020
tacgcgcaga aaaaaaggat ctcaagaaga tcctttgatc ttttctacgg ggtctgacgc  1080
tcagtggaac gaaaactcac gttaagggat tttggtcatg agattatcaa aaaggatctt  1140
cacctagatc cttttaaatt aaaaatgaag ttttaaatca atctaaagta tatatgagta  1200
aacttggtct gacagttacc aatgcttaat cagtgaggca cctatctcag cgatctgtct  1260
atttcgttca tccatagttg cctgactccc cgtcgtgtag ataactacga tacgggaggg  1320
cttaccatct ggccccagtg ctgcaatgat accgcgagag ccacgctcac cggctccaga  1380
tttatcagca ataaaccagc cagccggaag ggccgagcgc agaagtggtc ctgcaacttt  1440
atccgcctcc atccagtcta ttaattgttg ccgggaagct agagtaagta gttcgccagt  1500
taatagtttg cgcaacgttg ttgccattgc tacaggcatc gtggtgtcac gctcgtcgtt  1560
tggtatggct tcattcagct ccggttccca acgatcaagg cgagttacat gatcccccat  1620
gttgtgcaaa aaagcggtta gctccttcgg tcctccgatc gttgtcagaa gtaagttggc  1680
cgcagtgtta tcactcatgg ttatggcagc actgcataat tctcttactg tcatgccatc  1740
cgtaagatgc ttttctgtga ctggtgagta ctcaaccaag tcattctgag aatagtgtat  1800
gcggcgaccg agttgctctt gcccggcgtc aatacgggat aataccgcgc cacatagcag  1860
aactttaaaa gtgctcatca ttggaaaacg ttcttcgggg cgaaaactct caaggatctt  1920
accgctgttg agatccagtt cgatgtaacc cactcgtgca cccaactgat cttcagcatc  1980
ttttactttc accagcgttt ctgggtgagc aaaaacagga aggcaaaatg ccgcaaaaaa  2040
gggaataagg gcgacacgga aatgttgaat actcatactc ttcctttttc aatattattg  2100
aagcatttat cagggttatt gtctcatgag cggatacata tttgaatgta tttagaaaaa  2160
taaacaaata ggggttccgc gcacatttcc ccgaaaagtg ccacctgacg tctaagaaac  2220
cattattatc atgacattaa cctataaaaa taggcgtatc acgaggccct ttcgtctcgc  2280
gcgtttcggt gatgacggtg aaaacctctg acacatgcag ctcccggaga cggtcacagc  2340
ttgtctgtaa gcggatgccg ggagcagaca agcccgtcag ggcgcgtcag cgggtgttgg  2400
cgggtgtcgg ggctggctta actatgcggc atcagagcag attgtactga gagtgcacca  2460
tatgcggtgt gaaataccgc acagatgcgt aaggagaaaa taccgcatca ggcgccattc  2520
```

-continued

```
gccattcagg ctgcgcaact gttgggaagg gcgatcggtg cgggcctctt cgctattacg  2580
ccagctggcg aaagggggat gtgctgcaag gcgattaagt tgggtaacgc cagggttttc  2640
ccagtcacga cgttgtaaaa cgacggccag tgaattcgag ctcggtacct cgcgaatgca  2700
tctaga                                                             2706

SEQ ID NO: 186         moltype =   length =
SEQUENCE: 186
000

SEQ ID NO: 187         moltype =   length =
SEQUENCE: 187
000

SEQ ID NO: 188         moltype =   length =
SEQUENCE: 188
000

SEQ ID NO: 189         moltype =   length =
SEQUENCE: 189
000

SEQ ID NO: 190         moltype = DNA  length = 6426
FEATURE                Location/Qualifiers
variation              31..39
source                 1..6426
                       mol_type = other DNA
                       organism = synthetic construct
SEQUENCE: 190
ctgacacccg aacaggtggt cgccattgct nnnnnnnnng gaggacggcc agccttggag  60
tccatcgtag cccaattgtc caggcccgat cccgcgttgg ctgcgttaac gaatgaccat  120
ctggtggcgt tggcatgtct tggtggacga cccgcgctcg atgcagtcaa aaagggtctg  180
cctcatgctc ccgcattgat caaaagaacc aaccggcgga ttcccgagag aacttcccat  240
cgagtcgcgg gatcccaact agtcaaaagt gaactggagg agaagaaatc tgaacttcgt  300
cataaattga aatatgtgcc tcatgaatat attgaattaa ttgaaattgc cagaaattcc  360
actcaggata gaattcttga aatgaaggta atggaatttt ttatgaaagt ttatggatat  420
agaggtaaac atttgggtgg atcaaggaaa ccggacggag caatttatac tgtcggatct  480
cctattgatt acggtgtgat cgtggatact aaagcttata gcggaggtta taatctgcca  540
attggccaag cagatgaaat gcaacgatat gtcgaagaaa atcaaacacg aaacaaacat  600
atcaacccta atgaatggtg gaaagtctat ccatcttctg taacggaatt taagttttta  660
tttgtgagtg gtcactttaa aggaaactac aaagctcagc ttacacgatt aaatcatatc  720
actaattgta atggagctgt tcttagtgta gaagagcttt taattggtgg agaaatgatt  780
aaagccggca cattaacctt agaggaagtc agacggaaat ttaataacgg cgagataaac  840
ttttaagggc ccttcgaagg taagcctatc cctaaccctc tcctcggtct cgattctacg  900
cgtaccggtc atcatcacca tcaccattga gtttaaaccc gctgatcagc ctcgactgtg  960
ccttctagtt gccagccatc tgttgtttgc ccctcccccg tgccttcctt gaccctggaa  1020
ggtgccactc ccactgtcct ttcctaataa aatgaggaaa ttgcatcgca ttgtctgagt  1080
aggtgtcatt ctattctggg gggtggggtg gggcaggaca gcaaggggga ggattgggaa  1140
gacaatagca ggcatgctgg ggatgcggtg ggctctatgg cttctgaggc ggaaagaacc  1200
agctggggct ctagggggta tccccacgcg ccctgtagcg gcgcattaag cgcggcgggt  1260
gtggtggtta cgcgcagcgt gaccgctaca cttgccagcg ccctagcgcc cgctcctttc  1320
gctttcttcc cttcctttct cgccacgttc gccggctttc cccgtcaagc tctaaatcgg  1380
ggcatccctt tagggttccg atttagtgct ttacggcacc tcgaccccaa aaaacttgat  1440
tagggtgatg gttcacgtag tgggccatcg ccctgataga cggtttttcg ccctttgacg  1500
ttggagtcca cgttctttaa tagtggactc ttgttccaaa ctggaacaac actcaaccct  1560
atctcggtct attcttttga tttataaggg attttgggga tttcggccta ttggttaaaa  1620
aatgagctga tttaacaaaa atttaacgcg aattaattct gtggaatgtg tgtcagttag  1680
ggtgtggaaa gtccccaggc tccccaggca ggcagaagta tgcaaagcat gcatctcaat  1740
tagtcagcaa ccaggtgtgg aaagtcccca ggctccccag caggcagaag tatgcaaagc  1800
atgcatctca attagtcagc aaccatagtc ccgcccctaa ctccgcccat cccgccccta  1860
actccgccca gttccgccca ttctccgccc catggctgac taattttttt tatttatgca  1920
gaggccgagg ccgcctctgc ctctgagcta ttccagaagt agtgaggagg cttttttgga  1980
ggcctaggct tttgcaaaaa gctcccggga gcttgtatat ccattttcgg atctgatcag  2040
cacgtgttga caattaatca tcggcatagt atatcggcat agtataatac gacaaggtga  2100
ggaactaaac catggccaag cctttgtctc aagaagaatc caccctcatt gaaagagcaa  2160
cggctacaat caacagcatc cccatctctg aagactacag cgtcgccagc gcagctctct  2220
ctagcgacgg ccgcatcttc actggtgtca atgtatatca ttttactggg ggaccttgtg  2280
cagaactcgt ggtgctgggc actgctgctg ctgcggcagc tggcaacctg acttgtatcg  2340
tcgcgatcgg aaatgagaac aggggcatct tgagcccctg cggacggtgt cgacaggtgc  2400
ttctcgatct gcatcctggg atcaaagcga tagtgaagga cagtgatgga cagccgacgg  2460
cagttgggat tcgtgaattg ctgccctctg gttatgtgtg ggagggctaa gcacttcgtg  2520
gccgaggagc aggactgaca cgtgctacga gatttcgatt ccaccgccgc cttctatgaa  2580
aggttgggct tcggaatcgt tttccgggac gccggctgga tgatcctcca gcgcggggat  2640
ctcatgctgg agttcttcgc ccaccccaac ttgtttattg cagcttataa tggttacaaa  2700
taaagcaata gcatcacaaa tttcacaaat aaagcatttt tttcactgca ttctagttgt  2760
ggtttgtcca aactcatcaa tgtatcttat catgtctgta taccgtcgac ctctagctag  2820
agcttggcgt aatcatggtc atagctgttt cctgtgtgaa attgttatcc gctcacaatt  2880
ccacacaaca tacgagccgg aagcataaag tgtaaagcct ggggtgccta atgagtgagc  2940
taactcacat taattgcgtt gcgctcactg cccgctttcc agtcgggaaa cctgtcgtgc  3000
cagctgcatt aatgaatcgg ccaacgcgcg gggagaggcg gtttgcgtat tgggcgctct  3060
```

-continued

```
tccgcttcct cgctcactga ctcgctgcgc tcggtcgttc ggctgcggcg agcggtatca  3120
gctcactcaa aggcggtaat acggttatcc acagaatcag gggataacgc aggaaagaac  3180
atgtgagcaa aaggccagca aaaggccagg aaccgtaaaa aggccgcgtt gctggcgttt  3240
ttccataggc tccgcccccc tgacgagcat cacaaaaatc gacgctcaag tcagaggtgg  3300
cgaaacccga caggactata aagataccag gcgtttcccc ctggaagctc cctcgtgcgc  3360
tctcctgttc cgaccctgcc gcttaccgga tacctgtccg cctttctccc ttcgggaagc  3420
gtggcgcttt ctcaatgctc acgctgtagg tatctcagtt cggtgtaggt cgttcgctcc  3480
aagctgggct gtgtgcacga accccccgtt cagcccgacc gctgcgcctt atccggtaac  3540
tatcgtcttg agtccaaccc ggtaagacac gacttatcgc cactggcagc agccactggt  3600
aacaggatta gcagagcgag gtatgtaggc ggtgctacag agttcttgaa gtggtggcct  3660
aactacggct acactagaag gacagtattt ggtatctgcg ctctgctgaa gccagttacc  3720
ttcggaaaaa gagttggtag ctcttgatcc ggcaaacaaa ccaccgctgg tagcggtggt  3780
tttttgttt gcaagcagca gattacgcgc agaaaaaaag gatctcaaga agatcctttg  3840
atcttttcta cggggtctga cgctcagtgg aacgaaaact cacgttaagg gattttggtc  3900
atgagattat caaaaaggat cttcacctag atccttttaa attaaaaatg aagttttaaa  3960
tcaatctaaa gtatatatga gtaaacttgg tctgacagtt accaatgctt aatcagtgag  4020
gcacctatct cagcgatctg tctatttcgt tcatccatag ttgcctgact ccccgtcgtg  4080
tagataacta cgatacggga gggcttacca tctggcccca gtgctgcaat gataccgcga  4140
gacccacgct caccggctcc agatttatca gcaataaacc agccagccgg aagggccgag  4200
cgcagaagtg gtcctgcaac tttatccgcc tccatccagt ctattaattg ttgccgggaa  4260
gctagagtaa gtagttcgcc agttaatagt ttgcgcaacg ttgttgccat tgctacaggc  4320
atcgtggtgt cacgctcgtc gtttggtatg gcttcattca gctccggttc ccaacgatca  4380
aggcgagtta catgatcccc catgttgtgc aaaaaagcgg ttagctcctt cggtcctccg  4440
atcgttgtca gaagtaagtt ggccgcagtg ttatcactca tggttatggc agcactgcat  4500
aattctctta ctgtcatgcc atccgtaaga tgcttttctg tgactggtga gtactcaacc  4560
aagtcattct gagaatagtg tatgcggcga ccgagttgct cttgcccggc gtcaatacgg  4620
gataataccg cgccacatag cagaacttta aaagtgctca tcattggaaa acgttcttcg  4680
gggcgaaaac tctcaaggat cttaccgctg ttgagatcca gttcgatgta acccactcgt  4740
gcacccaact gatcttcagc atcttttact ttcaccagcg tttctgggtg agcaaaaaca  4800
ggaaggcaaa atgccgcaaa aaagggaata agggcgacac ggaaatgttg aatactcata  4860
ctcttccttt ttcaatatta ttgaagcatt tatcagggtt attgtctcat gagcggatac  4920
atatttgaat gtatttagaa aaataaacaa ataggggttc cgcgcacatt tccccgaaaa  4980
gtgccacctg acgtcgacgg atcgggagat ctcccgatcc cctatggtcg actctcagta  5040
caatctgctc tgatgccgca tagttaagcc agtatctgct ccctgcttgt gtgttggagg  5100
tcgctgagta gtgcgcgagc aaaatttaag ctacaacaag gcaaggcttg accgacaatt  5160
gcatgaagaa tctgcttagg gttaggcgtt ttgcgctgct tcgcgatgta cgggccagat  5220
atacgcgttg acattgatta ttgactagtt attaatagta atcaattacg gggtcattag  5280
ttcatagccc atatatggag ttccgcgtta cataacttac ggtaaatggc ccgcctggct  5340
gaccgcccaa cgacccccgc ccattgacgt caataatgac gtatgttccc atagtaacgc  5400
caatagggac tttccattga cgtcaatggg tggagtattt acggtaaact gcccacttgg  5460
cagtacatca agtgtatcat atgccaagta cgccccctat tgacgtcaat gacggtaaat  5520
ggcccgcctg gcattatgcc cagtacatga ccttatggga ctttcctact tggcagtaca  5580
tctacgtatt agtcatcgct attaccatgg tgatgcggtt ttggcagtac atcaatgggc  5640
gtggatagcg gtttgactca cggggatttc caagtctcca ccccattgac gtcaatggga  5700
gtttgttttg gcaccaaaat caacgggact ttccaaaatg tcgtaacaac tccgccccat  5760
tgacgcaaat gggcggtagg cgtgtacggt gggaggtcta tataagcaga gctctctggc  5820
taactagaga acccactgct tactggctta tcgaaattaa tacgactcac tatagggaga  5880
cccaagctgg ctagcaccat ggactacaaa gaccatgacg gtgattataa agatcatgac  5940
atcgattaca aggatgacga tgacaagatg gcccccaaga agaagaggaa ggtgggcatt  6000
caccgcgggg tacctatggt ggacttgagg acactcggtt attcgcaaca gcaacaggag  6060
aaaatcaagc ctaaggtcag gagcaccgtc gcgcaacacc acgaggcgct tgtggggcat  6120
ggcttcactc atgcgcatat tgtcgcgctt tcacagcacc ctgcggcgct tgggacggtg  6180
gctgtcaaat accaagatat gattgcggcc ctgcccgaag ccacgcacga ggcaattgta  6240
ggggtcggta aacagtggtc gggagcgcga gcacttgagg cgctgctgac tgtggcgggt  6300
gagcttaggg ggcctccgct ccagctcgac accgggcagc tgctgaagat cgcgaagaga  6360
gggggagtaa cagcggtaga ggcagtgcac gcctggcgca atgcgctcac cggggccccc  6420
ttgaac                                                             6426

SEQ ID NO: 191         moltype = DNA  length = 128
FEATURE                Location/Qualifiers
source                 1..128
                       mol_type = other DNA
                       organism = synthetic construct
SEQUENCE: 191
tctagaggtc tcattgaccc cagaccaggt agtcgcaatc gcgtcacatg acgggggaaa  60
gcaagccctg gaaaccgtgc aaaggttgtt gccggtcctt tgtcaagacc acggcagaga  120
ccggatcc                                                          128

SEQ ID NO: 192         moltype = DNA  length = 131
FEATURE                Location/Qualifiers
source                 1..131
                       mol_type = other DNA
                       organism = synthetic construct
SEQUENCE: 192
tctagaggtc tcacggcctg actcccgatc aagttgtagc gattgcgtcg catgacggag  60
ggaaacaagc attggagact gtccaacggc tccttcccgt gttgtgtcaa gcccacggag  120
agaccggatc c                                                      131

SEQ ID NO: 193         moltype = DNA  length = 131
```

```
FEATURE                Location/Qualifiers
source                 1..131
                       mol_type = other DNA
                       organism = synthetic construct
SEQUENCE: 193
tctagaggtc tcaacggttt gacgcctgca caagtggtcg ccatcgccag ccatgatggc  60
ggtaagcagg cgctggaaac agtacagcgc ctgctgcctg tactgtgcca ggatcatgag  120
agaccggatc c                                                       131

SEQ ID NO: 194         moltype = DNA  length = 131
FEATURE                Location/Qualifiers
source                 1..131
                       mol_type = other DNA
                       organism = synthetic construct
SEQUENCE: 194
tctagaggtc tcacatggac tgaccccaga ccaggtagtc gcaatcgcgt cacatgacgg  60
gggaaagcaa gccctggaaa ccgtgcaaag gttgttgccg gtcctttgtc aagaccacag  120
agaccggatc c                                                       131

SEQ ID NO: 195         moltype = DNA  length = 131
FEATURE                Location/Qualifiers
source                 1..131
                       mol_type = other DNA
                       organism = synthetic construct
SEQUENCE: 195
tctagaggtc tcaccacggc ctgaccccag accaggtagt cgcaatcgcg tcacatgacg  60
ggggaaagca agccctggaa accgtgcaaa ggttgttgcc ggtcctttgt caagaccaag  120
agaccggatc c                                                       131

SEQ ID NO: 196         moltype = DNA  length = 131
FEATURE                Location/Qualifiers
source                 1..131
                       mol_type = other DNA
                       organism = synthetic construct
SEQUENCE: 196
tctagaggtc tcaaccacgg cctgactccc gatcaagttg tagcgattgc gtcgcatgac  60
ggagggaaac aagcattgga gactgtccaa cggctccttc ccgtgttgtg tcaagcccag  120
agaccggatc c                                                       131

SEQ ID NO: 197         moltype = DNA  length = 131
FEATURE                Location/Qualifiers
source                 1..131
                       mol_type = other DNA
                       organism = synthetic construct
SEQUENCE: 197
tctagaggtc tcagcccacg gtttgacgcc tgcacaagtg gtcgccatcg ccagccatga  60
tggcggtaag caggcgctgg aaacagtaca gcgcctgctg cctgtactgt gccaggatag  120
agaccggatc c                                                       131

SEQ ID NO: 198         moltype = DNA  length = 131
FEATURE                Location/Qualifiers
source                 1..131
                       mol_type = other DNA
                       organism = synthetic construct
SEQUENCE: 198
tctagaggtc tcaggatcat ggactgaccc cagaccaggt agtcgcaatc gcgtcacatg  60
acgggggaaa gcaagccctg gaaaccgtgc aaaggttgtt gccggtcctt tgtcaagaag  120
agaccggatc c                                                       131

SEQ ID NO: 199         moltype = DNA  length = 131
FEATURE                Location/Qualifiers
source                 1..131
                       mol_type = other DNA
                       organism = synthetic construct
SEQUENCE: 199
tctagaggtc tcaaagacca cggcctgacc ccagaccagg tagtcgcaat cgcgtcacat  60
gacgggggaa agcaagccct ggaaaccgtg caaaggttgt tgccggtcct ttgtcaagag  120
agaccggatc c                                                       131

SEQ ID NO: 200         moltype = DNA  length = 140
FEATURE                Location/Qualifiers
source                 1..140
                       mol_type = other DNA
                       organism = synthetic construct
SEQUENCE: 200
tctagaggtc tcacaagacc acggcctgac tcccgatcaa gttgtagcga ttgcgtcgca  60
tgacggaggg aaacaagcat tggagactgt ccaacggctc cttcccgtgt tgtgtcaagc  120
ccatggaaga gaccggatcc                                              140
```

```
SEQ ID NO: 201         moltype = DNA  length = 128
FEATURE                Location/Qualifiers
source                 1..128
                       mol_type = other DNA
                       organism = synthetic construct
SEQUENCE: 201
tctagaggtc tcattgaccc cagaccaggt agtcgcaatc gcgtcaaacg gagggggaaa  60
gcaagccctg gaaaccgtgc aaaggttgtt gccggtcctt tgtcaagacc acggcagaga  120
ccggatcc                                                          128

SEQ ID NO: 202         moltype = DNA  length = 131
FEATURE                Location/Qualifiers
source                 1..131
                       mol_type = other DNA
                       organism = synthetic construct
SEQUENCE: 202
tctagaggtc tcacggcctg actcccgatc aagttgtagc gattgcgtcg aacggtggag  60
ggaaacaagc attggagact gtccaacggc tccttcccgt gttgtgtcaa gcccacggag  120
agaccggatc c                                                       131

SEQ ID NO: 203         moltype = DNA  length = 131
FEATURE                Location/Qualifiers
source                 1..131
                       mol_type = other DNA
                       organism = synthetic construct
SEQUENCE: 203
tctagaggtc tcaacggttt gacgcctgca caagtggtcg ccatcgcctc gaatggcggc  60
ggtaagcagg cgctggaaac agtacagcgc ctgctgcctg tactgtgcca ggatcatgag  120
agaccggatc c                                                       131

SEQ ID NO: 204         moltype = DNA  length = 131
FEATURE                Location/Qualifiers
source                 1..131
                       mol_type = other DNA
                       organism = synthetic construct
SEQUENCE: 204
tctagaggtc tcacatggac tgaccccaga ccaggtagtc gcaatcgcgt caaacggagg  60
gggaaagcaa gccctggaaa ccgtgcaaag gttgttgccg gtcctttgtc aagaccacag  120
agaccggatc c                                                       131

SEQ ID NO: 205         moltype = DNA  length = 131
FEATURE                Location/Qualifiers
source                 1..131
                       mol_type = other DNA
                       organism = synthetic construct
SEQUENCE: 205
tctagaggtc tcaccacggc ctgaccccag accaggtagt cgcaatcgcg tcaaacggag  60
ggggaaagca agccctggaa accgtgcaaa ggttgttgcc ggtcctttgt caagaccaag  120
agaccggatc c                                                       131

SEQ ID NO: 206         moltype = DNA  length = 131
FEATURE                Location/Qualifiers
source                 1..131
                       mol_type = other DNA
                       organism = synthetic construct
SEQUENCE: 206
tctagaggtc tcaaccacgg cctgactccc gatcaagttg tagcgattgc gtcgaacggt  60
ggagggaaac aagcattgga gactgtccaa cggctccttc ccgtgttgtg tcaagcccag  120
agaccggatc c                                                       131

SEQ ID NO: 207         moltype = DNA  length = 131
FEATURE                Location/Qualifiers
source                 1..131
                       mol_type = other DNA
                       organism = synthetic construct
SEQUENCE: 207
tctagaggtc tcagcccacg gtttgacgcc tgcacaagtg gtcgccatcg ccagcaatgg  60
cggcggtaag caggcgctgg aaacagtaca gcgcctgctg cctgtactgt gccaggatag  120
agaccggatc c                                                       131

SEQ ID NO: 208         moltype = DNA  length = 131
FEATURE                Location/Qualifiers
source                 1..131
                       mol_type = other DNA
                       organism = synthetic construct
SEQUENCE: 208
tctagaggtc tcaggatcat ggactgaccc cagaccaggt agtcgcaatc gcgtcaaacg  60
gagggggaaa gcaagccctg gaaaccgtgc aaaggttgtt gccggtcctt tgtcaagaag  120
agaccggatc c                                                       131
```

```
SEQ ID NO: 209          moltype = DNA  length = 131
FEATURE                 Location/Qualifiers
source                  1..131
                        mol_type = other DNA
                        organism = synthetic construct
SEQUENCE: 209
tctagaggtc tcaaagacca cggcctgacc ccagaccagg tagtcgcaat cgcgtcaaac  60
ggagggggaa agcaagccct ggaaaccgtg caaaggttgt tgccggtcct ttgtcaagag  120
agaccggatc c                                                       131

SEQ ID NO: 210          moltype = DNA  length = 140
FEATURE                 Location/Qualifiers
source                  1..140
                        mol_type = other DNA
                        organism = synthetic construct
SEQUENCE: 210
tctagaggtc tcacaagacc acggcctgac tcccgatcaa gttgtagcga ttgcgtccaa  60
cggtggaggg aaacaagcat tggagactgt ccaacggctc cttcccgtgt tgtgtcaagc  120
ccatggaaga gaccggatcc                                              140

SEQ ID NO: 211          moltype = DNA  length = 128
FEATURE                 Location/Qualifiers
source                  1..128
                        mol_type = other DNA
                        organism = synthetic construct
SEQUENCE: 211
tctagaggtc tcattgaccc cagaccaggt agtcgcaatc gcgtcaaaca ttgggggaaa  60
gcaagccctg gaaaccgtgc aaaggttgtt gccggtcctt tgtcaagacc acggcagaga  120
ccggatcc                                                           128

SEQ ID NO: 212          moltype = DNA  length = 131
FEATURE                 Location/Qualifiers
source                  1..131
                        mol_type = other DNA
                        organism = synthetic construct
SEQUENCE: 212
tctagaggtc tcacggcctg actcccgatc aagttgtagc gattgcgtcg aacattggag  60
ggaaacaagc attggagact gtccaacggc tccttcccgt gttgtgtcaa gcccacggag  120
agaccggatc c                                                       131

SEQ ID NO: 213          moltype = DNA  length = 131
FEATURE                 Location/Qualifiers
source                  1..131
                        mol_type = other DNA
                        organism = synthetic construct
SEQUENCE: 213
tctagaggtc tcaacggttt gacgcctgca caagtggtcg ccatcgccag caatattggc  60
ggtaagcagg cgctggaaac agtacagcgc ctgctgcctg tactgtgcca ggatcatgag  120
agaccggatc c                                                       131

SEQ ID NO: 214          moltype = DNA  length = 131
FEATURE                 Location/Qualifiers
source                  1..131
                        mol_type = other DNA
                        organism = synthetic construct
SEQUENCE: 214
tctagaggtc tcacatggac tgaccccaga ccaggtagtc gcaatcgcgt caaacattgg  60
gggaaagcaa gccctggaaa ccgtgcaaag gttgttgccg gtcctttgtc aagaccacag  120
agaccggatc c                                                       131

SEQ ID NO: 215          moltype = DNA  length = 131
FEATURE                 Location/Qualifiers
source                  1..131
                        mol_type = other DNA
                        organism = synthetic construct
SEQUENCE: 215
tctagaggtc tcaccacggc ctgaccccag accaggtagt cgcaatcgcg tcgaacattg  60
ggggaaagca agccctggaa accgtgcaaa ggttgttgcc ggtcctttgt caagaccaag  120
agaccggatc c                                                       131

SEQ ID NO: 216          moltype = DNA  length = 131
FEATURE                 Location/Qualifiers
source                  1..131
                        mol_type = other DNA
                        organism = synthetic construct
SEQUENCE: 216
tctagaggtc tcaaccatgg cctgactccc gatcaagttg tagcgattgc gtcgaacatt  60
ggagggaaac aagcattgga gactgtccaa cggctccttc ccgtgttgtg tcaagcccag  120
```

```
agaccggatc c                                                  131

SEQ ID NO: 217          moltype = DNA  length = 131
FEATURE                 Location/Qualifiers
source                  1..131
                        mol_type = other DNA
                        organism = synthetic construct
SEQUENCE: 217
tctagaggtc tcagcccacg gtttgacgcc tgcacaagtg gtcgccatcg cctccaatat  60
tggcggtaag caggcgctgg aaacagtaca gcgcctgctg cctgtactgt gccaggatag  120
agaccggatc c                                                  131

SEQ ID NO: 218          moltype = DNA  length = 131
FEATURE                 Location/Qualifiers
source                  1..131
                        mol_type = other DNA
                        organism = synthetic construct
SEQUENCE: 218
tctagaggtc tcaggatcat ggactgaccc cagaccaggt agtcgcaatc gcgtcgaaca  60
ttgggggaaa gcaagccctg gaaaccgtgc aaaggttgtt gccggtcctt tgtcaagaag  120
agaccggatc c                                                  131

SEQ ID NO: 219          moltype = DNA  length = 131
FEATURE                 Location/Qualifiers
source                  1..131
                        mol_type = other DNA
                        organism = synthetic construct
SEQUENCE: 219
tctagaggtc tcaaagacca cggcctgacc ccagaccagg tagtcgcaat cgcgtcgaac  60
attgggggaa agcaagccct ggaaaccgtg caaaggttgt tgccggtcct ttgtcaagag  120
agaccggatc c                                                  131

SEQ ID NO: 220          moltype = DNA  length = 140
FEATURE                 Location/Qualifiers
source                  1..140
                        mol_type = other DNA
                        organism = synthetic construct
SEQUENCE: 220
tctagaggtc tcacaagacc acggcctgac tcccgatcaa gttgtagcga ttgcgtcgaa  60
cattggaggg aaacaagcat tggagactgt ccaacggctc cttcccgtgt tgtgtcaagc  120
ccatggaaga gaccggatcc                                         140

SEQ ID NO: 221          moltype = DNA  length = 128
FEATURE                 Location/Qualifiers
source                  1..128
                        mol_type = other DNA
                        organism = synthetic construct
SEQUENCE: 221
tctagaggtc tcattgaccc cagaccaggt agtcgcaatc gcgaacaata atgggggaaa  60
gcaagccctg gaaaccgtgc aaaggttgtt gccggtcctt tgtcaagacc acggcagaga  120
ccggatcc                                                      128

SEQ ID NO: 222          moltype = DNA  length = 131
FEATURE                 Location/Qualifiers
source                  1..131
                        mol_type = other DNA
                        organism = synthetic construct
SEQUENCE: 222
tctagaggtc tcacggcctg actcccgatc aagttgtagc gattgcgaat aacaatggag  60
ggaaacaagc attggagact gtccaacggc tccttcccgt gttgtgtcaa gcccacggag  120
agaccggatc c                                                  131

SEQ ID NO: 223          moltype = DNA  length = 131
FEATURE                 Location/Qualifiers
source                  1..131
                        mol_type = other DNA
                        organism = synthetic construct
SEQUENCE: 223
tctagaggtc tcaacggttt gacgcctgca caagtggtcg ccatcgccaa caacaacggc  60
ggtaagcagg cgctggaaac agtacagcgc ctgctgcctg tactgtgcca ggatcatgag  120
agaccggatc c                                                  131

SEQ ID NO: 224          moltype = DNA  length = 131
FEATURE                 Location/Qualifiers
source                  1..131
                        mol_type = other DNA
                        organism = synthetic construct
SEQUENCE: 224
tctagaggtc tcacatggac tgaccccaga ccaggtagtc gcaatcgcga acaataatgg  60
```

```
gggaaagcaa gccctggaaa ccgtgcaaag gttgttgccg gtcctttgtc aagaccacag  120
agaccggatc c                                                       131

SEQ ID NO: 225         moltype = DNA  length = 131
FEATURE                Location/Qualifiers
source                 1..131
                       mol_type = other DNA
                       organism = synthetic construct
SEQUENCE: 225
tctagaggtc tcaccacggc ctgaccccag accaggtagt cgcaatcgcg aacaataatg  60
ggggaaagca agccctggaa accgtgcaaa ggttgttgcc ggtcctttgt caagaccaag  120
agaccggatc c                                                       131

SEQ ID NO: 226         moltype = DNA  length = 131
FEATURE                Location/Qualifiers
source                 1..131
                       mol_type = other DNA
                       organism = synthetic construct
SEQUENCE: 226
tctagaggtc tcaaccatgg cctgactccc gatcaagttg tagcgattgc gaataacaat  60
ggagggaaac aagcattgga gactgtccaa cggctccttc ccgtgttgtg tcaagcccag  120
agaccggatc c                                                       131

SEQ ID NO: 227         moltype = DNA  length = 131
FEATURE                Location/Qualifiers
source                 1..131
                       mol_type = other DNA
                       organism = synthetic construct
SEQUENCE: 227
tctagaggtc tcagcccacg gtttgacgcc tgcacaagtg gtcgccatcg ccaacaacaa  60
cggcggtaag caggcgctgg aaacagtaca gcgcctgctg cctgtactgt gccaggatag  120
agaccggatc c                                                       131

SEQ ID NO: 228         moltype = DNA  length = 131
FEATURE                Location/Qualifiers
source                 1..131
                       mol_type = other DNA
                       organism = synthetic construct
SEQUENCE: 228
tctagaggtc tcaggatcat ggactgaccc cagaccaggt agtcgcaatc gcgaacaata  60
atgggggaaa gcaagccctg gaaaccgtgc aaaggttgtt gccggtcctt tgtcaagaag  120
agaccggatc c                                                       131

SEQ ID NO: 229         moltype = DNA  length = 131
FEATURE                Location/Qualifiers
source                 1..131
                       mol_type = other DNA
                       organism = synthetic construct
SEQUENCE: 229
tctagaggtc tcaaagacca cggcctgacc ccagaccagg tagtcgcaat cgcgaacaat  60
aatgggggaa agcaagccct ggaaaccgtg caaaggttgt tgccggtcct ttgtcaagag  120
agaccggatc c                                                       131

SEQ ID NO: 230         moltype = DNA  length = 140
FEATURE                Location/Qualifiers
source                 1..140
                       mol_type = other DNA
                       organism = synthetic construct
SEQUENCE: 230
tctagaggtc tcacaagacc acggcctgac tcccgatcaa gttgtagcga ttgcgaataa  60
caatggaggg aaacaagcat tggagactgt ccaacggctc cttcccgtgt tgtgtcaagc  120
ccatggaaga gaccggatcc                                              140

SEQ ID NO: 231         moltype = DNA  length = 81
FEATURE                Location/Qualifiers
source                 1..81
                       mol_type = other DNA
                       organism = synthetic construct
SEQUENCE: 231
cctgcaggtc gaccgtctca gaacttgaag agaccgtacg tgatcgtggt ctcatggatt  60
gaagagacgg gtaccgagct c                                            81

SEQ ID NO: 232         moltype = DNA  length = 77
FEATURE                Location/Qualifiers
source                 1..77
                       mol_type = other DNA
                       organism = synthetic construct
SEQUENCE: 232
cctgcaggtc gaccgtctca ttgaagagac cgtactggat cgtggtctca cggcctgaag  60
```

```
agacgggtac cgagctc                                                77

SEQ ID NO: 233         moltype = DNA  length = 78
FEATURE                Location/Qualifiers
source                 1..78
                       mol_type = other DNA
                       organism = synthetic construct
SEQUENCE: 233
cctgcaggtc gaccgtctca ttgaagagac cgtactggat cgtggtctca acggtctgaa  60
gagacgggta ccgagctc                                               78

SEQ ID NO: 234         moltype = DNA  length = 79
FEATURE                Location/Qualifiers
source                 1..79
                       mol_type = other DNA
                       organism = synthetic construct
SEQUENCE: 234
cctgcaggtc gaccgtctca ttgaagagac cgtactggat cgtggtctca catggactga  60
agagacgggt accgagctc                                              79

SEQ ID NO: 235         moltype = DNA  length = 80
FEATURE                Location/Qualifiers
source                 1..80
                       mol_type = other DNA
                       organism = synthetic construct
SEQUENCE: 235
cctgcaggtc gaccgtctca ttgaagagac cgtactggat cgtggtctca ccacggcctg  60
aagagacggg taccgagctc                                             80

SEQ ID NO: 236         moltype = DNA  length = 81
FEATURE                Location/Qualifiers
source                 1..81
                       mol_type = other DNA
                       organism = synthetic construct
SEQUENCE: 236
cctgcaggtc gaccgtctca ttgaagagac cgtactggat cgtggtctca accacggcct  60
gaagagacgg gtaccgagct c                                           81

SEQ ID NO: 237         moltype = DNA  length = 82
FEATURE                Location/Qualifiers
source                 1..82
                       mol_type = other DNA
                       organism = synthetic construct
SEQUENCE: 237
cctgcaggtc gaccgtctca ttgaagagac cgtactggat cgtggtctca gcccacggtc  60
tgaagagacg ggtaccgagc tc                                          82

SEQ ID NO: 238         moltype = DNA  length = 83
FEATURE                Location/Qualifiers
source                 1..83
                       mol_type = other DNA
                       organism = synthetic construct
SEQUENCE: 238
cctgcaggtc gaccgtctca ttgaagagac cgtactggat cgtggtctca ggatcatgga  60
ctgaagagac gggtaccgag ctc                                         83

SEQ ID NO: 239         moltype = DNA  length = 84
FEATURE                Location/Qualifiers
source                 1..84
                       mol_type = other DNA
                       organism = synthetic construct
SEQUENCE: 239
cctgcaggtc gaccgtctca ttgaagagac cgtactggat cgtggtctca aagaccacgg  60
cctgaagaga cgggtaccga gctc                                        84

SEQ ID NO: 240         moltype = DNA  length = 85
FEATURE                Location/Qualifiers
source                 1..85
                       mol_type = other DNA
                       organism = synthetic construct
SEQUENCE: 240
cctgcaggtc gaccgtctca ttgaagagac cgtactggat cgtggtctca caagaccacg  60
gcctgaagag acgggtaccg agctc                                       85

SEQ ID NO: 241         moltype = DNA  length = 77
FEATURE                Location/Qualifiers
source                 1..77
                       mol_type = other DNA
                       organism = synthetic construct
```

```
SEQUENCE: 241
cctgcaggtc gaccgtctca ttgaagagac cgtactggat cgtggtctca tggactgaag  60
agacgggtac cgagctc                                                  77

SEQ ID NO: 242         moltype = AA  length = 21
FEATURE                Location/Qualifiers
source                 1..21
                       mol_type = protein
                       organism = synthetic construct
SEQUENCE: 242
GGTQALEAVL TALPRVCPGM V                                             21

SEQ ID NO: 243         moltype = AA  length = 21
FEATURE                Location/Qualifiers
source                 1..21
                       mol_type = protein
                       organism = synthetic construct
SEQUENCE: 243
GGTQALEAVL TALPRVCPGM V                                             21

SEQ ID NO: 244         moltype = DNA  length = 102
FEATURE                Location/Qualifiers
source                 1..102
                       mol_type = other DNA
                       organism = synthetic construct
SEQUENCE: 244
cagaccaccg agaggatcgt ggccatcggc accagccacg gcggcaccca ggccctggag  60
gccgtgctga ccgccctgcc cagggtgtgc cccggcatgg tg                      102

SEQ ID NO: 245         moltype = DNA  length = 3123
FEATURE                Location/Qualifiers
source                 1..3123
                       mol_type = other DNA
                       organism = synthetic construct
SEQUENCE: 245
gacggatcgg gagatctccc gatcccctat ggtcgactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
accatggact acaaagacca tgacggtgat tataaagatc atgacatcga ttacaaggat  960
gacgatgaca agatggcccc caagaagaag aggaaggtgg gcattcaccg cggggtacct  1020
atggtggact tgaggacact cggttattcg caacagcaac aggagaaaat caagcctaag  1080
gtcaggagca ccgtcgcgca acaccacgag gcgcttgtgg ggcatggctt cactcatgcg  1140
catattgtcg cgctttcaca gcaccctgcg gcgcttggga cggtggctgt caaataccaa  1200
gatatgattg cggccctgcc cgaagccacg cacgaggcaa ttgtaggggt cggtaaacag  1260
tggtcgggag cgcgagcact tgaggcgctg ctgactgtgg cgggtgagct tagggggcct  1320
ccgctccagc tcgacaccgg gcagctgctg aagatcgcga agagaggggg agtaacagcg  1380
gtagaggcag tgcacgcctg gcgcaatgcg ctcaccgggg ccccccttgaa ccagaccacc  1440
gagaggatcg tggccatcgg caccagccac ggcggcaccc aggccctgga ggccgtgctg  1500
accgccctgc ccagggtgtg ccccggcatg gtgcagacca ccgagaggat cgtggccatc  1560
ggcaccagcc acggcggcac ccaggccctg gaggccgtgc tgaccgccct gcccagggtg  1620
tgccccggca tggtgcagac caccgagagg atcgtggcca tcggcaccag ccacggcggc  1680
acccaggccc tggaggccgt gctgaccgcc ctgcccaggg tgtgccccgg catggtgcag  1740
accaccgaga ggatcgtggc catcggcacc agccacggcg gcacccaggc cctggaggcc  1800
gtgctgaccg ccctgcccag ggtgtgcccc ggcatggtgc agaccaccga gaggatcgtg  1860
gccatcggca ccagccacgg cggcacccag gccctggagg ccgtgctgac cgccctgccc  1920
agggtgtgcc ccggcatggt gcagaccacc gagaggatcg tggccatcgg caccagccac  1980
ggcggcaccc aggccctgga ggccgtgctg accgccctgc ccagggtgtg ccccggcatg  2040
gtgcagacca ccgagaggat cgtggccatc ggcaccagcc acggcggcac ccaggccctg  2100
gaggccgtgc tgaccgccct gcccagggtg tgccccggca tggtgcagac caccgagagg  2160
atcgtggcca tcggcaccag ccacggcggc acccaggccc tggaggccgt gctgaccgcc  2220
ctgcccaggg tgtgccccgg catggtgcag accaccgaga ggatcgtggc catcggcacc  2280
agccacggcg gcacccaggc cctggaggcc gtgctgaccg ccctgcccag ggtgtgcccc  2340
ggcatggtgc agaccaccga gaggatcgtg gccatcggca ccagccacgg cggcacccag  2400
gccctggagg ccgtgctgac cgccctgccc agggtgtgcc ccggcatggt gcagaccacc  2460
gagaggatcg tggccatcgg caccagccac ggcggcaccc aggccctgga ggccgtgctg  2520
accgccctgc ccagggtgtg ccccggcatg gtgcagacca ccgagaggat cgtggccatc  2580
ggcaccagcc acggcggcac ccaggccctg gaggccgtgc tgaccgccct gcccagggtg  2640
```

```
tgccccggca tggtgcagac caccgagagg atcgtggcca tcggcaccag ccacggcggc  2700
acccaggccc tggaggccgt gctgaccgcc ctgcccaggg tgtgccccgg catggtgcag  2760
accaccgaga ggatcgtggc catcggcacc agccacggcg gcacccaggc cctggaggcc  2820
gtgctgaccg ccctgcccag ggtgtgcccc ggcatggtgc tgacacccga acaggtggtc  2880
gccattgcta ataataacgg aggacggcca gccttggagt ccatcgtagc ccaattgtcc  2940
aggcccgatc ccgcgttggc tgcgttaacg aatgaccatc tggtggcgtt ggcatgtctt  3000
ggtggacgac ccgcgctcga tgcagtcaaa aagggtctgc ctcatgctcc cgcattgatc  3060
aaaagaacca accggcggat tcccgagaga acttcccatc gagtcgcggg atcccaacta  3120
gtc                                                                3123

SEQ ID NO: 246          moltype = AA  length = 18
FEATURE                 Location/Qualifiers
source                  1..18
                        mol_type = protein
                        organism = synthetic construct
SEQUENCE: 246
SSGGGGSGGG GGGSSRSS                                                18

SEQ ID NO: 247          moltype = AA  length = 7
FEATURE                 Location/Qualifiers
source                  1..7
                        mol_type = protein
                        organism = synthetic construct
SEQUENCE: 247
GGSSRSS                                                            7

SEQ ID NO: 248          moltype = AA  length = 34
FEATURE                 Location/Qualifiers
source                  1..34
                        mol_type = protein
                        organism = synthetic construct
SEQUENCE: 248
LTPDQVVAIA SNGGGKQALE TVQRLLPVLC QDHG                              34

SEQ ID NO: 249          moltype = AA  length = 34
FEATURE                 Location/Qualifiers
source                  1..34
                        mol_type = protein
                        organism = synthetic construct
SEQUENCE: 249
LTPAQVVAIA SNIGGKQALE TVQRLLPVLC QDHG                              34

SEQ ID NO: 250          moltype = AA  length = 34
FEATURE                 Location/Qualifiers
source                  1..34
                        mol_type = protein
                        organism = synthetic construct
SEQUENCE: 250
LTPDQVVAIA SHDGGKQALE TVQRLLPVLC QAHG                              34

SEQ ID NO: 251          moltype = AA  length = 34
FEATURE                 Location/Qualifiers
source                  1..34
                        mol_type = protein
                        organism = synthetic construct
SEQUENCE: 251
LTPEQVVAIA NNNGGKQALE TVQRLLPVLC QAHG                              34

SEQ ID NO: 252          moltype = AA  length = 29
FEATURE                 Location/Qualifiers
source                  1..29
                        mol_type = protein
                        organism = synthetic construct
SEQUENCE: 252
TTERIVAIGT STGGTQALEA VLTALPRVC                                    29

SEQ ID NO: 253          moltype = AA  length = 29
FEATURE                 Location/Qualifiers
source                  1..29
                        mol_type = protein
                        organism = synthetic construct
SEQUENCE: 253
TTERIVAIGT STGGTQALEA VLTALPRVC                                    29

SEQ ID NO: 254          moltype = AA  length = 29
FEATURE                 Location/Qualifiers
source                  1..29
                        mol_type = protein
                        organism = synthetic construct
```

```
SEQUENCE: 254
TTERIVAIGT STGGTQALEA VLTALPRVC                                    29

SEQ ID NO: 255         moltype = AA  length = 29
FEATURE                Location/Qualifiers
source                 1..29
                       mol_type = protein
                       organism = synthetic construct
SEQUENCE: 255
TTERIVAIGT STGGTQALEA VLTALPRVC                                    29

SEQ ID NO: 256         moltype = AA  length = 29
FEATURE                Location/Qualifiers
source                 1..29
                       mol_type = protein
                       organism = synthetic construct
SEQUENCE: 256
TTERIVAIGT STGGTQALEA VLTALPRVC                                    29

SEQ ID NO: 257         moltype = AA  length = 29
FEATURE                Location/Qualifiers
source                 1..29
                       mol_type = protein
                       organism = synthetic construct
SEQUENCE: 257
TTERIVAIGT STGGTQALEA VLTALPRVC                                    29

SEQ ID NO: 258         moltype = AA  length = 29
FEATURE                Location/Qualifiers
source                 1..29
                       mol_type = protein
                       organism = synthetic construct
SEQUENCE: 258
TTERIVAIGT STGGTQALEA VLTALPRVC                                    29

SEQ ID NO: 259         moltype = AA  length = 29
FEATURE                Location/Qualifiers
source                 1..29
                       mol_type = protein
                       organism = synthetic construct
SEQUENCE: 259
TTERIVAIGT STGGTQALEA VLTALPRVC                                    29

SEQ ID NO: 260         moltype = AA  length = 29
FEATURE                Location/Qualifiers
source                 1..29
                       mol_type = protein
                       organism = synthetic construct
SEQUENCE: 260
TTERIVAIGT STGGTQALEA VLTALPRVC                                    29

SEQ ID NO: 261         moltype = AA  length = 29
FEATURE                Location/Qualifiers
source                 1..29
                       mol_type = protein
                       organism = synthetic construct
SEQUENCE: 261
TTERIVAIGT STGGTQALEA VLTALPRVC                                    29

SEQ ID NO: 262         moltype = AA  length = 29
FEATURE                Location/Qualifiers
source                 1..29
                       mol_type = protein
                       organism = synthetic construct
SEQUENCE: 262
TTERIVAIGT STGGTQALEA VLTALPRVC                                    29

SEQ ID NO: 263         moltype = AA  length = 29
FEATURE                Location/Qualifiers
source                 1..29
                       mol_type = protein
                       organism = synthetic construct
SEQUENCE: 263
TTERIVAIGT STGGTQALEA VLTALPRVC                                    29

SEQ ID NO: 264         moltype = AA  length = 29
FEATURE                Location/Qualifiers
source                 1..29
                       mol_type = protein
```

```
                         organism = synthetic construct
SEQUENCE: 264
TTERIVAIGT STGGTQALEA VLTALPRVC                                          29

SEQ ID NO: 265           moltype = AA  length = 29
FEATURE                  Location/Qualifiers
source                   1..29
                         mol_type = protein
                         organism = synthetic construct
SEQUENCE: 265
TTERIVAIGT STGGTQALEA VLTALPRVC                                          29

SEQ ID NO: 266           moltype = AA  length = 29
FEATURE                  Location/Qualifiers
source                   1..29
                         mol_type = protein
                         organism = synthetic construct
SEQUENCE: 266
TTERIVAIGT STGGTQALEA VLTALPRVC                                          29

SEQ ID NO: 267           moltype = AA  length = 29
FEATURE                  Location/Qualifiers
source                   1..29
                         mol_type = protein
                         organism = synthetic construct
SEQUENCE: 267
TTERIVAIGT STGGTQALEA VLTALPRVC                                          29

SEQ ID NO: 268           moltype = AA  length = 29
FEATURE                  Location/Qualifiers
source                   1..29
                         mol_type = protein
                         organism = synthetic construct
SEQUENCE: 268
TTERIVAIGT STGGTQALEA VLTALPRVC                                          29

SEQ ID NO: 269           moltype = AA  length = 29
FEATURE                  Location/Qualifiers
source                   1..29
                         mol_type = protein
                         organism = synthetic construct
SEQUENCE: 269
TTERIVAIGT STGGTQALEA VLTALPRVC                                          29

SEQ ID NO: 270           moltype = AA  length = 29
FEATURE                  Location/Qualifiers
source                   1..29
                         mol_type = protein
                         organism = synthetic construct
SEQUENCE: 270
TTERIVAIGT STGGTQALEA VLTALPRVC                                          29

SEQ ID NO: 271           moltype = AA  length = 29
FEATURE                  Location/Qualifiers
source                   1..29
                         mol_type = protein
                         organism = synthetic construct
SEQUENCE: 271
TTERIVAIGT STGGTQALEA VLTALPRVC                                          29

SEQ ID NO: 272           moltype = AA  length = 29
FEATURE                  Location/Qualifiers
source                   1..29
                         mol_type = protein
                         organism = synthetic construct
SEQUENCE: 272
TTERIVAIGT STGGTQALEA VLTALPRVC                                          29

SEQ ID NO: 273           moltype = AA  length = 29
FEATURE                  Location/Qualifiers
source                   1..29
                         mol_type = protein
                         organism = synthetic construct
SEQUENCE: 273
TTERIVAIGT STGGTQALEA VLTALPRVC                                          29

SEQ ID NO: 274           moltype = AA  length = 29
FEATURE                  Location/Qualifiers
source                   1..29
```

```
                        mol_type = protein
                        organism = synthetic construct
SEQUENCE: 274
TTERIVAIGT STGGTQALEA VLTALPRVC                                      29

SEQ ID NO: 275          moltype = AA  length = 29
FEATURE                 Location/Qualifiers
source                  1..29
                        mol_type = protein
                        organism = synthetic construct
SEQUENCE: 275
TTERIVAIGT STGGTQALEA VLTALPRVC                                      29

SEQ ID NO: 276          moltype = AA  length = 30
FEATURE                 Location/Qualifiers
source                  1..30
                        mol_type = protein
                        organism = synthetic construct
SEQUENCE: 276
MTSEQIVAIG TSTGGTQALE AVLTALPRVC                                     30

SEQ ID NO: 277          moltype = AA  length = 29
FEATURE                 Location/Qualifiers
source                  1..29
                        mol_type = protein
                        organism = synthetic construct
SEQUENCE: 277
TTERIVAIGT STGGTQALET VLTALPRVC                                      29

SEQ ID NO: 278          moltype = AA  length = 29
FEATURE                 Location/Qualifiers
source                  1..29
                        mol_type = protein
                        organism = synthetic construct
SEQUENCE: 278
TTERIVAIGT STGGTQALET VLTALPRVC                                      29

SEQ ID NO: 279          moltype = AA  length = 23
FEATURE                 Location/Qualifiers
source                  1..23
                        mol_type = protein
                        organism = synthetic construct
SEQUENCE: 279
RIVAIGTSTG GTQALEVVLT ALP                                            23

SEQ ID NO: 280          moltype = AA  length = 29
FEATURE                 Location/Qualifiers
source                  1..29
                        mol_type = protein
                        organism = synthetic construct
SEQUENCE: 280
TTDRVVALGT STGGTQALEV VLRQLPVDC                                      29

SEQ ID NO: 281          moltype = AA  length = 29
FEATURE                 Location/Qualifiers
source                  1..29
                        mol_type = protein
                        organism = synthetic construct
SEQUENCE: 281
TTDRVVALGT STGGTQALEV VLRQLPVDC                                      29

SEQ ID NO: 282          moltype = AA  length = 29
FEATURE                 Location/Qualifiers
source                  1..29
                        mol_type = protein
                        organism = synthetic construct
SEQUENCE: 282
TTDRVVALGC STGGTQALEF ILRQLPRDC                                      29

SEQ ID NO: 283          moltype = AA  length = 29
FEATURE                 Location/Qualifiers
source                  1..29
                        mol_type = protein
                        organism = synthetic construct
SEQUENCE: 283
TTERVVALGT STGGTQALEV VLRTLPRVC                                      29

SEQ ID NO: 284          moltype = AA  length = 29
FEATURE                 Location/Qualifiers
```

```
source                  1..29
                        mol_type = protein
                        organism = synthetic construct
SEQUENCE: 284
TTERIVAIGT STGGTQALEA VLTALPRVC                                   29

SEQ ID NO: 285          moltype = DNA  length = 85
FEATURE                 Location/Qualifiers
source                  1..85
                        mol_type = other DNA
                        organism = synthetic construct
SEQUENCE: 285
gctctgatag gagccacata gggtggcaat caggattggt gacagaaaag ccccatcctt  60
aggcctcctc cttcctagtc tcctg                                        85

SEQ ID NO: 286          moltype = DNA  length = 112
FEATURE                 Location/Qualifiers
source                  1..112
                        mol_type = other DNA
                        organism = synthetic construct
SEQUENCE: 286
gctctggtac tgggtacttt tatctgtccc ctccacccca cagtggggcc actaggacag  60
gattggtgac agaaaagccc catccttagg cctcctcctt cctagtctcc tg          112

SEQ ID NO: 287          moltype = DNA  length = 111
FEATURE                 Location/Qualifiers
source                  1..111
                        mol_type = other DNA
                        organism = synthetic construct
SEQUENCE: 287
gctctggtac tgggtacttt tatctgtccc ctccacccca cagtggggcc actagggagg  60
attggtgaca gaaaagcccc atccttaggc ctcctccttc ctagtctcct g           111

SEQ ID NO: 288          moltype = DNA  length = 111
FEATURE                 Location/Qualifiers
source                  1..111
                        mol_type = other DNA
                        organism = synthetic construct
SEQUENCE: 288
gctctggtac tgggtacttt tatctgtccc ctccacccca cagtggggcc actaggcagg  60
attggtgaca gaaaagcccc atccttaggc ctcctccttc ctagtctcct g           111

SEQ ID NO: 289          moltype = DNA  length = 113
FEATURE                 Location/Qualifiers
source                  1..113
                        mol_type = other DNA
                        organism = synthetic construct
SEQUENCE: 289
gctctggtac tgggtacttt tatctgtccc ctccacccca cagtggggcc actagggaca  60
ggattggtga cagaaaagcc ccatccttag gcctcctcct tcctagtctc ctg         113

SEQ ID NO: 290          moltype = DNA  length = 113
FEATURE                 Location/Qualifiers
source                  1..113
                        mol_type = other DNA
                        organism = synthetic construct
SEQUENCE: 290
gctctggtac tgggtacttt tatctgtccc ctccacccca cagtggggcc actagggaca  60
ggattggtga cagaaaagcc ccatccttag gcctcctcct tcctagtctc ctg         113

SEQ ID NO: 291          moltype = DNA  length = 113
FEATURE                 Location/Qualifiers
source                  1..113
                        mol_type = other DNA
                        organism = synthetic construct
SEQUENCE: 291
gctctggtac tgggtacttt tatctgtccc ctccaccccc cagtggggcc actagggaca  60
ggattggtga cagaaaagcc ccatccttag gcctcctcct tcctagtctc ctg         113

SEQ ID NO: 292          moltype = DNA  length = 113
FEATURE                 Location/Qualifiers
source                  1..113
                        mol_type = other DNA
                        organism = synthetic construct
SEQUENCE: 292
gctctggtac tgggtacttt tatctgtccc ctccacccca cagtggggcc actagggaca  60
ggattggtga cagaaaagcc ccatccttag gcctcctcct tcctagtctc ctg         113

SEQ ID NO: 293          moltype = DNA  length = 112
```

```
FEATURE                Location/Qualifiers
source                 1..112
                       mol_type = other DNA
                       organism = synthetic construct
SEQUENCE: 293
gctctggtac tgggtacttt tatctgtccc ctccacccca caggggggcc actaggacag  60
gattggtgac agaaaagccc catccttagg cctcctcctt cctagtctcc tg          112

SEQ ID NO: 294         moltype = DNA  length = 103
FEATURE                Location/Qualifiers
source                 1..103
                       mol_type = other DNA
                       organism = synthetic construct
SEQUENCE: 294
gctctggttc tgggtacttt tatctgtccc ctccacccca cagtggggcc actagggaca  60
ggattggtga cagaaaagcc ccatccttag gcctcctcct tcc                    103

SEQ ID NO: 295         moltype = DNA  length = 108
FEATURE                Location/Qualifiers
source                 1..108
                       mol_type = other DNA
                       organism = synthetic construct
SEQUENCE: 295
gctctggttc tgggtacttt tatctgtccc ctccacccca cagtggggcc actaggaggg  60
ggacaggatt ggtgacagaa aagccccatc cttaggcctc ctccttcc               108

SEQ ID NO: 296         moltype = DNA  length = 59
FEATURE                Location/Qualifiers
source                 1..59
                       mol_type = other DNA
                       organism = synthetic construct
SEQUENCE: 296
gctctgggga cggacaggat tggtgacaga aaagccccat ccttaggcct cctccttcc   59

SEQ ID NO: 297         moltype = DNA  length = 102
FEATURE                Location/Qualifiers
source                 1..102
                       mol_type = other DNA
                       organism = synthetic construct
SEQUENCE: 297
gctctggttc tgggtacttt tatctgtccc ctccacccca cagtggggcc actaggacag  60
gattggtgac agaaaagccc catccttagg cctcctcctt cc                     102

SEQ ID NO: 298         moltype = DNA  length = 103
FEATURE                Location/Qualifiers
source                 1..103
                       mol_type = other DNA
                       organism = synthetic construct
SEQUENCE: 298
gctctggttc tgggtacttt tatctgtccc ctccacccca cagtggggcc actagggaca  60
ggattggtga cagaaaagcc ccatccttag gcctcctcct tcc                    103

SEQ ID NO: 299         moltype = DNA  length = 102
FEATURE                Location/Qualifiers
source                 1..102
                       mol_type = other DNA
                       organism = synthetic construct
SEQUENCE: 299
gctctggttc tgggtacttt tatctgtccc ctccacccca cagtggggcc actaggacag  60
gattggtgac agaaaagccc catccttagg cctcctcctt cc                     102

SEQ ID NO: 300         moltype = AA  length = 11
FEATURE                Location/Qualifiers
source                 1..11
                       mol_type = protein
                       organism = synthetic construct
SEQUENCE: 300
QTTERIVAIG T                                                       11

SEQ ID NO: 301         moltype = AA  length = 11
FEATURE                Location/Qualifiers
source                 1..11
                       mol_type = protein
                       organism = synthetic construct
SEQUENCE: 301
QTTERIVAIG T                                                       11
```

COMPOSITIONS AND METHODS FOR DIRECTING PROTEINS TO SPECIFIC LOCI IN THE GENOME

RELATED APPLICATIONS

This application is a continuation of U.S. application Ser. No. 15/580,675, filed Dec. 7, 2017, now U.S. Pat. No. 11,473,082, issued Oct. 18, 2022, which is a National Stage Application, filed under 35 U.S.C. § 371, of International Application No. PCT/US2016/037922, filed on Jun. 16, 2016, which claims priority to and the benefit of U.S. Provisional Application No. 62/181,162, filed Jun. 17, 2015, the contents of each of which are herein incorporated by reference in their entirety.

INCORPORATION OF SEQUENCE LISTING

The Sequence Listing XML associated with this application is provided electronically in XML file format and is hereby incorporated by reference into the specification. The name of the XML file containing the Sequence Listing XML is "POTH-003_C01US_ST26.xml". The XML file is 308,775 bytes in size, created on Apr. 27, 2023, and is being submitted electronically via USPTO Patent Center.

FIELD OF THE DISCLOSURE

The present invention is directed to compositions and methods for targeted gene modification.

BACKGROUND

There are many instances in which it would be desirable to localize a protein to a specific locus in the genome of an organism in order for the protein to carry out a specific function. One instance in which it is desirable to localize a protein to a specific location in the genome is in the case of gene editing. In such examples of gene editing tools, a DNA binding domain is fused to a nuclease domain through a covalent linkage via a peptide bond. The instant disclosure provides compositions and methods for fusion proteins for gene editing with superior efficacy.

SUMMARY

The disclosure provides compositions and methods for directing a protein to a specific locus or loci in a genome of an organism. Upon contact of the genome with a composition or polypeptide of the disclosure, one or more strand of the double-stranded DNA may be cut. If the cut is made in the presence of one or more DNA repair pathways or components thereof, may either interrupt gene expression or provide modification of the genomic sequence by insertion, deletion, or substitution of one or more base pairs. Compositions and methods of the disclosure provide superior and unexpectedly efficient nuclease activity at a target locus or loci in a genome.

The disclosure provides a fusion protein comprising, consisting essentially of or consisting of a DNA localization component and an effector molecule.

In certain embodiments of the fusion proteins of the disclosure, the DNA localization component may comprise, consist essentially of or consist of, at least one guide RNA (gRNA). In certain aspects of these embodiments, the DNA localization component may comprise, consist essentially of or consist of, two guide RNAs (gRNAs), wherein a first gRNA specifically binds to a first strand of a double-stranded DNA target sequence and a second gRNA specifically binds to a second strand of the double-stranded DNA target sequence.

In certain embodiments of the disclosure the DNA localization component may comprise, consist essentially of or consist of, at least one guide RNA (gRNA) and the effector molecule may comprise, consist essentially of or consist of a Cas9, a Cas9 nuclease domain or a fragment thereof. In certain embodiments of the disclosure the DNA localization component may comprise, consist essentially of or consist of, at least one guide RNA (gRNA) and the effector molecule may comprise, consist essentially of or consist of an inactivated Cas9 (dCas9) or an inactivated nuclease domain. In certain embodiments of the disclosure the DNA localization component may comprise, consist essentially of or consist of, at least one guide RNA (gRNA) and the effector molecule may comprise, consist essentially of or consist of an inactivated small Cas9 (dSaCas9). In each of these embodiments, the effector molecule may comprise, consist essentially of or consist of a Cas9, dCas9, dSaCas9, or nuclease domain thereof and a second endonuclease. The second endonuclease may comprise, consist essentially of or consist of a Type IIS endonuclease. The second endonuclease may comprise, consist essentially of or consist of a Type IIS endonuclease, including, but not limited to, one or more of AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BaaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051. In certain embodiments, the effector molecule may comprise, consist essentially of or consist of dCas9 or a nuclease domain thereof and a Type UIS endonuclease. The second endonuclease may comprise, consist essentially of or consist of a Type IIS endonuclease, including, but not limited to, one or more of AciI, Mn1, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of dCas9 or a nuclease domain thereof and not comprise, consist essentially of or consist of FokI. In certain embodiments, the effector molecule may comprise, consist essentially of or consist of a homodimer of a type IIS endonuclease, including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of a heterodimer of a type IIS endonuclease, including, but not limited to, one or more of AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

In certain embodiments of the fusion proteins of the disclosure, the DNA localization component may comprise, consist essentially of or consist of, a DNA-binding domain of a transcription activator-like effector nuclease (TALEN). In certain embodiments of the fusion proteins of the disclosure, the DNA localization component may comprise, consist essentially of or consist of, a DNA-binding domain of a TALEN (also referred to as a TAL protein) and the effector molecule may comprise an endonuclease. The DNA binding domain, or TAL protein, may be derived from *Xanthomonas*. The DNA binding domain, or TAL protein, may be derived from *Ralstonia.*

In certain embodiments of the fusion proteins of the disclosure, the DNA localization component may comprise, consist essentially of or consist of, a DNA-binding domain of a TALEN, or TAL protein, derived from *Xanthomonas* and the effector molecule may comprise, consist essentially of or consist of, a Type IIS endonuclease. The effector molecule may comprise, consist essentially of or consist of a Type IIS endonuclease, including, but not limited to, one or more of AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the fusion proteins of the disclosure, the DNA localization component may comprise, consist essentially of or consist of, a DNA-binding domain of a TALEN, or TAL protein, derived from *Xanthomonas* and the effector molecule may not comprise, consist essentially of or consist of FokI. In certain embodiments of the fusion proteins of the disclosure, the DNA localization component may comprise, consist essentially of or consist of, a DNA-binding domain of a TALEN, or TAL protein, derived from *Xanthomonas* and the effector molecule may not comprise, consist essentially of or consist of Clo051. In certain embodiments, the effector molecule may comprise, consist essentially of or consist of a homodimer of a type IIS endonuclease, including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of a heterodimer of a type IIS endonuclease, including, but not limited to, one or more of AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

In certain embodiments of the fusion proteins of the disclosure, the DNA localization component may comprise, consist essentially of or consist of, a DNA-binding domain of a TALEN, or TAL protein, derived from *Ralstonia* and the effector molecule may comprise, consist essentially of or consist of, a Type IIS endonuclease. The effector molecule may comprise, consist essentially of or consist of a Type IIS endonuclease, including, but not limited to, one or more of AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the fusion proteins of the disclosure, the DNA localization component may comprise, consist essentially of or consist of, a DNA-binding domain of a TALEN, or TAL protein, derived from *Ralstonia* and the effector molecule may not comprise, consist essentially of or consist of FokI. In certain embodiments, the effector molecule may comprise, consist essentially of or consist of a homodimer of a type IIS endonuclease, including, but not limited to, AciI, Mn1I, AlwI, BbvI, BccI, BceAI, BsmAI, BsmFI, BspCNI, BsrI, BtsCI, HgaI, HphI, HpyAV, MboII, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051. In certain embodiments, the effector molecule may comprise, consist essentially of or consist of a heterodimer of a type IIS endonuclease, including, but not limited to, one or more of AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

In certain embodiments of the fusion proteins of the disclosure, the effector molecule may comprise, consist essentially of or consist of, a heterodimer.

In certain embodiments of the fusion proteins of the disclosure, the effector molecule may comprise, consist essentially of or consist of, a homodimer. In certain embodiments of the fusion proteins of the disclosure, the effector molecule may comprise, consist essentially of or consist of, a homodimer of a type IIS endonuclease.

Effector molecules of the disclosure, including heterodimers and homodimers of the disclosure, may comprise, consist essentially of or consist of a nuclease or endonuclease. Effector molecules of the disclosure, including heterodimers and homodimers of the disclosure, may comprise, consist essentially of or consist of a Cas9, a Cas9 nuclease domain or a fragment thereof. The Cas9 may be or may comprise, consist essentially of or consist of an inactivated Cas9 (dCas9) or an inactivated nuclease domain. The Cas9 may be or may comprise, consist essentially of or consist of an inactivated small Cas9 (dSaCas9).

In certain embodiments of the disclosure, the effector molecule may comprise, consist essentially of or consist of a dCas9 or an inactivated nuclease domain thereof and a type IIS endonuclease. In certain embodiments of the disclosure, the effector molecule may comprise, consist essentially of or consist of a dCas9 or an inactivated nuclease domain thereof and a type IIS endonuclease, including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the disclosure, the effector molecule may comprise, consist essentially of or consist of a dCas9 or an inactivated nuclease domain thereof and not may not comprise, consist essentially of or consist of FokI.

In certain embodiments of the disclosure, the effector molecule may comprise, consist essentially of or consist of a dSaCas9 or an inactivated nuclease domain thereof and a type IIS endonuclease. In certain embodiments of the disclosure, the effector molecule may comprise, consist essentially of or consist of a dSaCas9 or an inactivated nuclease domain thereof and a type IIS endonuclease, including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051.

In certain embodiments of the disclosure, the effector molecule may comprise, consist essentially of or consist of a heterodimer of one or more type IIS endonucleases. In certain embodiments of the disclosure, the effector molecule may comprise, consist essentially of or consist of a heterodimer of one or more type IIS endonucleases, including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BaaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051.

In certain embodiments of the fusion proteins of the disclosure, the effector molecule may comprise, consist essentially of or consist of, a homodimer of type IIS endonucleases. In certain embodiments of the disclosure, the effector molecule may comprise, consist essentially of or consist of a homodimer of type IIS endonucleases, including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, FokI or Clo051.

Effector molecules of the disclosure, including heterodimers and homodimers of the disclosure, may comprise, consist essentially of or consist of a DNA cleavage domain of a TALEN. The TALEN may be derived from *Xanthomonas* or *Ralstonia.*

In certain embodiments of the disclosure, the effector molecule may comprise, consist essentially of or consist of a DNA cleavage domain of a TALEN, wherein the TALEN is derived from *Xanthomonas*, and a type IIS endonuclease. In certain embodiments of the disclosure, the effector molecule may comprise, consist essentially of or consist of a DNA cleavage domain of a TALEN, wherein the TALEN is derived from *Xanthomonas*, and a type IIS endonuclease, including, but not limited to, AciI, Mn1I, AlwI, BbvI, BccI, BceAI, BsmAI, BsmFI, BspCNI, BsrI, BtsCI, HgaI, HphI, HpyAV, MboII, My1I, PleI, SfaNI, AcuI, BciVI, BfuAI, BmgBI, BmrI, BpmI, BpuEI, BaaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments of the disclosure, the effector molecule may comprise, consist essentially of or consist of a DNA cleavage domain of a TALEN, wherein the TALEN is derived from *Xanthomonas*, and not may not comprise, consist essentially of or consist of FokI. In certain embodiments of the disclosure, the effector molecule may comprise, consist essentially of or consist of a DNA cleavage domain of a TALEN, wherein the TALEN is derived from *Xanthomonas*, and not may not comprise, consist essentially of or consist of Clo051.

In certain embodiments of the disclosure, the effector molecule may comprise, consist essentially of or consist of a DNA cleavage domain of a TALEN, wherein the TALEN is derived from *Ralstonia*, and a type IIS endonuclease. In certain embodiments of the disclosure, the effector molecule may comprise, consist essentially of or consist of a DNA cleavage domain of a TALEN, wherein the TALEN is derived from *Ralstonia*, and a type IIS endonuclease, including but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I, or Clo051.

Effector molecules of the disclosure, including heterodimers and homodimers of the disclosure, may comprise, consist essentially of or consist of AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments, the effector molecule may comprise, consist essentially of or consist of Clo051, BfiI or BmrI. In certain embodiments, the effector molecule may comprise, consist essentially of or consist of Clo051.

The disclosure provides a nucleic acid encoding a fusion protein of the disclosure.

The disclosure provides a vector comprising, consisting essentially of or consisting of, a nucleic acid of the disclosure. Preferably, the disclosure provides a vector comprising, consisting essentially of or consisting of, a nucleic acid encoding a fusion protein of the disclosure.

The disclosure provides a cell comprising a fusion protein, a nucleic acid, a vector or a composition of the disclosure. The cell may be in vivo, ex vivo or in vitro. The cell may be a unicellular or single-celled organism, including, for example, bacteria, archaea, protozoa, unicellular algae and/or unicellular fungi.

The disclosure provides a composition comprising a fusion protein, a nucleic acid, a vector or a cell of the disclosure. Compositions of the disclosure may further comprise, consist essentially of or consist of pharmaceutically-acceptable carrier.

The disclosure provides a multicellular organism comprising, consisting essentially of or consisting of, a fusion protein, a nucleic acid, a vector, a cell, or a composition of the disclosure. The multicellular organism may be a plant. The multicellular organism may be an animal. In certain embodiments, the animal is not a human or a human embryo or is not derived from either a human or a human embryo.

The disclosure provides a method for directing proteins to specific loci in a genome of an organism comprising providing to a genomic DNA sequence a fusion protein, a nucleic acid, a vector, a cell or a composition of the disclosure. In certain embodiments of this method, the fusion protein, the nucleic acid, the vector, the cell or the composition contacts the genomic DNA sequence in vivo, ex vivo, or in vitro. In certain embodiments of this method, the genomic DNA sequence is not a human genomic DNA sequence.

The disclosure provides a composition comprising, consisting essentially of or consisting of, a DNA localization component and an effector molecule, wherein the DNA localization component and the effector molecule are capable of operatively linking via a non-covalent linkage.

DNA localization components of the disclosure may comprise, consist essentially of or consist of, at least one guide RNA (gRNA). In certain embodiments of the compositions and methods of the disclosure, DNA localization components may comprise, consist essentially of or consist of, two (2) guide RNAs (gRNAs), wherein a first gRNA specifically binds to a first strand of a double-stranded DNA target sequence and a second gRNA specifically binds to a second strand of the double-stranded DNA target sequence. Alternatively, DNA localization components of the disclosure may comprise a DNA binding domain of a transcription activator-like effector nuclease (TALEN). Exemplary DNA binding domains of TALEN of the disclosure may be derived from *Xanthomonas* or *Ralstonia.*

Effector molecules of the disclosure may comprise, consist essentially of or consist of, a homodimer or a heterodimer. Effector molecules, including those effector molecules comprising a homodimer or a heterodimer, may comprise, consist essentially of or consist of, a nuclease. In preferred embodiments, the nuclease is an endonuclease. Effector molecules, including those effector molecules comprising a homodimer or a heterodimer, may comprise, consist essentially of or consist of, a Cas9, a Cas9 nuclease domain or a fragment thereof. In certain embodiments, the Cas9 is a catalytically inactive or "inactivated" Cas9 (dCas9). In certain embodiments, the Cas9 is a catalytically inactive or "inactivated" nuclease domain of Cas9. In preferred embodiments, the dCas9 is encoded by a shorter sequence that is derived from a full length, catalytically inactivated, Cas9, referred to herein as a "small" dCas9 or dSaCas9.

Effector molecules, including those effector molecules comprising a homodimer or a heterodimer, may comprise, consist essentially of or consist of Clo051, BfiI or BmrI. In preferred embodiments, effector molecules, including those effector molecules comprising a homodimer or a heterodimer, may comprise, consist essentially of or consist of Clo051.

Effector molecules, including those effector molecules comprising a heterodimer, may comprise, consist essentially of or consist of a Cas9, a Cas9 nuclease domain or a fragment thereof that forms a heterodimer with Clo051, BfiI or BmrI. In certain embodiments, effector molecules, including those effector molecules comprising a heterodimer, may comprise, consist essentially of or consist of a Cas9, a Cas9 nuclease domain or a fragment thereof that forms a heterodimer with Clo051.

Effector molecules, including those effector molecules comprising a heterodimer, may comprise, consist essentially of or consist of a dCas9 or inactivated nuclease domain thereof that forms a heterodimer with Clo051, BfiI or BmrI. In preferred embodiments, effector molecules, including those effector molecules comprising a heterodimer, may comprise, consist essentially of or consist of a dCas9 or inactivated nuclease domain thereof that forms a heterodimer with Clo051.

Effector molecules, including those effector molecules comprising a heterodimer, may comprise, consist essentially of or consist of a dSaCas9 that forms a heterodimer with Clo051, BfiI or BmrI. In preferred embodiments, effector molecules, including those effector molecules comprising a heterodimer, may comprise, consist essentially of or consist of a dSaCas9 that forms a heterodimer with Clo051.

Effector molecules, including those effector molecules comprising a homodimer, may comprise, consist essentially of or consist of a catalytically-inactive form of Cas9 (e.g. dCas9 or dSaCas9) or a fragment thereof and a homodimer comprising, consisting essentially of or consisting of Clo051, BfiI or BmrI. In certain embodiments, effector molecules, including those effector molecules comprising a homodimer, may comprise, consist essentially of or consist of a catalytically-inactive form of Cas9 (e.g. dCas9 or dSaCas9) or a fragment thereof and a homodimer comprising, consisting essentially of or consisting of Clo051.

Effector molecules, including those effector molecules comprising a homodimer or a heterodimer, may comprise, consist essentially of or consist of a DNA cleavage domain of a TALEN. Exemplary DNA cleavage domains of TALENs of the disclosure may be derived from *Xanthomonas* or *Ralstonia.*

Effector molecules, including those effector molecules comprising a heterodimer, may comprise, consist essentially of or consist of a DNA cleavage domain of a *Xanthomonas* TALEN that forms a heterodimer with Clo051, BfiI or BmrI. In preferred embodiments, effector molecules, including those effector molecules comprising a heterodimer, may comprise, consist essentially of or consist of a DNA cleavage domain of a *Xanthomonas* TALEN that forms a heterodimer with Clo051.

Effector molecules, including those effector molecules comprising a homodimer, may comprise, consist essentially of or consist of a DNA cleavage domain of a *Xanthomonas* TALEN and a homodimer comprising, consisting essentially of or consisting of Clo051, BfiI or BmrI. In certain embodiments, effector molecules, including those effector molecules comprising a homodimer, may comprise, consist essentially of or consist of a DNA cleavage domain of a *Xanthomonas* TALEN and a homodimer comprising, consisting essentially of or consisting of Clo051.

Effector molecules, including those effector molecules comprising a heterodimer, may comprise, consist essentially of or consist of a DNA cleavage domain of a *Ralstonia* TALEN that forms a heterodimer with Clo051, BfiI or BmrI. In preferred embodiments, effector molecules, including those effector molecules comprising a heterodimer, may comprise, consist essentially of or consist of a DNA cleavage domain of a *Ralstonia* TALEN that forms a heterodimer with Clo051.

Effector molecules, including those effector molecules comprising a homodimer, may comprise, consist essentially of or consist of a DNA cleavage domain of a *Ralstonia* TALEN and a homodimer comprising, consisting essentially of or consisting of Clo051, BfiI or BmrI. In certain embodiments, effector molecules, including those effector molecules comprising a homodimer, may comprise, consist essentially of or consist of a DNA cleavage domain of a *Ralstonia* TALEN and a homodimer comprising, consisting essentially of or consisting of Clo051.

Non-covalent linkages of the disclosure may comprise, consist essentially of or consist of an antibody fragment covalently attached to the effector molecule and which non-covalently binds directly to the DNA localization component. Non-covalent linkages of the disclosure may comprise, consist essentially of or consist of an antibody fragment covalently attached to the DNA localization component and which non-covalently binds directly to the effector component. Non-covalent linkages of the disclosure may comprise, consist essentially of or consist of an antibody fragment covalently attached to either the effector molecule or the DNA localization component and which non-covalently binds to an epitope tag covalently attached to the opposite component. Antibody fragments of the disclosure may comprise or consist of a single-chain variable fragment (scFv), a single domain antibody (sdAB), a small modular immunopharmaceutical (SMIP) molecule, or a nanobody.

Non-covalent linkages of the disclosure may comprise, consist essentially of or consist of a protein binding domain covalently attached to either the effector molecule or the DNA localization component and which non-covalently binds to the opposite component.

Non-covalent linkages of the disclosure may comprise, consist essentially of or consist of a protein covalently attached to either the effector molecule or the DNA localization component capable of binding to a protein covalently attached to the opposite component.

Non-covalent linkages of the disclosure may comprise, consist essentially of or consist of a small molecule covalently attached either to the effector molecule or the DNA localization component and which non-covalently binds to a protein or other small molecule covalently attached to the opposite component.

Non-covalent linkages of the disclosure may comprise, consist essentially of or consist of an antibody mimetic. Exemplary antibody mimetics of the disclosure comprise or consist of an organic compound that specifically binds a target sequence and has a structure distinct from a naturally-occurring antibody. Antibody mimetics may comprise or consist of a protein, a nucleic acid, or a small molecule. Antibody mimetics may comprise or consist of an affibody, an afflilin, an affimer, an affitin, an alphabody, an anticalin, and avimer, a DARPin, a Fynomer, a Kunitz domain peptide, or a monobody.

The disclosure provides a vector comprising a nucleic acid sequence that encodes for a DNA localization component, an effector molecule, and/or noncovalent-linkage of the disclosure.

The disclosure provides a polypeptide encoded by a vector of the disclosure. The disclosure provides a composition comprising a polypeptide encoded by a vector of the disclosure.

The disclosure provides a polypeptide comprising a DNA localization component and an effector molecule, wherein the DNA localization component and the effector molecule are capable of operatively linking via a non-covalent linkage. The disclosure provides a composition comprising a DNA localization component and an effector molecule, wherein the DNA localization component and the effector molecule are capable of operatively linking via a non-covalent linkage.

Compositions of the disclosure may comprise a pharmaceutically-acceptable carrier.

The disclosure provides a cell comprising a nucleic acid, a vector, a polypeptide, or a composition of the disclosure. The cell may be in situ, in vivo, ex vivo, or in vitro. Cells comprising a vector of the disclosure include single-celled organisms, including bacteria and archaea.

The disclosure provides a multicellular organism comprising a cell comprising a vector, polypeptide or composition of the disclosure. Exemplary multicellular organisms include, but are not limited to, a plant or an animal. In certain embodiments of the disclosure, an animal comprising a cell comprising a vector, polypeptide or composition of the disclosure is not a human. In certain embodiments of the disclosure, an animal comprising a cell comprising a vector, polypeptide or composition of the disclosure is not a human embryo.

The disclosure provides a method for directing proteins to specific loci in a genome of an organism comprising providing a composition, a nucleic acid, a vector, or a polypeptide of the disclosure to the genome. In certain embodiments of this method, composition, the nucleic acid, the vector, or the polypeptide are contact a genomic DNA sequence in vivo, ex vivo, or in vitro. In certain embodiments of this method, the genome is not a human genome.

The disclosure provides a method for modifying a genome of an organism comprising providing to a genomic DNA sequence or base pair a fusion protein, a nucleic acid, a vector, a cell or a composition according to the disclosure. In certain embodiments, the step of providing comprises bringing into contact a genomic sequence or base pair and at least one of the fusion protein, the nucleic acid, the vector, the cell or the composition. In certain aspects, contact between a genomic sequence or base pair and at least one of the fusion protein, the nucleic acid, the vector, the cell or the composition may be achieved through fluid communication.

According to this method, the modification of the genomic sequence or base pair may comprise a separation of a sequence and/or base pairs by an activity of an endonuclease. Alternatively, or in addition, the modification of the genomic sequence or base pair may comprise, consist essentially of or consist of a deletion, an insertion, a substitution, an inversion, and/or a relocation of a sequence or base pair. In certain embodiments, a DNA repair mechanism induces the deletion, insertion, substitution, inversion, and/or relocation. For example, when the DNA repair mechanism includes the Non-Homologous End Joining (NHEJ) DNA repair pathway, the NHEJ pathway may induce an insertions or deletions (InDels) at the target site, resulting in frameshifts and/or premature stop codons. Thus, when the DNA repair mechanism includes the Non-Homologous End Joining (NHEJ) DNA repair pathway, the NHEJ pathway may disrupt the open reading frame (ORF) of a target gene or genomic sequence. Disruption of the ORF of the target gene or genomic sequence may silence expression of the target gene or genomic sequence. For example, when the DNA repair mechanism includes the Homology Directed Repair (HDR) pathway, a repair template may be used to reconnect a single or double strand break in the genomic sequence. Repair templates of the disclosure may be used to insert desired sequences into the genome at the site of endonuclease activity. Exemplary repair templates of the disclosure may comprise an exogenous, artificial, and/or heterologous sequence.

Regardless of the mechanism or DNA repair pathway, inserted sequences of the disclosure may comprise an exogenous, artificial, and/or heterologous sequence. In certain embodiments, the genomic sequence comprising the insertion is non-naturally occurring. For example, when an insertion comprises an exogenous, artificial, and/or heterologous sequence, the resultant genomic sequence is non-naturally occurring.

The disclosure provides a genomic sequence modified according to a method of the disclosure.

The disclosure provides a cell comprising the genomic sequence.

The disclosure provides a cell comprising a modification resulting from a method of the disclosure. Modification of the cell or a genomic sequence thereof may be performed in vivo, ex vivo or in vitro. For example, a cell may be modified ex vivo or in vitro and administered to a subject. In certain embodiments, the modified cell or modified genomic sequence of the disclosure is neither a human cell nor a human genomic sequence. In certain embodiments, the modified cell or modified genomic sequence of the disclosure is neither a human embryonic cell nor a human embryonic genomic sequence.

DETAILED DESCRIPTION

Figure 1:
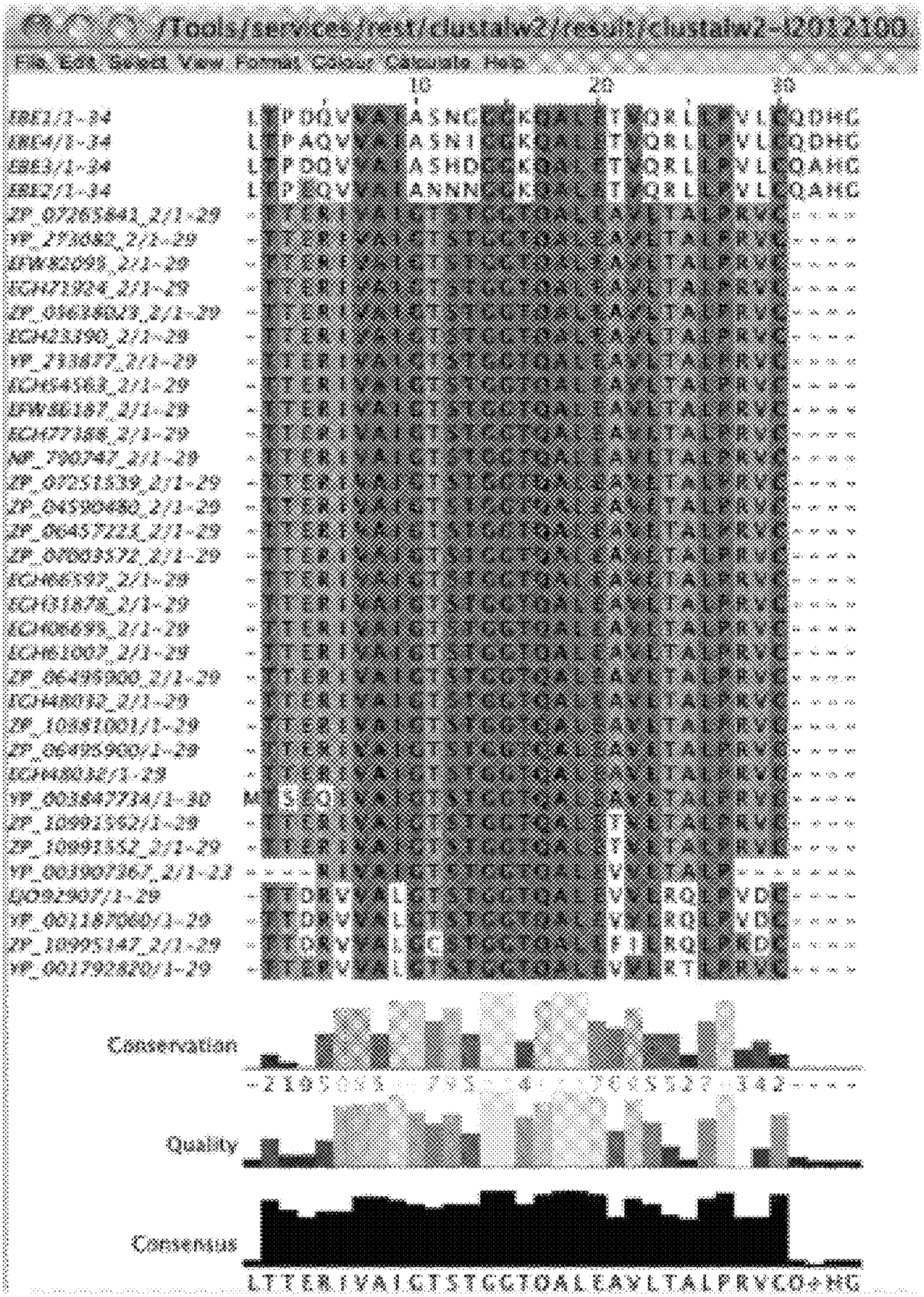
FIG. 1 is an alignment depicting a consensus sequence of a DNA-binding protein from *Xanthomonas* aligned via BLAST to methyltransferase sequences from bacterial strains. Based upon sequence alignment, the DNA binding function of the sequences are demonstrated. From top to bottom, SEQ ID Nos: 248 to 283 are shown, the consensus sequence TTERIVAIGTSTGGTOALEAVLTALPRVC (SEQ ID NO: 284).

Disclosed are compositions and methods for directing proteins to specific loci in the genome and uses thereof. In one aspect, the disclosed methods allow for directing proteins to specific loci in the genome of an organism, including the steps of providing a fusion protein comprising a DNA localization component and an effector molecule. Alternatively, the disclosed methods allow for directing proteins to specific loci in the genome of an organism, including the steps of providing a DNA localization component and an effector molecule, wherein the DNA localization component and the effector molecule are capable of being operatively linked via a non-covalent linkage. In certain embodiments of this method, the DNA localization component is capable of binding a specific DNA sequence.

DNA Localization Components

DNA localization components of the disclosure may be capable of binding a specific DNA sequence. The DNA localization component may be selected from, for example, a DNA-binding oligonucleotide, a DNA-binding protein, a DNA binding protein complex, and combinations thereof. Other suitable DNA binding components will be recognized by one of ordinary skill in the art.

DNA localization components may comprise an oligonucleotide directed to a specific locus or loci in the genome. The oligonucleotide may be selected from DNA, RNA, DNA/RNA hybrids, and combinations thereof.

DNA localization components may comprise a nucleotide binding protein or protein complex that binds an oligonucleotide when bound to a target DNA. The protein or protein complex may be capable of recognizing a feature selected from RNA-DNA heteroduplexes, R-loops, or combinations thereof. In one aspect, the DNA localization component may comprise a protein or protein complex capable of recognizing an R-loop selected from Cas9, Cascade complex, RecA, RNase H, RNA polymerase, DNA polymerase, or a combination thereof.

DNA localization components may comprise an engineered protein capable of binding to target DNA. In this aspect, the DNA localization component may comprise a protein capable of binding a DNA sequence selected from meganuclease, zinc finger array, transcription activator-like (TAL) array, and combinations thereof.

DNA localization components may comprise a protein that contains a naturally occurring DNA binding domain. The DNA localization component may comprise, for example, a protein comprising a naturally occurring DNA binding domain is selected from a bZIP domain, a Helix-loop-helix, a Helix-turn-helix, a HMG-box, a Leucine zipper, a Zinc finger, or a combination thereof.

Exemplary DNA localization components of the disclosure include, but are not limited to, a DNA-binding oligonucleotide, a DNA-binding protein, a DNA binding protein complex, and any combination thereof.

DNA localization components of the disclosure may comprise an oligonucleotide directed to a specific locus in the genome. Exemplary oligonucleotides include, but are not limited to, DNA, RNA, DNA/RNA hybrids, and any combination thereof.

DNA localization components of the disclosure may comprise a protein or a protein complex capable of recognizing a feature selected from RNA-DNA heteroduplexes, R-loops, and any combination thereof. Exemplary proteins or protein complexes capable of recognizing an R-loop include, but are not limited to, Cas9, Cascade complex, RecA, RNase H, RNA polymerase, DNA polymerase, and any combination thereof. In certain embodiments of the methods of the disclosure, the protein or protein complex capable of recognizing an R-loop comprises Cas9.

DNA localization components of the disclosure may comprise a protein capable of binding a DNA sequence selected from meganuclease, Zinc Finger array, TAL array, and any combination thereof.

DNA localization components of the disclosure may comprise a protein comprising a naturally occurring DNA binding domain. Exemplary naturally occurring DNA binding domains include, but are not limited to, a bZIP domain, a Helix-loop-helix, a Helix-turn-helix, a HMG-box, a Leucine zipper, a Zinc finger, and any combination thereof.

DNA localization components of the disclosure may comprise an oligonucleotide directed to a target location in a genome and a protein capable of binding to a target DNA sequence.

Effector Molecules

Methods of the disclosure comprise providing an effector molecule.

Exemplary effector molecules of the disclosure are capable of a predetermined effect at a specific locus in the genome.

Exemplary effector molecules of the disclosure include, but are not limited to, a transcription factor (activator or repressor), chromatin remodeling factor, nuclease, exonuclease, endonuclease, transposase, methytransferase, demethylase, acetyltransferase, deacetylase, kinase, phosphatase, integrase, recombinase, ligase, topoisomerase, gyrase, helicase, fluorophore, or any combination thereof.

Exemplary effector molecules of the disclosure may comprise a transposase. In other aspects, the effector molecule may comprise a PB transposase (PBase).

Exemplary effector molecules of the disclosure comprise a nuclease. Non-limiting examples of nucleases include restriction endonucleases, homing endonucleases, S1 Nuclease, mung bean nuclease, pancreatic DNase I, micrococcal nuclease, yeast HO endonuclease, or any combination thereof. In certain embodiments, the effector molecule comprises a restriction endonuclease. In certain embodiments, the effector molecule comprises a Type IIS restriction endonuclease.

Exemplary effector molecules of the disclosure may comprise an endonuclease. Non-limiting examples of the endonuclease include AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I and Clo051. In certain embodiments, the effector molecule comprises BmrI, BfiI, or Clo051. The effector molecule may comprise BmrI. The effector molecule may comprise BfiI. The effector molecule may comprise Clo051.

Linkages

The disclosure provides a fusion protein comprising, consisting essentially of or consisting of a DNA localization component and an effector molecule. When the polypeptides of the disclosure are fusion proteins, the nucleic acid sequences encoding one or more components of the fusion protein may be operably linked, for example, in an expression vector. Fusion proteins of the disclosure may be chimeric proteins. Fusion proteins of the disclosure may also include proteins encoded by one or more recombinant nucleic acid sequences. Fusion proteins may also include a linker region to operatively-link two components of the fusion protein. For example, the disclosure provides a fusion protein comprising, consisting essentially of or consisting of a DNA localization component and an effector molecule, operatively-linked by a linker region. In this embodiment, the DNA localization component, the linker region, and the effector molecule may be encoded by one or more nucleic acid sequences inserted into an expression cassette and/or expression vector such that translation of the nucleic acid sequence results in the fusion protein.

Polypeptides and compositions of the disclosure may comprise a non-covalent linkage between the DNA localization component and the effector molecule. The non-covalent linkage may comprise an antibody, an antibody fragment, an antibody mimetic, or a scaffold protein.

Exemplary non-covalent linkages of the disclosure may comprise an antibody fragment covalently attached to an effector molecule, which non-covalently binds directly to a DNA localization component.

Exemplary non-covalent linkages of the disclosure may comprise an antibody fragment covalently attached to a DNA localization component, non-covalently binds directly to an effector component.

Exemplary non-covalent linkages of the disclosure may comprise an antibody fragment covalently attached to either an effector molecule or a DNA localization component, which non-covalently binds to an epitope tag covalently attached to the opposite component. In certain embodiments of the disclosure, antibody fragments may comprise or consist of a single-chain variable fragment (scFv), a single domain antibody (sdAB), a small modular immunopharmaceutical (SMIP) molecule, or a nanobody.

Exemplary non-covalent linkages of the disclosure may comprise a protein binding domain covalently attached to either an effector molecule or a DNA localization component, which non-covalently binds to the opposite component Exemplary non-covalent linkages of the disclosure may comprise a protein covalently attached to either an effector molecule or a DNA localization component capable of binding to a protein covalently attached to the opposite component.

Non-covalent linkages of the disclosure may comprise or consist of an antibody mimetic. Exemplary antibody mimetics include, but are not limited to, an organic compound that specifically binds a target sequence and has a structure distinct from a naturally-occurring antibody. Moreover, Exemplary antibody mimetics include, but are not limited to, a protein, a nucleic acid, or a small molecule. In certain embodiments of the disclosure, the antibody mimetic comprises or consists of an affibody, an afflilin, an affimer, an affitin, an alphabody, an anticalin, and avimer, a DARPin, a Fynomer, a Kunitz domain peptide, or a monobody.

Exemplary non-covalent linkages of the disclosure may comprise a small molecule covalently attached either to an effector molecule or a DNA localization component, which non-covalently binds to a protein or other small molecule covalently attached to the opposite component.

Antibodies and fragments thereof, include, but are not limited to, single-chain variable fragment (scFv), single domain antibodies (sdAB), monobodies, and nanobodies. For example, the non-covalent linkage may comprise, a single-chain variable fragment (scFv) or a single domain antibody (sdAB) covalently attached to one or more effector molecules, and which is capable of a non-covalent association to the DNA localization component. In a further aspect, the non-covalent linkage may comprise a single-chain variable fragment (scFv) covalently attached to the DNA localization component and which non-covalently binds directly to the effector component. In a further aspect, the non-covalent linkage may comprise a single-chain variable fragment (scFv) covalently attached to either the effector molecule or the DNA localization component. The scFV may then non-covalently bind to an epitope tag covalently attached to the opposite component (i.e., to the DNA localization component or the effector molecule).

The non-covalent linkage may comprise, for example, an antibody mimetic. As used herein, the term "antibody mimetic" is intended to describe an organic compound that specifically binds a target sequence and has a structure distinct from a naturally-occurring antibody. Antibody mimetics may comprise a protein, a nucleic acid, or a small molecule. The target sequence to which an antibody mimetic of the disclosure specifically binds may be an antigen. Antibody mimetics may provide superior properties over antibodies including, but not limited to, superior solubility, tissue penetration, stability towards heat and enzymes (e.g. resistance to enzymatic degradation), and lower production costs. Exemplary antibody mimetics include, but are not limited to, an affibody, an afflilin, an affimer, an affitin, an alphabody, an anticalin, and avimer (also known as avidity multimer), a DARPin (Designed Ankyrin Repeat Protein), a Fynomer, a Kunitz domain peptide, and a monobody.

Affibody molecules of the disclosure comprise a protein scaffold comprising or consisting of one or more alpha helix without any disulfide bridges. Preferably, affibody molecules of the disclosure comprise or consist of three alpha helices. For example, an affibody molecule of the disclosure may comprise an immunoglobulin binding domain. An affibody molecule of the disclosure may comprise the Z domain of protein A.

Affilin molecules of the disclosure comprise a protein scaffold produced by modification of exposed amino acids of, for example, either gamma-B crystallin or ubiquitin. Affilin molecules functionally mimic an antibody's affinity to antigen, but do not structurally mimic an antibody. In any protein scaffold used to make an affilin, those amino acids that are accessible to solvent or possible binding partners in a properly-folded protein molecule are considered exposed amino acids. Any one or more of these exposed amino acids may be modified to specifically bind to a target sequence or antigen.

Affimer molecules of the disclosure comprise a protein scaffold comprising a highly stable protein engineered to display peptide loops that provide a high affinity binding site for a specific target sequence. Exemplary affimer molecules of the disclosure comprise a protein scaffold based upon a cystatin protein or tertiary structure thereof. Exemplary affimer molecules of the disclosure may share a common tertiary structure of comprising an alpha-helix lying on top of an anti-parallel beta-sheet.

Affitin molecules of the disclosure comprise an artificial protein scaffold, the structure of which may be derived, for example, from a DNA binding protein (e.g. the DNA binding protein Sac7d). Affitins of the disclosure selectively bind a target sequence, which may be the entirety or part of an antigen. Exemplary affitins of the disclosure are manufactured by randomizing one or more amino acid sequences on the binding surface of a DNA binding protein and subjecting the resultant protein to ribosome display and selection. Target sequences of affitins of the disclosure may be found, for example, in the genome or on the surface of a peptide, protein, virus, or bacteria. In certain embodiments of the disclosure, an affitin molecule may be used as a specific inhibitor of an enzyme. Affitin molecules of the disclosure may include heat-resistant proteins or derivatives thereof.

Alphabody molecules of the disclosure may also be referred to as Cell-Penetrating Alphabodies (CPAB). Alphabody molecules of the disclosure comprise small proteins (typically of less than 10 kDa) that bind to a variety of target sequences (including antigens). Alphabody molecules are capable of reaching and binding to intracellular target sequences. Structurally, alphabody molecules of the disclosure comprise an artificial sequence forming single chain alpha helix (similar to naturally occurring coiled-coil structures). Alphabody molecules of the disclosure may comprise a protein scaffold comprising one or more amino acids that are modified to specifically bind target proteins. Regardless of the binding specificity of the molecule, alphabody molecules of the disclosure maintain correct folding and thermostability.

Anticalin molecules of the disclosure comprise artificial proteins that bind to target sequences or sites in either proteins or small molecules. Anticalin molecules of the disclosure may comprise an artificial protein derived from a human lipocalin. Anticalin molecules of the disclosure may be used in place of, for example, monoclonal antibodies or fragments thereof. Anticalin molecules may demonstrate superior tissue penetration and thermostability than monoclonal antibodies or fragments thereof. Exemplary anticalin molecules of the disclosure may comprise about 180 amino acids, having a mass of approximately 20 kDa. Structurally, anticalin molecules of the disclosure comprise a barrel structure comprising antiparallel beta-strands pairwise connected by loops and an attached alpha helix. In preferred embodiments, anticalin molecules of the disclosure comprise a barrel structure comprising eight antiparallel beta-strands pairwise connected by loops and an attached alpha helix.

Avimer molecules of the disclosure comprise an artificial protein that specifically binds to a target sequence (which may also be an antigen). Avimers of the disclosure may recognize multiple binding sites within the same target or within distinct targets. When an avimer of the disclosure recognize more than one target, the avimer mimics function of a bi-specific antibody. The artificial protein avimer may comprise two or more peptide sequences of approximately 30-35 amino acids each. These peptides may be connected via one or more linker peptides. Amino acid sequences of one or more of the peptides of the avimer may be derived from an A domain of a membrane receptor. Avimers have a rigid structure that may optionally comprise disulfide bonds and/or calcium. Avimers of the disclosure may demonstrate greater heat stability compared to an antibody.

DARPins (Designed Ankyrin Repeat Proteins) of the disclosure comprise genetically-engineered, recombinant, or chimeric proteins having high specificity and high affinity for a target sequence. In certain embodiments, DARPins of the disclosure are derived from ankyrin proteins and, optionally, comprise at least three repeat motifs (also referred to as repetitive structural units) of the ankyrin protein. Ankyrin proteins mediate high-affinity protein-protein interactions. DARPins of the disclosure comprise a large target interaction surface.

Fynomers of the disclosure comprise small binding proteins (about 7 kDa) derived from the human Fyn SH3 domain and engineered to bind to target sequences and molecules with equal affinity and equal specificity as an antibody.

Kunitz domain peptides of the disclosure comprise a protein scaffold comprising a Kunitz domain. Kunitz domains comprise an active site for inhibiting protease activity. Structurally, Kunitz domains of the disclosure comprise a disulfide-rich alpha+beta fold. This structure is exemplified by the bovine pancreatic trypsin inhibitor. Kunitz domain peptides recognize specific protein structures and serve as competitive protease inhibitors. Kunitz domains of the disclosure may comprise Ecallantide (derived from a human lipoprotein-associated coagulation inhibitor (LACI)).

Monobodies of the disclosure are small proteins (comprising about 94 amino acids and having a mass of about 10 kDa) comparable in size to a single chain antibody. These genetically engineered proteins specifically bind target sequences including antigens. Monobodies of the disclosure may specifically target one or more distinct proteins or target sequences. In preferred embodiments, monobodies of the disclosure comprise a protein scaffold mimicking the structure of human fibronectin, and more preferably, mimicking the structure of the tenth extracellular type III domain of fibronectin. The tenth extracellular type III domain of fibronectin, as well as a monobody mimetic thereof; contains seven beta sheets forming a barrel and three exposed loops on each side corresponding to the three complementarity determining regions (CDRs) of an antibody. In contrast to the structure of the variable domain of an antibody, a monobody lacks any binding site for metal ions as well as a central disulfide bond. Multispecific monobodies may be optimized by modifying the loops BC and FG. Monobodies of the disclosure may comprise an adnectin.

The non-covalent linkage may comprise, for example, a scaffold protein. Scaffold proteins of the disclosure include, for example, antibody mimetics of the disclosure. Scaffold proteins of the disclosure further include, for example, small modular immunopharmaceutical (SMIP) molecules, a domain antibody, and a nanobody.

SMIP molecules of the disclosure are artificial proteins comprising one or more sequences or portions of an immunoglobulin (antibody) that are monospecific for a target sequence or antigen. SMIPs of the disclosure may substitute for the use of a monoclonal antibody. Structurally, SMIPs are single chain proteins comprising a binding region, a hinge region (i.e. a connector), and an effector domain. The binding region of a SMIP may comprise a modified single-chain variable fragment (scFv). SMIPs may be produced from genetically-modified cells as dimers.

Domain antibodies of the disclosure comprise a single monomeric variable antibody domain (i.e. either heavy or light variable domain). Domain antibodies of the disclosure demonstrate the same antigen specificity as a whole and intact antibody. Domain antibodies of the disclosure may be manufactured, at least in part, by immunization of dromedaries, camels, llamas, alpacas or sharks with the desired antigen and subsequent isolation of the mRNA coding for heavy-chain antibodies.

Nanobodies of the disclosure comprise a VHH single domain antibody. Nanobodies of the disclosure may comprise single domain antibodies of the disclosure.

Non-covalent linkages may comprise a protein binding domain covalently attached to either the effector molecule or the DNA localization component and which is capable of a non-covalent interaction with the opposite component. Non-limiting examples of protein binding domains include, for example, SH2, SH3, PTB, LIM, SAM, PDZ, FERM, CH, Pleckstin, WW, WS×WS, and the E3 ligase domain.

Non-covalent linkages may comprise a protein covalently attached to either the effector molecule or the DNA localization component that is capable of binding to a protein covalently attached to the opposite component. Non-limiting examples include any two proteins that interact non-covalently. Such proteins are readily identified via the Database of Interacting Proteins (DIP), STRING, BioGRID, MIPS, or the like.

Non-covalent linkage may comprise a small molecule covalently attached either to an effector molecule or a DNA localization component, and is capable of forming a non-covalent bond to a protein or other small molecule covalently attached to the opposite component. One such example would include biotin attached to an oligonucleotide and avidin covalently linked to an effector molecule.

The above described methods and compositions may be used, for example, in situations in which a particular protein may have several functions. Transposase proteins, for example, must perform several steps to achieve the desired function, including transposon recognition, cleavage of DNA to excise a transposon, movement of a transposon sequence to a new genomic location, recognition of a new target site, and cleavage of DNA to integrate the transposon at a new locus. In certain aspects, it may be desirable to direct a transposase to integrate a transposon at a particular site in the genome. In these aspects, this could be carried out by, for example, adding a heterologous protein with site-specific DNA binding activity. However, the heterologous protein with site-specific DNA binding activity would only be required during the target site recognition step, and the presence of this protein at earlier stages in the process described above may be detrimental to the other steps. As such, in this aspect, a temporary association of the heterologous protein with site-specific DNA binding activity with the transposase would allow the transposase to be directed to the genomic site of interest while allowing for the other steps of the process to be carried out with limited interference of the protein due to the non-covalent binding.

As another example, it may be desirable to have an enzymatic protein, such as a nuclease, methylase, deacetylase, etc. to temporarily interact with a specific DNA binding domain so that its activity occurs at a specific location in the genome. For example, it may be desired to cause a Clo051 restriction nuclease to temporarily interact with a Cas9 protein that is catalytically inactive for DNA cleavage.

In one aspect, the linker comprises a non-covalent linkage between the DNA binding element and the effector. For example, in one aspect, phage display (PhD) may be used to produce single-chain variable fragment (scFv) antibodies or single domain antibodies (sdAbs) against a particular target. PhD may be used to identify a scFv antibody against an effector, for example piggyBBac (PB) transposase that provides a linkage. A large diversity in scFv affinity may be obtained by limiting the stringency of the affinity selection process. In one aspect, the linkage may be between PB transposase (PBase) and a modular DNA binding domain such as a polydactyl zinc finger, a TAL array, or a dCas9 protein (with associated guide RNA). In some aspects, a scFv antibody with a faster off-rate may provide permissive "breathing" of the complex. In other aspects, conformation and/or flexibility of an effector and DNA binding element may be critical. Non-covalent linkages may provide conformational pliability to the disclosed gene editing compositions. Alternatively, slower off-rates (and a higher Kd) of an scFv that binds particular epitopes of an effector may provide an optimal stability and conformation of the gene editing complex that would not otherwise be obtainable through traditional peptide linkage. A near-exhaustive search among scFv antibodies allows one to select from among a large diversity of possible conformations of a gene editing complex. A PhD strategy creates such diversity through the generation of unique monovalent scFvs against multiple unique epitopes.

Furthermore, a non-covalent linkage method, such as that achieved through the use of a scFv antibody, may employ an unmodified and native effector (e.g., PB). This provides a reversible associate between the effector and the DNA binding element, which may circumvent any permanent interference with the activity of an effector that may occur when it is subjected to covalent linkage. Certain non-covalent associations could introduce steric hindrances that compromise the effector reaction. As several activities may be involved (site recognition, strand cleavage, transposon binding and integration) it is likely that each separate step may be differentially affected by a particular steric hindrance. For example, if transposase association with the DNA transposon (during transposon mobilization from one genomic site to another) has a very slow off-rate, then it would be detrimental to have a very high affinity association between a DNA binding element-scFv and the PBase that disrupts this association. However, if the DNA binding element-scFv protein binds with a lower, but significant affinity, it could be temporarily displaced during transposon mobilization. It is possible that such an early step could involve temporary dissociation of DNA binding factor-scFv with the PBase, with subsequent reassembly of the complex at later steps to create a fully functional and DNA binding factor-enabled site-specific transposase.

Dual Reporter Plasmid

Polypeptides of the disclosure may be introduced into a dual reporter plasmid to validate the efficiency of polypeptides comprising a nuclease to cut DNA at the targeted site.

Figure 5:
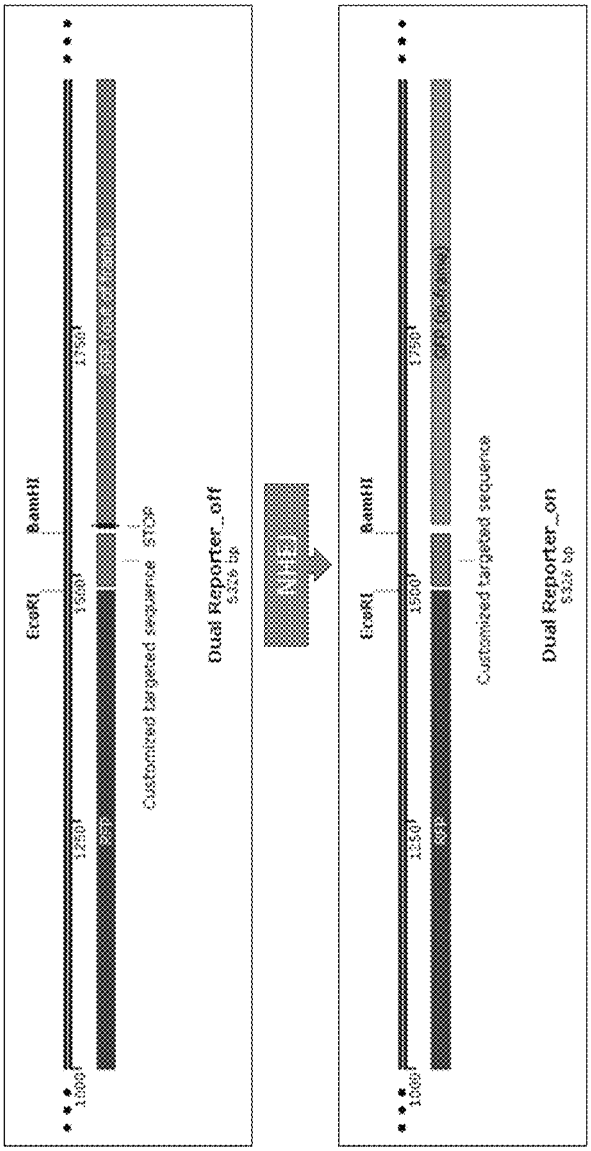
FIG. 5 is a schematic depicting of the use of a dual-reporter plasmid for validating efficiency of specific binding and endonuclease activity for polypeptide constructs of the disclosure.

FIG. 5 depicts a use of an exemplary dual reporter plasmid of the disclosure that may be used to validate the efficiency of polypeptide specific binding to a target sequence and subsequent endonuclease activity at that site. According to the plasmid depicted in FIG. 5 and further described in Example 8, expression of the red fluorescent protein (RFP) under the control of a constitutive reporter illustrates transfection efficiency of the plasmid. According to the plasmid depicted in FIG. 5 and further described in Example 8, expression of the green fluorescent protein (GFP) under the control of a promoter, the activity of which is induced by a targeted double-strand break and subsequent repair by non-homologous end joining (NHEJ) repair, illustrates the efficacy of the nuclease activity of the polypeptide of the disclosure that specifically targets the customized target sequence of the plasmid.

Figure 6:
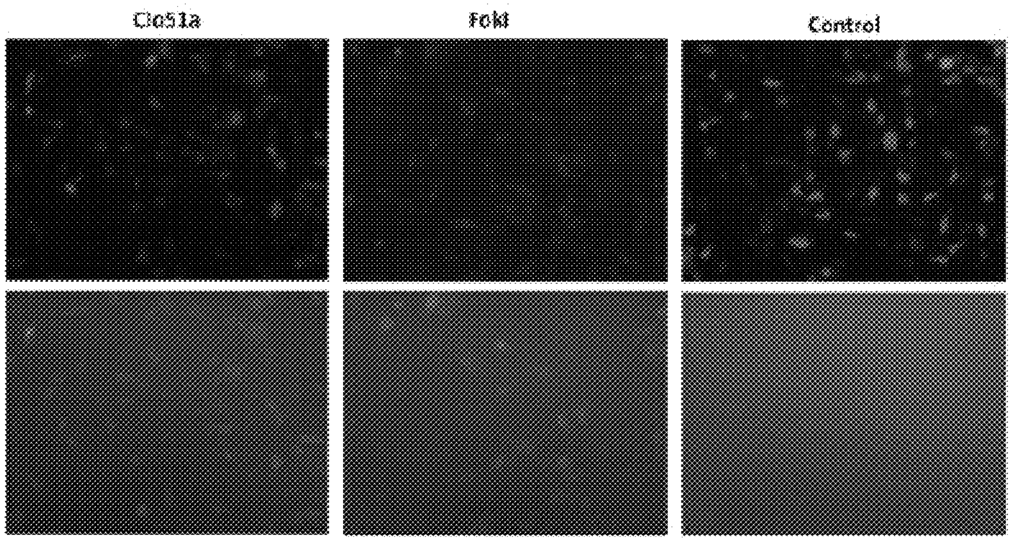
FIG. 6 is a series of photographs depicting the endonuclease activity of an AAVS1 (adeno-associated virus integration site 1) vector indicator 22 hours post-transfection. AAVS1 is an exemplary dual-reporter plasmid of the disclosure that is also depicted in FIG. 5. Endonuclease activity of Clo051 and FokI are shown relative to an endonuclease-free control.

FIG. 6 demonstrates the endonuclease activity of an AAVS1 vector containing at least a nuclease domain of either Clo051 or FokI relative to an endonuclease-free control, Among the photographs in the top row, expression of the red fluorescent protein (RFP) under the control of a constitutive reporter illustrates transfection efficiency of the plasmid. Compared to the positive control, the vector containing Clo051 demonstrates superior transfection efficiency compared to the vector containing FokI. Among the photographs in the bottom row, expression of the green fluorescent protein (GFP) under the control of a promoter, the activity of which is induced by a targeted double-strand break and subsequent repair by non-homologous end joining (NHEJ) repair, illustrates the efficacy of the nuclease activity of either Clo051 or FokI compared to the negative control lacking an endonuclease domain. Compared to the negative control, the vector containing Clo051 demonstrates greater nuclease activity compared to the vector containing FokI.

Cas9 Constructs

Polypeptides of the disclosure include a DNA localization component and an effector molecule. In some embodiments, the polypeptide is a fusion protein comprising, consisting essentially of or consisting of a DNA localization component and an effector molecule. Alternatively, the polypeptide may comprise, consist essentially of or consist of a DNA localization component and an effector molecule, wherein the DNA localization component and the effector molecule are capable of operatively linking via a covalent or non-covalent linkage.

In certain embodiments of the compositions of the disclosure, the DNA localization component comprises one or more guide RNAs (gRNAs) and the effector comprises a type IIS endonuclease. In certain embodiments, effectors of the disclosure may comprise an endonuclease homodimer or heterodimer. In certain embodiments, the effector may comprise an endonuclease homodimer or heterodimer comprising, consisting essentially or consisting of a catalytic domain of a form of Cas9 and a type IIS endonuclease or, alternatively, two distinct type II endonucleases. In certain embodiments, the effector may comprise an endonuclease homodimer comprising, consisting essentially or consisting of two identical type II endonucleases.

Exemplary Cas9 constructs may include a catalytically inactive Cas9 (dCas9) and an effector. For example, Cas9 construct of the disclosure may include an effector comprising a type IIS endonuclease including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments, the effector molecule comprises BmrI, BfiI, or Clo051. In certain embodiments, the effector comprises a homodimer comprising a type IIS endonuclease including, but not limited to, AciI, Mn1I, AlwI, BbvI, BccI, BceAI, BsmAI, BsmFI, BspCNI, BsrI, BtsCI, HgaI, HphI, HpyAV, MboII, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051.

Exemplary Cas9 constructs may include a catalytically inactive small Cas9 (dSaCas9) and an effector. For example, Cas9 construct of the disclosure may include an effector comprising a type 1S endonuclease including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051. In certain embodiments, the effector molecule comprises BmrI, BfiI, or Clo051. In certain embodiments, the effector comprises a homodimer comprising a type IIS endonuclease including, but not limited to, AciI, Mn1I, AlwI, BbvI, BccI, BceAI, BsmAI, BsmFI, BspCNI, BsrI, BtsCI, HgaI, HphI, HpyAV, Mbo1I, My1I, PleI, SfaNI, AcuI, BciVI, BfuAI, BmgBI, BmrI, BpmI, BpuEI, BsaI, BseRI, BsgI, BsmI, BspMI, BsrBI, BsrBI, BsrDI, BtgZI, BtsI, EarI, EciI, MmeI, NmeAIII, BbvCI, Bpu10I, BspQI, SapI, BaeI, BsaXI, CspCI, BfiI, MboII, Acc36I or Clo051.

Alignment of the small *Staphylococcus aureus* Cas9 (SaCas9) (SEQ ID NO: 20) aligned to a full-length *Staphylococcus pyogenes* Cas9 (SpCas9) (SEQ ID NO: 21)

```
SpCas9   MDKKYSIGLDIGTNSVGWAVITDEYKVPSKKFKVLGNTDRHSIKKNLIGALLFDSG--ET
SaCas9   mkrnyilgldigitsvgygiidyetrdvid-----------------agvrlfkeanven
         *.::* :***** .***:.:*  * :     .                *. **...  *.

SpCas9   AEATRLKRTARRRYTRRKNRICYLQEIFSNEMAKVDDSFFHRLEESFLVEEDKKHERHPI
SaCas9   negrrskrgarrlkrrrrhriqrvkkllfdyn--------------lltdhselsginp-
          *. * ** ***   **:.**  ::::: :                :*.:..:    .*

SpCas9   FGNIVDEVAYHEKYPTIYHLRKKLVDSTDKADLRLIYLALAHMIKFRGHFLIEGDLNPDN
SaCas9   ---------year---vkglsqklse-------eefsaallhlakrrgvhnvn-------
                  *. :    :  * :** :        . :  ** *: * ** . ::

SpCas9   SDVDKLFIQLVQTYNQLFEENPINASGVDAKAILSARLSKSRRLENLIAQLPGEKKNGLF
SaCas9   ------------------------------------------------------------

SpCas9   GNLIALSLGLTPNFKSNFDLAEDAKLQLSKDTYDDDLDNLLAQIGDQYADLFLAAKNLSD
SaCas9   ------------------eveed---------------------tgn-------------
                           :: **                      *:

SpCas9   AILLSDILRVNTEITKAPLSASMIKRYDEHHQDLTLLKALVR--QQLPEKYKEIFFDQSK
SaCas9   ----------------------------------elstkeqisrnskaleekyvae-----
                                           :*:  : : *  : * ***

SpCas9   NGYAGYIDGGASQEEFYKFIKPILEKMDGTEELLVKLNREDLLRKQRTFDNGSIPHQIHL
SaCas9   ---------------------lqlerlkkdgevrgsin---------rfkts-----dyv
                               **::.   *:  .:*           *...       ::

SpCas9   GELHAILRRQEDFYPFLKDNREKIEKILTFRIPYYVGPLARGNSRFAWMTRKSEETITPW
SaCas9   keakqllkvqkayhqldqsfidtyidlletrrtyyegpge--gspfgwkdik------ew
          * : :*: *: :: : :.  :.  .:*  *  ** **     * *.*   *       *

SpCas9   NFEEVVDKGASAQSFIERMTNFDKNLPNEKVLPKHSLLYEYFTVYNELTKVKYVTEGMRK
SaCas9   yeml-----------mghctyfpeelrsvk----yaynadlynalndlnnlvitrden--
                        : : * * ::* . *    ::   : :.. *:*.::  . :

SpCas9   PAFLSGEQKKAIVDLLFKTNRKVTVKQLKEDYFKKIECFDSVEISGVEDRFNASLGTYHD
SaCas9   -ekleyyekfqiienvfkqkkkptlkqiakeilvneedikgyrvtstgkpeftnlkvyhd
            *.  :*  *:: :** ::* *:**: :: : : * :.. .::.. .   :.* .***

SpCas9   LLKIIKDKDFLDNEENEDILEDIVLTLTLFEDREMIEERLKTYAHLFDDKVMK-QLKRRR
SaCas9   ikditarkeiiena---elldqiakiltiyqssediqeeltnlnseltqeeieqisnlkg
         : .*   *::::*    ::*::*.  **::. * *:*.*..    : :: ::   : :

SpCas9   YTGWGRLSRKLINGIRDKQSGKTILDFLKSDGFANRNFMQLIHDDSLTFKEDIQKAQVSG
SaCas9   ytgthnlslkainlildelwh-----------tndnqiaifnrl----klvpkkvdlsq
         ***  .** * ** * *:              :* * : ::.       *   :*.::*

SpCas9   QGDSLHEHIANLAGSPAIKKGILQTVKVVDELVKVMGRHKPENIVIEMARENQTTQKG--
SaCas9   qkeipttlvddfilspvvkrsfiqsikvinaiikkygl--pndiiielareknskdaqkm
         * :      : ::  **.:*:.::*::**:: ::*  *   *::*:**:***::.:

SpCas9   ----QKNSRERMKRIEEGIKELGSQILKEHPVENTQLQNEKLYLYYLQNGRDMYVDQELD
SaCas9   inemqkrnrqtnerieeiirt--------tgkenakyliekiklhdmqegkclysleaip
             **..*:  :**** *:             **::  **: *: :*:*: :*  :  :

SpCas9   ----INRLSDYDVDHIVPQSFLKDDSIDNKVLTRSDKNRGKSDNVPSEEVVKKM-----K
SaCas9   ledllnnpfnyevdhiiprsvsfdnsfnnkvlvkqeenskkgnrtpfqylsssdskisye
             :*.  :*:****:*:*.  *:*::****.:.::*  *.:..* :  : ..      :

SpCas9   NYWRQLLNAKL----ITQRKFDNLTKAERGGLSELDKAGFIKRQLVETRQITKHVAQILD
SaCas9   tfkkhilnlakgkgrisktkkeyl-leerdinrfsvqkdfinrnlvdtryatrglmnllr
         .: :::**       *:: * : *   **        :  **:*:**:**  *: : ::*
```

-continued

```
SpCas9   SRMNTKYDENDKLIREVKVITLKSKLVSDFRKDFQFYKVREINNYHHAHDAYLNAVVGTA
SaCas9   syfrvn-------nldvkvksinggftsflrrkwkfkkernkgykhhaedaliian----
         * :..:         :*** :::. :.* :*:.::* * *:    ***.** : *

SpCas9   LIKKYPKLESEFVYGDYKVYDVRKMIAKSEQEIGKATAKYFFYSNIMNFFKTEITLANGE
SaCas9   ---------adfifkewkkldkakkvmenqmf-----------------------eekq
                  ::*:: ::*  *  * : :.:                        : :

SpCas9   IRKRPLIETNGETGEIVWDK--------GRDFATVRKVLSMPQVNIVKKTEVQ-------
SaCas9   aesmpeieteqeykeifitphqikhikdfkdykyshrvdkkpnrelindtlystrkddkg
          .. * ***: *  **.             :*:   ::* . *: ::::.*   .

SpCas9   --------TGGFSKES----ILPKRNSDKLIARKKDWDPK----------KYGGFDSPTV
SaCas9   ntlivnninglydkdndkikklinkspekl;my--hhdpqtyqkiklimeqygdeknply
                .* :.*:.     * ::. :**:     . **:           :** ..*

SpCas9   AYSVLVV------AKVEKGK-SKKLKSVKELLGITIMERSSFEKNPIDFLEAKGYKEVKK
SaCas9   kyyeetgnyltkyskkdngpvikkikyygnklnahl-----------di--tddypnsrn
          *   .        :* ::*   **:*   : *   :            *:  :. * : ::

SpCas9   DL-IIKLPKYSL-FELENGRKRMLASA--GELQKGNELALPSKYVNFLYLASHYEKLKGS
SaCas9   kvvklslkpyrfdvyldngvykfvtvknldvikkenyyevn---------skcyeeakkl
         .:  :.*  * : . *:**  ::::      ::* *   :          :. **: *

SpCas9   PEDNEQKQLFVEQHKHYLDEIIEQISEFSKRVI------------LADANLDKVLSAYNK
saCas9   kkisnqae-fia--sfynndlikingelyrvigvnndllnrievnmidityreylenmnd
          : .:* : *:   ..* :::*:  .*: : :              : * .  : *.  *.

SpCas9   HRDKPIREQAENIIHLFTLTNLGAPAAFKYFDTTIDRKRYTSTKEVLDATLIHQSITGLY
SaCas9   krpp-------riiktia----sktqsikkystdi--------------------lgnly
         :*          .**: ::     .    ::* :.* *                   :  **

SpCas9   ETRID----LSQLGGD
SaCas9   evkskkhpqiikkg--
         *.: .    : : *
```

Small Cas9 (SaCas9)

The disclosure provides compositions comprising a small, Cas9 (Cas9) operatively-linked to an effector. In certain embodiments, the disclosure provides a fusion protein comprising, consisting essentially of or consisting of a DNA localization component and an effector molecule, wherein the effector comprises a small, Cas9 (Cas9). In certain embodiments, a small Cas9 construct of the disclosure may comprise an effector comprising a type IIS endonuclease.

Amino acid sequence of *Staphylococcus aureus* Cas9 with an active catalytic site.

```
                                                      (SEQ ID NO: 22)
  1  mkrnyilgld igitsvgygi idyetrdvid agvrlfkean vennegrrsk rgarrlkrrr

 61  rhriqrvkkl lfdynlltdh selsginpye arvkglsqkl seeefsaall hlakrrgvhn

121  vneveedtgn elstkeqisr nskaleekyv aelqlerlkk dgevrgsinr fktsdyvkea

181  kqllkvqkay hqldqsfidt yidlletrrt yyegpgegsp fgwkdikewy emlmghctyf

241  peelrsvkya ynadlynaln dlnnlvitrd enekleyyek fqiienvfkq kkkptlkqia

301  keilvneedi kgyrvtstgk peftnlkvyh dikditarke iienaelldq iakiltiyqs

361  sediqeeltn lnseltqeei eqisnlkgyt gthnlslkai nlildelwht ndnqiaifnr

421  lklvpkkvdl sqqkeipttl vddfilspvv krsfiqsikv inaiikkygl pndiiielar

481  eknskdaqkm inemqkrnrq tnerieeiir ttgkenakyl iekiklhdmq egkclyslea

541  ipledllnnp fnyevdhiip rsvsfdnsfn nkvlvkqeen skkgnrtpfq ylsssdskis

601  yetfkkhiln lakgkgrisk tkkeylleer dinrfsvqkd finrnlvdtr yatrglmnll

661  rsyfrvnnld vkvksinggf tsflrrkwkf kkernkgykh haedaliian adfifkewkk

721  ldkakkvmen qmfeekqaes mpeieteqey keifitphqi khikdfkdyk yshrvdkkpn

781  relindtlys trkddkgntl ivnnlnglyd kdndklkkli nkspekllmy hhdpqtyqkl
```

-continued

```
841   klimeqygde knplykyyee tgnyltkysk kdngpvikki kyygnklnah ldittddypns
901   rnkvvklslk pyrfdvyldn gvykfvtvkn ldvikkenyy evnskcyeea kklkkisnqa
961   efiasfynnd likingelyr vigvnndlln rievnmidit yreylenmnd krppriikti
1021  asktqsikky stdilgnlye vkskkhpqii kkg
```

Inactivated, Small Cas9 (dSaCas9)

The disclosure provides compositions comprising an inactivated, small, Cas9 (dSaCas9) operatively-linked to an effector. In certain embodiments, the disclosure provides a fusion protein comprising, consisting essentially of or consisting of a DNA localization component and an effector molecule, wherein the effector comprises a small, inactivated Cas9 (dSaCas9). In certain embodiments, a small, inactivated Cas9 (dSaCas9) construct of the disclosure may comprise an effector comprising a type IIS endonuclease.

dSaCas9 Sequence: D10A and N580A mutations (bold, capitalized, and underlined) inactivate the catalytic site.

-continued

```
STGQHFRLFIRHGPLQVTAEEGGFTCYGLSKGGFVPWFGTEGRGSLLTCG
DVEENPGPMPKKKRKVEGIKSNISLLKDELRGQISHISHEYLSLIDLAFD
SKQNRLFEMKVLELLVNEYGFKGRHLGGSRKPDGIVYSTTLEDNFGIIVD
TKAYSEGYSLPISQADEMERYVRENSNRDEEVNPNKWWENFSEEVKKYYF
VFISGSFKGKFEEQLRRLSMTTGVNGSAVNVVNLLLGAEKIRSGEMTIEE
LERAMFNNSEFILKYGGGGSDKKYSIGLAIGTNSVGWAVITDEYKVPSKK
```

(SEQ ID NO: 23)

```
1     mkrnyilglA igitsvgygi idyetrdvid agvrlfkean vennegrrsk rgarrlkrrr
61    rhriqrvkkl lfdynlltdh selsginpye arvkglsqkl seeefsaall hlakrrgvhn
121   vneveedtgn elstkeqisr nskaleekyv aelqlerlkk dgevrgsinr fktsdyvkea
181   kqllkvqkay hqldqsfidt yidlletrrt yyegpgegsp fgwkdikewy emlmghctyf
241   peelrsvkya ynadlynaln dlnnlvitrd enekleyyek fqiienvfkq kkkptlkqia
301   keilvneedi kgyrvtstgk peftnlkvyh dikditarke iienaelldq iakiltiyqs
361   sediqeeltn lnseltqeei eqisnlkgyt gthnlslkai nlildelwht ndnqiaifnr
421   lklvpkkvdl sqqkeipttl vddfilspvv krsfiqsikv inaiikkygl pndiiielar
481   eknskdaqkm inemqkrnrq tnerieeiir ttgkenakyl iekiklhdmq egkclyslea
541   ipledllnnp fnyevdhiip rsvsfdnsfn nkvlvkqeeA skkgnrtpfq ylsssdskis
601   yetfkkhiln lakgkgrisk tkkeylleer dinrfsvqkd finrnlvdtr yatrglmnll
661   rsyfrvnnld vkvksinggf tsflrrkwkf kkernkgykh haedaliian adfifkewkk
721   ldkakkvmen qmfeekqaes mpeieteqey keifitphqi khikdfkdyk yshrvdkkpn
781   relindtlys trkddkgntl ivnnlnglyd kdndklkkli nkspekllmy hhdpqtyqkl
841   klimeqygde knplykyyee tgnyltkysk kdngpvikki kyygnklnah ldittddypns
901   rnkvvklslk pyrfdvyldn gvykfvtvkn ldvikkenyy evnskcyeea kklkkisnqa
961   efiasfynnd likingelyr vigvnndlln rievnmidit yreylenmnd krppriikti
1021  asktqsikky stdilgnlye vkskkhpqii kkg
```

Figure 9:
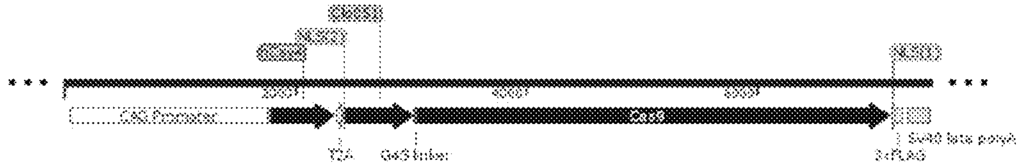
FIG. 9 is a schematic depiction of the Csy4-T2A-Clo051-G4Slinker-dCas9 construct map.

Exemplary Cas9 constructs of the disclosure include, but are not limited to, Clo051-Cas9. FIG. 9 provides a construct map for an exemplary vector of the disclosure, Csy4-T2A-Clo051-G4Slinker-dCas9. The corresponding amino acid sequence for this construct is provided below:

(SEQ ID NO: 24)

```
MGDHYLDIRLRPDPEFPPAQLMSVLFGKLHQALVAQGGDRIGVSFPDLDE
SRSRLGERLRIHASADDLRALLARPWLEGLRDHLQFGEPAVVPHPTPYRQ
VSRVQAKSNPERLRRRLMRRHDLSEEEARKRIPDTVARALDLPFVTLRSQ
```

-continued

```
FKVLGNTDRHSIKKNLIGALLFDSGETAEATRLKRTARRRYTRRKNRICY
LQEIFSNEMAKVDDSFFHRLEESFLVEEDKKHERHPIFGNIVDEVAYHEK
YPTIYHLRKKLVDSTDKADLRLIYLALAHMIKFRGHFLIEGDLNPDNSDV
DKLFIQLVQTYNQLFEENPINASGVDAKAILSARLSKSRRLENLIAQLPG
EKKNGLFGNLIALSLGLTPNFKSNFDLAEDAKLQLSKDTYDDDLDNLLAQ
IGDQYADLFLAAKNLSDAILLSDILRVNTEITKAPLSASMIKRYDEHHQD
LTLLKALVRQQLPEKYKEIFFDQSKNGYAGYIDGGASQEEFYKFIKPILE
KMDGTEELLVKLNREDLLRKQRTFDNGSIPHQIHLGELHAILRRQEDFYP
```

-continued

```
FLKDNREKIEKILTFRIPYYVGPLARGNSRFAWMTRKSEETITPWNFEEV

VDKGASAQSFIERMTNFDKNLPNEKVLPKHSLLYEYFTVYNELTKVKYVT

EGMRKPAFLSGEQKKAIVDLLFKTNRKVTVKQLKEDYFKKIECFDSVEIS

GVEDRFNASLGTYHDLLKIIKDKDFLDNEENEDILEDIVLTLTLFEDREM

IEERLKTYAHLFDDKVMKQLKRRRYTGWGRLSRKLINGIRDKQSGKTILD

FLKSDGFANRNFMQLIHDDSLTFKEDIQKAQVSGQGDSLHEHIANLAGSP

AIKKGILQTVKVVDELVKVMGRHKPENIVIEMARENQTTQKGQKNSRERM

KRIEEGIKELGSQILKEHPVENTQLQNKLYLYYLQNGRDMYVDQELDINR

LSDYDVDAIVPQSFLKDDSIDNKVLTRSDKNRGKSDNVPSEEVVKKMKNY

WRQLLNAKLITQRKFDNLTKAERGGLSELDKAGFIKRQLVETRQITKHVA

QILDSRMNTKYDENDKLIREVKVITLKSKLVSDFRKDFQFYKVREINNYH

HAHDAYLNAVVGTALIKKYPKLESEFVYGDYKVYDVRKMIAKSEQEIGKA

TAKYFFYSNIMNFFKTEITLANGEIRKRPLIETNGETGEIVWDKGRDFAT

VRKVLSMPQVNIVKKTEVQTGGFSKESILPKRNSDKLIARKKDWDPKKYG

GFDSPTVAYSVLVVAKVEKGKSKKLKSVKELLGITIMERSSFEKNPIDFL

EAKGYKEVKKDLIIKLPKYSLFELENGRKRMLASAGELQKGNELALPSKY

VNFLYLASHYEKLKGSPEDNEQKQLFVEQHKHYLDEIIEQISEFSKRVIL

ADANLDKVLSAYNKHRDKPIREQAENIIHLFTLTNLGAPAAFKYFDTTID

RKRYTSTKEVLDATLIHQSITGLYETRIDLSQLGGD
```

Figure 10:
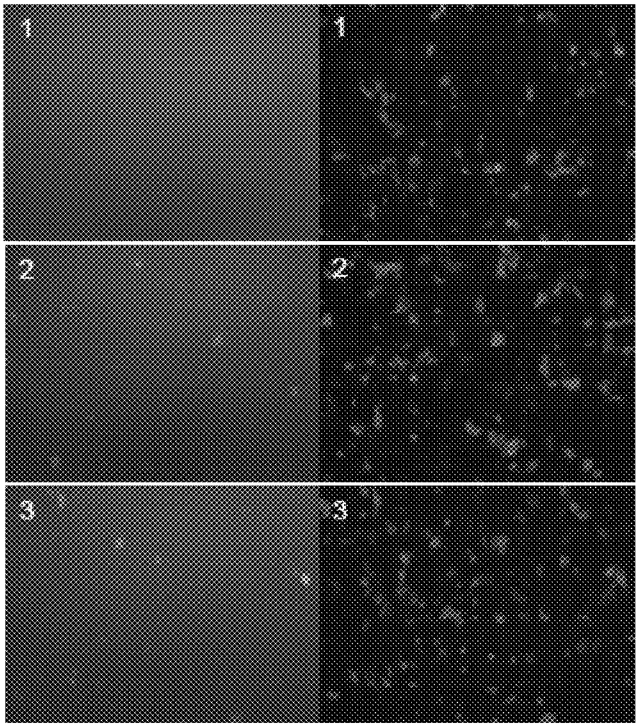
FIG. 10 is a series of photographs depicting Clo051-Cas9 activity. Condition (1) shows the pCagsClo051C4RGN plasmid (that encodes for Clo051-dCas9) transfected with a non-specific guide RNA (gRNA) and an indicator, the combination of which serve as a negative control for this experiment. Condition (2) shows the pCagsClo051C4RGN plasmid (that encodes for CLo051-dCas9) transfected with NG-AAVS1-gRNA and an indicator. Condition (3) shows the pCagsC4RGN plasmid (that encodes for FokI-dCas9) transfected with NG-AAVS1-gRNA and an indicator, the combination of which serve as a positive control in this experiment.

FIG. 10 demonstrates that an exemplary Clo051-Cas9 construct, including the Csy4-T2A-Clo051-G4Slinker-dCas9 construct, of the disclosure is active.

Cas9 may be combined with any nuclease, including but not limited to Clo051, BfiI and BmrI. Exemplary sequences for the nuclease domains of Clo051, BfiI and BmrI are provided below.

An exemplary Clo051 nuclease domain may comprise, consist essentially of or consist of the amino acid sequence of:

```
                                          (SEQ ID NO: 25)
EGIKSNISLLKDELRGQISHISHEYLSLIDLAFDSKQNRLFEMKVLELLV

NEYGFKGRHLGGSRKPDGIVYSTTLEDNFGIIVDTKAYSEGYSLPISQAD

EMERYVRENSNRDEEVNPNKWWENFSEEVKKYYFVFISGSFKGKFEEQLR

RLSMTTGVNGSAVNVVNLLLGAEKIRSGEMTIEELERAMFNNSEFILKY.
```

An exemplary BfiI nuclease domain may comprise, consist essentially of or consist of, the amino acid sequence below wherein the catalytic residues include H105, K107, N125, and E136:

```
                                          (SEQ ID NO: 26)
MNFFSLHPNVYATGRPKGLIGMLENVWVSNHTPGEGTLYLISGFSNYNGG

VRFYETFTEHINQGGRVIAILGGSTSQRLSSRQVVEELLNRGVEVHIINR

KRILHAKLYGTSNNLGESLVVSSGNFTGPGMSQNIEASLLLDNNTTQSMG

FSWNDMISEMLNQNWHIHNMTNATDASPGWNLLYDERTTNLTL
```

An exemplary BmrI nuclease domain may comprise, consist essentially of or consist of, the amino acid sequence below wherein the catalytic residues include H105, K107, N125, and E136: MNYFSLHPNVYATGRPKGLINMLESVWISNQKPGDGTMYLISGFANYNGGIRFYETFTEHINHGGKVIAILGGSTSQRLSSKQVVAELVSRGVDVYIINRKRLLHAKLYGSSSNSGESLVVSSGNFTGPGMSQNVEASLLLDNNTTSSMGFSWNGMVNSMLDQKWQINL SNSNPTSPSWNLLYDERTTNLTL (SEQ ID NO: 27)

Transcriptional Activator-Like (TAL) Proteins

Transcription factors with programmable DNA binding domains provide a means to create an exogenous biological circuit in an endogenous system and create designer proteins that bind to pre-determined DNA sequences or individual nucleic acids. Modular DNA binding domains have been identified in transcriptional activator-like (TAL) proteins, or, more specifically, transcriptional activator-like effector nucleases (TALENs), thereby allowing for the de novo creation of synthetic transcription factors that bind to DNA sequences of interest and, if desirable, also allowing a second domain present on the protein or polypeptide to perform an activity related to DNA. TAL proteins have been derived from the organisms *Xanthomonas* and *Ralstonia.*

*Xanthomonas*

The disclosure provides polypeptides derived from *Xanthomonas* amino acid sequences or amino acid sequences related thereto, nucleic acids encoding the same, compositions comprising the same, kits comprising the same, non-human transgenic animals comprising the same, and methods of using the same.

As described herein, effector proteins derived from *Xanthomonas*, including TAL proteins, may be used as part of a larger targeted chimeric protein (i.e. a component of a chimeric protein). Chimeric effector proteins of the disclosure, including those comprising or consisting of a TAL protein, or any component thereof, may demonstrate accessory activities related to nucleic acids such as nuclease activity. For instance, in some embodiments, a polypeptide or pronucleases that can facilitate homologous recombination in genome engineering may be used as a component of a chimeric protein. In certain embodiments, a transcription factor may be used as a component of a chimeric protein, making the resultant chimeric protein particularly useful for therapeutic compositions and uses thereof requiring a very high level of specificity (including therapeutic compositions and uses thereof directed against pathogens (e.g., viruses)).

Polypeptides or proteins of the disclosure may be derived from polypeptides or proteins found in *Xanthomonas*. Polypeptides or proteins of the disclosure may contain one or more sequences that are neither identical to any polypeptide or protein found in *Xanthomonas* nor naturally-occurring in *Xanthomonas*.

Polypeptides or proteins of the disclosure may comprise at least a first domain and a second domain, wherein the first domain comprises at least one coding sequence for a nucleic acid recognition element and the second domain comprises at least one coding sequence for a nucleic acid effector element.

The disclosure provides a preferred *Xanthomonas*-TALE-Clo051 (XTC) polypeptide. This polypeptide comprises a TAL DNA-binding domain derived from *Xanthomonas* fused to the Clo051 endonuclease.

Figure 3:
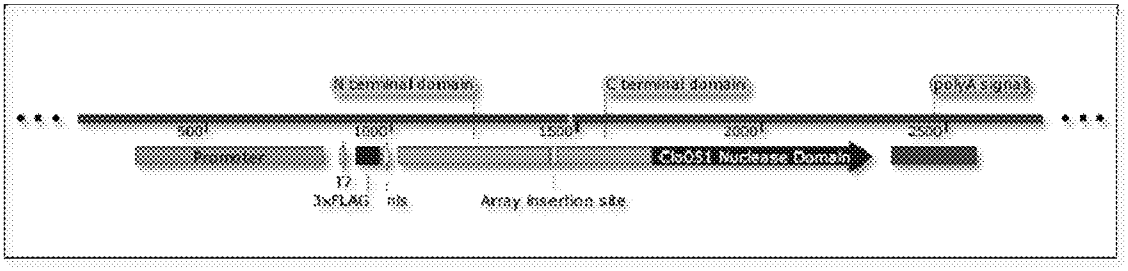
FIG. 3 is a construct map depicting an exemplary *Xanthomonas*-TALE-Clo051 (XTC) Empty Backbone of the disclosure.
Figure 4:
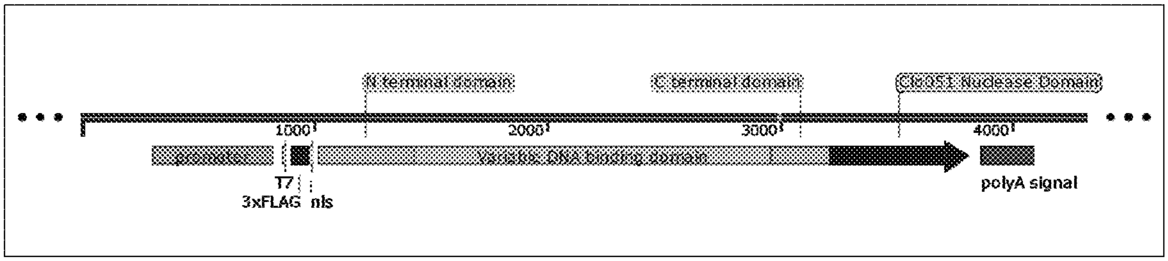
FIG. 4 is a construct map depicting an exemplary XTC cloned DNA binding domain of the disclosure. Customized TALE arrays can be cloned into the XTC backbone to target 16-20 bp specific DNA sequences.

FIGS. 3 and 4 provide a construct map corresponding to an exemplary empty backbone and cloned DNA binding domain for the XTC polypeptide.

In certain embodiments of the XTC polypeptide, the N-terminal domain sequence comprises a T7 promotor and a nuclear localization signal (NLS) in a 3×FLAG® System Expression Vector. The amino acid sequence encoding a

*Xanthomonas* TAL DNA-binding domain comprises: "MDYKDHDGDYKDHDIDYKDDDDK MAPKKKRKVGIHRGVPMVDLRTLGYSQQQQEKIKPKVRSTVAQHHEALVGHGFTH AHIVALSQHPAALGTVAVKYQDMIAALPEATHEAIVGVGKQWSGARALEALLTVA GELRGPPL QLDTGQLLKIAKRGGVTAVEAVHAWRNALTGAPLN" (SEQ ID NO: 28), wherein the sequence "MDYK DHDGDYKDHDIDYKDDDDK" (SEQ ID NO: 29) is a 3×FLAG® epitope tag and the *Xanthomonas* TAL DNA-binding domain is encoded by the sequence

```
                                          (SEQ ID NO: 30)
"MAPKKKRKVGIHRGVPMVDLRTLGYSQQQQEKIKPKVRSTVAQHHEAL
VGHGFTHAHIVALSQHPAALGTVAVKYQDMIAALPEATHEAIVGVGKQW
SGARALEALLTVAGELRGPPLQLDTGQLLKIAKRGGVTAVEAVHAWRNA
LTGAPLN".
```

The C-terminal Domain sequence of the XTC polypeptide may comprise one of four potential sequences. Variable amino acid positions are denoted by the letter "X". The consensus sequence of the XTC C-terminal Domain comprises "LTPEQVVAIAXXGGRPALESIVAQLSRPDPALAALTNDHLVALACLGGRPALDAV KKGLPHAPALIKRTNRRIPERTSHRVAGS" (SEQ ID NO: 31) wherein the bolded "XXX" positions are variable.

In a first embodiment of the sequence of the XTC C-terminal Domain, the XXX variable amino acids are "NNN" and specify a glycine (G). The complete sequence for this first embodiment of the sequence of the XTC C-terminal Domain is (SEQ ID NO: 32)
"LTPEQVVAIANNNGGRPALESIVAQLSRPDPALAALTNDHLVALACLGG
RPALDAVKKGLPHAPALIKRTNRRIPERTSHRVAGS".

In a second embodiment of the sequence of the XTC C-terminal Domain, the XXX variable amino acids are "SNG" and specify a threonine (T). The complete sequence for this second embodiment of the sequence of the XTC C-terminal Domain is (SEQ ID NO: 33)
"LTPEQVVAIASNGGGRPALESIVAQLSRPDPALAALTNDHLVALACLGG
RPALDAVKKGLPHAPALIKRTNRRIPERTSHRVAGS".

In a third embodiment of the sequence of the XTC C-terminal Domain, the XXX variable amino acids are "SID" and specify a cysteine (C). The complete sequence for this third embodiment of the sequence of the XTC C-terminal Domain is (SEQ ID NO: 34)
"LTPEQVVAIASHDGGRPALESIVAQLSRPDPALAALTNDHLVALACLGG
RPALDAVKKGLPHAPALIKRTNRRIPERTSHRVAGS".

In a fourth embodiment of the sequence of the XTC C-terminal Domain, the XXX variable amino acids are "SNI" and specify an alanine (A). The complete sequence for this fourth embodiment of the sequence of the XTC C-terminal Domain is (SEQ ID NO: 35)
"LTPEQVVAIASNIGGRPALESIVAQLSRPDPALAALTNDHLVALACLGG
RPALDAVKKGLPHAPALIKRTNRRIPERTSHRVAGS".

Preferred *Xanthomonas*-TALE-Clo051 (XTC) polypeptides of the disclosure comprise a Clo051 nuclease domain comprising, consisting essentially of or consisting of the amino acid sequence of

```
                                          (SEQ ID NO: 36)
"EGIKSNISLLKDELRGQISHISHEYLSLIDLAFDSKQNRLFEMKVLELL
VNEYGFKGRHLGGSRKPDGIVYSTTLEDNFGIIVDTKAYSEGYSLPISQA
DEMERYVRENSNRDEEVNPNKWWENFSEEVKKYYFVFISGSFKGKFEEQL
RRLSMTTGVNGSAVNVVNLLLGAEKIRSGEMTIEELERAMFNNSEFILK
Y".
```

Figure 7:
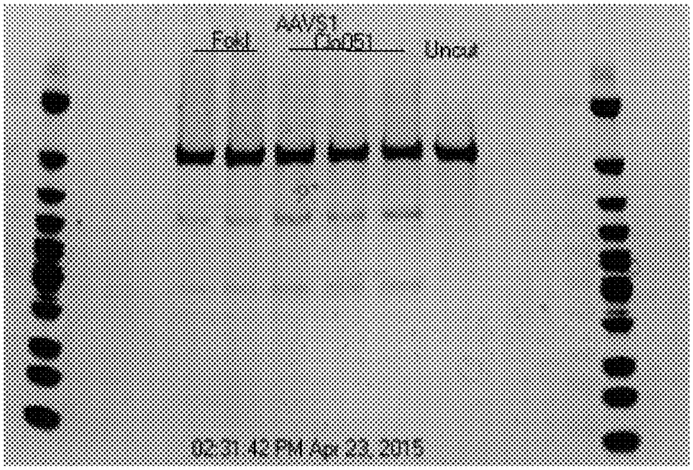
FIG. 7 is a photograph of a gel depicting the results of a Cell Assay with TALE-Clo051. Cutting efficiency of TALE-Clo051 (average cutting efficiency of replicates of 8.1%) was compared to the cutting efficiency of TALE-FokI. Average cutting efficiency of replicates of TALE-Clo051 was 8.1% compared to the average cutting efficiency of replicates of TALE-FokI, which was 7.1%. Thus, TALE-Clo051 has a superior cutting efficiency to TALE-FokI.

As shown in FIG. 7, for example, *Xanthomonas*-TALE-Clo051 (XTC) polypeptides of the disclosure, including TALE-Clo051, demonstrate superior cutting efficiency compared to TALE-FokI. In this experiment, endonuclease activity (cutting efficiency) was determined in a CEL I mismatch endonuclease assay using either TALE-Clo051 or TALE-FokI. Cell assays are described in greater detail in Kulinski et al. The CEL I Enzymatic Mutation Detection Assay, BioTechniques 29(1):44-48 (July 2000) (the contents of which are herein incorporated by reference). Moreover, FIG. 8 depicts another comparison of endonuclease activity, also demonstrated by CEL I assay, between XTN TALEN compositions of the disclosure and alternative TALEN constructs that are not encompassed by the disclosure.

Figure 8:
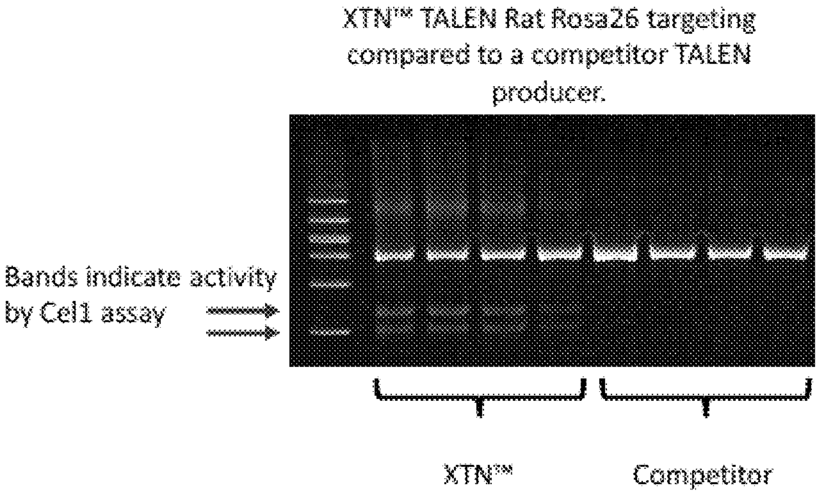
FIG. 8 is a photograph of a gel depicting a Cell assay comparing the relative nuclease activity of the *Xanthomonas*-TALE-Nuclease (XTN) TALEN of the disclosure to TALEN not encompassed by this disclosure. XTN TALENS of the disclosure have significantly higher activity than TALENs not encompassed by this disclosure.

The results of the assay shown in FIG. 8 indicate that XTN TALENS of the disclosure have significantly higher activity than TALENS known in the art.

Figure 11:
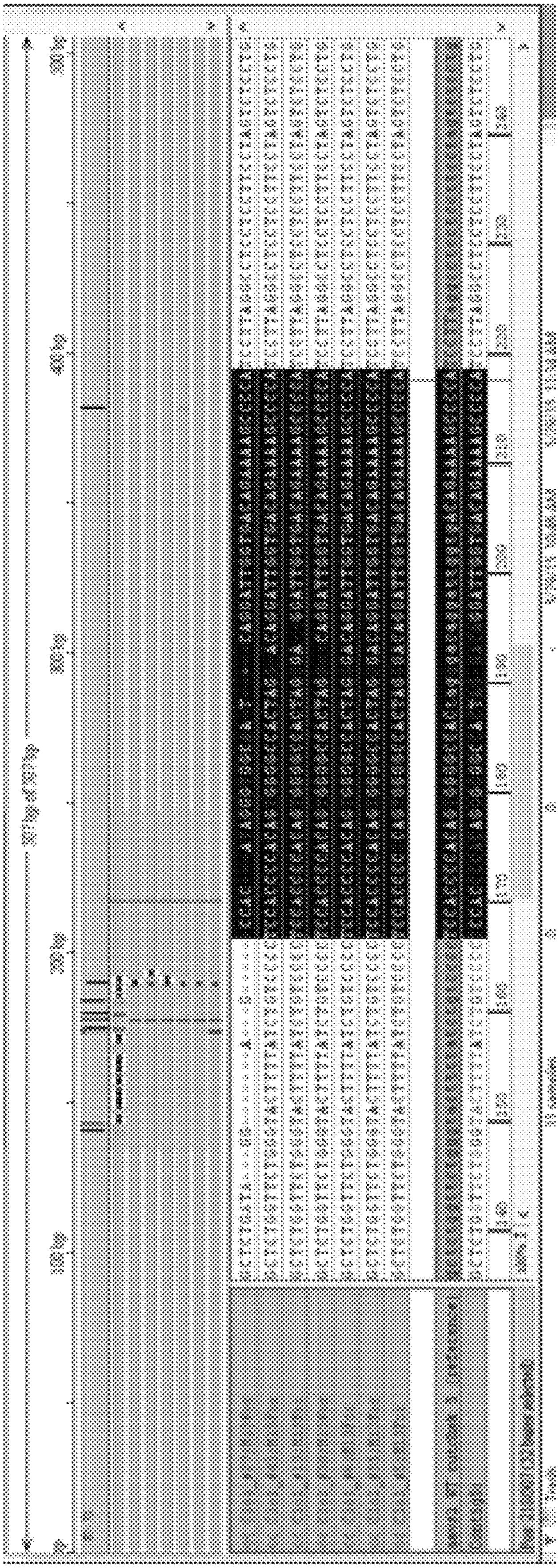
FIG. 11 is a photograph of an alignment of clones of Clo051-XTN. The AAV1 locus was amplified from Clo051-XTN treated samples, TOPO cloned, and 48 clones from each sample were sequenced. Sequencing results indicated that 43 Clo051-XTN clones contained usable sequence. Four of the 43 Clo051-XTN clones had an indel (an insertion or deletion of bases in the sequence) for a 9.3% rate of indel. Among these four Clo051-XTN clones, one clone (#43) has a single base pair (1 bp) deletion, two clones (#13 and 38) have a two base pair (2 bp) deletion, and one clone (#27) has a −52/+24 indel. From top to bottom, SEQ ID Nos 285 to 293 are shown.
Figure 12:
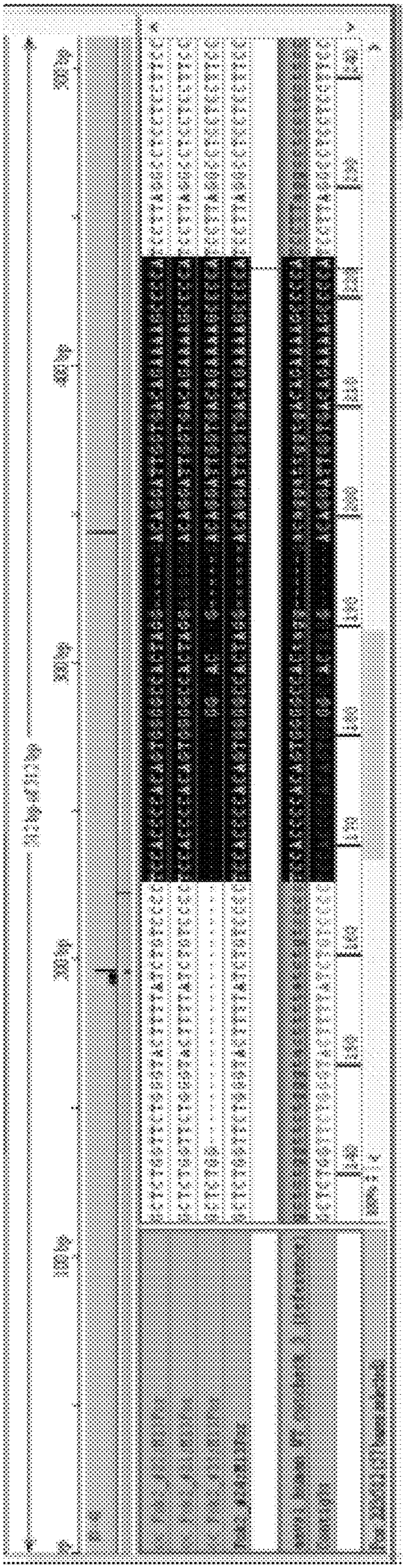
FIG. 12 is a photograph of an alignment of clones of FokI-XTN. The AAV1 locus was amplified from FokI-XTN treated samples, TOPO cloned, and 48 clones from each sample were sequenced. Sequencing results indicated that 46 FokI-XTN clones contained usable sequence. Three of the 46 FokI-XTN clones had an indel (an insertion or deletion of bases in the sequence) for a 6.5% rate of indel. Among these three unique FokI-XTN clones, one clone (#24) has a single base pair (1 bp) deletion, one clone (#21) have a five base pair (5 bp) insertion, and one clone (#35) has a −47/+4 indel. From top to bottom, SEQ ID Nos 294 to 299 are shown.

FIG. 11 depicts an alignment of XTN-Clo051 clones (encoding an XTC polypeptide of the disclosure). Sequence analysis revealed a low rate of insertion or deletion (indel) in the DNA sequences of these clones.

Figure 13:
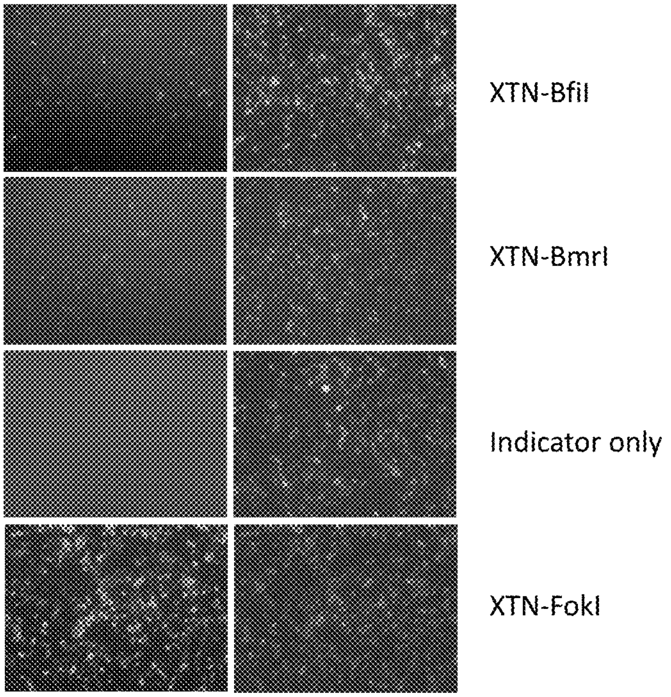
FIG. 13 is a series of photographs depicting the results of transfection and nuclease activity in HEK293 cells treated with either TAL-BfiI (XTN-BfiI) or TAL-BmrI (XTN-BmrI), when compared to treatment with XTN-FokI used herein as a positive control. Indicator only condition used as a negative control. Pictures were captured three days after transfection of the cells with AAVS1 XTN (one or XTN-BfiI, XTN-BmrI or XTN-FokI) with an indicator.

XTN compositions of the disclosure may include any endonuclease, including, but not limited to, *Xanthomonas*-TALE-BfiI and *Xanthomonas*-TALE-BmrI. The activity of these XTN compositions transfected into HEK293 cells is demonstrated in FIG. 13.

An exemplary BfiI nuclease domain may comprise, consist essentially of or consist of, the amino acid sequence below wherein the catalytic residues include H105, K107, N125, and E136:

```
                                          (SEQ ID NO: 37)
MNFFSLHPNVYATGRPKGLIGMLENVWVSNHTPGEGTLYLISGFSNYNGG
VRFYETFEHINQGGRVIAILGGSTSQRLSSRQVVEELLNRGVEVHIINRK
RILHAKLYGTSNNLGESLVVSSGNFTGPGMSQNIEASLLLDNNTTQSMGF
SWNDMISEMLNQNWHIHNMTNATDASPGWNLLYDERTTNLTL
```

An exemplary BmrI nuclease domain may comprise, consist essentially of or consist of, the amino acid sequence below wherein the catalytic residues include H105, K107, N125, and E136:

(SEQ ID NO: 38)

```
MNYFSLHPNVYATGRPKGLINMLESVWISNQKPGDGTMYLISGFANYNGG

IRFYETFTEHINHGGKVIAILGGSTSQRLSSKQVVAELVSRGVDVYIINR

KRLLHAKLYGSSSNSGESLVVSSGNFTGPGMSQNVEASLLLDNNTTSSMG

FSWNGMVNSMLDQKWQIHNLSNSNPTSPSWNLLYDERTTNLTL
```

*Ralstonia*

The disclosure provides polypeptides derived from *Ralstonia* amino acid sequences or amino acid sequences related thereto, nucleic acids encoding the same, compositions comprising the same, kits comprising the same, non-human transgenic animals comprising the same, and methods of using the same.

Repeat variable diresidues (RVDs) of *Ralstonia* effectors correspond to the nucleotides in their target sites in a direct, linear fashion, one RVD to one nucleotide, with some degeneracy and no apparent context dependence. This finding represents a mechanism for protein-DNA recognition that enables target site prediction for new target-specific *Ralstonia* effectors.

As described herein, effector proteins derived from *Ralstonia*, including TAL proteins, may be used as part of a larger targeted chimeric protein (i.e. a component of a chimeric protein). Chimeric effector proteins of the disclosure, including those comprising or consisting of a TAL protein, or any component thereof, may demonstrate accessory activities related to nucleic acids such as nuclease activity. For instance, in some embodiments, a polypeptide or pronucleases that can facilitate homologous recombination in genome engineering may be used as a component of a chimeric protein. In certain embodiments, a transcription factor may be used as a component of a chimeric protein, making the resultant chimeric protein particularly useful for therapeutic compositions and uses thereof requiring a very high level of specificity (including therapeutic compositions and uses thereof directed against pathogens (e.g., viruses)).

Polypeptides or proteins of the disclosure may be derived from polypeptides or proteins found in *Ralstonia*. Polypeptides or proteins of the disclosure may contain one or more sequences that are neither identical to any polypeptide or protein found in *Ralstonia* nor naturally-occurring in *Ralstonia*.

Polypeptides or proteins of the disclosure may comprise at least a first domain and a second domain, wherein the first domain comprises at least one coding sequence for a nucleic acid recognition element and the second domain comprises at least one coding sequence for a nucleic acid effector element.

As used throughout the disclosure, the term "RTN" refers to a *Ralstonia* TALE Nuclease. RTNs of the disclosure may refer to a polypeptide or protein that comprises at least a first domain wherein the first domain comprises at least one coding sequence for a nucleic acid recognition element derived from an amino acid sequence derived from *Ralstonia*. RTNs of the disclosure may refer to a polypeptide or proteins of the invention that comprise at least a first domain and a second domain, wherein the first domain comprises at least one coding sequence for a nucleic acid recognition element derived from an amino acid sequence derived from *Ralstonia* and the second domain comprises a amino acid that is an effector protein. RTNs of the disclosure may refer to a polypeptide or proteins of the invention that comprise at least a first domain and a second domain, wherein the first domain comprises at least one coding sequence for a nucleic acid recognition element derived from an amino acid sequence derived from *Ralstonia* and the second domain comprises a amino acid that is a nuclease.

RTN DNA binding specificity depends on the number and order of repeat domains in the DNA binding domain. For example, repeats may comprise from about 30 to about 40 amino acids. Alternatively, repeats may comprise from about 32 to about 38 amino acids, from about 33 to about 37 amino acids, from about 34 to about 35 amino acids, from about 33 to about 36 amino acids, or from about 33 to about 35 amino acids. Repeats may consist of 34 to 35 amino acids, consist of 33 to 35 amino acids, or consist of 34 to 36 amino acids.

Nucleotide binding specificity of repeat domains of the disclosure may be determined by the 12 and 13 amino acids of each repeat domain.

Polypeptides or proteins of the disclosure may comprise at least one RVD sequence selected from the following: SI, SN, SH, NP, NH, NT, NK, NN, ND, HN, HY, HD, HH, RN, RS, and GS. Polypeptides or proteins of the disclosure may comprise at least one RVD sequence in any combination selected from the following: SI, SN, SH, NP, NH, NT, NK, NN, ND, HN, HY, HD, HH, RN, RS, NG and GS; wherein SI, SN, SH, NP, and NH bind any nucleic acid base; wherein NT, NK, and NN bind adenine; wherein ND, HN, HY, HD, and HH bind adenine and/or guanine; wherein NG binds thymine; wherein RN, RS, and GS bind guanine. Polypeptides or proteins of the disclosure may comprise at least one RVD sequence in any combination selected from the following: SI, SN, SH, NP, NH, NT, NK, NN, ND, HN, HY, HD, HH, RN, RS, NG and GS; wherein SI, SN, SH, NP, and NH bind any nucleic acid base; wherein NK binds guanine, and NN binds adenine or guanine; wherein ND, HN, HY, HD, and HH bind cytosine; wherein NG binds thymine; wherein RN, RS, and GS bind guanine. Polypeptides or proteins of the disclosure may comprise at least one RVD sequence in any combination selected from the following: SI, SN, SH, NP, NH, NT, NK, NN, ND, HN, HY, HD, HH, RN, RS, NG and GS; wherein SI binds adenine; SN binds guanine and/or adenine, SH, NP, and NH bind any nucleic acid base; wherein NK binds guanine; and NN binds adenine and/or guanine; wherein ND binds cytosine, HN binds guanine, HY, HD, and HH bind cytosine; wherein NG binds thymine; wherein RN binds guanine and/or adenine; wherein RS and GS binds guanine. Polypeptides or proteins of the disclosure may comprise at least one RVD sequence in any combination wherein at least one of the RVD sequences is NP, ND, or HN; and wherein NP binds cytosine, adenine, and guanine; wherein ND binds cytosine; and wherein HN binds adenine and/or guanine.

Polypeptides or proteins of the disclosure may comprise, consist essentially of, or consist of SEQ ID NO: 1.

Polypeptides or proteins of the disclosure may comprise, consist essentially of, or consist of SEQ ID NO: 1, wherein $X_1X_2$ bind to a single nucleic acid. Polypeptides or proteins of the disclosure may comprise, consist essentially of, or consist of SEQ ID NO: 1, wherein $X_1X_2$ bind to at least one nucleic acid.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein $X_1$=naturally occurring or non-naturally amino acid and wherein $X_2$=naturally occurring or non-naturally amino acid.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein, in any combination, $X_1$ and $X_2$ are independently variable, $X_1$=A, N, H, R or G; and $X_2$=I, N, H, K, Y, T, D, S, or P.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein $X_1$=S and $X_2$=I.

Polypeptides or proteins of the disclosure may comprise at least 80%, 85%, 90%, 95%, 96%, 97%, 98%, or 99% sequence identity to LSTEQVVAIASX$_1$X$_2$GGKQALEAVKAQLLVLRAAPYE (SEQ ID NO: 1); wherein $X_1$=S and $X_2$=N.

Polypeptides or proteins of the disclosure may comprise at least 80% sequence identity to SEQ ID NO: 1. Polypeptides or proteins of the disclosure may comprise at least 90% sequence identity to SEQ ID NO: 1. Polypeptides or proteins of the disclosure may comprise at least 91% sequence identity to SEQ ID NO: 1. Polypeptides or proteins of the disclosure may comprise at least 92% sequence identity to SEQ ID NO: 1. Polypeptides or proteins of the disclosure may comprise at least 93% sequence identity to SEQ ID NO: 1. Polypeptides or proteins of the disclosure may comprise at least 94% sequence identity to SEQ ID NO: 1. Polypeptides or proteins of the disclosure may comprise at least 95% sequence identity to SEQ ID NO: 1. Polypeptides or proteins of the disclosure may comprise at least 96% sequence identity to SEQ ID NO: 1. Polypeptides or proteins of the disclosure may comprise at least 97% sequence identity to SEQ ID NO: 1. Polypeptides or proteins of the disclosure may comprise at least 98% sequence identity to SEQ ID NO: 1. Polypeptides or proteins of the disclosure may comprise at least 99% sequence identity to SEQ ID NO: 1.

Polypeptides or proteins of the disclosure may comprise at least 80% sequence identity to SEQ ID NO:1 and comprise more than one of the amino acid substitution in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 90° % sequence identity to SEQ ID NO:1 and comprise more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 95% sequence identity to SEQ ID NO:1 and comprise more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 99% sequence identity to SEQ ID NO:1 and comprise more than one of the amino acid substitutions in any of the polypeptides chosen from SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 80%, 85%, 90%, 91%, 92%, 93%, 94%, 95%, 96%, 97%, 98%, or 99% sequence identity to SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least one, two, three, or four polypeptide sequences selected from polypeptides comprising at least 80%, 85%, 90%, 91%, 92%, 93%, 94%, 95%, 96%, 97%, 98%, or 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Polypeptides or proteins of the disclosure may comprise at least 80%, 85%, 90%, 95%, 96%, 97%, 98%, or 99% sequence identity to

```
                                    (SEQ ID NO: 2)
LSTEQVVAIASSIGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                    (SEQ ID NO: 3)
LSTEQVVAIASSNGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                    (SEQ ID NO: 4)
LSTEQVVAIASSHGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                    (SEQ ID NO: 5)
LSTEQVVAIASNPGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                    (SEQ ID NO: 6)
LSTEQVVAIASNHGGKQALEAVKAQLLVLRAAPYE.
```

Polypeptides or proteins of the disclosure may comprise at least 80%, 85%, 90%, 95%, 96%, 97%, 98%, or 99% sequence identity to

```
                                    (SEQ ID NO: 7)
LSTEQVVAIASNTGGKQALEAVKAQLLVLRAAPYE.
```

Polypeptides or proteins of the disclosure may comprise at least 80%, 85%, 90%, 95%, 96%, 97%, 98%, or 99% sequence identity to (SEQ ID NO: 8)
LSTEQVVAIASNKGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 9)
LSTEQVVAIASNPGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 10)
LSTEQVVAIASNNGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 11)
LSTEQVVAIASNDGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 12)
LSTEQVVAIASNGGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 13)
LSTEQVVAIASHNGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 14)
LSTEQVVAIASHYGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 15)
LSTEQVVAIASHDGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 16)
LSTEQVVAIASHHGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 17)
LSTEQVVAIASRNGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 18)
LSTEQVVAIASRSGGKQALEAVKAQLLVLRAAPYE.

Polypeptides or proteins of the disclosure may comprise at least 80%, 85%, 90%, 95%, 96%, 97%, 98%, or 99% sequence identity to (SEQ ID NO: 19)
LSTEQVVAIASGSGGKQALEAVKAQLLVLRAAPYE.

Polypeptides or proteins of the disclosure may comprise, consist essentially of or consist of any combination of polypeptide sequences with at least 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO: 18, and SEQ ID NO:19.

Polypeptides or proteins of the disclosure may comprise, consist essentially of or consist of any combination of a polypeptide sequences with at least 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO: 18, and SEQ ID NO:19, wherein the 12' and 13' amino acid of at least one of the polypeptide sequences binds at least one nucleic acid.

Polypeptides or proteins of the disclosure may comprise, consist essentially of or consist of any combination of a polypeptide sequences with 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO: 18, and SEQ ID NO:19.

Polypeptides or proteins of the disclosure may comprise, consist essentially of or consist of a first domain and a second domain, wherein the first domain is a nucleic acid recognition domain that comprises, consists essentially of or consists of at least one combination of polypeptide sequences with 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19.

Polypeptides or proteins of the disclosure may comprise, consist essentially of or consist of a first domain and a second domain, wherein the first domain is a nucleic acid recognition domain that comprises, consists essentially of or consists of at least one combination of a polypeptide sequences with 80%, 85%, 90%, 91%, 92%, 93%, 94%, 95%, 96%, 97%, 98%, or 99% sequence identity to the polypeptides chosen from: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and SEQ ID NO:19; wherein the $12^{th}$ and $13^{th}$ amino acid of at least one polypeptide sequence bind a nucleic acid.

The disclosure also provides nucleic acids encoding any one or more of the polypeptides or proteins described above. Nucleic acids of the disclosure may comprise, comprise essentially of, or consist of nucleic acid sequences that encode at least 2, 3, 4, 5 or more polypeptides chosen from polypeptides comprising at least 80%, 85%, 90%, 91%, 92%, 93%, 94%, 95%, 96%, 97%, 98%, or 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, or SEQ ID NO:19.

Compositions

The disclosure provides nucleic acid sequences that encode any protein or polypeptide described herein. Compositions of the disclosure may comprise, consist essentially of, or consist of at least one nucleic acid sequence that encodes a protein or polypeptide described herein. Compositions of the disclosure may comprise, consist essentially of, or consist of a plurality of (i.e. one or more) nucleic acid sequences that encode any protein or polypeptide described herein. Compositions of the disclosure may comprise, consist essentially of, or consist of at least one amino acid sequence described herein. Compositions of the disclosure may comprise, consist essentially of, or consist of a plurality of (i.e. one or more) amino acid sequences described herein.

The disclosure provides vectors comprising, consisting essentially of or consisting of any one or more of the nucleic acid sequences of the disclosure encoding any one or more of the proteins of the disclosure. In some embodiments, the vector is a plasmid. In some embodiments, the vector is a retrovirus. Retrovirus vectors of the disclosure may comprise, for example, long terminal-repeats, a psi packaging signal, a cloning site, and a sequence encoding a selectable marker.

The disclosure provides cells comprising any one or more of the nucleic acids or vectors of the disclosure. In some embodiments, the cell is a sperm or an egg.

The disclosure provides kits comprising: a vector comprising a nucleic acid encoding any one or more of the proteins of the disclosure.

The disclosure provides non-human, transgenic animals comprising a nucleic acid molecule encoding any one or more of the proteins of the disclosure.

Organisms of the disclosure are unicellular or multicellular. Multicellular organisms may include, but are not limited to, vertebrates. Exemplary vertebrate animals may include, but are not limited to, mammals. Exemplary vertebrate animals may include, but are not limited to, non-human mammals.

Expression Cassettes and Vectors

The DNA sequences of the invention can be provided in expression cassettes for expression in any prokaryotic or eukaryotic cell and/or organism of interest including, but not limited to, bacteria, fungi, algae, plants, and animals. Exemplary cassettes include 5' and 3' regulatory sequences operably linked to a DNA sequence of the invention.

As used throughout the disclosure, the term "operably linked" refers to a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the DNA sequence to be under the transcriptional regulation of the regulatory regions. The expression cassette may additionally contain selectable marker genes.

Exemplary expression cassettes may include in the 5'-3' direction of transcription, a transcriptional and translational initiation region (i.e., a promoter), a DNA sequence of the invention, and a transcriptional and translational termination region (i.e., termination region) functional in plants or other organism or non-human host cell. The regulatory regions (i.e., promoters, transcriptional regulatory regions, and translational termination regions) and/or the DNA sequence of the invention may be native/autologous to the host cell or to each other. Alternatively, the regulatory regions and/or DNA sequence of the invention may be heterologous to the host cell or to each other. As used throughout the disclosure, the term "heterologous" refers to a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

Termination regions of the disclosure may be native with a transcriptional initiation region, may be native with the operably linked DNA sequence of interest, may be native with the host, or may be derived from another source (i.e., foreign or heterologous) to the promoter, the DNA sequence of interest, the plant host, or any combination thereof. Convenient termination regions for use in plants are available from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671-674; Sanfacon et al. (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acids Res. 15:9627-9639.

Polynucleotides of the disclosure may be optimized for increased expression in a transformed organism. That is, the polynucleotides can be synthesized using codons preferred by the host for improved expression. See, for example, Campbell and Gown (1990) Plant Physiol. 92:1-11 for a discussion of host-preferred codon usage. Methods are available in the art for synthesizing host-preferred gene, particularly plant-preferred genes. See, for example, U.S. Pat. Nos. 5,380,831, and 5,436,391, and Murray et al. (1989) Nucleic Acids Res. 17:477-498, herein incorporated by reference.

Additional sequence modifications may be used to enhance gene expression in a cellular host. Exemplary sequence modifications include, but are not limited to, elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

Expression cassettes of the disclosure may contain 5' leader sequences. Such leader sequences can act to enhance translation. Translation leaders are known in the art and include, for example: picornavirus leaders, for example, EMCV leader (Encephalomyocarditis 5' noncoding region) (Elroy-Stein et al. (1989) Proc. Natl. Acad. Sci. USA 86:6126-6130); potyvirus leaders, for example, TEV leader (Tobacco Etch Virus) (Gallie et al. (1995) Gene 165(2):233-238), MDMV leader (Maize Dwarf Mosaic Virus) (Virology 154:9-20), and human immunoglobulin heavy-chain binding protein (BiP) (Macejak et al. (1991) Nature 353:90-94); untranslated leader from the coat protein mRNA of alfalfa mosaic virus (AMV RNA 4) (Tabling et al. (1987) Nature 325:622-625); tobacco mosaic virus leader (TMV) (Gallie et al. (1989) in Molecular Biology of RNA, ad. Cech (Liss, New York), pp. 237-256); and maize chlorotic mottle virus leader (MCMV) (Lommel et al. (1991) Virology 81:382-385). See also, Della-Cioppa et al. (1987) Plant Physiol. 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The disclosure provides viral vectors comprising any one or more than one nucleic acid sequence disclosed herein. The viral vector is optionally selected from the group comprising a retroviral vector, an adenoviral vector, an adeno-associated viral vector, spumaviral, a lentiviral vector and a plasmid or other vector, such as transposons, described in the application. The retroviral vector optionally comprises an oncoretroviral vector. The retroviral vector optionally comprises a lentiviral vector.

Numerous plant transformation vectors and methods for transforming plants are available. See, for example, An, G. et al. (1986) Plant Pysiol., 81:301-305; Fry, J., et al. (1987) Plant Cell Rep. 6:321-325; Block, M. (1988) Theor. Appl Genet. 76:767-774; Hinchee, et al. (1990) Stadler. Genet. Symp. 203212.203-212; Cousins, et al. (1991) Aust. J. Plant Physiol. 18:481-494; Chee, P. P. and Slightom, J. L. (1992) Gene. 118:255-260; Christou, et al. (1992) Trends. Biotechnol. 10:239-246; D'Halluin, et al. (1992) Bio/Technol. 10:309-314; Dhir, et al. (1992) Plant Physiol. 99:81-88; Casas et al. (1993) Proc. Nat. Acad Sci. USA 90:11212-11216; Christou, P. (1993) In Vitro Cell. Dev. Biol.-Plant; 29P:119-124; Davies, et al. (1993) Plant Cell Rep. 12:180-183; Dong, J. A. and Mchughen, A. (1993) Plant Sci. 91:139-148; Franklin, C. I. and Trieu, T. N. (1993) Plant. Physiol. 102:167; Golovkin, et al. (1993) Plant Sci. 90:41-52; Guo Chin Sci. Bull. 38:2072-2078; Asano, et al. (1994) Plant Cell Rep. 13; Ayeres N. M. and Park, W. D. (1994) Crit. Rev. Plant. Sci. 13:219-239; Barcelo, et al. (1994) Plant. J. 5:583-592; Becker, et al. (1994) Plant. J. 5:299-307; Borkowska et al. (1994) Acta. Physiol Plant. 16:225-230; Christou, P. (1994) Agro. Food. Ind. Hi Tech. 5: 17-27; Eapen et al. (1994) Plant Cell Rep. 13:582-586; Hartman, et al. (1994) Bio-Technology 12: 919923; Ritala, et al. (1994) Plant. Mol. Biol. 24:317-325; and Wan, Y. C. and Lemaux, P. G. (1994) Plant Physiol. 104:3748.

Pharmaceutical Compostions

Compositions of the disclosure may be pharmaceutical compositions. Pharmaceutical compositions of the disclosure may be used to treat patients having diseases, disorders or abnormal physical states, and comprise an acceptable carrier, auxiliary or excipient.

The pharmaceutical compositions are optionally administered by ex vivo and in vivo methods such as electroporation, DNA microinjection, liposome DNA delivery, and virus vectors that have RNA or DNA genomes including retrovirus vectors, lentivirus vectors, Adenovirus vectors and Adeno-associated virus (AAV) vectors, Semliki Forest Virus. Derivatives or hybrids of these vectors are also useful.

Dosages to be administered depend on patient needs, on the desired effect and on the chosen route of administration. The expression cassettes are optionally introduced into the cells or their precursors using ex vivo or in vivo delivery vehicles such as liposomes or DNA or RNA virus vectors. They are also optionally introduced into these cells using physical techniques such as microinjection or chemical methods such as coprecipitation.

The pharmaceutical compositions are typically prepared by known methods for the preparation of pharmaceutically acceptable compositions which are administered to patients, and such that an effective quantity of the nucleic acid molecule is combined in a mixture with a pharmaceutically acceptable vehicle. Suitable vehicles are described, for example in Remington's Pharmaceutical Sciences (*Remington's Pharmaceutical Sciences*, Mack Publishing Company, Easton, Pa., USA). Any selectable marker gene can be used in the present invention.

On this basis, the pharmaceutical compositions could include an active compound or substance, such as a nucleic acid molecule, in association with one or more pharmaceutically acceptable vehicles or diluents, and contained in buffered solutions with a suitable pH and isoosmotic with the physiological fluids. The methods of combining the expression cassettes with the vehicles or combining them with diluents are well known to those skilled in the art. The composition could include a targeting agent for the transport of the active compound to specified sites within cells. The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as .beta.-galactosidase and fluorescent proteins such as green fluorescent protein (GFP) (Su et al. (2004) Biotechnol Bioeng 85:610-9 and Fetter et al. (2004) Plant Cell 16:215-28), cyan florescent protein (CYP) (Bolte et al. (2004) J. Cell Science 117:943-54 and Kato et al. (2002) Plant Physiol 129:913-42), and yellow florescent protein (PhiYFP™ from Evrogen, see, Bolte et al. (2004) J. Cell Science 117:943-54). For additional selectable markers, see generally, Yarranton (1992) Curr. Opin. Biotech. 3:506-511; Christopherson et al. (1992) Proc. Natl. Acad. Sci. USA 89:6314-6318; Yao et al. (1992) Cell 71:63-72; Reznikoff (1992) Mol. Microbiol. 6:2419-2422; Barkley et al. (1980) in The Operon, pp. 177-220; Hu et al. (1987) Cell 48:555-566; Brown et al. (1987) Cell 49:603-612; Figge et al. (1988) Cell 52:713-722; Deuschle et al. (1989) Proc. Natl. Acad. Aci. USA 86:5400-5404; Fuerst et al. (1989) Proc. Natl. Acad. Sci. USA 86:2549-2553; Deuschle et al. (1990) Science 248:480-483; Gossen (1993) Ph.D. Thesis, University of Heidelberg; Reines et al. (1993) Proc. Natl. Acad. Sci. USA 90:1917-1921; Labow et al. (1990) Mol. Cell. Biol. 10:3343-3356; Zambretti et al. (1992) Proc. Natl Acad. Sci. USA 89:3952-3956; Baim et al. (1991) Proc. Natl. Acad. Sci. USA 88:5072-5076; Wyborski et al. (1991) Nucleic Acids Res. 19:4647-4653; Hillenand-Wissman (1989) Topics Mol. Struc. Biol. 10:143-162; Degenkolb et al. (1991) Antimicrob. Agents Chemother. 35:1591-1595; Kleinschnidt et al. (1988) Biochemistry 27:1094-1104; Bonin (1993) Ph.D. Thesis, University of Heidelberg; Gossen et al. (1992) Proc. Natl. Acad. Sci. USA 89:5547-5551; Oliva et al. (1992) Antimicrob. Agents Chemother. 36:913-919; Hlavka et al. (1985) Handbook of Experimental Pharmacology, Vol. 78 (Springer-Verlag, Berlin); Gill et al. (1988) Nature 334:721-724. Such disclosures are herein incorporated by reference.

Genetically-Modified Cells and Organisms

The disclosure provides a eukaryotic cell comprising a mutation, a heterologous gene, a variant and/or another genetic modification caused by introduction of one or more nucleic acids or polypeptides described herein.

The disclosure provides a mammalian cell comprising a mutation, a heterologous gene, a variant and/or another genetic modification caused by introduction of one or more nucleic acids or polypeptides described herein.

The disclosure provides a human cell comprising any one or combination of proteins or nucleic acid sequences disclosed herein. For example, the disclosure provides a human cell comprising a mutation, a heterologous gene, a variant, and/or another genetic modification caused by introduction of one or more nucleic acids or polypeptides described herein. Alternatively, the disclosure provides non-human cells comprising a mutation, a heterologous gene, a variant and/or another genetic modification caused by introduction of one or more nucleic acids or polypeptides described herein.

The disclosure provides an insect cell comprising a mutation, a heterologous gene, a variant and/or other genetic modification caused by introduction of one or more nucleic acids or polypeptides described herein.

The disclosure provides a fish cell comprising a mutation, a heterologous gene, a variant and/or other genetic modification caused by introduction of one or more nucleic acids or polypeptides described herein.

The disclosure provides a plant cell comprising a mutation, a heterologous gene, a variant and/or other genetic modification caused by introduction of one or more nucleic acids or polypeptides described herein.

The disclosure provides plants (and portions or parts thereof), seeds, plant cells and other non-human host cells transformed with the isolated nucleic acid molecules of the disclosure and the proteins or polypeptides encoded by the nucleic acid molecules (including coding regions thereof) of the disclosure. Polypeptides and DNA molecules described herein may be introduced into animal and human cells as well as cells of other organisms, including, but not limited to, fungi or plants.

Compositions of the disclosure may be used for site-specific modification of the genome of any cell, including, but not limited to, stem cells and gametes. Exemplary stem cells include pluripotent cells, totipotent cells, somatic stem cells, spermatogonial stem cells (SSCs), embryonic stem (ES) cells, induced pluripotent stem (iPS) cells, embryos, germ cells, primordial germ cells (PGCs), plant tube cells, pollen cells, and spores.

Site-specific engineering of stem cells results in altered function of gene(s) or gene product(s) and genetically modified organisms, and cell or tissue culture models are produced from these engineered stem cells. Modified stem cells and organisms include knockout and knockin cells and organisms.

Genetically modified organisms created by site-specific engineering using the compositions and methods of the disclosure, include, but not limited to mammals (e.g. rats, mice, pigs, rabbits, guinea pigs, dogs, non-human primates, mini-pigs) as well as plants (e.g., maize, soybean, rice, potato, wheat, tobacco, tomato, and *Arabidopsis*, as well as the descendants and ancestors of such organisms).

Gene Therapy

The application includes methods and compositions for providing a coding nucleic acid molecule to the cells of an individual such that expression of the coding nucleic acid molecule in the cells provides the biological activity or phenotype of the polypeptide encoded by the coding nucleic acid molecule. The method also relates to a method for providing an individual having a disease, disorder or abnormal physical state with a biologically active polypeptide by administering a nucleic acid molecule of the present application. The method may be performed ex vivo or in vivo. Gene therapy methods and compositions are demonstrated, for example, in U.S. Pat. Nos. 5,869,040, 5,639,642, 5,928,214, 5,911,983, 5,830,880, 5,910,488, 5,854,019, 5,672,344, 5,645,829, 5,741,486, 5,656,465, 5,547,932, 5,529,774, 5,436,146, 5,399,346 and 5,670,488, 5,240,846. The amount of polypeptide will vary with the subject's needs. The optimal dosage of vector may be readily determined using empirical techniques, for example by escalating doses (see U.S. Pat. No. 5,910,488 for an example of escalating doses). Vectors containing the nucleic acid molecules of the application are typically administered to mammals, preferably humans, in gene therapy using techniques described below. The polypeptides produced from the nucleic acid molecules are also optionally administered to mammals, preferably humans. The application relates to a method of medical treatment of a mammal in need thereof, preferably a human, by administering to the mammal a vector of the application or a cell containing a vector of the application. A recipient, preferably human, who develops an adverse event, such as graft versus host disease, is typically administered a drug, such as AZT, that is a substrate for the modified tmpk molecules of the application. Diseases, such as blood diseases or neural diseases (neurodegenerative), that are readily treated are described in this application and known in the art (e.g. diseases, such as thalassemia or sickle cell anemia that are treated by administering a globin gene as described in Canadian patent application no. 2,246,005). Blood diseases treatable by stem cell transplant include leukemias, myelodysplastic syndromes, stem cell disorders, myeloproliferative disorders, lymphoproliferative disorders phagocyte disorders, inherited metabolic disorders, histiocytic disorders, inherited erythrocyte abnormalities, inherited immune system disorders, inherited platelet abnormalities, plasma cell disorders, malignancies (See also, Medical Professional's Guide to Unrelated Donor Stem Cell Transplants, 4th Edition). Stem cell nerve diseases to be treated by neural stem cell transplantation include diseases resulting in neural cell damage or loss, (e.g. paralysis, Parkinson's disease, Alzheimer's disease, ALS, multiple sclerosis). The vector of the application is useful as a stem cell marker and to express genes that cause stem cells to differentiate (e.g. growth factor).

Various approaches to gene therapy may be used. The disclosure provides a method for providing a human with a therapeutic polypeptide including: introducing human cells into a human, the human cells having been treated in vitro or ex vivo to insert therein a vector of the application, the human cells expressing in vivo in the human a therapeutically effective amount of the therapeutic polypeptide.

The method also relates to a method for producing a stock of recombinant virus by producing virus suitable for gene therapy comprising modified DNA encoding globin. This method preferably involves transfecting cells permissive for virus replication (the virus containing modified globin) and collecting the virus produced.

Cotransfection (DNA and marker on separate molecules) may be employed (see eg U.S. Pat. Nos. 5,928,914 and 5,817,492). As well, a detection cassette or marker (such as Green Fluorescent Protein marker or a derivative, CD19 or CD25) may be used within the vector itself (preferably a viral vector).

Methods of the disclosure may be used to mutate any eukaryotic stem cell, including, but not limited to, haploid, diploid, triploid, tetraploid, or aneuploid. In one embodiment, the cell is diploid. Stem cells in which the methods of the present invention can be advantageously used include, but are not limited to stem cells such as somatic stem cells, SSCs, ES cells, iPS cells, embryos, or any cell capable of developing into one or more organisms.

The disclosure provides a method to produce a site-specific knockout, knock-in or otherwise genetically modified stem cell. The site-specific mutation is generated using a composition of the disclosure that cleaves the desired site, followed by NHEJ repair, resulting in deletion mutations. The site-specific mutation can be produced in spermatogonial stem cells (SSCs) which are used to generate heterozygous or homozygous genetically modified organisms.

The disclosure provides a method to produce a site-specific knockout, knock-in or otherwise genetically modified stem cell. The site-specific mutation is generated using a composition of the disclosure that the desired site resulting in deletion mutations. The site specific mutation is produced in embryonic stem (ES) cells, which are used to generate heterozygous or homozygous genetically modified organisms.

The disclosure provides methods to produce a site-specific knockout, knock-in or otherwise genetically modified stem cell. The site specific mutation is generated using a composition that cleaves the desired site resulting in deletion mutations. The site-specific mutation is produced in induced pluripotent stem (iPS) cells, which are used to generate heterozygous or homozygous genetically modified organisms.

The disclosure provides methods to produce a site-specific knockout, knockin or otherwise genetically modified stem cell. The site specific mutation is generated using a composition that cleaves the desired site resulting in deletion mutations. The site-specific mutation is produced in embryos which are used to generate heterozygous or homozygous genetically modified organisms.

The disclosure provides methods to mutate cells within the organism or within the native environment as in tissue explants (e.g., in vivo or in situ). Alternatively, tissues or stem cells isolated from the organism using art-known methods and genes can be mutated according to the methods of the disclosure. The tissues or stem cells are either maintained in culture (e.g., in vitro), or re-implanted into a tissue or organism (e.g., ex vivo).

Methods of Making XTNs and RTNs

Similar to the architecture described in the FLASH assembly method of the disclosure, the disclosure provides a preferred assembly method to construct TALE repeat arrays in which three distinct TALE repeat backbones that differ slightly in their amino acid and DNA sequences occur in a repeated pattern. The first, amino-terminal TALE repeat in an array was designated as a unit. This is followed by β, and γ units and then an α unit that is substantially identical to the first α unit, except for the different positioning of a Type IIS restriction site on the 5' and 3' end (required to enable creation of a unique overhangs needed for cloning into an organized array). The α unit is then followed again by repeats of β and γ units.

For each of four repeat variable di-residues (RVDs) that specifies one of the four DNA bases (NI=A, HD=C, NN=G, NG=T), 10 plasmids were synthesized (IDT) and generated, for a library total of forty pRVD plasmids (ampicillin selectable marker). For example, 10 plasmids were generated for the RVD NI such that NI-1 was an α unit, NI-2 was a β unit, NI-3 was a γ unit, NI-4 was an α unit and so on. For all of these pRVD plasmids, the sequence encoding the TALE repeat domain is flanked by BsaI restriction sites such that the overhangs generated by digestion of any pRVD plasmids encoding units designed to be adjacent to one another (eg. 1 and 2, 2 and 3 etc) with BasI are complementary to each other.

Assembly of pRVDs into XTNs was achieved in two broad steps:

- Step 1a: Clone pRVDs 1 through 10 (specifying the first 10 targeted nucleotides) into pIN-X.
- Step 1b: Clone pRVDs 1 up to 10 (specifying the 11th up to 20th targeted nucleotide) into pIN-Z.
- Step 2: Clone the pIN-X array and the pIN-Z array of TALE repeat backbones into the correct XTN-expression backbone to produce an XTN targeting up to 20 specified nucleotide sequence.

With respect to Step 1a: pRVDs (pRVDs 1 through 10) are selected in the correct order to match the first ten targeted DNA sequences. 100 ng of each pRVD is mixed with 100 ng of pIN-X in a single 20 ul reaction containing 1 ul BsaI (10U, NEB) and 1 ul T4 DNA ligase (2000U, NEB) in T4 DNA ligase buffer (NEB). The reaction is then incubated in a thermocycler to 10 cycles of 5 min at 37° C. and 10 min at 16° C., then heated to 50° C. for 5 min and then 80° C. for 5 min. The mixture is then used to transform *E. coli* cells and plated on LB agar containing 50 ug/ml Kanamycin. Colonies are then screened by colony PCR and sequenced to identify clones that contain the desired 10RVD array.

With respect to Step 1b: pRVDs are selected in the correct order to match the 11th through (upto) 20th targeted DNA sequence. 100 ng of each pRVD is mixed with 100 ng of pIN-Z and the procedure described in Step 1a above is replicated to identify desired clones.

With respect to Step 2: 150 ng of each pIN-X and pIN-Z plasmids containing the intermediary repeat arrays is mixed with 150 ng of the desired XTN expression plasmid in a single 20 ul reaction containing 1 ul BsmBI (10U NEB) and 1 ul T4 DNA ligase (2000U NEB) in T4 DNA ligase buffer (NEB). The reaction is treated and used to transform *E coli* as in Step 1a, except Ampicillin (100 ug/ml) is used in place of Kanamycin for selection of transformants. Clones are screened by colony PCR and sequenced to identify desired clones.

XTN Intermediate plasmids pIN-X and pIN-Z: pIN-X and pIN-Z are Kanamycin selectable plasmids that contain two sites each for BsaI and BsmBI such that when digested with BsaI, produce overhangs that complement the BsaI overhangs of pRVD-1 and pRVD-10 to incorporate an array of pRVDs 1 through 10 into the intermediate plasmids. Several versions of pIN-X have been generated for use depending on the number of repeats to be incorporated (6 through 10 repeats). When intermediate plasmids are digested with BsmBI, overhangs (that flank the cloned TALE repeat arrays) are generated that are complementary to the BsmBI overhangs of each other and that of the XTN expression backbones. This enables generation of an XTN of this architecture: N-terminal sequence—TALE repeat array (10 repeats from pIN-X)— TALE repeat array (6 to 10 repeats from pIN-Z)— C-terminal sequence—Nuclease.

XTN Expression Backbones: Similar to the FLASH system of the disclosure, the last targeted nucleotide specified by the final half Effector Binding Element (EBE), is incorporated in the expression backbone and hence there are four expression backbones that each specify the last targeted nucleotide to be A, C, T or G. The expression backbone contains the XTN N-terminal sequence, the C-terminal sequence linked to a particular obligate dimer nuclease such as FokI (Clo51, BfiI, BmrI).

Methods of Use

The disclosure provides methods of modifying genetic material of a cell or at least one cell of an organism (multicellular or unicellular), the method comprising administering directly to the cell or at least one cell of the organism one or more of the nucleic acids or polypeptides of the disclosure.

Polypeptides of the disclosure may be provided or administered as a nucleic acid encoding the protein. In some embodiments, the nucleic acid encoding the protein is administered with a second nucleic acid sequence that encodes an effector.

The disclosure provide methods for constructing new repeat units and testing the specific binding activities of artificially constructed repeat units specifically recognizing base pairs in a target DNA sequence. The number of repeat units to be used in a repeat domain may be varied for optimal specific binding. Generally, at least 1.5 repeat units are considered as a minimum, although typically at least about 8 repeat units are used. The repeat units are not required to be complete repeat units because repeat units of half the size may be used. Moreover, polypeptides and methods of making and using the polypeptides of the disclosure depend on repeat domains with a particular number of repeat units. Thus, a polypeptide of the disclosure may comprise, for example, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 30.5, 31, 31.5, 32, 32.5, 33, 33.5, 34, 34.5, 35, 35.5, 36, 36.5, 37, 37.5, 38, 38.5, 39, 39.5, 40, 40.5, 41, 41.5, 42, 42.5, 43, 43.5, 44, 44.5, 46, 46.5, 47, 47.5, 48, 48.5, 49, 49.5, 50, 50.5 or more repeat units.

Polypeptides of the disclosure may comprise a repeat domain with repeat units wherein in the repeat units hypervariable regions are included which determine recognition of a base pair in a target DNA sequence. For example, each repeat unit of the repeat domains of the disclosure may include a hypervariable region which determines recognition of one base. pair in a target DNA sequence. Alternatively, 1 or 2 repeat units in a repeat domain may be included which do not specifically recognize a base pair in a target DNA sequence.

Considering the recognition code disclosed herein, a modular arrangement of repeat units is contemplated wherein each repeat unit is responsible for the specific recognition of one base pair in a target DNA sequence. Consequently, in this modular arrangement, a sequence of repeat units may correspond to a sequence of base pairs in a target DNA sequence so that 1 repeat unit corresponds to one base pair.

The disclosure provides a method for selectively recognizing a base pair in a target DNA sequence by a polypeptide that comprises at least one repeat domain, the at least one repeat domain comprising a plurality of repeat units, wherein each repeat unit comprises at least one RVD region. RVD regions of the disclosure determine recognition of a base pair or nucleotide in a target DNA sequence. More specifically, the RVD regions of the disclosure include those amino acids in a DNA-binding polypeptide responsible for selective recognition of base pairs in a target DNA sequence. Having defined these recognition codes (i.e. RVD regions), the disclosure provides a general principle for recognizing specific base pairs in a target DNA sequence by selected amino acids in a polypeptide. Distinct types of monomers that are part of a repeat unit array (or polymer) of varying amino acid length have the capacity to recognize one defined/specific base pair. Within each repeat unit forming a repeat domain, a RVD region is responsible for the specific recognition of a base pair in a target DNA sequence.

Thus, the disclosure provides not only a method for selectively recognizing a base pair in a target DNA sequence by a polypeptide comprising at least one repeat domain comprising repeat units, but also methods for generating target DNA sequences that are selectively recognized by repeat domains in a polypeptide. These polypeptides are useful as molecular biology tools for cloning, mutagenizing or otherwise altering an isolated nucleic acid sequence or other in vivo sequence. The polypeptides and methods of use described herein provide an efficient means of selective mutagenesis.

The disclosure also provides a method for constructing and/or making a polypeptide that recognizes a specific DNA sequence. Polypeptides of the disclosure comprise at least one repeat monomer of the disclosure and can be constructed by a modular approach. This modular approach may include preassembling repeat units in target vectors that, subsequently, may be assembled into a final destination vector. DNA constructs of the disclosure may be codon optimized to recombinantly produce and/or secrete recombinant polypeptides of the disclosure. Any recombinant system in the art can be used to produce a recombinant protein of the disclosure. Exemplary recombinant systems include, but not limited to, baculovirus cells, eukaryotic cells (e.g. mammalian cells), or bacterial cells.

When a target DNA sequence is known, compositions and methods of the disclosure may be used to construct of a modular series of repeat units, including specific recognition amino acid sequences, and assemble these repeat units into a polypeptide in the appropriate order to enable recognition of and specific binding to the desired target DNA sequence. Any polypeptide can be modified by combination with a modular repeat unit DNA-binding domain of the disclosure. Such examples include polypeptides that are transcription activator and repressor proteins, resistance-mediating proteins, nucleases, topoisomerases, ligases, integrases, recombinases, resolvases, methylases, acetylases, demethylases, deacetylases, and any other polypeptide capable of modifying DNA, RNA, or proteins.

The modular repeat unit DNA-binding domain of the disclosure may be combined with a cell compartment localization signal (e.g. a nuclear localization signal), to function at any other regulatory regions, including, but not limited to, transcriptional regulatory regions and translational termination regions.

Modularly designed repeat units of the disclosure may be combined with an endonuclease domain capable of cleaving DNA when brought into proximity with DNA (for example, as a result of binding by the repeat domain). Such endonucleolytic breaks stimulate the rate of homologous recombination in eukaryotes, including fungi, plants, and animals. The ability to simulate homologous recombination at a specific site as a result of a site-specific endonucleolytic break allows the recovery of transformed cells that have integrated a DNA sequence of interest at the specific site, at a much higher frequency than is possible without having made the site-specific break. In addition, endonucleolytic breaks such as those caused by polypeptides formed from a repeat domain and an endonuclease domain are sometimes repaired by the cellular DNA metabolic machinery in a way that alters the sequence at the site of the break, for instance by causing a short insertion or deletion at the site of the break compared to the unaltered sequence. These sequence alterations can cause inactivation of the function of a gene or protein, for instance by altering a protein-coding sequence to make a non-functional protein, modifying a splice site so that a gene transcript is not properly cleaved, making a non-functional transcript, and/or changing the promoter sequence of a gene so that it can no longer by appropriately transcribed.

Breaking DNA using site specific endonucleases can increase the rate of homologous recombination in the region of the breakage. In some embodiments, the Clo051 endonuclease may be utilized in an effector to induce DNA breaks. The Clo051 endonuclease domain functions independently of the DNA binding domain and cuts a double stranded DNA typically as a dimer. For example, an effector could be constructed that contains a repeat domain for recognition of a desired target DNA sequence as well as a Clo051 endonuclease domain to induce DNA breakage at or near the target DNA sequence. Utilization of such effectors enables the generation of targeted changes in genomes (including, for example, additions, deletions and other modifications, analogous to those uses reported for zinc finger nucleases as per Bibikova et al. (2003) Science 300, 764; Urnov et al. (2005) Nature 435, 646; Wright et al. (2005) The Plant Journal 44:693-705; and U.S. Pat. Nos. 7,163,824 and 7,001,768, all of which are herein incorporated by reference in their entireties).

Any other endonuclease domain may be operably-linked with heterologous DNA binding domains to be utilized as an effector. The Clo051 endonuclease is one such non-limiting example. Prior to use of a particular endonuclease, if not already present, the recognition site of that endonuclease must be introduced at the desired location to enhance homologous recombination at that site.

Novel endonucleases may be designed and/or synthesize by, for example, modifying known endonucleases or making chimeric versions of one or more such endonucleases that recognize novel target DNA sequences, thus paving the way for generation of such engineered endonuclease domains to cleave endogenous target DNA sequences of interest (Chevalier et al. (2002) Molecular Cell 10:895-905; WO2007/060495; WO2009/095793; Fajardo-Sanchez et al. (2008) Nucleic Acids Res. 36:2163-2173, both of which are incorporated by reference in their entireties). It is contemplated with respect to the compositions and methods of the disclosure that endonuclease domains may be similarly engineered to render the DNA-binding activity non-functional but preserve the DNA cleaving activity of a known endonuclease to induce DNA breaks similar to those induced by the known endonuclease (for example, similar to those breaks induced by the use of Clo051 described above). In such applications, target DNA sequence recognition would preferably be provided by the repeat domain of the effector but DNA cleavage would be accomplished by the engineered endonuclease domain.

Effectors of the disclosure may include a repeat domain with specific recognition for a desired specific target sequence. In preferred embodiments, the effector specifically binds to an endogenous chromosomal DNA sequence. The specific nucleic acid sequence or more preferably specific endogenous chromosomal sequence can be any sequence in a nucleic acid region where it is desired to enhance homologous recombination. For example, the nucleic acid region may be a region which contains a gene in which it is desired to introduce a mutation, such as a point mutation or deletion, or a region into which it is desired to introduce a gene conferring a desired phenotype.

The disclosure provides methods of generating a modified plant in which a desired addition has been introduced. The methods can include obtaining a plant cell that includes an endogenous target DNA sequence into which it is desired to introduce a modification; generating a double-stranded cut within the endogenous target DNA sequence with an effector that includes a repeat domain that binds to an endogenous target DNA sequence and an endonuclease domain; introducing an exogenous nucleic acid that includes a sequence homologous to at least a portion of the endogenous target DNA into the plant cell under conditions which permit homologous recombination to occur between the exogenous nucleic acid and the endogenous target DNA sequence; and generating a plant from the plant cell in which homologous recombination has occurred. These methods may be applied to generate genetically modified plant and animal cells in vivo, in vitro or ex vivo. The target DNA sequence may be artificial or naturally occurring. These methods may be used in any organism (such non-limiting organisms to include animals, humans, fungi, oomycetes bacteria and viruses) using techniques and methods known in the art and utilized for such purposes in such organisms.

Modularly designed repeat domains of the disclosure may be combined with one or more domains responsible for the modulation or control of the expression of a gene, including, but not limited to, plant genes, animal genes, fungal genes, oomycete genes, viral genes, and/or human genes. Methods for modulating gene expression by generating DNA-binding polypeptides containing zinc finger domains have been described (U.S. Pat. Nos. 7,285,416, 7,521,241, 7,361,635, 7,273,923, 7,262,054, 7,220,719, 7,070,934, 7,013,219, 6,979,539, 6,933,113, 6,824,978, each of which is hereby herein incorporated by reference in its entirety). Effectors of the *Xanthomonas* and/or *Ralstonia* family, for example, may be modified to bind to specific target DNA sequences. Such polypeptides include, for example, transcription activators or repressor proteins of transcription that are modified by the methods of the disclosure to specifically bind to genetic control regions in a promoter of or other regulatory region for a gene of interest in order to activate, repress or otherwise modulate transcription of the gene.

Target DNA sequences of the disclosure may be modified to be specifically recognized by a naturally occurring repeat domain or by a modified repeat domain. As one example, the target DNA sequences for members of the *Xanthomonas* and/or *Ralstonia* family may be inserted into promoters to generate novel controllable promoters that can be induced by the corresponding effector. Secondary inducible systems may be constructed using a trans-activator and a target gene, wherein the trans-activator is a polypeptide wherein the polypeptide comprises at least a repeat domain comprising repeat units of the present invention that bind to the target gene and induce expression. The trans-activator and the target gene may be introduced into one cell line but may also be present in different cell lines and later be introgressed. Disease-resistant plants may be generated by inserting the target DNA sequence of a repeat domain containing polypeptide of the present invention in front of a gene that, after expression, leads to a defense reaction of the plant by activating a resistance-mediating gene.

Custom DNA-binding polypeptides may be constructed by rearranging repeat unit types resulting in the generation of repeat domains with novel target DNA binding specificity. Individual repeat units of the disclosure are nearly identical at the DNA level which precludes classical cloning strategies. The compositions and methods of the disclosure provide a quick and inexpensive strategy to assemble custom polypeptides with repeat domains. To improve cloning versatility such polypeptides, the disclosure provides a two-step assembly method. This method may be used to assemble polypeptides with novel repeat types to study their target DNA recognition and binding specificity.

Using the compositions and methods of the disclosure, DNA sequences may be generated to enable binding by a repeat domain containing polypeptide of the disclosure by introducing base pairs into any DNA region or specific regions of a gene, or into a genetic control element, to specifically target a polypeptide having a repeat domain comprised of repeat units that will bind a modified DNA sequence to facilitate specific recognition and binding to each other.

Polypeptides of the disclosure may be synthetically manufactured using known amino acid chemistries familiar to one of ordinary skill in organic chemistry synthesis. Such procedures include both solution and solid phase procedures, e.g., using either Boc or Fmoc methodologies.

Compounds of the disclosure may be synthesized using solid phase synthesis techniques.

The disclosure also provides a method for targeted modulation of gene expression by constructing modular repeat units specific for a target DNA sequence of interest, modifying a polypeptide by the addition of the repeat monomers so as to enable the polypeptide to now recognize the target DNA, introducing or expressing the modified polypeptide in a prokaryotic or eukaryotic cell so as to enable the modified polypeptide to recognize the target DNA sequence, and modulating the expression of the target gene in the cell as a result of such recognition.

The disclosure also provides a method for directed modification of a target DNA sequence by the construction of a polypeptide including at least a repeat domain of the present invention that recognizes the target DNA sequence and that the polypeptide also contains a functional domain capable of modifying the target DNA (such as via site specific recombination, restriction or integration of donor target sequences) thereby enabling targeted DNA modifications in complex genomes.

The disclosure further provides for the production of modified polypeptides including at least a repeat domain comprising repeat units wherein a hypervariable region within each of the repeat units determines selective recognition of a base pair in a target DNA sequence. The disclosure provides DNA that encodes for a polypeptide containing a repeat domain as described above.

The disclosure provides a method for selectively recognizing base pairs in a target DNA sequence by a polypeptide wherein the polypeptide comprises at least a repeat domain comprising repeat units wherein each repeat unit contains a hypervariable region which determines recognition of a base pair in the target DNA sequence wherein consecutive repeat units correspond to consecutive base pairs in the target DNA sequence.

The disclosure provides a method of modulating expression of a target gene in a cell. Exemplary cells include, but are not limited to, a plant cell, a human cell, an animal cell, a fungal cell or any other living cell. Cells of the disclosure may contain a polypeptide of the disclosure that comprises at least a repeat domain comprising repeat units. Repeat units of the disclosure comprise a hypervariable region. Each repeat unit is responsible for the recognition of 1 base pair in a target DNA sequence. Polypeptides of the disclosure are introduced either as DNA encoding for a polypeptide or the polypeptide is introduced per se into the cell by methods described herein. Regardless of how the polypeptide is introduced into a cell, polypeptides of the disclosure comprise at least one repeat domain that specifically recognizes and preferably binds to a target DNA sequence of base pairs and modulates the expression of a target gene. Preferably, all repeat units contain a hypervariable region which determines recognition of base pairs in a target DNA sequence.

Examples of peptide sequences which can be linked to an polypeptide or RTN of the disclosure, for facilitating uptake of effectors into cells, include, but are not limited to: an 11 amino acid peptide of the tat protein of HIV; a 20 residue peptide sequence which corresponds to amino acids 84 103 of the p16 protein (see Fahraeus et al. (1996) Current Biology 6:84); the third helix of the 60-amino acid long homeodomain of Antennapedia (Derossi et al. (1994) J. Biol. Chem. 269:10444); the h region of a signal peptide such as the Kaposi fibroblast growth factor (K-FGF) h region; or the VP22 translocation domain from HSV (Elliot & O'Hare (1997) Cell 88:223 233). Other suitable chemical moieties that provide enhanced cellular uptake may also be chemically linked to effectors. As described herein, effectors can be designed to recognize any suitable target site, for regulation of expression of any endogenous gene of choice. Examples of endogenous genes suitable for regulation include VEGF, CCR5, ER.alpha., Her2/Neu, Tat, Rev, HBV C, S, X, and P, LDL-R, PEPCK, CYP7, Fibrinogen, ApoB, Apo E, Apo(a), renin, NF-.kappa.B, I-.kappa.B, TNF-.alpha., FAS ligand, amyloid precursor protein, atrial naturetic factor, ob-leptin, ucp-1, IL-1, IL-2, IL-3, IL-4, IL-5, IL-6, IL-12, G-CSF, GM-CSF, Epo, PDGF, PAF, p53, Rb, fetal hemoglobin, dystrophin, eutrophin, GDNF, NGF, IGF-1, VEGF receptors flt and flk, topoisomerase, telomerase, bcl-2, cyclins, angiostatin, IGF, ICAM-1, STATS, c-myc, c-myb, TH, PTI-1, polygalacturonase, EPSP synthase, FAD2-1, delta-12 desaturase, delta-9 desaturase, delta-15 desaturase, acetyl-CoA carboxylase, acyl-ACP-thioesterase, ADP-glucose pyrophosphorylase, starch synthase, cellulose synthase, sucrose synthase, senescence-associated genes, heavy metal chelators, fatty acid hydroperoxide lyase, viral genes, protozoal genes, fungal genes, and bacterial genes. In general, suitable genes to be regulated include, but are not limited to, cytokines, lymphokines, growth factors, mitogenic factors, chemotactic factors, onto-active factors, receptors, potassium channels, G-proteins, signal transduction molecules, disease resistance genes, and other disease-related genes.

Toxin molecules may be used to transport polypeptides across cell membranes. Often, such molecules are composed of at least two parts (called "binary toxins"): a translocation or binding domain or polypeptide and a separate toxin domain or polypeptide. Typically, the translocation domain or polypeptide binds to a cellular receptor, and then the toxin is transported into the cell. Several bacterial toxins, including *Clostridium perfringens* iota toxin, diphtheria toxin (DT), *Pseudomonas* exotoxin A (PE), pertussis toxin (PT), *Bacillus anthracis* toxin, and pertussis adenylate cyclase (CYA), have been used in attempts to deliver peptides to the cell cytosol as internal or amino-terminal fusions (Arora et al. (1993) J. Biol. Chem. 268:3334 3341; Perelle et al. (1993) Infect. Immun. 61:5147 5156 (1993); Stenmark et al. (1991) J. Cell Biol. 113:1025 1032 (1991); Donnelly et al. (1993) Proc. Natl. Acad. Sci. USA 90:3530 3534; Carbonetti et al. (1995) Abstr. Annu. Meet. Am. Soc. Microbiol. 95:295; Sebo et al. (1995) Infect. Immun. 63:3851 3857; Klimpel et al. (1992) Proc. Natl. Acad. Sci. USA 89:10277 10281; and Novak et al. (1992) J. Biol. Chem. 267:17186 17193).

Effectors can also be introduced into an animal cell, preferably a mammalian cell, via liposomes and liposome derivatives such as immunoliposomes. The term "liposome" refers to vesicles comprised of one or more concentrically ordered lipid bilayers, which encapsulate an aqueous phase. The aqueous phase typically contains the compound to be delivered to the cell, in this case an effector. The liposome fuses with the plasma membrane, thereby releasing the effector into the cytosol. Alternatively, the liposome is phagocytosed or taken up by the cell in a transport vesicle. Once in the endosome or phagosome, the liposome either degrades or fuses with the membrane of the transport vesicle and releases its contents.

The disclosure provides methods of generating a non-human, transgenic animal comprising a germline mutation comprising: introducing a vector comprising a nucleotide sequence encoding one or more of the proteins of the disclosure into a cell of the non-human, transgenic animal. Compositions of the disclosure may be administered to an organism locally or systemically.

The disclosure provides methods of mutagenizing the germ line of a non-human, transgenic animal comprising: introducing a nucleic acid molecule encoding one or more of the proteins of the disclosure into a cell under conditions sufficient to generate a transgenic animal.

Definitions

As used throughout the disclosure, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more standard deviations. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

The disclosure provides isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

The disclosure provides fragments and variants of the disclosed DNA sequences and proteins encoded by these DNA sequences. As used throughout the disclosure, the term "fragment" refers to a portion of the DNA sequence or a portion of the amino acid sequence and hence protein encoded thereby. Fragments of a DNA sequence comprising coding sequences may encode protein fragments that retain biological activity of the native protein and hence DNA recognition or binding activity to a target DNA sequence as herein described. Alternatively, fragments of a DNA sequence that are useful as hybridization probes generally do not encode proteins that retain biological activity or do not retain promoter activity. Thus, fragments of a DNA sequence may range from at least about 20 nucleotides, about 50 nucleotides, about 100 nucleotides, and up to the full-length polynucleotide of the invention.

Nucleic acids or proteins of the disclosure can be constructed by a modular approach including preassembling monomer units and/or repeat units in target vectors that can subsequently be assembled into a final destination vector. Polypeptides of the disclosure may comprise repeat monomers of the disclosure and can be constructed by a modular approach by preassembling repeat units in target vectors that can subsequently be assembled into a final destination vector. The disclosure provides polypeptide produced by this method as well nucleic acid sequences encoding these polypeptides. The disclosure provides host organisms and cells comprising nucleic acid sequences encoding polypeptides produced this modular approach.

The term "antibody" is used in the broadest sense and specifically covers single monoclonal antibodies (including agonist and antagonist antibodies) and antibody compositions with polyepitopic specificity. It is also within the scope hereof to use natural or synthetic analogs, mutants, variants, alleles, homologs and orthologs (herein collectively referred to as "analogs") of the antibodies hereof as defined herein. Thus, according to one embodiment hereof, the term "antibody hereof" in its broadest sense also covers such analogs. Generally, in such analogs, one or more amino acid residues may have been replaced, deleted and/or added, compared to the antibodies hereof as defined herein.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, $F(ab')_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CHI in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s). The term further includes single domain antibodies ("sdAB") which generally refers to an antibody fragment having a single monomeric variable antibody domain, (for example, from camelids). Such antibody fragment types will be readily understood by a person having ordinary skill in the art.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

The term "comprising" is intended to mean that the compositions and methods include the recited elements, but do not exclude others. "Consisting essentially of" when used to define compositions and methods, shall mean excluding other elements of any essential significance to the combination when used for the intended purpose. Thus, a composition consisting essentially of the elements as defined herein would not exclude trace contaminants or inert carriers. "Consisting of shall mean excluding more than trace elements of other ingredients and substantial method steps. Embodiments defined by each of these transition terms are within the scope of this invention.

The term "effector molecule" means a molecule, such as a protein or protein domain, oftentimes an enzymatic protein, capable of exerting a localized effect in a cell. The effector molecule may take a variety of different forms, including selectively binding to a protein or to DNA, for example, to regulate a biological activity. Effector molecules may have a wide variety of different activities, including, but not limited to nuclease activity, increasing or decreasing enzyme activity, increasing or decreasing gene expression, or affecting cell signaling. Other examples of effector molecules will be readily appreciated by one having ordinary skill in the art.

The term "epitope tag", or otherwise "affinity tag", refers to a short amino acid sequence or peptide enabling a specific interaction with a protein or a ligand.

The term "epitope" refers to an antigenic determinant of a polypeptide. An epitope could comprise three amino acids in a spatial conformation, which is unique to the epitope. Generally, an epitope consists of at least 4, 5, 6, or 7 such amino acids, and more usually, consists of at least 8, 9, or 10 such amino acids. Methods of determining the spatial conformation of amino acids are known in the art, and include, for example, x-ray crystallography and two-dimensional nuclear magnetic resonance.

As used herein, "expression" refers to the process by which polynucleotides are transcribed into mRNA and/or the process by which the transcribed mRNA is subsequently being translated into peptides, polypeptides, or proteins. If the polynucleotide is derived from genomic DNA, expression may include splicing of the mRNA in a eukaryotic cell.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" or "regulation" of gene expression refers to a change in the activity of a gene. Modulation of expression can include, but is not limited to, gene activation and gene repression.

The term "operatively linked" or its equivalents (e.g., "linked operatively") means two or more molecules are positioned with respect to each other such that they are capable of interacting to affect a function attributable to one or both molecules or a combination thereof.

Non-covalently linked components and methods of making and using non-covalently linked components, are disclosed. The various components may take a variety of different forms as described herein. For example, non-covalently linked (i.e., operatively linked) proteins may be used to allow temporary interactions that avoid one or more problems in the art. The ability of non-covalently linked components, such as proteins, to associate and dissociate enables a functional association only or primarily under circumstances where such association is needed for the desired activity. The linkage may be of duration sufficient to allow the desired effect.

A method for directing proteins to a specific locus in a genome of an organism is disclosed. The method may comprise the steps of providing a DNA localization component and providing an effector molecule, wherein the DNA localization component and the effector molecule are capable of operatively linking via a non-covalent linkage.

The term "scFv" refers to a single-chain variable fragment. scFv is a fusion protein of the variable regions of the heavy (VH) and light chains (VL) of immunoglobulins, connected with a linker peptide. The linker peptide may be from about 5 to 40 amino acids or from about 10 to 30 amino acids or about 5, 10, 15, 20, 25, 30, 35, or 40 amino acids in length. Single-chain variable fragments lack the constant Fc region found in complete antibody molecules, and, thus, the common binding sites (e.g., Protein G) used to purify antibodies. The term further includes a scFv that is an intrabody, an antibody that is stable in the cytoplasm of the cell, and which may bind to an intracellular protein.

The term "single domain antibody" means an antibody fragment having a single monomeric variable antibody domain which is able to bind selectively to a specific antigen. A single-domain antibody generally is a peptide chain of about 110 amino acids long, comprising one variable domain (VH) of a heavy-chain antibody, or of a common IgG, which generally have similar affinity to antigens as whole antibodies, but are more heat-resistant and stable towards detergents and high concentrations of urea. Examples are those derived from camelid or fish antibodies. Alternatively, single-domain antibodies can be made from common murine or human IgG with four chains.

The terms "specifically bind" and "specific binding" as used herein refer to the ability of an antibody, an antibody fragment or a nanobody to preferentially bind to a particular antigen that is present in a homogeneous mixture of different antigens. In certain embodiments, a specific binding interaction will discriminate between desirable and undesirable antigens in a sample, in some embodiments more than about ten- to 100-fold or more (e.g., more than about 1000- or 10,000-fold). "Specificity" refers to the ability of an immunoglobulin or an immunoglobulin fragment, such as a nanobody, to bind preferentially to one antigenic target versus a different antigenic target and does not necessarily imply high affinity.

A "target site" or "target sequence" is a nucleic acid sequence that defines a portion of a nucleic acid to which a binding molecule will bind, provided sufficient conditions for binding exist.

The terms "nucleic acid" or "oligonucleotide" or "polynucleotide" refer to at least two nucleotides covalently linked together. The depiction of a single strand also defines the sequence of the complementary strand. Thus, a nucleic acid may also encompass the complementary strand of a depicted single strand. A nucleic acid of the disclosure also encompasses substantially identical nucleic acids and complements thereof that retain the same structure or encode for the same protein.

Probes of the disclosure may comprise a single stranded nucleic acid that can hybridize to a target sequence under stringent hybridization conditions. Thus, nucleic acids of the disclosure may refer to a probe that hybridizes under stringent hybridization conditions.

Nucleic acids of the disclosure may be single- or double-stranded. Nucleic acids of the disclosure may contain double-stranded sequences even when the majority of the molecule is single-stranded. Nucleic acids of the disclosure may contain single-stranded sequences even when the majority of the molecule is double-stranded. Nucleic acids of the disclosure may include genomic DNA, cDNA, RNA, or a hybrid thereof. Nucleic acids of the disclosure may contain combinations of deoxyribo- and ribo-nucleotides. Nucleic acids of the disclosure may contain combinations of bases including uracil, adenine, thymine, cytosine, guanine, inosine, xanthine hypoxanthine, isocytosine and isoguanine. Nucleic acids of the disclosure may be synthesized to comprise non-natural amino acid modifications. Nucleic acids of the disclosure may be obtained by chemical synthesis methods or by recombinant methods.

Nucleic acids of the disclosure, either their entire sequence, or any portion thereof, may be non-naturally occurring. Nucleic acids of the disclosure may contain one or more mutations, substitutions, deletions, or insertions that do not naturally-occur, rendering the entire nucleic acid sequence non-naturally occurring. Nucleic acids of the disclosure may contain one or more duplicated, inverted or repeated sequences, the resultant sequence of which does not naturally-occur, rendering the entire nucleic acid sequence non-naturally occurring. Nucleic acids of the disclosure may contain modified, artificial, or synthetic nucleotides that do not naturally-occur, rendering the entire nucleic acid sequence non-naturally occurring.

Given the redundancy in the genetic code, a plurality of nucleotide sequences may encode any particular protein. All such nucleotides sequences are contemplated herein.

As used throughout the disclosure, the term "operably linked" refers to the expression of a gene that is under the control of a promoter with which it is spatially connected. A promoter can be positioned 5' (upstream) or 3' (downstream) of a gene under its control. The distance between a promoter and a gene can be approximately the same as the distance between that promoter and the gene it controls in the gene from which the promoter is derived. Variation in the distance between a promoter and a gene can be accommodated without loss of promoter function.

As used throughout the disclosure, the term "promoter" refers to a synthetic or naturally-derived molecule which is capable of conferring, activating or enhancing expression of a nucleic acid in a cell. A promoter can comprise one or more specific transcriptional regulatory sequences to further enhance expression and/or to alter the spatial expression and/or temporal expression of same. A promoter can also comprise distal enhancer or repressor elements, which can be located as much as several thousand base pairs from the start site of transcription. A promoter can be derived from sources including viral, bacterial, fungal, plants, insects, and animals. A promoter can regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

As used throughout the disclosure, the term "substantially complementary" refers to a first sequence that is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540, or more nucleotides or amino acids, or that the two sequences hybridize under stringent hybridization conditions.

As used throughout the disclosure, the term "substantially identical" refers to a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 180, 270, 360, 450, 540 or more nucleotides or amino acids, or with respect to nucleic acids, if the first sequence is substantially complementary to the complement of the second sequence.

As used throughout the disclosure, the term "variant" when used to describe a nucleic acid, refers to (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

As used throughout the disclosure, the term "vector" refers to a nucleic acid sequence containing an origin of replication. A vector can be a viral vector, bacteriophage, bacterial artificial chromosome or yeast artificial chromosome. A vector can be a DNA or RNA vector. A vector can be a self-replicating extrachromosomal vector, and preferably, is a DNA plasmid.

As used throughout the disclosure, the term "variant" when used to describe a peptide or polypeptide, refers to a peptide or polypeptide that differs in amino acid sequence by the insertion, deletion, or conservative substitution of amino acids, but retain at least one biological activity. Variant can also mean a protein with an amino acid sequence that is substantially identical to a referenced protein with an amino acid sequence that retains at least one biological activity.

A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157: 105-132 (1982). The hydropathic index of an amino acid is based on a consideration of its hydrophobicity and charge. Amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference.

Substitution of amino acids having similar hydrophilicity values can result in peptides retaining biological activity, for example immunogenicity. Substitutions can be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "conservative" amino acid substitutions may be defined as set out in Tables A, B, or C below. In some embodiments, fusion polypeptides and/or nucleic acids encoding such fusion polypeptides include conservative substitutions have been introduced by modification of polynucleotides encoding polypeptides of the invention. Amino acids can be classified according to physical properties and contribution to secondary and tertiary protein structure. A conservative substitution is a substitution of one amino acid for another amino acid that has similar properties. Exemplary conservative substitutions are set out in Table A.

TABLE A

Conservative Substitutions I

| Side chain characteristics | | Amino Acid |
|---|---|---|
| Aliphatic | Non-polar | GAPILVF |
| | Polar-uncharged | CSTMNQ |
| | Polar-charged | DEKR |
| Aromatic | | HFWY |
| Other | | NQDE |

Alternately, conservative amino acids can be grouped as described in Lehninger, (Biochemistry, Second Edition; Worth Publishers, Inc. NY, N.Y. (1975), pp. 71-77) as set forth in Table B.

TABLE B

Conservative Substitutions II

| Side Chain Characteristic | | Amino Acid |
|---|---|---|
| Non-polar ) (hydrophobic | Aliphatic: | A L I V P |
| | Aromatic: | F W Y |
| | Sulfur-containing: | M |
| | Borderline: | G Y |
| Uncharged-polar | Hydroxyl: | S T Y |
| | Amides: | N Q |
| | Sulfhydryl: | C |
| | Borderline: | G Y |
| Positively Charged (Basic): | | K R H |
| Negatively Charged (Acidic): | | D E |

Alternately, exemplary conservative substitutions are set out in Table C.

TABLE C

Conservative Substitutions III

| Original Residue | Exemplary Substitution |
|---|---|
| Ala (A) | Val Leu Ile Met |
| Arg (R) | Lys His |

TABLE C-continued

| Conservative Substitutions III | |
|---|---|
| Original Residue | Exemplary Substitution |
| Asn (N) | Gln |
| Asp (D) | Glu |
| Cys (C) | Ser Thr |
| Gln (Q) | Asn |
| Glu (E) | Asp |
| Gly (G) | Ala Val Leu Pro |
| His (H) | Lys Arg |
| Ile (I) | Leu Val Met Ala Phe |
| Leu (L) | Ile Val Met Ala Phe |
| Lys (K) | Arg His |
| Met (M) | Leu Ile Val Ala |
| Phe (F) | Trp Tyr Ile |
| Pro (P) | Gly Ala Val Leu Ile |
| Ser (S) | Thr |
| Thr (T) | Ser |
| Trp (W) | Tyr Phe Ile |
| Tyr (Y) | Trp Phe Thr Ser |
| Val (V) | Ile Leu Met Ala |

It should be understood that the polypeptides of the disclosure are intended to include polypeptides bearing one or more insertions, deletions, or substitutions, or any combination thereof, of amino acid residues as well as modifications other than insertions, deletions, or substitutions of amino acid residues. Polypeptides or nucleic acids of the disclosure may contain one or more conservative substitution.

As used throughout the disclosure, the term "more than one" of the aforementioned amino acid substitutions refers to 2, 3, 4, 5, 6, 7, 8, 9, 10, 11, 12, 13, 14, 15, 16, 17, 18, 19, or 20 or more of the recited amino acid substitutions. The term "more than one" may refer to 2, 3, 4, or 5 of the recited amino acid substitutions.

Polypeptides and proteins of the disclosure, either their entire sequence, or any portion thereof, may be non-naturally occurring. Polypeptides and proteins of the disclosure may contain one or more mutations, substitutions, deletions, or insertions that do not naturally-occur, rendering the entire amino acid sequence non-naturally occurring. Polypeptides and proteins of the disclosure may contain one or more duplicated, inverted or repeated sequences, the resultant sequence of which does not naturally-occur, rendering the entire amino acid sequence non-naturally occurring. Polypeptides and proteins of the disclosure may contain modified, artificial, or synthetic amino acids that do not naturally-occur, rendering the entire amino acid sequence non-naturally occurring.

As used throughout the disclosure, "sequence identity" may be determined by using the stand-alone executable BLAST engine program for blasting two sequences (bl2seq), which can be retrieved from the National Center for Biotechnology Information (NCBI) ftp site, using the default parameters (Tatusova and Madden, FEMS Microbiol Lett., 1999, 174, 247-250; which is incorporated herein by reference in its entirety). The terms "identical" or "identity" when used in the context of two or more nucleic acids or polypeptide sequences, refer to a specified percentage of residues that are the same over a specified region of each of the sequences. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) can be considered equivalent. Identity can be performed manually or by using a computer sequence algorithm such as BLAST or BLAST 2.0.

As used throughout the disclosure, the term "endogenous" refers to nucleic acid or protein sequence naturally associated with a target gene or a host cell into which it is introduced.

As used throughout the disclosure, the term "exogenous" refers to nucleic acid or protein sequence not naturally associated with a target gene or a host cell into which it is introduced, including non-naturally occurring multiple copies of a naturally occurring nucleic acid, e.g., DNA sequence, or naturally occurring nucleic acid sequence located in a non-naturally occurring genome location.

The disclosure provides methods of introducing a polynucleotide construct comprising a DNA sequence into a host cell. By "introducing" is intended presenting to the plant the polynucleotide construct in such a manner that the construct gains access to the interior of the host cell. The methods of the invention do not depend on a particular method for introducing a polynucleotide construct into a host cell, only that the polynucleotide construct gains access to the interior of one cell of the host. Methods for introducing polynucleotide constructs into bacteria, plants, fungi and animals are known in the art including, but not limited to, stable transformation methods, transient transformation methods, and virus-mediated methods.

By "stable transformation" is intended that the polynucleotide construct introduced into a plant integrates into the genome of the host and is capable of being inherited by progeny thereof. By "transient transformation" is intended that a polynucleotide construct introduced into the host does not integrate into the genome of the host.

As used throughout the disclosure, the term "genetically modified plant (or transgenic plant)" refers to a plant which comprises within its genome an exogenous polynucleotide. Generally, and preferably, the exogenous polynucleotide is stably integrated into the genome such that the polynucleotide is passed on to successive generations. The exogenous polynucleotide may be integrated into the genome alone or as part of a recombinant expression cassette. "Transgenic" is used herein to include any cell, cell line, callus, tissue, plant part or plant, the genotype of which has been altered by the presence of exogenous nucleic acid including those trans genies initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used throughout the disclosure, the term "modifying" is intended to mean that the sequence is considered modified simply by the binding of the polypeptide. It is not intended to suggest that the sequence of nucleotides is changed, although such changes (and others) could ensue following binding of the polypeptide to the nucleic acid of interest. In some embodiments, the nucleic acid sequence is DNA.

Modification of the nucleic acid of interest (in the sense of binding thereto by a polypeptide modified to contain modular repeat units) could be detected in any of a number of methods (e.g. gel mobility shift assays, use of labelled polypeptides-labels could include radioactive, fluorescent, enzyme or biotin/streptavidin labels). Modification of the nucleic acid sequence of interest (and detection thereof) may be all that is required (e.g. in diagnosis of disease). Desirably, however, further processing of the sample is performed. Conveniently the polypeptide (and nucleic acid sequences specifically bound thereto) is separated from the rest of the sample. Advantageously the polypeptide-DNA complex is bound to a solid phase support, to facilitate such separation. For example, the polypeptide may be present in an acrylamide or agarose gel matrix or, more preferably, is immobilized on the surface of a membrane or in the wells of a microtitre plate.

All percentages and ratios are calculated by weight unless otherwise indicated.

All percentages and ratios are calculated based on the total composition unless otherwise indicated.

Every maximum numerical limitation given throughout this disclosure includes every lower numerical limitation, as if such lower numerical limitations were expressly written herein. Every minimum numerical limitation given throughout this disclosure will include every higher numerical limitation, as if such higher numerical limitations were expressly written herein. Every numerical range given throughout this disclosure will include every narrower numerical range that falls within such broader numerical range, as if such narrower numerical ranges were all expressly written herein.

The values disclosed herein are not to be understood as being strictly limited to the exact numerical values recited. Instead, unless otherwise specified, each such value is intended to mean both the recited value and a functionally equivalent range surrounding that value. For example, a value disclosed as "20 μm" is intended to mean "about 20 μm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the disclosure have been illustrated and described, various other changes and modifications can be made without departing from the spirit and scope of the disclosure. The scope of the appended claims includes all such changes and modifications that are within the scope of this disclosure.

EXAMPLES

In order that the invention disclosed herein may be more efficiently understood, examples are provided below. It should be understood that these examples are for illustrative purposes only and are not to be construed as limiting the invention in any manner. Throughout these examples; molecular cloning reactions, and other standard recombinant DNA techniques, were carried out according to methods described in Maniatis et al., Molecular Cloning—A Laboratory Manual, 2nd ed., Cold Spring Harbor Press (1989), using commercially available reagents, except where otherwise noted.

Example 1

Generating Nucleic Acid Vectors with *Ralstonia* TALs (RTALs) with Functional Analysis Cluster analysis and review of sequence homologies of *Ralstonia* genome revealed the sequence of SEQ ID NO: 1 which is homologous to known TAL sequences.

Nucleic acid sequences that encode the polypeptides of the claimed invention are made through molecular biology techniques known to those with ordinary skill in the art. DNA sequences, for instance, are synthesized with the XbaI and/or SalI restriction sites flanking each nucleic acid sequence that encodes the polyproteins of the present invention. Polymerase chain reaction is performed to amplify the DNA with certain restriction endonuclease sites. Sequences are gel-purified, isolated, and reconstituted in water or suitable buffer for ligation reactions. A plasmid that encodes a protein with effector function (such as nuclease function) that comprises requisite regulatory elements is ligated to one or more of the nucleic acid sequences that encode the following sequences at the plasmid multiple cloning sites:

```
a.
                                     (SEQ ID NO: 39)
LSTEQVVAIAS NK GGKQALEAVKAHLLDLLGAPYV

b.
                                     (SEQ ID NO: 40)
LSTEQVVAIAS NN GGKQALEAVKAQLLELRAAPYE

c.
                                     (SEQ ID NO: 41)
LSTAQVVAIAS NG GGKQALEGIGEQLLKLRTAPYG

d.
                                     (SEQ ID NO: 42)
LSTAQVVAIAS HD GGKPALEAVWAKLPVLRGVPYA

e.
                                     (SEQ ID NO: 43)
LSTEQVVTIAS SI GGKQALEAVKVQLPVLRAAPYE
```

Plasmid sequences are transformed in suitable bacteria for production of high copy numbers of plasmid. Plasmids containing at least one polypeptide above can be selected using antibiotic selection, isolated and purified from bacterial cells using techniques known to those skilled in the art.

Plasmids are built and in-vitro testing of expressed DNA-binding polypeptides is validated using the methods described in *Nature Biotechnology* 2012 May; 30(5):460-5. "FLASH assembly of TALENs for high-throughput genome editing." Reyon D, Tsai S Q, Khayter C, Foden J A, Sander J D, Joung J K, which is incorporated by reference in its entirety.

Construction of a Plasmid Archive Encoding Pre-Assembled TALE Repeats

TALE repeat arrays were constructed using the same architecture first described by Miller, J. C. et al. ("A TALE nuclease architecture for efficient genome editing.", *Nat Biotechnol.* 2011; 29:143-148; the contents of which are herein incorporated by reference) in which distinct TALE repeat backbones that differ slightly in their amino acid and DNA sequences occur in a repeated pattern. The first, amino-terminal TALE repeat in an array was designated as the α unit. This a unit is followed by β, γ and δ units and then an ε unit that is essentially identical to the α unit, except for the different positioning of a Type IIS restriction site on the 5' end (required to enable creation of a unique overhang on the α unit needed for cloning). The ε unit is then followed again by repeats of β, γ, δ and ε units. Due to constraints related to creation of a 3'end required for cloning, slightly modified DNA sequences were required for TALE repeat arrays that end with a carboxyterminal γ or ε unit.

Preparation of TALE repeat-encoding DNA fragments for FLASH assembly

To prepare DNA fragments encoding a units for use in FLASH assembly, 20 rounds of PCR are performed with each a unit plasmid as a template using primers oJS2581 (5'-Biotin-TCTAGAGAAGACAAGAACCTGACC-3') (SEQ ID NO: 44) and oJS2582(5'-GGATCCGGTCTC-TrAAGGCCGTGG-3') (SEQ ID NO: 45). The resulting PCR products are biotinylated on the 5' end. Each a PCR product is then digested with 40 units of BsaI-HF restriction enzyme to generate 4 bp overhangs, purified using the QIAquick PCR purification kit (QIAGEN) according to manufacturer's instructions except that the final product will be eluted in 50 μl of 0.1×EB.

To prepare DNA fragments encoding polypeptide repeats, 10 μg of each of these plasmids are digested with 50 units of BbsI restriction enzyme in NEBuffer 2 for 2 hours at 37° C. followed by serial restriction digests performed in NEBuffer 4 at 37° C. using 100 units each of XbaI, BamHI-HF, and SalI-HF enzymes that are added at 5 minute intervals. The latter set of restriction digestions are designed to cleave the plasmid backbone to ensure that this larger DNA fragment will not interfere with subsequent ligations performed during the FLASH assembly process. These restriction digest reactions are then purified using the QIAquick PCR purification kit (QIAGEN) according to manufacturer's instructions, except that the final product will be eluted in 180 μl of 0.1×EB.

Automated FLASH Assembly

All steps of FLASH assembly are performed using a Sciclone G3 liquid-handling workstation (Caliper) or similar device sold by another company in 96-well plates and using a SPRIplate 96-ring magnet (Beckman Coulter Genomics) and a DynaMag-96 Side magnet (Life Technologies). In the first step of FLASH, a biotinylated α unit fragment is ligated to the first βγδε fragment and then the resulting αβγδε fragments are bound to Dynabeads MyOne C1 streptavidin-coated magnetic beads (Life Technologies) in 2×B&W Buffer. Beads are then drawn to the side of the well by placing the plate on the magnet and then washed with 100 μl B&W buffer with 0.005% Tween 20 (Sigma) and again with 100 μl 0.1 mg/ml bovine serum albumin (BSA) (New England Biolabs). Additional βγδε fragments are ligated by removing the plate from the magnet, resuspending the beads in solution in each well, digesting the bead-bound fragment with BsaI-HF restriction enzyme, placing the plate on the magnet, washing with 100 μl B&W/Tween20 followed by 100 μl of 0.1 mg/ml BSA, and then ligating the next fragment. This process is repeated multiple times with additional βγδε units to extend the bead-bound fragment. The last fragment to be ligated is always a β, βγ*, βγδ, or δε* unit to enable cloning of the full-length fragment into expression vectors (note that fragments that end with a δε* unit will always be preceded by ligation of a βγ unit).

The final full-length bead-bound fragment is digested with 40 units of BsaI-HF restriction enzyme followed by 25 units of BbsI restriction enzyme (New England Biolabs). Digestion with BbsI released the fragment from the beads and generates a unique 5' overhang for cloning of the fragment: Digestion with BsaI-HF results in creation of a unique 3' overhang for cloning.

Subcloning of TALE Repeat Array-Encoding DNA Fragments into TALEN Expression Vectors DNA fragments encoding our FLASH assembled TALE repeat arrays are subcloned into TALE expression vectors. In some experiments, there are 4 or more separate plasmids. In some experiments, vectors include a CMV promoter, a translational start codon optimized for mammalian cell expression, a triple FLAG epitope tag, a nuclear localization signal, amino acids 153 to 288 from the TALE 13 protein (as numbered by Miller, J. C. et al. (*Nat Biotechnol.* 2011; 29:143-148; the contents of which are herein incorporated by reference), two unique and closely positioned Type IIS BsmBI restriction sites, a 0.5 TALE repeat domain encoding RVDs, amino acids 715 to 777 from the TALE 13 protein, and the wild-type FokI cleavage domain.

All DNA fragments assembled by FLASH possess overhangs that enable directional cloning into any of the expression vectors that are digested with BsmBI. Standard TALEN expression vectors (each possessing a different 0.5 TALE repeat) are available from suppliers such as Addgene and full sequences of these plasmids are freely available on a web page dedicated to these constructs: www.addgene.org/talengineering/expressionvectors/ for synthetic construction.

To prepare a TALEN expression vector for subcloning, 5 μg of plasmid DNA is digested with 50 units of BsmBI restriction enzyme (New England Biolabs) in NEBuffer 3 for 8 hours at 55 degrees C. Digested DNA will be purified using 90 μl of Ampure XP beads (Agencourt) according to manufacturer's instructions and diluted to a final concentration of 5 ng/μl in 1 mM TrisHCl. FLASH-assembled TALE repeat arrays are ligated into TALEN expression vectors using 400 U of T4 DNA Ligase (New England Biolabs). Ligation products are transformed into chemically competent XL-1 Blue cells. Typically, six colonies are picked for each ligation and plasmid DNA is isolated by an alkaline lysis miniprep procedure. Simultaneously, the same colonies are screened by PCR using primers oSQT34 (5'-GACGGTGGCTGTCAAATACCAAGATATG-3') (SEQ ID NO: 46) and oSQT35 (5'-TCTCCTCCAGTTCACTIT-TGACTAGTrGGG-3') (SEQ ID NO: 47). PCR products are analyzed on a QIAxcel capillary electrophoresis system (Qiagen). Miniprep DNA from clones that contain correctly sized PCR products are sent for DNA sequence confirmation with primers oSQTI (5'-AGTAACAGCGGTAGAGGCAG-3') (SEQ ID NO: 48), oSQT3 (5'-ATTGGGCTAC-GATGGACTCC-3') (SEQ ID NO: 49), and oJS2980 (5'-TTAATTCAATATATTCATGAGGCAC-3') (SEQ ID NO: 50); oSQTI anneals at the 5' end of the TALE repeat array coding sequence and enables sequencing of the amino-terminal half of the assembled array, oSQT3 anneals at the 3' end of the TALE repeat array coding sequence and enables sequencing of the carboxy-terminal half of the assembled array, and oJS2980 primes within the coding sequence of the FokI domain (downstream of oSQT3) and enables sequencing and verification of the carboxy-terminal 0.5 TALE repeat domain.

Six colonies for each assembly are screened as described above, followed by six additional colonies if necessary. With this approach, one or more sequence-verified clones are generated for >90% of assembly reactions. These percentages are derived primarily from experiments designed to construct DNA fragments encoding 16.5 TALE repeats.

EGFP TALEN Activity and Toxicity Assays

EGFP reporter assays are performed in a clonal U2OS human cell line bearing an integrated construct that constitutively expresses an EGFP-PEST fusion protein. This clonal line is derived from a polyclonal U2OS EGFP-PEST reporter line. Clonal U2OS EGFP-PEST cells are cultured in Advanced DMEM (Life Technologies) supplemented with 10% FBS, 2 mM GlutaMax (Life Technologies), penicillin/streptomycin, and 400 μg/ml G418. Cells are transfected in triplicate with 500 ng of each TALEN plasmid DNA and 50 ng ptdTomato-N1 plasmid DNA using a Lonza 4D-Nucleofector System, Solution SE, and program DN-100 according to manufacturer's instructions. 1 μg of ptdTomato-N1 plasmid alone is transfected in triplicate as a negative control. Cells are assayed for EGFP and tdTomato expression at 2 and 5 days post-transfection using a BD FACSAriaII flow cytometer.

PCR Amplification and Sequence Verification of Endogenous Human Genes

PCR reactions to amplify targeted loci are performed.

Standard PCR conditions with Phusion Hot Start 1 high-fidelity DNA polymerase (Thermo-Fisher) are performed according to manufacturer's instructions for 35 cycles (98° C., 10 s denaturation; 68° C., 15 s annealing; 72° C., 30 s extension). For loci that do not amplify under standard conditions one of the following modifications is used: 1) the addition of betaine to a final concentration of 1.8M, 2) touchdown PCR ([98° C., 10 s; 72-62° C., −1° C./cycle, 15 s; 72° C., 30 s]$_{10\ cycles}$, [98° C., 10 s; 62° C., −1° C./cycle, 15 s; 72° C., 30 s]$_{25\ cycles}$) with 1.8M betaine, and 3) the addition of 3% or 5% DMSO and an annealing temperature of 65° C. PCR products are analyzed for correct size on a QIAxcel capillary electrophoresis system. Correctly sized products are treated with ExoSap-IT (Affymetrix) to remove unincorporated nucleotides or primers and sent for DNA sequencing to confirm the endogenous gene sequence.

T7 Endonuclease I Assay for Quantifying NHEJ-Mediated Mutation of Endogenous Human Genes U2OS-EGFP cells are cultured and transfected in duplicate as described above. Genomic DNA is isolated from cells transfected with TALEN-encoding or control plasmids using a high-throughput magnetic-bead based purification system (Agencourt DNAdvance) according to the manufacturer's instructions. PCR to amplify endogenous loci are performed for 35 cycles as described above and fragments were purified with Ampure XP (Agencourt) according to manufacturer's instructions. 200 ng of purified PCR product are denatured and reannealed in NEBuffer 2 (New England Biolabs) using a thermocycler with the following protocol (95° C., 5 min; 95-85° C. at −2° C./s; 85-25° C. at −0.1° C./s; hold at 4° C.). 33 Hybridized PCR products were treated with 10 U of T7 Endonuclease I at 37° C. for 15 minutes in a reaction volume of 20 μl. Reactions are stopped by the addition of 2 μl 0.5 M EDTA, purified with Ampure XP, and quantified on a QIAxcel capillary electrophoresis system using method OM500. The sum of the area beneath TALEN-specific cleavage peaks (expressed as a percentage of the parent amplicon peak, denoted fraction cleaved) is used to estimate gene modification levels using the following equation as previously described.

$$(\%\ \text{gene modification}=100\times(1-(1-\text{fraction cleaved})^{1/2})$$

Example 2

RTN Constructs

Five fragments shown below were synthesized and each cloned into a modified pUC57: pUC57-ΔBsaI (vectors as disclosed in Juong et. al. FLASH assembly paper. The modified pUC57: pUC57-ΔBsaI contains single basepair change to disrupt a BsaI site) with XbaI and BamHI.

RTN1 EBEs:

```
NK (SEQ ID NO: 51):
 XbaI BbsI
ATGCA T^CTAGA-GAAGACAA^CTGA-

GCACCGAGCAGGTGGTGGCCATCGCCAGCAACAAGGGCGGCAAGCAGGCC

CTGGAGGCCGTGAAGGCCCACCTGCTGGACCTGCTGGGCGCCCCCTACGA

G-CTGA^AGAGACC-G^GATCC(CGGGC)            BsaI
 BamHI

NN (SEQ ID NO: 52):
ATGCA

TCTAGAGAAGACAACTGAGCACCGAGCAGGTGGTGGCCATCGCCAGCAAC

AACGGCGGCAAGCAGGCCCTGGAGGCCGTGAAGGCCCAGCTGCTGGAGCT

GAGGGCCGCCCCCTACGAGCTGAAGAGACCGGATCC CGGGC

NG (SEQ ID NO: 53):
ATGCA

TCTAGAGAAGACAACTGAGCACCGagCAGGTGGTGGCCATCGCCAGCAAC

GGCGGCGGCAAGCAGGCCCTGGAGGGCATCGGCGAGCAGCTGCTGAAGCT

GAGGACCGCCCCCTACGAGCTGAAGAGACCGGATCC CGGGC

HD (SEQ ID NO: 54):
ATGCA

TCTAGAGAAGACAACTGAGCACCGagCAGGTGGTGGCCATCGCCAGCCAC

GACGGCGGCAAGCCCGCCCTGGAGGCCGTGTGGGCCAAGCTGCCCGTGCT

GAGGGGCGTGCCCTACGAGCTGAAGAGACCGGATCC CGGGC

SI (SEQ ID NO: 55):
ATGCA

TCTAGAGAAGACAACTGAGCACCGAGCAGGTGGTGACCATCGCCAGCAG

CATCGCGGCAAGCAGGCCCTGGAGGCCGTGAAGGTGCAGCTGCCCGTGC

TGAGGGCCCCCCCTACGAGCTGAAGAGACCGGATCC CGGGC
```

For proof of principle, these cloned fragments are used to generate chimeric proteins of six repeat units fused to FokI nuclease, i.e. a chimeric protein that targets a string of A (C, T and G) nucleotides. These chimeric proteins are then tested for binding/targeting efficiency to desired DNA bases using a reporter construct.

Once the binding efficiency of these units are confirmed, a library of *Ralstonia* EBEs are generated that are a copy of FLASH TALEN's *Xanthomonas* EBE library. This library can then be used to generate *Ralstonia* TALENs following the exact protocol of the FLASH TALEN system.

Example 3

Generating Nucleic Acid Vectors with Methylesterase

Additional sequences cloned from other species or cloned from the same species may be used functionally as an enzyme either by itself or in series as a monomer or polymer (protein fusion) for performing any of the experiments disclosed herein with DNA recognition. A RVD identification consensus sequence was created using sequence optimization techniques known in the art. A BLAST search was performed across methlyesterase sequences in bacterial species (see FIG. 1). The following polypeptides were identified as having DNA base pair recognition capability similar to the nucleic acid sequences and polypeptides disclosed herein SEQ ID NO: 1-19:

TABLE D

| TAL EBE against methylesterases | | | | |
|---|---|---|---|---|
| #1 | | | | |
| Xanthomonas Consensus EBEs | | | | |
| LTPDQVVAIASNGGGKQALETVQRLLPVLCQDHG | | | | (SEQ ID NO: 56) |
| LTPEQVVAIANNNGGKQALETVQRLLPVLCQAHG | | | | (SEQ ID NO: 57) |
| LTPDQVVAIASHDGGKQALETVQRLLPVLCQAHG | | | | (SEQ ID NO: 58) |
| LTPAQVVAIASNIGGKQALETVQRLLPVLCQDHG | | | | (SEQ ID NO: 59) |
| EJO92907 | 166 | TTDRVVALGTSTGGTQALEVVLRQLPVDC | 194 | (SEQ ID NO: 60) |
| YP_001187060 | 166 | TTDRVVALGTSTGGTQALEVVLRQLPVDC | 194 | (SEQ ID NO: 61) |
| YP_003847734 | 169 | MTSEQIVAIGTSTGGTQALEAVLTALPRVC | 198 | (SEQ ID NO: 62) |
| ZP_08780698 | 167 | TTDRVVAIGTSTGGTALEVVLTALPRVC | 195 | (SEQ ID NO: 63) |
| YP_004846745 | 185 | TTERIVAIGTSTGGTALETVLHRLPATC | 213 | (SEQ ID NO: 64) |
| YP_005027668 | 186 | TTDKIIAIGTSTGGTALEAVLTKLPAVC | 214 | (SEQ ID NO: 65) |
| ZP_10991552 | 174 | TTERIVAIGTSTGGTQALETVLTALPRVC | 202 | (SEQ ID NO: 66) |
| YP_001792820 | 162 | TTERVVALGTSTGGTALEVVLRTLPRVC | 190 | (SEQ ID NO: 67) |
| EKE17764 | 172 | TTDOLIAIGTSTGGTQALEAILTKLPATC | 200 | (SEQ ID NO: 68) |
| ZP_03698248 | 178 | TTERIVAIGTSTGGTALETVLPRLPATC | 206 | (SEQ ID NO: 69) |
| EGH48032 | 11 | TTERIVAIGTSTGGTALEAVLTALPRVC | 39 | (SEQ ID NO: 70) |
| ZP_06495900 | 1 | TTERIVAIGTSTGGTALEAVLTALPRVC | 29 | (SEQ ID NO: 71) |
| ZP_10381001 | 76 | TTERIVAIGTSTGGTALEAVLTALPRVC | 104 | (SEQ ID NO: 72) |
| ZP_10442431 | 158 | TSDKVVAIGASTGGTQALELLLTGLPAVC | 186 | (SEQ ID NO: 73) |
| #2 | | | | |
| ZP_10991552 | 174 | TTERIVAIGTSTGGTALETVLTALPRVC | 202 | (SEQ ID NO: 74) |
| EGH48032 | 11 | TTERIVAIGTSTGGTQALEAVLTALPRVC | 39 | (SEQ ID NO: 75) |
| ZP_06495900 | 1 | TTERIVAIGTSTGGTQALEAVLTALPRVC | 29 | (SEQ ID NO: 76) |
| EGH61007 | 172 | TTERIVAIGTSTGGTALEAVLTALPRVC | 200 | (SEQ ID NO: 77) |
| EGH06695 | 172 | TTERIVAIGTSTGGTQALEAVLTALPRVC | 200 | (SEQ ID NO: 78) |
| EGH31878 | 172 | TTERIVAIGTSTGGTQALEAVLTALPRVC | 200 | (SEQ ID NO: 79) |
| EGH66597 | 172 | TTERIVAIGTSTGGTQALEAVLTALPRVC | 200 | (SEQ ID NO: 80) |
| ZP_07003572 | 172 | TTERIVAIGTSTGGTQALEAVLTALPRVC | 200 | (SEQ ID NO: 81) |
| ZP_06457223 | 172 | TTERIVAIGTSTGGTQALEAVLTALPRVC | 200 | (SEQ ID NO: 82) |
| ZP_04590480 | 172 | TTERIVAIGTSTGGTQALEAVLTALPRVC | 200 | (SEQ ID NO: 83 |
| ZP_07251539 | 172 | TTERIVAIGTSTGGTQALEAVLTALPRVC | 200 | (SEQ ID NO: 84) |
| NP_790747 | 172 | TTERIVAIGTSTGGTQALEAVLTALPRVC | 200 | (SEQ ID NO: 85) |
| EGH77388 | 172 | TTERIVAIGTSTGGTQALEAVLTALPRVC | 200 | (SEQ ID NO: 86) |
| EFW86187 | 172 | TTERIVAIGTSTGGTQALEAVLTALPRVC | 200 | (SEQ ID NO: 87) |
| EGH54563 | 172 | TTERIVAIGTSTGGTQALEAVLTALPRVC | 200 | (SEQ ID NO: 88) |
| YP_233877 | 172 | TTERIVAIGTSTGGTALEAVLTALPRVC | 200 | (SEQ ID NO: 89) |
| EGH23390 | 172 | TTERIVAIGTSTGGTQALEAVLTALPRVC | 200 | (SEQ ID NO: 90) |
| ZP_05638023 | 172 | TTERIVAIGTSTGGTQALEAVLTALPRVC | 200 | (SEQ ID NO: 91) |
| EGH71924 | 106 | TTERIVAIGTSTGGTQALEAVLTALPRVC | 134 | (SEQ ID NO: 92) |
| EFW82095 | 172 | TTERIVAIGTSTGGTQALEAVLTALPRVC | 200 | (SEQ ID NO: 93) |
| ZP_07265841 | 172 | TTERIVAIGTSTGGTQALEAVLTALPRVC | 200 | (SEQ ID NO: 94) |
| YP_273082 | 172 | TTERIVAIGTSTGGTALEAVLTALPRVC | 200 | (SEQ ID NO: 95) |
| YP_004030667 | 117 | FSQADIVRIADNIGGAQALKAVLEHGPTL | 145 | (SEQ ID NO: 96) |
| YP_004030667 | 186 | ADIVKIASNGGGAQALEAVAMHGSTLCE | 213 | (SEQ ID NO: 97) |
| YP_004030667 | 153 | ADIVKIAGNGGGARALKAVVMHGPTLCE | 180 | (SEQ ID NO: 98) |
| ZP_10995147 | 155 | TTDRVVALGCSTGGTQALEFILRQLPRDC | 183 | (SEQ ID NO: 99) |
| EGH56182 | 30 | ALAAAVGGKGALEVPANLIPANCE | 53 | (SEQ ID NO: 100) |
| YP_003907367 | 173 | RIVAIGTSTGGTQALEVVLTALP | 195 | (SEQ ID NO: 101) |
| EBE1 | | LTPDQVVAIASNGGGKQALETVQRLLPVLCQDHG | 34 | (SEQ ID NO: 102) |
| EBE4 | | LTPAQVVAIASNIGGKQALETVQRLLPVLCQDHG | 34 | (SEQ ID NO: 103) |
| EBE3 | | LTPDQVVAIASHDGGKQALETVQRLLPVLCQAHG | 34 | (SEQ ID NO: 104) |
| EBE2 | | LTPEQVVAIANNNGGKQALETVQRLLPVLCQAHG | 34 | (SEQ ID NO: 105) |
| ZP_07265841_2 | | -TTERIVAIGTSTGGTQALEAVLTALPRVC---- | 29 | (SEQ ID NO: 106) |
| YP_273082_2 | | -TTERIVAIGTSTGGTQALEAVLTALPRVC---- | 29 | (SEQ ID NO: 107) |
| EFW82095_2 | | -TTERIVAIGTSTGGTQALEAVLTALPRVC---- | 29 | (SEQ ID NO: 108) |
| EGH71924_2 | | -TTERIVAIGTSTGGTQALEAVLTALPRVC---- | 29 | (SEQ ID NO: 109) |
| ZP_05638023_2 | | -TTERIVAIGTSTGGTQALEAVLTALPRVC---- | 29 | (SEQ ID NO: 110) |
| EGH23390_2 | | -TTERIVAIGTSTGGTQALEAVLTALPRVC---- | 29 | (SEQ ID NO: 111) |
| YP_233877_2 | | -TTERIVAIGTSTGGTQALEAVLTALPRVC---- | 29 | (SEQ ID NO: 112) |
| EGH54563_2 | | -TTERIVAIGTSTGGTQALEAVLTALPRVC---- | 29 | (SEQ ID NO: 113) |
| EFW86187_2 | | -TTERIVAIGTSTGGTQALEAVLTALPRVC---- | 29 | (SEQ ID NO: 114) |
| EGH77388_2 | | -TTERIVAIGTSTGGTQALEAVLTALPRVC---- | 29 | (SEQ ID NO: 115) |
| NP_790747_2 | | -TTERIVAIGTSTGGTQALEAVLTALPRVC---- | 29 | (SEQ ID NO: 116) |
| ZP_07251539_2 | | -TTERIVAIGTSTGGTQALEAVLTALPRVC---- | 29 | (SEQ ID NO: 117) |
| ZP_04590480_2 | | -TTERIVAIGTSTGGTQALEAVLTALPRVC---- | 29 | (SEQ ID NO: 118) |
| ZP_06457223_2 | | -TTERIVAIGTSTGGTQALEAVLTALPRVC---- | 29 | (SEQ ID NO: 119) |
| ZP_07003572_2 | | -TTERIVAIGTSTGGTQALEAVLTALPRVC---- | 29 | (SEQ ID NO: 120) |
| EGH66597_2 | | -TTERIVAIGTSTGGTQALEAVLTALPRVC---- | 29 | (SEQ ID NO: 121) |
| EGH31878_2 | | -TTERIVAIGTSTGGTQALEAVLTALPRVC---- | 29 | (SEQ ID NO: 122) |
| EGH06695_2 | | -TTERIVAIGTSTGGTQALEAVLTALPRVC---- | 29 | (SEQ ID NO: 123) |
| EGH61007_2 | | -TTERIVAIGTSTGGTQALEAVLTALPRVC---- | 29 | (SEQ ID NO: 124) |
| ZP_06495900_2 | | -TTERIVAIGTSTGGTQALEAVLTALPRVC---- | 29 | (SEQ ID NO: 125) |

TABLE D-continued

| TAL EBE against methylesterases | | | |
|---|---|---|---|
| EGH48032_2 | -TTERIVAIGTSTGGTQALEAVLTALPRVC---- | 29 | (SEQ ID NO: 126) |
| ZP_10381001 | -TTERIVAIGTSTGGTQALEAVLTALPRVC---- | 29 | (SEQ ID NO: 127) |
| ZP_06495900 | -TTERIVAIGTSTGGTQALEAVLTALPRVC---- | 29 | (SEQ ID NO: 128) |
| EGH48032 | -TTERIVAIGTSTGGTQALEAVLTALPRVC---- | 29 | (SEQ ID NO: 129) |
| YP_003847734 | MTSEQIVAIGTSTGGTQALEAVLTALPRVC---- | 30 | (SEQ ID NO: 130) |
| ZP_10991552 | -TTERIVAIGTSTGGTQALETVLTALPRVC---- | 29 | (SEQ ID NO: 131) |
| ZP_10991552_2 | -TTERIVAIGTSTGGTQALETVLTALPRVC---- | 29 | (SEQ ID NO: 132) |
| YP_003907367_2 | ----RIVAIGTSTGGTQALEVVLTALP------- | 23 | (SEQ ID NO: 133) |
| EJO92907 | -TTDRVVAIGTSTGGTQALEVVLRQLPVDC---- | 29 | (SEQ ID NO: 134) |
| YP_001187060 | -TTDRVVALGTSTGGTQALEVVLRQLPVDC---- | 29 | (SEQ ID NO: 135) |
| ZP_10995147_2 | -TTDRVVALGCSTGGTQALEFILRQLPRDC---- | 29 | (SEQ ID NO: 136) |
| YP_001792820 | -TTERVVALGTSTGGTQALEVVLRTLPRVC---- | 29 | (SEQ ID NO: 137) |
| ZP_08780698 | -TTDRVVAIGTSTGGTQALEVVLTALPRVC---- | 29 | (SEQ ID NO: 138) |
| YP_004846745 | -TTERIVAIGTSTGGTQALETVLHRLPATC---- | 29 | (SEQ ID NO: 139) |
| ZP_03698248 | -TTERIVAIGTSTGGTQALETVLPRLPATC---- | 29 | (SEQ ID NO: 140) |
| YP_005027668 | -TTDKIIAIGTSTGGTQALEAVLTKLPAVC---- | 29 | (SEQ ID NO: 141) |
| EKE17764 | -TTDQUAIGTSTGGTQALEAILTKLPATC---- | 29 | (SEQ ID NO: 142) |
| ZP_10442431 | -TSDKVVAIGASTGGTQALELLLTGLPAVC---- | 29 | (SEQ ID NO: 143) |
| YP_004030667_2b | ---ADIVKIASNGGGAQALEAVAMHGSTLCE--- | 28 | (SEQ ID NO: 144) |
| YP_004030667_2c | ---ADIVKIAGNGGGARALKAVVMHGPTLCE--- | 28 | (SEQ ID NO: 145) |
| YP_004030667_2a | FSQADIVRIADNIGGAQALKAVLEHGPTL----- | 29 | (SEQ ID NO: 146) |
| EGH56182_2 | -------ALAAAVGGKGALEVPANLIPANCE--- | 24 | (SEQ ID NO: 147) |

Example 4

Figure 2:
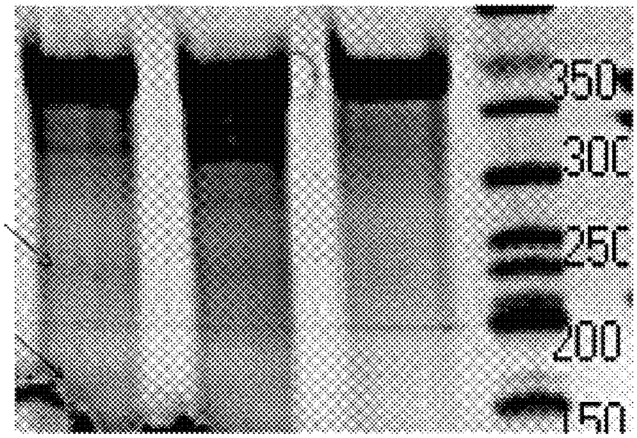
FIG. 2 is a photograph of a gel electrophoresis demonstrating RTN functionality.

A pair of Bmpr2 specific EBEs (*Ralstonia* DNA binding domain, 16EBEs each) are gene synthesized and cloned into XTN-BB (*Xanthomonas* TAL backbone fused to FokI). These constructs are co-transfected into Rat C6 cells and gDNA extracted after 48 hrs for Cell surveyor nuclease assay. A successful assay should produce 240 bp and 150 bp subpopulations from the original 400 bp amplicon of the locus. The results are shown in the FIG. 2.

The assay reveals the expected 250 bp and 150 bp bands in the *Ralstonia* and *Xanthomonas* TALEN transfected cells, which are absent in the WT negative control. This indicates that the *Ralstonia* EBEs target this locus and the fusion of FokI nuclease to *Ralstonia* EBEs lead to targeted digestion of genomic DNA. Using the 250 bp band, 5.75% for XTN, 1.82% for RTN. Using the 150 bp band, 3.66% for XTN, 5.43% for RTN.

| | |
|---|---|
| Bmpr2 Target site (SEQ ID NO: 148) | **T-T-GATA-GTCG-CCTT-ATG-T**tttggatacagaatgt**T-GAC-AGGT-AAAC-GAAA-T-A** |
| Fwd RTN | TGATAGTCGCCTTATG (SEQ ID NO: 149) |
| Rev RTN | ATTTGGTTTACCTGTC (SEQ ID NO: 150) |

Note:
the first and the last nucleotide of the targeted site (underlined) are not specified by the RTNs. These are specified by the Xanthomonas TALEN backbone.

Bmpr2 FWD RTN EBEs' amino acid sequence:

(SEQ ID NO: 151)
LSTAQVVAIAS NG GGKQALEGIGEQLLKLRTAPYG (SEQ ID NO: 152)
LSTEQVVAIAS NK GGKQALEAVKAHLLDLLGAPYV (SEQ ID NO: 153)
LSTEQVVAIAS NN GGKQALEAVKAQLLELRAAPYE (SEQ ID NO: 154)
LSTAQVVAIAS NG GGKQALEGIGEQLLKLRTAPYG (SEQ ID NO: 155)
LSTEQVVAIAS NN GGKQALEAVKAQLLELRAAPYE (SEQ ID NO: 156)
LSTEQVVAIAS NK GGKQALEAVKAHLLDLLGAPYV (SEQ ID NO: 157)
LSTAQVVAIAS NG GGKQALEGIGEQLLKLRTAPYG (SEQ ID NO: 158)
LSTAQVVAIAS HD GGKPALEAVWAKLPVLRGVPYA (SEQ ID NO: 159)
LSTEQVVAIAS NK GGKQALEAVKAHLLDLLGAPYV

-continued (SEQ ID NO: 160)
LSTAQVVAIAS HD GGKPALEAVWAKLPVLRGVPYA (SEQ ID NO: 161)
LSTAQVVAIAS HD GGKPALEAVWAKLPVLRGVPYA (SEQ ID NO: 162)
LSTAQVVAIAS NG GGKQALEGIGEQLLKLRTAPYG (SEQ ID NO: 163)
LSTAQVVAIAS NG GGKQALEGIGEQLLKLRTAPYG (SEQ ID NO: 164)
LSTEQVVAIAS NN GGKQALEAVKAQLLELRAAPYE (SEQ ID NO: 165)
LSTAQVVAIAS NG GGKQALEGIGEQLLKLRTAPYG (SEQ ID NO: 166)
LSTEQVVAIAS NK GGKQALEAVKAHLLDLLGAPYV Bmpr2 FWD RTN DNA sequence:
(Bolded font: synthesized Ralstonia EBEs) This sequence is contiguous (SEQ ID NO: 167):
GACGGATCGGGAGATCTCCCGATCCCCTATGGTCGACTCTCAGTACAATCTGCTCTGATGCCGCATAGTTAAGCCAGTATCTGCTCCCT GCTTGTGTGTTGGAGGTCGCTGAGTAGTGCGCGAGCAAAATTTAAGCTACAACAAGGCAAGGCTTGACCGACAATTGCATGAAGAAT CTGCTTAGGGTTAGGCGTTTTGCGCTGCTTCGCGATGTACGGGCCAGATATACGCGTTGACATTGATTATTGACTAGTTATTAATAGTA ATCAATTACGGGGTCATTAGTTCATAGCCCATATATGGAGTTCCGCGTTACATAACTTACGGTAAATGGCCCGCCTGGCTGACCGCCC AACGACCCCCGCCCATTGACGTCAATAATGACGTATGTTCCCATAGTAACGCCAATAGGGACTTTCCATTGACGTCAATGGGTGGAgT ATTTACGGTAAACTGCCCACTTGGCAGTACATCAAGTGTATCATATGCCAAGTACGCCCCCTATTGACGTCAATGACGGTAAATGGCC CGCCTGGCATTATGCCCAGTACATGACCTTATGGGACTTTCCTACTTGGCAGTACATCTACGTATTAGTCATCGCTATTACCATGGTGA TGCGGTTTTGGCAGTACATCAATGGGCGTGGATAGCGGTTTGACTCACGGGGATTTCCAAGTCTCCACCCCATTGACGTCAATGGGAG TTTGTTTTGGCACCAAAATCAACGGGACTTTCCAAAATGTCGTAACAACTCCGCCCCATTGACGCAAATGGGCGGTAGGCGTGTACGG TGGGAGGTCTATATAAGCAGAGCTCTCTGGCTAACTAGAGAACCCACTGCTTACTGGCTTATCGAAATTAATACGACTCACTATAGGG AGACCCAAGCTGGCTAGCACCATGGACTACAAAGACCATGACGGTGATTATAAAGATCATGACATCGATTACAAGGATGACGATGAC AAGATGGCCCCCAAGAAGAAGAGGAAGGTGGGCATTCACCGCGGGGTACCTATGGTGGACTTGAGGACACTCGGTTATTCGCAACAG CAACAGGAGAAAATCAAGCCTAAGGTCAGGAGCACCGTCGCGCAACACCACGAGGCGCTTGTGGGGCATGGCTTCACTCATGCGCAT ATTGTCGCGCTTTCACAGCACCCTGCGGCGCTTGGGACGGTGGCTGTCAAATACCAAGATATGATTGCGGCCCTGCCCGAAGCCACGC ACGAGGCAATTGTAGGGGTCGGTAAACAGTGGTCGGGAGCGCGAGCACTTGAGGCGCTGCTGACTGTGGCGGGTGAGCTTAGGGGGC CTCCGCTCCAGCTCGACACCGGGCAGCTGCTGAAGATCGCGAAGAGAGGGGGAGTAACAGCGGTAGAGGCAGTGCACGCCTGGCGC

AATGCGCTCACCGGGGCCCCCTTGAAC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

-continued

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGCGGAGGACGGCCAGCCTTGGAGTCCATCGTAGCCCAATTGTCCAGGCCC

GATCCCGCGTTGGCTGCGTTAACGAATGACCATCTGGTGGCGTTGGCATGTCTTGGTGGACGACCCGCGCTTGATGCAGTCAAAAAGG

GTCTGCCTCATGCTCCCGCATTGATCAAAAGAACCAACCGGCGGATTCCCGAGAGAACTTCCCATCGAGTCGCGGGATCCCAACTAGT

CAAAAGTGAACTGGAGGAGAAGAAATCTGAACTTCGTCATAAATTGAAATATGTGCCTCATGAATATATTGAATTAATTGAAATTGCC

AGAAATTCCACTCAGGATAGAATTCTTGAAATGAAGGTAATGGAATTTTTTATGAAAGTTTATGGATATAGAGGTAAACATTTGGGTG

GATCAAGGAAACCGGACGGAGCAATTTATACTGTCGGATCTCCTATTGATTACGGTGTGATCGTGGATACTAAAGCTTATAGCGGAGG

TTATAATCTGCCAATTGGCCAAGCAGATGAAATGCAACGATATGTCGAAGAAAATCAAACACGAAACAAACATATCAACCCTAATGA

ATGGTGGAAAGTCTATCCATCTTCTGTAACGGAATTTAAGTTTTTATTTGTGAGTGGTCCTTTAAAGGAAACTACAAAGCTCAGCTTA

CACGATTAAATCATATCACTAATTGTAATGGAGCTGTTCTTAGTGTAGAAGAGCTTTTAATTGGTGGAGAAATGATTAAAGCCGGCTTT

ATTAACCTTAGAGGAAGTCAGACGGAAATTTAATAACGGCGAGATAAACTTTTAAGGGCCCTTCGAAGGTAAGCCTATCCCTAACCCT

CTCCTCGGTCTCGATTCTACGCGTACCGGTCATCATCACCATCACCATTGAGTTTAAACCCGCTGATCAGCCTCGACTGTGCCTTCTAG

TTGCCAGCCATCTGTTGTTTGCCCCTCCCCCGTGCCTTCCTTGACCCTGGAAGGTGCCACTCCCACTGTCCTTTCCTAATAAAATGAGG

AAATTGCATCGCATTGTCTGAGTAGGTGTCATTCTATTCTGGGGGGTGGGGTGGGGCAGGACAGCAAGGGGGAGGATTGGGAAGACA

ATGCAGGCATGCTGGGGATGCGGTGGGCTCTATGGCTTCTGAGGCGGAAAGAACCAGCTGGGGCTCTAGGGGGTATCCCCATGCGC

CCTGTAGCGGCGCATTAAGCGCGGCGGGTGTGGTGGTTACGCGCAGCGTGACCGCTACACTTGCCAGCGCCCTAGCGCCCGCTCCTTT

CGCTTTCTTCCCTTCCTTTCTCGCCACGTTCGCCGGCTTTCCCCGTCAAGCTCTAAATCGGGGCATCCTTTTAGGGTTCCGATTTAGTGC

TTTACGGCACCTCGACCCCAAAAAACTTGATTAGGGTGATGGTTCACGTAGTGGGCCATCGCCCTGATAGACGGTTTTTCGCCCTTTGA

CGTTGGAGTCCACGTTCTTTAATAGTGGACTCTTGTTCCATTACTGGAACAACACTCAACCCTATCTCGGTCTATTTTCTGATTTATAA

GGGATTTTGGGGATTTCGGCCTATTGGTTAAAAAATGAGCTGATTTAACAAAAATTTAACGCGAATTAATTCTGTGGAATGTGTGTCA

GTTAGGGTGTGGAAAGTCCCCAGGCTCCCCAGGCAGGCAGAAGTATGCAAAGCATGCATCTCAATTAGTCAGCAACCAGGTGTGGAA

-continued

AGTCCCCAGGCTCCCCAGCAGGCAGAAGTATGCAAAGCATGCATCTCAATTAGTCAGCAACCATAGTCCCGCCCCTAACTCCGCCCAT

CCCGCCCCTAACTCCGCCCAGTTCCGCCCATTCTCCGCCCCATGGCTGACTAATTTTTTTTATTTATGCAGAGGCCGAGGCCGCCTCTG

CCTCTGAGCTATTCCAGAAGTAGTGAGGAGGCTTTTTTGGAGGCCTAGGCTTTTTCAAAAAGCTCCCGGGAGCTTGTATATCCATTTTC

GGATCTGATCAGCACGTGTTGACAATTAATCATCGGCATAGTATATCGGCATAGTATAATACGACAAGGTGAGGAACTAAACCATGG

CCAAGCCTTTGTCTCAAGAAGAATCCACCCTCATTGAAAGAGCAACGGCTACAATCAACAGCATCCCCATCTCTGAAGACTACAGCGT

CGCCAGCGCAGCTCTCTCTAGCGACGGCCGCATCTTCACTGGTGTCAATGTATATCATTTTACTGGGGGACCTTGTGCAGAACTCGTGG

TGCTGGGCACTGCTGCTGCTGCGGCAGCTGGCAACCTGACTTGTATCGTCGCGATCGGAAATGAGAACAGGGGCATCTTGAGCCCCTG

CGGACGGTGTCGACAGGTGCTTCTCGATCTGCATCTGGGATCAAAGCGATAGTGAAGGACAGTGATGGACAGCCGACGGCAGTTGG

GATTCGTGAATTGCTGCCCTCTGGTTATGTGTGGGAGGGCTAAGCACTTCGTGGCCGAGGAGCAGGACTGACACGTGCTACGAGATTT

CGATTCCACCGCCGCCTTCTATGAAAGGTTGGGCTTCGGAATCGTTTTCCGGGACGCCGGCTGGATGATCCTCCAGCGCGGGGATCTC

ATGCTGGAGTTCTTCGCCCACCCCAACTTGTTTATTGCAGCTTATAATGGTTACAAATAAAGCAATAGCATCACAAATTTCACAAATA

AAGCATTTTTTTcACTGCATTCTAGTTGTGGTTTGTCCAAACTCATCAATGTATCTTATCATGTCTGTATACCGTCGACCTCTAGCTAGA

GCTTGGCGTAATCATGGTCATAGCTGTTTCCTGTGTGAAATTGTTATCCGCTCACAATTCCACACAACATACGAGCCGGAAGCATAAA

GTGTAAAGCCTGGGGTGCCTAATGAGTGAGCTAACTCACATTAATTGCGTTGCGCTCACTGCCCGCTTCCAGTCGGGAAACCTGTCG

TGCCAGCTGCATTAATGAATCGGCCAACGCGCGGGGAGAGGCGGTTTGCGTATTGGGCGCTCTTCCGCTTCCTCGCTCACTGACTCGC

TGCGCTCGGTCGTTCGGCTGCGGCGAGCGGTATCAGCTCACTCAAAGGCGGTAATACGGTTATCCACAGAATTCAGGGGATAACGCAG

GAAAGAACATGTGAGCAAAAGGCCAGCAAAAGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGACTATAAAGATACCAGGCGTTTCCCCCTGGAA

GCTCCCTCGTGCGCTCTCCTGTTCCGACCCTGCCGCTTACCGGATACCTGTCCGCCTTTCTCCCTTCGGGAAGCGTGGCGCTTTCTCAAT

GCTCACGCTGTAGGTATCTCAGTTCGGTGTAGGTCGTTCGCTCCAAGCTGGGCTTTTGTGCACGAACCCCCCGTTCAGCCCGACCGCTG

CGCCTTTTTCCGGTAACTATCGTCTTGAGTCCAACCCGGTAAGACACGACTTATCGCCACTTTGCAGCAGCCACTGGTAACAGGTTTTA

GCAGAGCGAGGTATGTAGGCGGTGCTACAGAGTTTTTTGAAGTGGTGGCCTAACTACGGCTACACTAGAAGGACAGTATTTGGTATCTGC

GCTCTGCTGAAGCCAGTTACCTTCGGAAAAAGAGTTGGTAGCTCTTGATCCGGCATTACAAACCACCGCTGGTAGCGGTGGTTTTTTTG

TTTGCAAGCAGCAGATTACGCGCAGAAAAAAAGGATCTCAAGAAGATCCTTTGATCTTTTCTACGGGGTCTGACGCTCAGTGGAACGA

AAACTCACGTTAAGGGATTTTGGTCTTTGAGATTATCAAAAAGGATCTTCACCTAGATCCTTTTAAATTAAAAATGAAGTTTTAAATCA

ATCTAAAGTATATATGAGTAAACTTGGTCTGACAGTTACCAATGCTTAATCAGTGAGGCACCTATCTCAGTGATCTGTCTATTTTGTTC

ATCCATAGTTGCCTGACTCCCCGTCGTGTAGATAACTACGATACGGGAGGGCTTACCATCTGGCCCCAGTGCTGCAATGATACCGCGA

GACCCACGCTCACCGGCTCCAGATTTATCAGCAATAAACCAGCCAGCCGGAAGGGCCGAGCGCAGAAGTGGTCCTGCAACTTTATCC

GCCTCCATCCAGTCTATTAATTGTTGCCGGGAAGCTAGAGTAAGTAGTTCGCCAGTTAATAGTTTGCGCAACGTTGTTGCCATTGCTAC

AGGCATCGTGGTGTCACGCTCGTCGTTTGGTATGGCTTCATTCAGCTCCGGTTCCCAACGATCAAGGCGAGTTACATGATCCCCCATGT

TGTGCAAAAAAGCGGTTAGCTCCTTCGGTCCTCCGATCGTTGTCAGAAGTAAGTTGGCCGCAGTGTTATCACTCATGGTTATGGCAGC

ACTGCATATTCTCTTACTGTCATGCCATCCGTAAGATGCTTTTCTGTGACTGGTGAGTACTCAACCAAGTCATTCTGAGAATAGTGTA

TTCGGCGACCGAGTTGCTCTTGCCCGGCGTCAATACGGGATAATACCGCGCCACATAGCAGAACTTTAAAAGTGCTCATCATTGGAAA

ACGTTCTTCGGGGCGAAAACTCTCAAGGATCTTACCGCTGTTGAGATCCAGTTCGATGTAACCCACTCGTGCACCCAACTGATCTTCA

GCATCTTTTACTTTCACCAGCGTTTCTGGGTGAGCAAAAACAGGAAGGCAAAATGCCGCAAAAAAGGGAATAAGGGCGACACGGAAA

TGTTGAATACTCATACTCTTCCTTTTTCAATATTATTGAAGCATTTATCAGGGTTATTGTCTCATGAGCGGATACATATTTGAATGTATT

TAGAAAAATAAACAAATAGGGGTTCCGCGCACATTTCCCCGAAAAGTGCCACCTGACGTC

Bmpr2 REV RTN EBEs' amino acid sequence:

(SEQ ID NO: 168)

LSTEQVVAIAS NN GGKQALEAVKAQLLELRAAPYE (SEQ ID NO: 169)

LSTAQVVAIAS NG GGKQALEGIGEQLLKLRTAPYG

-continued (SEQ ID NO: 170)
LSTAQVVAIAS NG GGKQALEGIGEQLLKLRTAPYG (SEQ ID NO: 171)
LSTAQVVAIAS NG GGKQALEGIGEQLLKLRTAPYG (SEQ ID NO: 172)
LSTAQVVAIAS HD GGKPALEAVWAKLPVLRGVPYA (SEQ ID NO: 173)
LSTEQVVAIAS NK GGKQALEAVKAHLLDLLGAPYV (SEQ ID NO: 174)
LSTAQVVAIAS NG GGKQALEGIGEQLLKLRTAPYG (SEQ ID NO: 175)
LSTAQVVAIAS NG GGKQALEGIGEQLLKLRTAPYG (SEQ ID NO: 176)
LSTAQVVAIAS NG GGKQALEGIGEQLLKLRTAPYG (SEQ ID NO: 177)
LSTEQVVAIAS NN GGKQALEAVKAQLLELRAAPYE (SEQ ID NO: 178)
LSTAQVVAIAS HD GGKPALEAVWAKLPVLRGVPYA (SEQ ID NO: 179)
LSTAQVVAIAS HD GGKPALEAVWAKLPVLRGVPYA (SEQ ID NO: 180)
LSTAQVVAIAS NG GGKQALEGIGEQLLKLRTAPYG (SEQ ID NO: 181)
LSTEQVVAIAS NK GGKQALEAVKAHLLDLLGAPYV (SEQ ID NO: 182)
LSTAQVVAIAS NG GGKQALEGIGEQLLKLRTAPYG (SEQ ID NO: 183)
LSTAQVVAIAS HD GGKPALEAVWAKLPVLRGVPYA Bmpr2 REV RTN DNA Sequence:
(Bolded Font: synthesized Ralstonia EBEs) this sequence is contiguous (SEQ ID NO: 184):
GACGGATCGGGAGATCTCCCGATCCCCTATGGTCGACTCTCAGTACAATCTGCTCTGATGCCGCATAGTTAAGCCAGTATCTGCTCCCT GCTTGTGTGTTGGAGGTCGCTGAGTAGTGCGCGAGCAAAATTTAAGCTACAACAAGGCAAGGCTTGACCGACAATTGCATGAAGAAT CTGCTTAGGGTTAGGCGTTTTGCGCTGCTTCGCGATGTACGGGCCAGATATACGCGTTGACATTGATTATTGACTAGTTATTAATAGTA ATCAATTACGGGGTCATTAGTTCATAGCCCATATATGGAGTTCCGCGTTACATAACTTACGGTAAATGGCCCGCCTGGCTGACCGCCC AACGACCCCCGCCCATTGACGTCAATAATGACGTATGTTCCCATAGTAACGCCAATAGGGACTTTCCATTGACGTCAATGGGTGGAgT ATTTACGGTAAACTGCCCACTTGGCAGTACATCAAGTGTATCATATGCCAAGTACGCCCCCTATTGACGTCAATGACGGTAAATGGCC CGCCTGGCATTATGCCCAGTACATGACCTTATGGGACTTTCCTACTTGGCAGTACATCTACGTATTAGTCATCGCTATTACCATGGTGA TGCGGTTTTGGCAGTACATCAATGGGCGTGGATAGCGGTTTGACTCACGGGGATTTCCAAGTCTCCACCCCATTGACGTCAATGGGAG TTTGTTTTGGCACCAAAATCAACGGGACTTTCCAAAATGTCGTAACAACTCCGCCCCATTGACGCAAATGGGCGGTAGGCGTGTACGG TGGGAGGTCTATATAAGCAGAGCTCTCTGGCTAACTAGAGAACCCACTGCTTACTGGCTTATCGAAATTAATACGACTCACTATAGGG AGACCCAAGCTGGCTAGCACCATGGACTACAAAGACCATGACGGTGATTATAAAGATCATGACATCGATTACAAGGATGACGATGAC AAGATGGCCCCCAAGAAGAAGAGGAAGGTGGGCATTCACCGCGGGGTACCTATGGTGGACTTGAGGACACTCGGTTATTCGCAACAG CAACAGGAGAAAATCAAGCCTAAGGTCAGGAGCACCGTCGCGCAACACCACGAGGCGCTTGTGGGGCATGGCTTCACTCATGCGCAT ATTGTCGCGCTTTCACAGCACCCTGCGGCGCTTGGGACGGTGGCTGTCAAATACCAAGATATGATTGCGGCCCTGCCCGAAGCCACGC ACGAGGCAATTGTAGGGGTCGGTAAACAGTGGTCGGGAGCGCGAGCACTTGAGGCGCTGCTGACTGTGGCGGGTGAGCTTAGGGGGC CTCCGCTCCAGCTCGACACCGGGCAGCTGCTGAAGATCGCGAAGAGAGGGGGAGTAACAGCGGTAGAGGCAGTGCACGCCTGGCGC

AATGCGCTCACCGGGGCCCCCTT

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

-continued

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAC

GGCGGCAAGCAGGCCCTGGAGGCCGTGAAGGCCCAGCTGCTGGAGCTGAGGGCCGCCCCCTACGAG

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGAGCAGGTGGTGGCCATCGCCAGCAACAAG

GGCGGCAAGCAGGCCCTGGAGGCCGTGAAGGCCCACCTGCTGGACCTGCTGGGCGCCCCCTACGTG

CTGAGCACCGCCCAGGTGGTGGCCATCGCCAGCAACGGC

GGCGGCAAGCAGGCCCTGGAGGGCATCGGCGAGCAGCTGCTGAAGCTGAGGACCGCCCCCTACGGC

CTGAGCACCGCCCAGGTGGTGGCCATCGCCAGCCACGAC

GGCGGCAAGCCCGCCCTGGAGGCCGTGTGGGCCAAGCTGCCCGTGCTGAGGGGCGTGCCCTACGCC

CTGAGCACCGAGCAGGTGGTGACCATCGCCAGC

AGCATCGGAGGACGGCCAGCCTTGGAGTCCATCGTAGCCCAATTGTCCAGGCCCGATCCCGCGTTGGCTGCGTTAACGAATGACCATC

TGGTTTGCGTTGGCATGTCTTGGTGGACGACCCGCGCTCGATGCAGTCAAAAAGGGTCTGCCTCATGCTCCCGCATTGATCAAAAGAAC

CAACCGGCGGATTCCCGAGAGAACTTCCCATCGAGTCGCGGGATCCCAACTAGTCAAAAGTGAACTGGAGGAGAAGAAATCTGAACT

TCGTCATAAATTGAAATATGTGCCTCATGAATATATTGAATTAATTGAAATTGCCAGAAATTCCACTCAGGATAGAATTCTTGAAATG

AAGGTAATGGAATTTTTTATGAAAGTTTATGGATATAGAGGTTAACATTTGGGTGGATCAAGGAAACCGGACGGAGCAATTTATACT

GTCGGATCTCCTATTGATTACGGTGTGATCGTGGATACTAAAGCTTATAGCGGAGGTTATAATCTGCCAATTGGCCAAGCAGATGAAA

TGCAACGATATGTCGAAGAAAATCAAACACGAAACAAACATATCAACCCTAATGAATGGTGGAAAGTCTATCCATCTTCTGTAACGG

AATTTAAGTTTTTATTTGTGAGTGGTTACTTTAAAGGAAACTACAAAGCTCAGCTTACACGATTAAATCATATCACTAATTGTAATGGA

GCTGTTCTTAGTGTAGAAGAGCTTTTAATTGGTGGAGAAATGATTAAAGCCGGCACATTAACCTTAGAGGAAGTCAGACGGAAATTTA

-continued

ATAACGGCGAGATAAACTTTTAAGGGCCCTTCGAAGGTAAGCCTATCCCTAACCCTCTCCTCCGTCTCGATTCTACGCCTACCGGTCAT

CATCACCATCACCATTGAGTTTAAACCCGCTGATCAGCCTCGACTGTGCCTTCTAGTTGCCAGCCATCTGTTGTTTGCCCCTCCCCCGT

GCCTTCCTTGACCCTGGAAGGTGCCACTCCCACTGTCCTTTCCTAATAAAATGAGGAAATTGCATCGCATTGTCTGAGTAGGTGTCATT

CTATTCTGGGGGGTGGGGTGGGGCAGGACAGCAAGGGGGAGGATTGGGAAGACAATAGCAGGCATGCTGGGGATGCGGTGGGCTCT

ATGGCTTCTGAGGCGGAAAGAACCAGCTGGGGCTCTAGGGGGTATCCCCACGCGCCCTGTAGCGGCGCATTAAGCGCGGCGGGTGTG

GTGGTTACGCGCAGCGTGACCGCTACACTTGCCAGCGCCCTAGCGCCCGCTCCTTTCGCTTTCTTCCCTTCCTTTCTCGCCACGTTCGCC

GGCTTTCCCCGTCAAGCTCTAAATCGGGGCATCCCTTTAGGGTTCCGATTTAGTTTCTTTACGGCACCTCGACCCCAAAAAACTTGATTA

GGGTGATGGTTCACGTAGTGGGCCATCGCCCTGATAGACGGTTTTTCGCCCTTTGACGTTGGAGTCCACGTTCTTTAATAGTGGACTCT

TGTTCCAAACTGGAACAACACTCAACCCTATCTCGGTCTATTCTTTTGATTTATAAGGGATTTTGGGGATTTCGGCCTATTGGTTAAAA

AATGAGCTGATTTAACAAAAATTTAACGCGAATTAATTCTGTGGAATGTGTGTCAGTTAGGGTGTGGAAAGTCCCCAGGCTCCCCAGG

CAGGCAGAAGTATGCAAAGCATGCATCTCAATTAGTCAGCAACCAGGTGTGGAGTCCCCAGGCTCCCCAGCAGGCAGAAGTATGC

AAAGCATGCATCTCAATTAGTCAGCAACCATAGTCCCGCCCCTAACTCCGCCCATCCCGCCCCTAACTCCGCCCAGTTCCGCCCATTCT

CCGCCCCATGGCTGACTAATTTTTTTTATTTATGCAGAGGCCGAGGCCGCCTCTGCCTCTGAGCTATTCCAGAAGTAGTGAGGAGGCTT

TTTTGGAGGCCTAGGCTTTTGCAAAAAGCTCCCGGGAGCTTGTATATCCATTTTCGGATCTGATCAGCACGTGTTGACAATTAATCATC

GGCATAGTATATCGGCATAGTATAATACGACAAGGTGAGGAACTAAACCATGGCCAAGCCTTTGTCTCAAGAAGAATCCACCCTCATT

GAAAGAGCAACGGCTACAATCAACAGCATCCCCATCTCTGAAGACTACAGCGTCGCCAGCGCAGCTCTCTCTAGCGACGGCCGCATC

TTCACTGGTGTCAATGTATATCATTTTACTGGGGGACCTTTTTGCAGAACTCGTGGTGCTGGGCACTGCTGCTGCTGCGGCAGCTGGCA

ACCTGACTTGTATCGTCGCGATCGGAAATGAGAACAGGGGCATCTTGAGCCCCTGCGGACGGTGTCGACAGGTGCTTCTCGATCTGCA

TCCTGGGATCAAAGCGATAGTGAAGGACAGTGATGGACAGCCGACGGCAGTTGGGATTCGTGAATTGCTGCCCTCTGGTTATGTGTGG

GAGGGCTAAGCACTTCGTGGCCGAGGAGCAGGACTGACACGTGCTACGAGATTTCGATTCCACCGCCGCCTTCTATGAAAGGTTGGG

CTTCGGAATCGTTTTCCGGGACGCCGGCTGGATGATCCTCCAGCGCGGGGATCTCATGCTGGAGTTCTTCGCCCACCCCAACTTGTTTA

TTGCAGCTTATAATGGTTACAAATAAAGCAATAGCATCACAAATTTCACAAATAAAGCATTTTTTTCACTGCATTCTAGTTGTGGTTTG

TCCAAACTCATCAATGTATCTTATCATGTCTGTATACCGTCGACCTCTAGCTAGAGCTTGGCGTAATCATGGTCATAGCTGTTTCCTGT

GTGAAATTGTTATCCGCTCACAATTCCACACAACATACGAGCCGGAAGCATAAAGTGTAAAGCCTGGGGTGCCTAATGAGTGAGCTA

ACTCACATTAATTGCGTTGCGCTCACTGCCCGCTTTCCAGTCGGGAAACCTGTCGTGCCAGCTGCATTAATGAATCGGCCAACGCGCG

GGGAGAGGCGGTTTGCGTATTGGGCGCTTTTCCGCTTCCTCGCTCACTGACTCGCTGCGCTCGGTCGTTCGGCTGCGGCGAGCGGTATC

AGCTCACTCAAAGGCGGTAATACGGTTATCCACAGAATCAGGGGATAACGCAGGAAAGAACATGTGAGCAAAAGGCCAGCAAAAGG

CCAGGAACCGTAAAAAGGCCGCGTTGCTGGCGTTTTTCCATAGGCTCCGCCCCCCTGACGAGCATCACAAAAATCGACGCTCAAGTCA

GAGGTGGCGAAACCCGACAGGACTATAAAGATACCAGGCGTTTCCCCCTGGAAGCTCCCTCGTGCGCTCTCCTGTTCCGACCCTGCCG

TTTACCGGATACCTGTCCGCCTTTCTCCCTTCGGGAAGCGTGGCGCTTTCTCAATGCTCACGCTGTAGGTATCTCAGTTCGGTGTAGGT

CGTTCGCTCCAAGCTGGGCTGTGTGCACGAACCCCCCGTTCAGCCCGACCGCTGCGCCTTATCCGGTAACTATCGTCTTGAGTCCAACC

CGGTAAGACACGACTTATCGCCACTGGCAGCAGCCACTGGTAACAGGATTAGCAGAGCGAGGTATGTAGGCGGTGCTACAGAGTTCT

TGAAGTGGTGGCCTAACTACGGCTACACTAGAAGGACAGTATTTGGTATCTGCGCTCTGCTGAGCCGTTCCCTTCGGAAAAAGAGT

TGGTAGCTCTTGATCCGGCAAACAAACCACCGCTGGTAGCGGTGGTTTTTTTGTTTGCAAGCAGCAGATTACGCGCAGAAAAAAAGGA

TTCTCAAGAAGATCCTTTGATCTTTTCTACGGGGTCTGACGCTCAGTGGAACGAAAACTCACGTTAAGGGATTTTGGTCATGAGATTATC

AAAAAGGATCTTCACCTAGATCCTTTTAAATTAAAAATGAAGTTTTAAATCAATCTAAAGTATATATGAGTAAACTTGGTCTGACAGT

TACCAATGCTTAATCAGTGAGGCACCTATCTCAGCGATCTGTCTATTTCGTTCATCCATAGTTGCCTGACTCCCCGTCGTGTAGATAAC

TACGATACGGGAGGGCTTACCATCTGGCCCCAGTGCTGCAATGATACCGCGAGACCCATGCTCACCGGCTCCAGATTTATCAGCAATA

AACCAGCCAGCCGGAAGGGCCGAGCGCAGAAGTGGTCCTGCAACTTTATCCGCCTCCATCCAGTCTATTAATTGTTGCCGGGAAGCTA

GAGTAAGTAGTTCGCCAGTTAATAGTTTGCGCAACGTTGTTGCCATTGCTACAGGCATCGTGGTGTCACGCTCGTCGTTTGGTATGGCT

TCATTCAGCTCCGGTTCCCAACGATCAAGGCGAGTTACATGATCCCCCATGTTGTGCAAAAAAGCGGTTAGCTCCTTCGGTCCTCCGAT

-continued

```
CGTTGTCAGAAGTAAGTTGGCCGCAGTGTTATCATTCATGGTTATGGCAGCACTGCATAATTCTCTTACTGTCATGCCATCCGTAAGAT

GCTTCCTGTGACTGGTGAGTACTCAACCAAGTCATTCTGAGAATAGTGTATGCGGCGACCGAGTTGCTCTTGCCCGGCGTCAATACG

GGATAATACCGCGCCACATAGCAGAACTTTAAAAGTGCTCATCATTGGAAAACGTTCTTCGGGGCGAAAACTCTCAAGGATCTTACCG

CTGTTGAGATCCAGTTCGATGTAACCCACTCGTGCACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTTGAATACTCATACTCTTCCTTTTTCAATATTATTG

AAGCATTTATCAGGGTTATTGTCTCATGAGCGGATACATATTTGAATGTATTTAGAAAAATAAACAAATAGGGGTTCCGCGCACATTT

CCCCGAAAAGTGCCACCTGACGTC
```

Example 5

A library of *Ralstonia* EBEs and backbone vectors were made which could be used to assemble full length *Ralstonia* DNA binding domains into *Ralstonia* or *Xanthomonas* TALEN backbones, utilizing the golden gate assembly method. The RTNs were co-transfected into the Rat C6 cell line and gDNA extracted for analysis 48 hrs post transfection. A 420 bp gDNA fragment containing the RTN binding site was amplified by PCR. This amplicon was then subjected to the Cell assay using Surveyor Mutation Detection Kit (Transgenomic) as per manufacturer protocol. In brief, the amplicon is denatured into single stranded DNA and slowly re-annealed back to double stranded DNA. During this process, considering the original pool was a mixture of WT and mutated sequences, there will be cross hybridization between WT and mutant strands leading to formation of heteroduplexes. Upon treatment of this re-annealed pool with the Surveyor Nuclease, it recognizes the heteroduplexes and cleaves them, which generated two shorter fragments from (255 bp and 165 bp) the original amplicon (420 bp).

Terminology pRVD: plasmid containing a single *Ralstonia* EBE. Individual EBEs were gene synthesized and cloned in FLASH-XTN sub-array backbone (XbaI, BamHI).

pFus X: a sub-array plasmid that holds the first 10 EBEs of any given RTN. The required piece was gene synthesized and cloned into pHSG-298 (SacI, SbfI).

pFUS Z: a sub-array plasmid that holds EBE 11 up to the second-last EBE of any given RTN. Eg: Z4 holds EBEs 11-14, Z5 holds EBEs 11-15 and Z6 holds EBEs 11-16. Gene synthesized and cloned into pHSG-298 (SacI, SbfI).

XTN-bb: *Xanthomonas* TAL backbone that contains the N-terminal and C-terminal *Xanthomonas* TAL domains fused to FokI nuclease. This backbone specifies a T nucleotide 5' of the target sequence specified by the EBEs. It also contains the last half EBE that specifies the last nucleotide of the targeted sequence. Therefore there are four XTN-bb plasmids, each specifying a different final nucleotide of the targeted sequence (same as FLASH XTN backbones).

All plasmids are stored at 150 ng/ul in 0.1×TE buffer.

Methods: (building a 16EBE DNA binding domain and cloning it into a *Xanthomonas* TALEN backbone).

Assembly of a custom TALEN or TAL effector construct involves two steps: (i) assembly of repeat modules (pRVDs) into sub-arrays of 1-10 repeats and (ii) joining of the sub-arrays into a backbone to make the final construct.

Construction of a TALEN monomer with a 17 RVD array (5'-TGATAGTCGC-CTTATG-T-3'): Select from the pRVD plasmids those that encode RVDs 1-10 in the array using plasmids numbered in that order. For example, the plasmid for the first RVD would be gRTN-1T, the second gRTN-2G, the third gRTN-3A etc. Modules from these plasmids are cloned into sub-array plasmid pFUS-X. Next, select modules for RVDs 11-16 in the 16 RVD array again starting with plasmids numbered from 1. Thus for RVD 11 gRTN-1C would be used, for RVD 12 gRTN-2T, etc. The pFUS-Z plasmids are numbered 1-10 and should be selected according to the number of EBEs going in. Thus, in our example, pFUS-Z6 should be used.

The pRVDs and sub-array plasmids (150 ng each) are subjected to digestion and ligation in a single 20 μl reaction containing 1 μl BsaI (10 U, New England BioLabs) and 1 μl T4 DNA Ligase (2000 U, New England BioLabs) in T4 DNA ligase buffer (New England BioLabs). The reaction is incubated in a thermocycler for 10 cycles of 5 min at 37° C. and 10 min at 16° C., then heated to 50° C. for 5 min and then 80° C. for 5 min. Then, 1 μl 25 mM ATP and 1 μl Plasmid Safe DNase (10 U, Epicentre) are added. The mixture is incubated at 37° C. for 1 h, then used to transform *Escherichia coli* cells. Cells are plated on LB agar containing 50 mg/ml Kanamycin, overnight at 37° C.

Up to six colonies from each transformation were screened with M13 forward (fwd) and reverse (rev) primers, via colony PCR, to identify clones that contain a full-length sub-array. Full length pFUS-X sub-array clones should produce a 1.1 kb band and full-length pFUS-Z6 clones should produce a 700 bp band (add or subtract 105 bp for each EBE more or less). Cultures were started overnight cultures of a full-length pFUS-X and a full-length pFUS-Z6 clone.

Plasmid DNA was isolated from the pFUS-X and pFUS-Z cultures. Sub-arrays were joined into one of the four backbone plasmids. A 20 μl digestion and ligation reaction mixture is prepared with 150 ng each of the pFUS-X and pFUS-Z plasmids, 150 ng of the backbone plasmid, in this case XTN-bbT, 1 μl Esp3I (10U, Thermo Scientific) and 1 μl T4 DNA Ligase (2000U, New England Biolabs) in T4 DNA ligase buffer. The reaction is then incubated in a thermocycler for 3 cycles of 10 min at 37° C. and 15 min at 16° C. The reaction is then incubated at 37° C. for an additional 30 min and heated to 50° C. for 5 min, then 80° C. for 5 min. After cooling to room temperature, 1 μl 25 mM ATP and 1 μl Plasmid Safe DNase (10U, Epicenter) were added and incubated at 37° C. for 1 hr. The reaction is then used to transform *E. coli* as above, except that Plasmid Safe. Also, in this step, ampicillin (100 mg/ml) is used in place of Kanamycin for selection of transformants.

Up to three colonies were screened from each transformation via colony PCR with XTN-VF and XTN-VR2 primers and started overnight cultures of 1 full length clone for each RTN (2.1 kb band indicates 17EBE array). We then isolated plasmid DNA and identify clones containing the final, full-length repeat array by DNA sequencing with XTN-VF, XTN-VR1 and XTN-VR2.

XbaI and BamHI digested XTN sub-array backbone (sites underlined) (SEQ ID NO: 185):
(BamHI)GGATCCCGGGCCCGTCGACTGCAGAGGCCTGCATGCAAGCTTG
GCGTAATCATGGTCATAGCTGTTTCCTGTGTGAAATTGTTATCCGCTCAC
AATTCCACACAACATACGAGCCGGAAGCATAAAGTGTAAAGCCTGGGGTG
CCTAATGAGTGAGCTAACTCACATTAATTGCGTTGCGCTCACTGCCCGCT
TTCCAGTCGGGAAACCTGTCGTGCCAGCTGCATTAATGAATCGGCCAACG
CGCGGGGAGAGGCGGTTTGCGTATTGGGCGCTCTTCCGCTTCCTCGCTCA
CTGACTCGCTGCGCTCGGTCGTTCGGCTGCGGCGAGCGGTATCAGCTCAC
TCAAAGGCGGTAATACGGTTATCCACAGAATCAGGGGATAACGCAGGAAA
GAACATGTGAGCAAAAGGCCAGCAAAAGGCCAGGAACCGTAAAAAGGCCG
CGTTGCTGGCGTTTTTCCATAGGCTCCGCCCCCCTGACGAGCATCACAAA
AATCGACGCTCAAGTCAGAGGTGGCGAAACCCGACAGGACTATAAAGATA
CCAGGCGTTTCCCCCTGGAAGCTCCCTCGTGCGCTCTCCTGTTCCGACCC
TGCCGCTTACCGGATACCTGTCCGCCTTTCTCCCTTCGGGAAGCGTGGCG
CTTTCTCATAGCTCACGCTGTAGGTATCTCAGTTCGGTGTAGGTCGTTCG
CTCCAAGCTGGGCTGTGTGCACGAACCCCCCGTTCAGCCCGACCGCTGCG
CCTTATCCGGTAACTATCGTCTTGAGTCCAACCCGGTAAGACACGACTTA
TCGCCACTGGCAGCAGCCACTGGTAACAGGATTAGCAGAGCGAGGTATGT
AGGCGGTGCTACAGAGTTCTTGAAGTGGTGGCCTAACTACGGCTACACTA
GAAGAACAGTATTTGGTATCTGCGCTCTGCTGAAGCCAGTTACCTTCGGA
AAAAGAGTTGGTAGCTCTTGATCCGGCAAACAAACCACCGCTGGTAGCGG
TGGTTTTTTTGTTTGCAAGCAGCAGATTACGCGCAGAAAAAAAGGATCTC
AAGAAGATCCTTTGATCTTTTCTACGGGGTCTGACGCTCAGTGGAACGAA
AACTCACGTTAAGGGATTTTGGTCATGAGATTATCAAAAAGGATCTTCAC
CTAGATCCTTTTAAATTAAAAATGAAGTTTTAAATCAATCTAAAGTATAT
ATGAGTAAACTTGGTCTGACAGTTACCAATGCTTAATCAGTGAGGCACCT
ATCTCAGCGATCTGTCTATTTCGTTCATCCATAGTTGCCTGACTCCCCGT
CGTGTAGATAACTACGATACGGGAGGGCTTACCATCTGGCCCCAGTGCTG
CAATGATACCGCGAGAgCCACGCTCACCGGCTCCAGATTTATCAGCAATA
AACCAGCCAGCCGGAAGGGCCGAGCGCAGAAGTGGTCCTGCAACTTTATC
CGCCTCCATCCAGTCTATTAATTGTTGCCGGGAAGCTAGAGTAAGTAGTT
CGCCAGTTAATAGTTTGCGCAACGTTGTTGCCATTGCTACAGGCATCGTG
GTGTCACGCTCGTCGTTTGGTATGGCTTCATTCAGCTCCGGTTCCCAACG
ATCAAGGCGAGTTACATGATCCCCCATGTTGTGCAAAAAAGCGGTTAGCT
CCTTCGGTCCTCCGATCGTTGTCAGAAGTAAGTTGGCCGCAGTGTTATCA
CTCATGGTTATGGCAGCACTGCATAATTCTCTTACTGTCATGCCATCCGT
AAGATGCTTTTCTGTGACTGGTGAGTACTCAACCAAGTCATTCTGAGAAT
AGTGTATGCGGCGACCGAGTTGCTCTTGCCCGGCGTCAATACGGGATAAT
ACCGCGCCACATAGCAGAACTTTAAAAGTGCTCATCATTGGAAAACGTTC -continued TTCGGGGCGAAAACTCTCAAGGATCTTACCGCTGTTGAGATCCAGTTCGA
TGTAACCCACTCGTGCACCCAACTGATCTTCAGCATCTTTTACTTTCACC
AGCGTTTCTGGGTGAGCAAAAACAGGAAGGCAAAATGCCGCAAAAAAGGG
AATAAGGGCGACACGGAAATGTTGAATACTCATACTCTTCCTTTTTCAAT
ATTATTGAAGCATTTATCAGGGTTATTGTCTCATGAGCGGATACATATTT
GAATGTATTTAGAAAAATAAACAAATAGGGGTTCCGCGCACATTTCCCCG
AAAAGTGCCACCTGACGTCTAAGAAACCATTATTATCATGACATTAACCT
ATAAAAATAGGCGTATCACGAGGCCCTTTCGTCTCGCGCGTTTCGGTGAT
GACGGTGAAAACCTCTGACACATGCAGCTCCCGGAGACGGTCACAGCTTG
TCTGTAAGCGGATGCCGGGAGCAGACAAGCCCGTCAGGGCGCGTCAGCGG
GTGTTGGCGGGTGTCGGGGCTGGCTTAACTATGCGGCATCAGAGCAGATT
GTACTGAGAGTGCACCATATGCGGTGTGAAATACCGCACAGATGCGTAAG
GAGAAAATACCGCATCAGGCGCCATTCGCCATTCAGGCTGCGCAACTGTT
GGGAAGGGCGATCGGTGCGGGCCTCTTCGCTATTACGCCAGCTGGCGAAA
GGGGGATGTGCTGCAAGGCGATTAAGTTGGGTAACGCCAGGGTTTTCCCA
GTCACGACGTTGTAAAACGACGGCCAGTGAATTCGAGCTCGGTACCTCGC
GAATGCATCTAGA(XbaI)

Underlined sequences overlap with sub-arrays pFUS-X and pFUS-Z.

(SEQ ID NO: 186)
XTN-bbA: NNNNNNNNN is replaced with TCTAACATC (SEQ ID NO: 187)
XTN-bbC: NNNNNNNNN is replaced with TCCCACGAC (SEQ ID NO: 188)
XTN-bbG: NNNNNNNNN is replaced with AATAATAA (SEQ ID NO: 189)
XTN-bbT: NNNNNNNNN is replaced with TCTAATGGG (SEQ ID NO: 190)
pFUS-Z overlap CTGACACCCGAACAGGTGGTCGCCATTGC
TNNNNNNNN
GGAGGACGGCCAGCCTTGGAGTCCATCGTAGCCCAATTGTCCAGGCCCGA
TCCCGCGTTGGCTGCGTTAACGAATGACCATCTGGTGGCGTTGGCATGTC
TTGGTGGACGACCCGCGCTCGATGCAGTCAAAAAGGGTCTGCCTCATGCT
CCCGCATTGATCAAAAGAACCAACCGGCGGATTCCCGAGAGAACTTCCCA
TCGAGTCGCGGGATCCCAACTAGTCAAAAGTGAACTGGAGGAGAAGAAAT
CTGAACTTCGTCATAAATTGAAATATGTGCCTCATGAATATATTGAATTA
ATTGAAATTGCCAGAAATTCCACTCAGATAGAATTCTTGAAATGAAGGTA
ATGGAATTTTTTATGAAAGTTTATGGATATAGAGGTAAACATTTGGGTGG
ATCAAGGAAACCGGACGGAGCAATTTATACTGTCGGATCTCCTATTGATT
ACGGTGTGATCGTGGATACTAAAGCTTATAGCGGAGGTTATAATCTGCCA
ATTGGCCAAGCAGATGAAATGCAACGATATGTCGAAGAAAATCAAACACG
AAACAAACATATCAACCCTAATGAATGGTGGAAAGTCTATCCATCTTCTG -continued TAACGGAATTTAAGTTTTTATTTGTGAGTGGTCACTTTAAAGGAAACTAC
AAACTCAGCTTACACGATTAAATCATATCACTAATTGTAATGGAGCTGTT
CTTAGTGTAGAAGAGCTTTTAATTGGTGGAGAAATGATTAAAGCCGGCAC
ATTAACCTTAGAGGAAGTCAGACGGAAATTTAATAACGGCGAGATAAACT
TTTAAGGGCCCTTCGAAGGTAAGCCTATCCCTAACCCTCTCCTCGGTCTC
GATTCTACGCGTACCGGTCATCATCACCATCACCATTGAGTTTAAACCCG
CTGATCAGCCTCGACTGTGCCTTCTAGTTGCCAGCCATCTGTTGTTTGCC
CCTCCCCCGTGCCTTCCTTGACCCTGGAAGGTGCCACTCCCACTGTCCTT
TCCTAATAAAATGAGGAAATTGCATCGCATTGTCTGAGTAGGTGTCATTC
TATTCTGGGGGGTGGGGTGGGGCAGGACAGCAAGGGGGAGGATTGGGAAG
ACAATAGCAGGCATGCTGGGGATGCGGTGGGCTCTATGGCTTCTGAGGCG
GAAAGAACCAGCTGGGGCTCTAGGGGGTATCCCCACGCGCCCTGTAGCGG
CGCATTAAGCGCGGCGGGTGTGGTGGTTACGCGCAGCGTGACCGCTACAC
TTGCCAGCGCCCTAGCGCCCGCTCCTTTCGCTTTCTTCCCTTCCTTTCTC
GCCACGTTCGCCGGCTTTCCCCGTCAAGCTCTAAATCGGGGCATCCCTTT
AGGGTTCCGATTTAGTGCTTTACGGCACCTCGACCCCAAAAAACTTGATT
AGGGTGATGGTTCACGTAGTGGGCCATCGCCCTGATAGACGGTTTTTCGC
CCTTTGACGTTGGAGTCCACGTTCTTTAATAGTGGACTCTTGTTCCAAAC
TGGAACAACACTCAACCCTATCTCGGTCTATTCTTTTGATTTATAAGGGA
TTTTGGGGATTTCGGCCTATTGGTTAAAAAATGAGCTGATTTAACAAAAA
TTTAACGCGAATTAATTCTGTGGAATGTGTGTCAGTTAGGGTGTGGAAAG
TCCCCAGGCTCCCCAGGCAGGCAGAAGTATGCAAAGCATGCATCTCAATT
AGTCAGCAACCAGGTGTGGAAAGTCCCCAGGCTCCCCAGCAGGCAGAAGT
ATGCAAAGCATGCATCTCAATTAGTCAGCAACCATAGTCCCGCCCCTAAC
TCCGCCCATCCCGCCCCTAACTCCGCCCAGTTCCGCCCATTCTCCGCCCC
ATGGCTGACTAATTTTTTTTATTTATGCAGAGGCCGAGGCCGCCTCTGCC
TCTGAGCTATTCCAGAAGTAGTGAGGAGGCTTTTTTGGAGGCCTAGGCTT
TTGCAAAAAGCTCCCGGGAGCTTGTATATCCATTTTCGGATCTGATCAGC
ACGTGTTGACAATTAATCATCGGCATAGTATATCGGCATAGTATAATACG
ACAAGGTGAGGAACTAAACCATGGCCAAGCCTTTGTCTCAAGAAGAATCC
ACCCTCATTGAAAGAGCAACGGCTACAATCAACAGCATCCCCATCTCTGA
AGACTACAGCGTCGCCAGCGCAGCTCTCTCTAGCGACGGCCGCATCTTCA
CTGGTGTCAATGTATATCATTTTACTGGGGGACCTTGTGCAGAACTCGTG
GTGCTGGGCACTGCTGCTGCTGCGGCAGCTGGCAACCTGACTTGTATCGT
CGCGATCGGAAATGAGAACAGGGGCATCTTGAGCCCCTGCGGACGGTGTC
GACAGGTGCTTCTCGATCTGCATCCTGGGATCAAAGCGATAGTGAAGGAC
AGTATGGACAGCCGACGGCAGTTGGGATTCGTGAATTGCTGCCCTCTGGT
TATGTGTGGGAGGGCTAAGCACTTCGTGGCCGAGGAGCAGGACTGACACG
TGCTACGAGATTTCGATTCCACCGCCGCCTTCTATGAAAGGTTGGGCTTC
GGAATCGTTTTCCGGGACGCCGGCTGGATGATCCTCCAGCGCGGGGATCT
CATGCTGGAGTTCTTCGCCCACCCCAACTTGTTTATTGCAGCTTATAATG -continued GTTACAAATAAAGCAATAGCATCACAAATTTCACAAATAAAGCATTTTTT
TCACTGCATTCTAGTTGTGGTTTGTCCAAACTCATCAATGTATCTTATCA
TGTCTGTATACCGTCGACCTCTAGCTAGAGCTTGGCGTAATCATGGTCAT
AGCTGTTTCCTGTGTGAAATTGTTATCCGCTCACAATTCCACACAACATA
CGAGCCGGAAGCATAAAGTGTAAAGCCTGGGGTGCCTAATGAGTGAGCTA
ACTCACATTAATTGCGTTGCGCTCACTGCCCGCTTTCCAGTCGGGAAACC
TGTCGTGCCAGCTGCATTAATGAATCGGCCAACGCGCGGGGAGAGGCGGT
TTGCGTATTGGGCGCTCTTCCGCTTCCTCGCTCACTGACTCGCTGCGCTC
GGTCGTTCGGCTGCGGCGAGCGGTATCAGCTCACTCAAAGGCGGTAATAC
GGTTATCCACAGAATCAGGGGATAACGCAGGAAAGAACATGTGAGCAAAA
GGCCAGCAAAAGGCCAGGAACCGTAAAAAGGCCGCGTTGCTGGCGTTTTT
CCATAGGCTCCGCCCCCCTGACGACATCACAAAAATCGACGCTCAAGTCA
GAGGTGGCGAAACCCGACAGGACTATAAAGATACCAGGCGTTTCCCCCTG
GAAGCTCCCTCGTGCGCTCTCCTGTTCCGACCCTGCCGCTTACCGGATAC
CTGTCCGCCTTTCTCCCTTCGGGAAGCGTGGCGCTTTCTCAATGCTCACG
CTGTAGGTATCTCAGTTCGGTGTAGGTCGTTCGCTCCAAGCTGGGCTGTG
TGCACGAACCCCCCGTTCAGCCCGACCGCTGCGCCTTATCCGGTAACTAT
CGTCTTGAGTCCAACCCGGTAAGACACGACTTATCGCCACTGGCAGCAGC
CACTGGTAACAGGATTAGCAGAGCGAGGTATGTAGGCGGTGCTACAGAGT
TCTTGAAGTGGTGGCCTAACTACGGCTACACTAGAAGGACAGTATTTGGT
ATCTGCGCTCTGCTGAAGCCAGTTACCTTCGGAAAAAGAGTTGGTAGCTC
TTGATCCGGCAAACAAACCACCGCTGGTAGCGGTGGTTTTTTTGTTTGCA
AGCAGCAGATTACGCGCAGAAAAAAAGGATCTCAAGAAGATCCTTTGATC
TTTTCTACGGGGTCTGACGCTCAGTGGAACGAAAACTCACGTTAAGGGAT
TTTGGTCATGAGATTATCAAAAAGGATCTTCACCTAGATCCTTTTAAATT
AAAAATGAAGTTTTAAATCAATCTAAAGTATATATGAGTAAACTTGGTCT
GACAGTTACCAATGCTTAATCAGTGAGGCACCTATCTCAGCGATCTGTCT
ATTTCGTTCATCCATAGTTGCCTGACTCCCCGTCGTGTAGATAACTACGA
TACGGGAGGGCTTACCATCTGGCCCCAGTGCTGCAATGATACCGCGAGAC
CCACGCTCACCGGCTCCAGATTTATCAGCAATAAACCAGCCAGCCGGAAG
GGCCAGCGCAGAAGTGGTCCTGCAACTTTATCCGCCTCCATCCAGTCTAT
TAATTGTTGCCGGGAAGCTAGAGTAAGTAGTTCGCCAGTTAATAGTTTGC
GCAACGTTGTTGCCATTGCTACAGGCATCGTGGTGTCACGCTCGTCGTTT
GGTATGGCTTCATTCAGCTCCGGTTCCCAACGATCAAGGCGAGTTACATG
ATCCCCCATGTTGTGCAAAAAAGCGGTTAGCTCCTTCGGTCCTCCGATCG
TTGTCAGAAGTAAGTTGGCCGCAGTGTTATCACTCATGGTTATGGCAGCA
CTGCATAATTCTCTTACTGTCATGCCATCCGTAAGATGCTTTTCTGTGAC
TGGTGAGTACTCAACCAAGTCATTCTGAGAATAGTGTATGCGGCGACCGA
GTTGCTCTTGCCCGGCGTCAATACGGGATAATACCGCGCCACATAGCAGA
ACTTTAAAAGTGCTCATCATTGGAAAACGTTCTTCGGGGCGAAAACTCTC -continued

```
AAGGATCTTACCGCTGTTGAGATCCAGTTCGATGTAACCCACTCGTGCAC
CCAACTGATCTTCAGCATCTTTTACTTTCACCAGCGTTTCTGGGTGAGCA
AAAACAGGAAGGCAAAATGCCGCAAAAAAGGGAATAAGGGCGACACGGAA
ATGTTGAATACTCATACTCTTCCTTTTTCAATATTATTGAAGCATTTATC
AGGGTTATTGTCTCATGAGCGGATACATATTTGAATGTATTTAGAAAAAT
AAACAAATAGGGGTTCCGCGCACATTTCCCCGAAAAGTGCCACCTGACGT
CGACGGATCGGGAGATCTCCCGATCCCCTATGGTCGACTCTCAGTACAAT
CTGCTCTGATGCCGCATAGTTAAGCCAGTATCTGCTCCCTGCTTGTGTGT
TGGAGGTCGCTGAGTAGTGCGCGAGCAAAATTTAAGCTACAACAAGGCAA
GGCTTGACCGACAATGCATGAAGAATCTGCTTAGGGTTAGGCGTTTTGCG
CTGCTTCGCGATGTACGGGCCAGATATACGCGTTGACATTGATTATTGAC
TAGTTATTAATAGTAATCAATTACGGGGTCATTAGTTCATAGCCCATATA
TGGAGTTCCGCGTTACATAACTTACGGTAAATGGCCCGCCTGGCTGACCG
CCCAACGACCCCCGCCCATTGACGTCAATAATGACGTATGTTCCCATAGT
AACGCCAATAGGGACTTTCCATTGACGTCAATGGGTGGAgTATTTACGGT
AAACTGCCCACTTGGCAGTACATCAAGTGTATCATATGCCAAGTACGCCC
CCTATTGACGTCAATGACGGTAAATGGCCCGCCTGGCATTATGCCCAGTA
CATGACCTTATGGGACTTTCCTACTTGGCAGTACATCTACGTATTAGTCA
TCGCTATTACCATGGTGATGCGGTTTTGGCAGTACATCAATGGGCGTGGA
TAGCGGTTTGACTCACGGGGATTTCCAAGTCTCCACCCCATTGACGTCAA
TGGGAGTTTGTTTTGGCACCAAAATCAACGGGACTTTCCAAAATGTCGTA
ACAACTCCGCCCCATTGACGCAAATGGGCGGTAGGCGTGTACGGTGGGAG
GTCTATATAAGCAGAGCTCTCTGGCTAACTAGAGAACCCACTGCTTACTG
GCTTATCGAAATTAATACGACTCACTATAGGGAGACCCAAGCTGGCTAGC
ACCATGGACTACAAAGACCATGACGGTGATATAAAGATCATGACATCGAT
TACAAGGATGACGATGACAAGATGGCCCCCAAGAAGAAGAGGAAGGTGGG
CATTCACCGCGGGGTACCTATGGTGGACTTGAGGACACTCGGTTATTCGC
AACAGCAACAGGAGAAAATCAAGCCTAAGGTCAGGAGCACCGTCGCGCAA
CACCACGAGGCGCTTGTGGGGCATGGCTTCACTCATGCGCATATTGTCGC
GCTTTCACAGCACCCTGCGGCGCTTGGGACGGTGGCTGTCAAATACCAAG
ATATGATTGCGGCCCTGCCCGAAGCCACGCACGAGGCAATTGTAGGGGTC
GGTAAACAGTGGTCGGGAGCGCGAGCACTTGAGGCGCTGCTGACTGTGGC
GGGTGAGCTTAGGGGGCCTCCGCTCCAGCTCGACACCGGGCAGCTGCTGA
AGATCGCGAAGAGAGGGGGAGTAACAGCGGTAGAGGCAGTGCACGCCTGG
CGCAATGCGCTCACCGGGGCCCCCTTGAAC pFUS-X overlap
```

BamHI and XbaI flanked pRVD fragments (gene synthesized, BamHI-EBE-XbaI)):

```
gXTN-1C:
                                        (SEQ ID NO: 191)
TCTAGAGGTCTCATTGACCCCAGACCAGGTAGTCGCAATCGCGTCAcatg
acGGGGGAAAGCAAGCCCTGGAAACCGTGCAAAGGTTGTTGCCGGTCCTT
TGTCAAGACCACGGCAGAGACCGGATCC

gXTN-2C:
                                        (SEQ ID NO: 192)
TCTAGAGGTCTCACGGCctgactcccgatcaagttgtagcgattgcgtcg
CATGACggagggaaacaagcattggagactgtccaacggctccttcccgt
gttgtgtcaagcccacggAGAGACCGGATCC

gXTN-3C:
                                        (SEQ ID NO: 193)
TCTAGAGGTCTCAacggtTTGACGCCTGCACAAGTGGTCGCCATCGCCAG
CcatgatGGCGGTAAGCAGGCGCTGGAAACAGTACAGCGCCTGCTGCCTG
TACTGTGCCAGGATCATGAGAGACCGGATCC

gXTN-4C:
                                        (SEQ ID NO: 194)
TCTAGAGGTCTCACATGGActgaccccagaccaggtagtcgcaatcgcgt
caCATGACgggggaaagcaagccctggaaaccgtgcaaaggttgttgccg
gtcattgtcaagaccacAGAGACCGGATCC

gXTN-5C:
                                        (SEQ ID NO: 195)
TCTAGAGGTCTCAccacggcCTGACCCCAGACCAGGTAGTCGCAATCGCG
TCAcatgacGGGGGAAAGCAAGCCCTGGAAACCGTGCAAAGGTTGTTGCC
GGTCCTTTGTCAAGACCAAGAGACCGGATCC

gXTN-6C:
                                        (SEQ ID NO: 196)
TCTAGAGGTCTCAACCACGGCctgactcccgatcaagttgtagcgattgc
gtcgCATGACggagggaaacaagcattggagactgtccaacggctccttc
ccgtgttgtgtcaagcccAGAGACCGGATCC

gXTN-7C:
                                        (SEQ ID NO: 197)
TCTAGAGGTCTCAgcccacggtTTGACGCCTGCACAAGTGGTCGCCATCG
CCAGCCATGATGGCGGTAAGCAGGCGCTGGAAACAGTACAGCGCCTGCTG
CCTGTACTGTGCCAGGATAGAGACCGGATCC

gXTN-8C:
                                        (SEQ ID NO: 198)
TCTAGAGGTCTCAGGATCATGGActgaccccagaccaggtagtcgcaatc
gcgtcacatgacgggggaaagcaagccctggaaaccgtgcaaaggttgtt
gccggtcattgtcaagaAGAGACCGGATCC

gXTN-9C:
                                        (SEQ ID NO: 199)
TCTAGAGGTCTCAaagaccacggcCTGACCCCAGACCAGGTAGTCGCAAT
CGCGTCAcatgacGGGGGAAAGCAAGCCCTGGAAACCGTGCAAAGGTTGT
TGCCGGTCCTTTGTCAAGAGAGACCGGATCC
```

gXTN-10C:

(SEQ ID NO: 200)

TCTAGAGGTCTCACAAGACCACGGCctgactcccgatcaagttgtagcga
ttgcgtcgcatgacggagggaaacaagcattggagactgtccaacggctc
cttcccgtgttgtgtcaagcccaTggAAGAGACCGGATCC gXTN-1T:

(SEQ ID NO: 201)

TCTAGAGGTCTCATTGACCCCAGACCAGGTAGTCGCAATCGCGTCAAACG
GAGGGGGAAAGCAAGCCCTGGAAACCGTGCAAAGGTTGTTGCCGGTCCTT
TGTCAAGACCACGGCAGAGACCGGATCC gXTN-2T:

(SEQ ID NO: 202)

TCTAGAGGTCTCACGGCctgactcccgatcaagttgtagcgattgcgtcg
AACGGTggagggaaacaagcattggagactgtccaacggctccttcccgt
gttgtgtcaagcccacggAGAGACCGGATCC gXTN-3T:

(SEQ ID NO: 203)

TCTAGAGGTCTCAacggtTTGACGCCTGCACAAGTGGTCGCCATCGCCTC
GAATGGCGGCGGTAAGCAGGCGCTGGAAACAGTACAGCGCCTGCTGCCTG
TACTGTGCCAGGATCATGAGAGACCGGATCC gXTN-4T:

(SEQ ID NO: 204)

TCTAGAGGTCTCACATGGActgaccccagaccaggtagtcgcaatcgcgt
caaacggagggggaaagcaagccctggaaaccgtgcaaaggttgttgccg
gtcctagtcaagaccacAGAGACCGGATCC gXTN-5T:

(SEQ ID NO: 205)

TCTAGAGGTCTCAccacggcCTGACCCCAGACCAGGTAGTCGCAATCGCG
TCAaacggaGGGGGAAAGCAAGCCCTGGAAACCGTGCAAAGGTTGTTGCC
GGTCCTTTGTCAAGACCAAGAGACCGGATCC gXTN-6T:

(SEQ ID NO: 206)

TCTAGAGGTCTCAACCACGGCctgactcccgatcaagttgtagcgattgc
gtcgAACGGTggagggaaacaagcattggagactgtccaacggctccttc
ccgtgttgtgtcaagcccAGAGACCGGATCC gXTN-7T:

(SEQ ID NO: 207)

TCTAGAGGTCTCAgcccacggtTTGACGCCTGCACAAGTGGTCGCCATCG
CCAGCaatggcGGCGGTAAGCAGGCGCTGGAAACAGTACAGCGCCTGCTG
CCTGTACTGTGCCAGGATAGAGACCGGATCC gXTN-8T:

(SEQ ID NO: 208)

TCTAGAGGTCTCAGGATCATGGActgaccccagaccaggtagtcgcaatc
gcgtcaAACGGAgggggaaagcaagccctggaaaccgtgcaaaggttgtt
gccggtcattgtcaagaAGAGACCGGATCC gXTN-9T:

(SEQ ID NO: 209)

TCTAGAGGTCTCAaagaccacggcCTGACCCCAGACCAGGTAGTCGCAAT
CGCGTCAAACGGAGGGGGAAAGCAAGCCCTGGAAACCGTGCAAAGGTTGT
TGCCGGTCCTTTGTCAAGAGAGACCGGATCC gXTN-10T:

(SEQ ID NO: 210)

TCTAGAGGTCTCACAAGACCACGGCctgactcccgatcaagttgtagcga
ttgcgtccaacggtggagggaaacaagcattggagactgtccaacggctc
cttcccgtgttgtgtcaagcccaTggAAGAGACCGGATCC gXTN-1A:

(SEQ ID NO: 211)

TCTAGAGGTCTCATTGACCCCAGACCAGGTAGTCGCAATCGCGTCAaaca
ttGGGGGAAAGCAAGCCCTGGAAACCGTGCAAAGGTTGTTGCCGGTCCTT
TGTCAAGACCACGGCAGAGACCGGATCC gXTN-2A:

(SEQ ID NO: 212)

TCTAGAGGTCTCACGGCctgactcccgatcaagttgtagcgattgcgtcg
aacattggagggaaacaagcattggagactgtccaacggctccttcccgt
gttgtgtcaagcccacggAGAGACCGGATCC gXTN-3A:

(SEQ ID NO: 213)

TCTAGAGGTCTCAacggtTTGACGCCTGCACAAGTGGTCGCCATCGCCAG
CaatattGGCGGTAAGCAGGCGCTGGAAACAGTACAGCGCCTGCTGCCTG
TACTGTGCCAGGATCATGAGAGACCGGATCC gXTN-4A:

(SEQ ID NO: 214)

TCTAGAGGTCTCACATGGActgaccccagaccaggtagtcgcaatcgcgt
caAACATTgggggaaagcaagccctggaaaccgtgcaaaggttgttgccg
gtcattgtcaagaccacAGAGACCGGATCC gXTN-5A:

(SEQ ID NO: 215)

TCTAGAGGTCTCAccacggcCTGACCCCAGACCAGGTAGTCGCAATCGCG
TCGAACATTGGGGGAAAGCAAGCCCTGGAAACCGTGCAAAGGTTGTTGCC
GGTCCTTTGTCAAGACCAAGAGACCGGATCC gXTN-6A:

(SEQ ID NO: 216)

TCTAGAGGTCTCAACCAtGGCctgactcccgatcaagttgtagcgattgc
gtcgaacattggagggaaacaagcattggagactgtccaacggctccttc
ccgtgttgtgtcaagcccAGAGACCGGATCC gXTN-7A:

(SEQ ID NO: 217)

TCTAGAGGTCTCAgcccacggtTTGACGCCTGCACAAGTGGTCGCCATCG
CCTCCAATATTGGCGGTAAGCAGGCGCTGGAAACAGTACAGCGCCTGCTG
CCTGTACTGTGCCAGGATAGAGACCGGATCC gXTN-8A:

(SEQ ID NO: 218)

TCTAGAGGTCTCAGGATCATGGActgaccccagaccaggtagtcgcaatc
gcgtcgaacattgggggaaagcaagccctggaaaccgtgcaaaggttgtt
gccggtcattgtcaagaAGAGACCGGATCC gXTN-9A:

(SEQ ID NO: 219)

TCTAGAGGTCTCAaagaccacggcCTGACCCCAGACCAGGTAGTCGCAAT
CGCGTCGAACATTGGGGGAAAGCAAGCCCTGGAAACCGTGCAAAGGTTGT
TGCCGGTCCTTTGTCAAGAGAGACCGGATCC -continued gXTN-10A:

(SEQ ID NO: 220)

TCTAGAGGTCTCACAAGACCACGGCctgactcccgatcaagttgtagcga ttgcgtcgAACATTggagggaaacaagcattggagactgtccaacggctc cttcccgtgttgtgtcaagcccaTggAAGAGACCGGATCC gXTN-1G:

(SEQ ID NO: 221)

TCTAGAGGTCTCATTGACCCCAGACCAGGTAGTCGCAATCGCGaacaata atGGGGGAAAGCAAGCCCTGGAAACCGTGCAAAGGTTGTTGCCGGTCCTT

TGTCAAGACCACGGCAGAGACCGGATCC gXTN-2G:

(SEQ ID NO: 222)

TCTAGAGGTCTCACGGCctgactcccgatcaagttgtagcgattgcgaat aacaatggagggaaacaagcattggagactgtccaacggctccttcccgt gttgtgtcaagcccacggAGAGACCGGATCC gXTN-3G:

(SEQ ID NO: 223)

TCTAGAGGTCTCAacggtTTGACGCCTGCACAAGTGGTCGCCATCGCCAA

CAACAACGGCGGTAAGCAGGCGCTGGAAACAGTACAGCGCCTGCTGCCTG

TACTGTGCCAGGATCATGAGAGACCGGATCC gXTN-4G:

(SEQ ID NO: 224)

TCTAGAGGTCTCACATGGActgaccccagaccaggtagtcgcaatcgcga acaataatgggggaaagcaagccctggaaaccgtgcaaaggttgttgccg gtcattgtcaagaccacAGAGACCGGATCC gXTN-5G:

(SEQ ID NO: 225)

TCTAGAGGTCTCAccacggcCTGACCCCAGACCAGGTAGTCGCAATCGCG

AACAATAATGGGGGAAAGCAAGCCCTGGAAACCGTGCAAAGGTTGTTGCC

GGTCCTTTGTCAAGACCAAGAGACCGGATCC gXTN-6G:

(SEQ ID NO: 226)

TCTAGAGGTCTCAACCAtGGCctgactcccgatcaagttgtagcgattgc gaataacaatggagggaaacaagcattggagactgtccaacggctccttc ccgtgttgtgtcaagcccAGAGACCGGATCC gXTN-7G:

(SEQ ID NO: 227)

TCTAGAGGTCTCAgcccacggtTTGACGCCTGCACAAGTGGTCGCCATCG

CCAACAACAACGGCGGTAAGCAGGCGCTGGAAACAGTACAGCGCCTGCTG

CCTGTACTGTGCCAGGATAGAGACCGGATCC gXTN-8G:

(SEQ ID NO: 228)

TCTAGAGGTCTCAGGATCATGGActgaccccagaccaggtagtcgcaatc gcgaacaataatgggggaaagcaagccctggaaaccgtgcaaaggttgtt gccggtcctttgtcaagaAGAGACCGGATCC gXTN-9G:

(SEQ ID NO: 229)

TCTAGAGGTCTCAaagaccacggcCTGACCCCAGACCAGGTAGTCGCAAT

CGCGAACAATAATGGGGGAAAGCAAGCCCTGGAAACCGTGCAAAGGTTGT

TGCCGGTCCTTTGTCAAGAGAGACCGGATCC

-continued gXTN-10G:

(SEQ ID NO: 230)

TCTAGAGGTCTCACAAGACCACGGCctgactcccgatcaagttgtagcga ttgcgaataacaatggagggaaacaagcattggagactgtccaacggctc cttcccgtgttgtgtcaagcccaTggAAGAGACCGGATCC SbfI and SacI Flanked pFUS Fragments (Gene Synthesized, SbfI-pFUS-SacI)

pFUS-X:

(SEQ ID NO: 231)

(SbfI) CCTGCAGGTCGACCGTCTCAGAACTTGAAGAGACCGTACGTGAT

CGTGGTCTCATggaTTGAAGAGACG GGTACCGAGCTC (SacI)

pFUS-Z1:

(SEQ ID NO: 232)

CCTGCAGGTCGACCGTCTCATTGAAGAGACCGTACTGgatcgtGGTCTCA

CGGCctgaAGAGACGGGTACCGAGCTC pFUS-Z2:

(SEQ ID NO: 233)

CCTGCAGGTCGACCGTCTCATTGAAGAGACCGTACTGgatcgtGGTCTCA acggtctgaAGAGACGGGTACCGAGCTC pFUS-Z3:

(SEQ ID NO: 234)

CCTGCAGGTCGACCGTCTCATTGAAGAGACCGTACTGgatcgtGGTCTCA

CATGGActgaAGAGACGGGTACCGAGCTC pFUS-Z4:

(SEQ ID NO: 235)

CCTGCAGGTCGACCGTCTCATTGAAGAGACCGTACTGgatcgtGGTCTCA ccacggcctgaAGAGACGGGTACCGAGCTC pFUS-Z5:

(SEQ ID NO: 236)

CCTGCAGGTCGACCGTCTCATTGAAGAGACCGTACTGgatcgtGGTCTCA

ACCACGGCctgaAGAGACGGGTACCGAGCTC pFUS-Z6:

(SEQ ID NO: 237)

CCTGCAGGTCGACCGTCTCATTGAAGAGACCGTACTGgatcgtGGTCTCA gcccacggtctgaAGAGACGGGTACCGAGCTC pFUS-Z7:

(SEQ ID NO: 238)

CCTGCAGGTCGACCGTCTCATTGAAGAGACCGTACTGgatcgtGGTCTCA

GGATCATGGActgaAGAGACGGGTACCGAGCTC pFUS-Z8:

(SEQ ID NO: 239)

CCTGCAGGTCGACCGTCTCATTGAAGAGACCGTACTGgatcgtGGTCTCA aagaccacggcctgaAGAGACGGGTACCGAGCTC pFUS-Z9:

(SEQ ID NO: 240)

CCTGCAGGTCGACCGTCTCATTGAAGAGACCGTACTGgatcgtGGTCTCA

CAAGACCACGGCctgaAGAGACGGGTACCGAGCTC pFUS-Z10:

(SEQ ID NO: 241)

CCTGCAGGTCGACCGTCTCATTGAAGAGACCGTACTGgatcgtGGTCTCA

TggActgaAGAGACGGGTACCGAGCTC

Example 7

Methylesterases and Methyltransferases 34aa Consensus EBE:

(SEQ ID NO: 300)
QTTERIVAIGT nn (nn is replaced with relevant RVD)

(SEQ ID NO: 242)
GGTQALEAVLTALPRVCPGMV

Backtranseq of 34aa (SEQ ID NO: 301)
QTTERIVAIGT

SH (SH is anon-specific RVD (SEQ ID NO: 243)
GGTQALEAVLTALPRVCPGMV
and (SEQ ID NO: 244)
CAGACCACCGAGAGGATCGTGGCCATCGGCACCAGCCACGGCGGCACCCA

GGCCCTGGAGGCCGTGCTGACCGCCCTGCCCAGGGTGTGCCCCGGCATGG

TG

Methylesterase EBE (14EBEs in XTN Backbone) (SEQ ID NO: 245):

Bold Font: Methylesterase EBEs. All with non-specific RVD SH in this example.

Black Font: FLASH XTN Backbone.

GACGGATCGGGAGATCTCCCGATCCCCTATGGTCGACTCTCAGTACAATCTGCTCTGATGCCGCATAGTTAAGCCAGTATCTGCTCCCT

GCTTGTGTGTTGGAGGTCGCTGAGTAGTGCGCGAGCAAAATTTAAGCTACAACAAGGCAAGGCTTGACCGACAATTGCATGAAGAAT

CTGCTTAGGGTTAGGCGTTTTGCGCTGCTTCGCGATGTACGGGCCAGATATACGCGTTGACATTGATTATTGACTAGTTATTAATAGTA

ATCAATTACGGGGTCATTAGTTCATAGCCCATATATGGAGTTCCGCGTTACATAACTTACGGTAAATGGCCCGCCTGGCTGACCGCCC

AACGACCCCCGCCCATTGACGTCAATAATGACGTATGTTCCCATAGTAACGCCAATAGGGACTTTCCATTGACGTCAATGGGTGGAgT

ATTTACGGTAAACTGCCCACTTGGCAGTACATCAAGTGTATCATATGCCAAGTACGCCCCCTATTGACGTCAATGACGGTAAATGGCC

CGCCTGGCATTATGCCCAGTACATGACCTTATGGGACTTTCCTACTTGGCAGTACATCTACGTATTAGTCATCGCTATTACCATGGTGA

TGCGGTTTTGGCAGTACATCAATGGGCGTGGATAGCGGTTTGACTCACGGGGATTTCCAAGTCTCCACCCCATTGACGTCAATGGGAG

TTTGTTTTGGCACCAAAATCAACGGGACTTTCCAAAATGTCGTAACAACTCCGCCCCATTGACGCAAATGGGCGGTAGGCGTGTACGG

TGGGAGGTCTATATAAGCAGAGCTCTCTGGCTAACTAGAGAACCCACTGCTTACTGGCTTATCGAAATTAATACGACTCACTATAGGG

AGACCCAAGCTGGCTAGCACCATGGACTACAAAGACCATGACGGTGATTATAAAGATCATGACATCGATTACAAGGATGACGATGAC

AAGATGGCCCCCAAGAAGAAGAGGAAGGTGGGCATTCACCGCGGGGTACCTATGGTGGACTTGAGGACACTCGGTTATTCGCAACAG

CAACAGGAGAAAATCAAGCCTAAGGTCAGGAGCACCGTCGCGCAACACCACGAGGCGCTTGTGGGGCATGGCTTCACTCATGCGCAT

ATTGTCGCGCTTTCACAGCACCCTGCGGCGCTTGGGACGGTGGCTGTCAAATACCAAGATATGATTGCGGCCCTGCCCGAAGCCACGC

ACGAGGCAATTGTAGGGGTCGGTAAACAGTGGTCGGGAGCGCGAGCACTTGAGGCGCTGCTGACTGTGGCGGGTGAGCTTAGGGGGC

CTCCGCTCCAGCTCGACACCGGGCAGCTGCTGAAGATCGCGAAGAGAGGGGGAGTAACAGCGGTAGAGGCAGTGCACGCCTGGCGC

AATGCGCTCACCGGGGCCCCCTTGAAC

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

-continued

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CAGACCACCGAGAGGATCGTGGCCATCGGCACCAGCCACGGCGGCACCCAGGCCCTGGAGGCCGTGCTGACCGCCCTGCCC

AGGGTGTGCCCCGGCATGGTG

CTGACACCCGAACAGGTGGTCGCCATTGCTAATAATAACGGAGGACGGCCAGCCTTGGAGTCCATCGTAGCCCAATTGTCCAGGCCC

GATCCCGCGTTGGCTGCGTTAACGAATGACCATCTGGTGGCGTTGGCATGTCTTGGTGGACGACCCGCGCTCGATGCAGTCAAAAAGG

GTCTGCCTCATGCTCCCGCATTGATCAAAAGAACCAACCGGCGGATTCCCGAGAGAACTTCCCATCGAGTCGCGGGATCCCAACTAGT

C

Example 8: Generation of an Exemplary Non-Covalent Linkage

Phage display is used to identify a scFv antibody against a FLAG affinity tag that provides an optimal linkage. A large diversity in scFv affinity is obtained by limiting the stringency of the affinity selection process. This diversity may represent a key advantage of a PhD approach for identifying a successful linkage between a FLAG affinity tag and a scFv with affinity for the FLAG tag. In some instances, a single-chain variable fragment (scFv) antibody with a faster off-rate may provide permissive "breathing" of a scFv-FLAG complex. A near-exhaustive search among scFv antibodies allows one to select from among a large diversity of possible conformations of scFv-FLAG affinity tag complexes. A PhD strategy may create such diversity through the generation of unique monovalent scFvs against the FLAG epitope.

A non-covalent linkage method, such as that achieved through the use of a scFv antibody employs a protein fused to a scFv that provides a reversible association between a FLAG affinity tag and the scFv, which may circumvent any permanent interference with the target protein that may occur when it is subjected to covalent linkage.

Immunization for Producing Anti-FLAG Antibodies.

An antibody library is produced from immunized rabbits as is well known in the art. Six New Zealand White rabbits are immunized each with 200 pg of a FLAG affinity tag peptide sequence plus adjuvant, and serum is collected six weeks after immunization for determining antibody titers. Titers are determined by ELISAs on immobilized FLAG affinity tag and the animals with the highest titers (at least 1:1000) are sacrificed for isolating the spleen and bone marrow. If rabbits do not produce sufficient titers, a naïve library from embryonic rabbit tissue is used. This provides an unbiased collection of un-rearranged heavy and light chain genes. Total RNA is extracted from tissues using Trizol (Invitrogen), and cDNA synthesis is performed with the iScript cDNA synthesis kit (BioRad).

Generating scFv Gene Fusions.

To isolate expressed variable regions of heavy and light chain genes from rabbit, several primers are used. Eight primers are used for kappa and lambda light chain amplification and five primers are used for heavy chain gene amplification. Primers also contain the coding sequence for an 18 amino acid linker sequence (SSGGGGSGGGGGGSSRSS) (SEQ ID NO: 246), which links the variable regions of the heavy and light chains (VII and VL). This longer linker sequence provides better stability of monomeric forms of scFv fragments. The PCR products of the VH and VL genes overlap in this linker region and can then be assembled by overlap-extension (OLE) PCR (FIG. 1). PCR products are then digested with SfiI, ligated with SfiI-digested pComb3H, and DNA will then be size-selected by gel electrophoresis. This plasmid enables phagemid display of an scFv fused to the pill coat protein. About 5 molecules of pill phage coat protein is present on each phage particle. The pComb3H plasmid expresses the scFv-plll fusion at a level such that about one or two molecules are integrated with wild-type pill (which is provided by helper phage). Since up to 1012 phage particles can be generated in a single preparation, a very large number of scFvs can thus be screened. In PhD the scFv coding sequence is always linked to the phage particle displaying the protein, so subsequent DNA sub-cloning is conveniently achieved.

Producing and Screening the Phage Library.

Ligated plasmid DNA (50 to 100 ng) is electroporated into ER2538 *E. coli* (New England Biolabs). *E. coli* will then be recovered by shaking for 1 hour at 37° C. in 5 mLs of SOC. Phage is produced with the VCSM13 helper phage, which has a defective origin of replication. Phage particles will be precipitated with PEG-8000 and then isolated by further centrifugation. This phage prep is the primary library, and will be affinity selected by "panning." Double recognition panning is performed in which the phage elution is re-incubated with the immobilized antigen, washed, and eluted again. This helps eliminate non-specific phage. To test each round of selection, phage pools are assayed by ELISAs for affinity to the PB antigen. PB or BSA are coated to 96-well plates, incubated with phage, and then incubated with a horseradish peroxidase (HRP) conjugated anti-M13 antibody, which recognizes the M13 phage coat protein. An increasing ELISA titer indicates successful affinity selection of each phage pool.

Transferring the scFv Library into a Lentiviral Vector, and Expansion in *E. coli*.

Phagemid DNA is isolated from bacteria after the 2nd (R2) and 3rd (R3) rounds of panning by infecting *E. coli* with each phage pool, selecting with carbenicillin, followed by standard plasmid preparation. Plasmid DNA is digested with Sfi1 to liberate the scFv coding sequence, and ligated upstream of the E2c coding sequence within the pLVX-IRES-ZsGreen1 (Clontech) vector. The E2c coding sequence also has a short linker sequence (GGSSRSS) (SEQ ID NO: 247) and creates a fusion of the scFv library to the N-terminal portion of E2c. The two ensuing plasmid libraries (R2 and R3) will then be prepared as in Aim 2, for production of two lentivirus libraries.

Lentivirus Library Production

For production of lentivirus particles, the Lenti-X HT Packaging System (Clontech) is used, which produces viral titers as high as $5\times10^8$ infectious units per mL. Virus is produced according to the manufacturer's specifications. Viral supernatants are titered on HepG2 and Huh7 cells, followed by FACS fluorescence produced by the ZsGreen1 reporter to count transduced cells.

In another aspect, a method for screening for scFvs is disclosed. In this aspect, scFvs that are stable in the cytoplasm may be identified by forming a fusion protein between the scFv and EGFP and expressing in a surrogate mammalian cell line.

What is claimed is:

1. A method for directing proteins to specific loci in a genome of an organism comprising contacting a genomic DNA sequence with a composition comprising a DNA localization component and an effector molecule, or a nucleic acid encoding the DNA localization component and the effector molecule, (a) wherein the DNA localization component comprises at least one guide RNA (gRNA), and (b) wherein the effector molecule comprises a fusion protein, wherein the fusion protein comprises (i) an inactivated Cas9 (dCas9) or an inactivated nuclease domain thereof and (ii) Clo051 or a nuclease domain thereof.

2. The method of claim 1, wherein the composition or nucleic acid contacts the genomic DNA sequence in vivo, ex vivo, or in vitro.

3. The method of claim 1, wherein the genomic DNA sequence is not a human genomic DNA sequence.

4. A method for modifying a genome of at least a cell of an organism comprising contacting a genomic DNA sequence with a composition comprising a DNA localization component and an effector molecule, or a nucleic acid encoding the DNA localization component and the effector molecule, (a) wherein the DNA localization component comprises at least one guide RNA (gRNA), and (b) wherein the effector molecule comprises a fusion protein, wherein the fusion protein comprises (i) an inactivated Cas9 (dCas9) or an inactivated nuclease domain thereof and (ii) Clo051 or a nuclease domain thereof.

5. The method of claim 4, wherein a double-strand break is introduced into the genomic sequence by Clo051 or a nuclease domain thereof.

6. The method of claim 5, wherein a DNA repair mechanism induces a deletion, insertion, substitution, inversion, and/or relocation.

7. The method of claim 6, wherein the DNA repair mechanism induces an insertion at the genomic sequence, and wherein the insertion comprises an exogenous, artificial, and/or heterologous sequence.

8. The method of claim 7, wherein the genomic sequence comprising the insertion is non-naturally occurring.

9. The method of claim 4, wherein the modification occurs in vivo, ex vivo or in vitro.

10. The method of claim 4, wherein the cell is not a human cell or a human embryonic cell.

11. The method of claim 1, wherein the proteins are directed to specific loci in a genome of a pluripotent stem cell, an embryonic stem cell, or an induced pluripotent stem cell in an organism.

12. The method of claim 4, wherein the genomic DNA is in a pluripotent stem cell, an embryonic stem cell, or an induced pluripotent stem cell.

13. A composition comprising a DNA localization component and an effector molecule, (a) wherein the DNA localization component comprises at least one guide RNA (gRNA), and (b) wherein the effector molecule comprises a fusion protein, wherein the fusion protein comprises (i) an inactivated Cas9 (dCas9) or an inactivated nuclease domain thereof and (ii) Clo051 or a nuclease domain thereof.

* * * * *